US011975061B2

(12) United States Patent
Curtiss, III

(10) Patent No.: US 11,975,061 B2
(45) Date of Patent: May 7, 2024

(54) PROTECTIVE IMMUNITY ENHANCED *SALMONELLA* VACCINE (PIESV) AGAINST *BRUCELLA* SPP

(71) Applicant: UNIVERSITY OF FLORIDA RESEARCH FOUNDATION, INCORPORATED, Gainesville, FL (US)

(72) Inventor: Roy Curtiss, III, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 17/273,801

(22) PCT Filed: Sep. 5, 2019

(86) PCT No.: PCT/US2019/049825
§ 371 (c)(1),
(2) Date: Mar. 5, 2021

(87) PCT Pub. No.: WO2020/051381
PCT Pub. Date: Mar. 12, 2020

(65) Prior Publication Data
US 2022/0023408 A1    Jan. 27, 2022

Related U.S. Application Data

(60) Provisional application No. 62/727,394, filed on Sep. 5, 2018.

(51) Int. Cl.
*A23K 10/16*   (2016.01)
*A61K 39/02*   (2006.01)
*A61K 39/00*   (2006.01)

(52) U.S. Cl.
CPC ...... *A61K 39/098* (2013.01); *A61K 2039/522* (2013.01); *A61K 2039/523* (2013.01); *A61K 2039/70* (2013.01)

(58) Field of Classification Search
None
See application file for complete search history.

(56) References Cited

U.S. PATENT DOCUMENTS

2014/0065188 A1   3/2014   Finlay et al.

FOREIGN PATENT DOCUMENTS

| WO | 2018124393 | | 5/2018 |
|---|---|---|---|
| WO | 2018140717 | A1 | 8/2018 |
| WO | 2020051381 | A1 | 3/2020 |

OTHER PUBLICATIONS

Yang, Xinghong et al., "Selection of Protective Epitopes for *Brucella melitensis* by DNA Vaccination", Infection and Immunity, Nov. 2005, vol. 73, No. 11, pp. 7297-7303.
Yang, Xinghong et al., "Progress in *Brucella* vaccine development", Front Biol (Beijing), Feb. 1, 2013, vol. 8, No. 1, pp. 60-77.
PCT/US2019/049825, PCT Search Report & Written Opinion, dated Jan. 31, 2020, 14 pages.
Ahman, Heidi et al., "Does dependency of antibody response in infants and children to pneumoccal polysaccharides conjugated to tetanus toxoid", Vaccine, vol. 17, 1999, pp. 2726-2732.
Ameiss, Keith et al., "Deliver of woodchuck hepatitis virus-like particle presented influenza M2e by recombinant attenuated *Salmonella* displaying a delayed lysis phenotype", Vaccine, vol. 28, 2010, pp. 6704-6713.
Beckett, F.W. et al., "The Effect Of Reduced-Dose *Brucella abortus* Strain 19 Vaccination In Accredited Dairy Herds", Br. vet. J., vol. 141, 1985, pp. 507-514.
Bertani, G., "Studies On Lysogenesis", I. The mode of phage liberation by lysogenic *Escherichia coli*. J Bacteriol., 1951; vol. 62, No. 3, pp. 293-300.
Biagini Raymond E. et al., "Comparison of a Multiplexed Fluorescent Covalent Microsphere Immunoassay and an Enzyme-Linked Immunosorbent Assay for Measurement of Human Immunoglobulin G Antibodies to Anthrax Toxins", Clinical and Diagnostic Laboratory Immunology, Jan. 2004, vol. 11, No. 1, pp. 50-55.
Blasco, J.m. et al., "Immunization with *Brucella melitensis* Rev 1 against *Brucella ovis* Infection of Rams", Veterinary Microbiology, vol. 14, 1987, pp. 381-392.
Bowden, R.A. et al., "Evaluation of immunogenicity and protective activity in BALB/c mice of the 25-kDa major outer-membrane protein of *Brucella melitensis* (Omp25) expresses in *Escherichia coli*", J. Med. Microbiol., vol. 47, 1998, pp. 39-48.
Clapp, Beata et al., "Nasal Vaccination Stimulates CD8+ T Cells for Potent Protection Against Mucosal *Brucella melitensis* Challenge", Immunol Cell Biol., May 2016, vol. 94, No. 5, pp. 496-508.
Corbel MJ., "Brucellosis: an overview", Emerg Infect Dis., 1997, vol. 3, No. 2, pp. 213-221.
Curtiss III, Roy et al., "Induction of Host Immune Responses Using *Salmonella*-Vectored Vaccines", Virulence Mechanisms of Bacterial Pathogens, 4th ed., 2007, pp. 297-313.

(Continued)

Primary Examiner — Jennifer E Graser
(74) Attorney, Agent, or Firm — Timothy H. Van Dyke; WOLTER, VAN DYKE, DAVIS, PLLC

(57) ABSTRACT

Bacterial pathogens have evolved means to succeed as pathogens by infecting without recognition by receptors triggering innate immunity, by suppressing induction of immunity and by inducing immune responses to antigens that confer no protectives immunity. Embodiments described herein circumvent these abilities in *Salmonella* so as to provide a vector system that induces maximal protective immune responses. Another major problem in using live attenuated bacterial vaccine vectors is the accumulation of attenuating mutations that confer a virulence and safety but which decrease the ability of the vaccine to invade cells in the MALT to colonize and persist in internal effector lymphoid tissues. The embodiments disclosed herein solve this problem in multiple ways by using regulated delayed in vivo shut off of virulence genes, regulated delayed synthesis of recombinant protective antigens and regulated delayed lysis in vivo to confer biological containment with no persistence of vaccine cells and no survival if excreted.

10 Claims, 72 Drawing Sheets

Specification includes a Sequence Listing.

(56) References Cited

OTHER PUBLICATIONS

Curtiss III, Roy et al., "*Salmonella enterica serovar typhimurium* Strains with Regulated Delayed Attenuation In Vivo", Infection and Immunity, Mar. 2009, vol. 77, No. 3, pp. 1071-1082.
Dean, Anna S. et al., "Clinical Manifestations of Human Brucellosis: A Systematic Review and Meta-Analysis", PLoS Negl Trop Dis., 2012, vol. 6, issue, 12, 9 pages.
Ehretsmann, CLaude P. et al., "Specificity of *Escherichia coli* endoribonuclease RNase E: in vivo and in vitro analysis of mutants in a bacteriophage T4 mRNA processing site", Genes & Development, vol. 6, 1992, pp. 149-159.
Franco, Maria Pia et al., "Human brucellosis", The Lancet Infectious diseases, 2007, vol. 7, No. 12, pp. 775-786.
Franz, David R. et al., "Clinical recognition and management of patients exposed to biological warfare agents", Jama—Journal of the American Medical Association, 1997, vol. 278, No. 5, pp. 399-411.
Ghasemi A. et al. "Simultaneous immunization of mice with Omp31 and TF provides protection against *Brucella melitensis* infection", Vaccine, 2015, vol. 33, No. 42, pp. 5532-5538.
Ghasemi A. et al. "Immune reactivity of *Brucella melitensis*-vaccinated rabbit serum with recombinant Omp31 and DnaK proteins", Iran J Microbiol., 2013, vol. 5, No. 1, pp. 9-23.
Ghasemi A. et al. "In silico analysis of chimeric TF, Omp31 and BP26 fragments of *Brucella melitensis* for development of a multi subunit vaccine candidate", Iran J Basic Med Sci., 2014, vol. 17, No. 3, pp. 172-180.
Gomez, Gabriel et al., "Immunogenic and Invasive Properties of *Brucella melitensis* 16M Outer Membrane Protein Vaccine Candidates Identified via a Reverse Vaccinology Approach", PLoS ONE, Mar. 2013, vol. 8, issue 3, 10 pages.
Gunn, Bronwym M. et al., "Construction of recombinant attenuated *Salmonella enterica serovar typhimurium* vaccine vector strains for safety in newborn and infant mice", Clin Vaccine Immunol., 2010, vol. 17, No. 3, pp. 354-362.
Herzberg, Mendel et al., "Immunization against *Brucella* infection", III. Response of mice and guinea pigs to injection of viable and nonviable suspensions of a streptomycin-dependent mutant of *Brucella melitensis*., J Bacteriol., 1955, vol. 69, No. 4, pp. 432-435.
Hitchcock, Penny J. et al., "Morphological heterogeneity among *Salmonella* lipopolysaccharide chemotypes in silver-stained polyacrylamide gels", Journal of bacteriology, 1983, vol. 154, No. 1, pp. 269-277.
Kang, Ho et al., "Immune responses to recombinant pneumococcal PspA antigen delivered by live attenuated *Salmonella enterica serovar typhimurium* vaccine", Infect Immun., 2002, vol. 70, No. 4, pp. 1739-1749.
Kong, Qingke et al., "Regulated delayed expression of rfaH in an attenuated *Salmonella enterica serovar typhimurium* vaccine enhances immunogenicity of outer membrane proteins and a heterologous antigen", Infect Immun., 2009, vol. 77, No. 12, pp. 5572-5582.
Konjufca, Vjollca et al., "Immunogenicity of recombinant attenuated *Salmonella enterica serovar typhimurium* vaccine strains carrying a gene that encodes *Eimeria tenella* antigen SO7", Infect Immun., 2008, vol. 76, No. 12, pp. 5745-5753.
Kruse, Hilde et al., "Wildlife as Source of Zoonotic Infections", Emerging Infectious Diseases, vol. 10, No. 12, Dec. 2004, 2067-2072.
Lalsiamthara, Jonathan et al., "Intermediate rough *Brucella abortus* S19Δper mutant is DIVA enable, safe to pregnant guinea pigs and conf FIG. 3
FIG. 3A
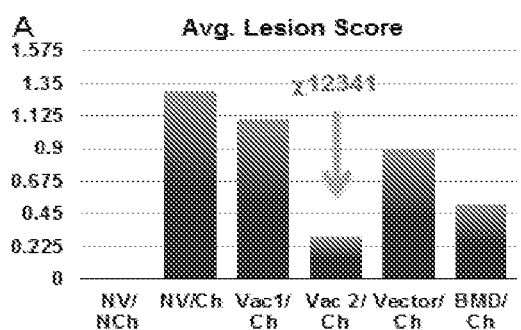
FIG. 3B
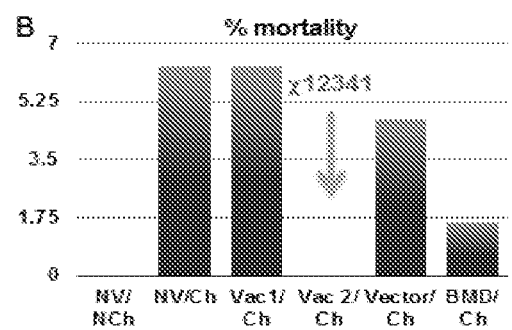
FIG. 3C
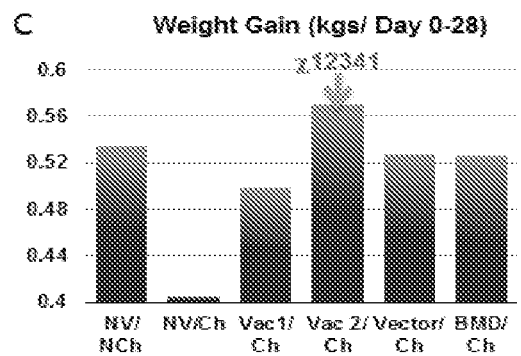
FIG. 3D
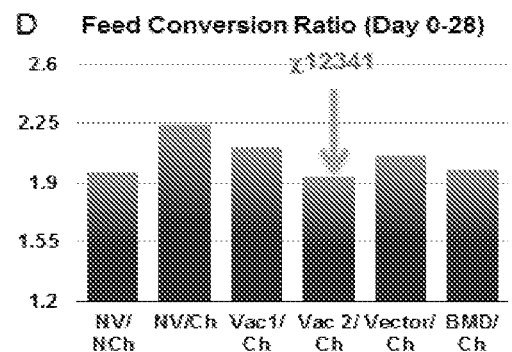

FIG. 5 Western Blot Results – χ6212(pYA232)

M = PAGE Ruler Pre-stained Protein Ladder
1 = Not Induced
2 = Induced

Positive Results as determined in previous experiment:
pG8R110 with *bp26*, pG8R110 with *omp22*, pG8R110 with *tf* pG8R111 with *bp26* pG8R114 with *omp22*, pG8R114 with *bp26*, pG8R114 with *tf*, pG8R114 with *omp25*

Positive Results as determined in second experiment: pG8R241, pG8R242, pG8R243, pG8R247, pG8R249, pG8R250, pG8R251

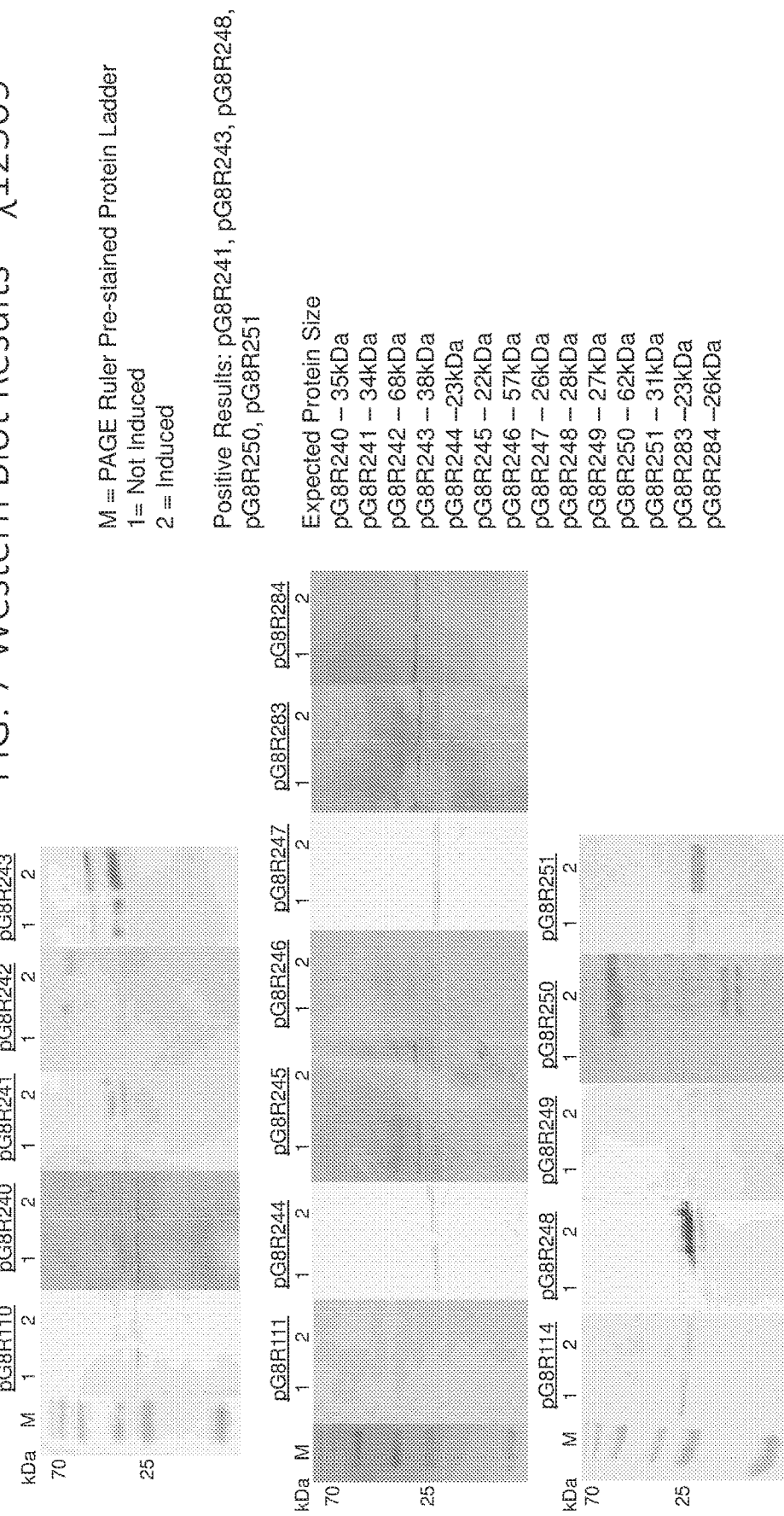

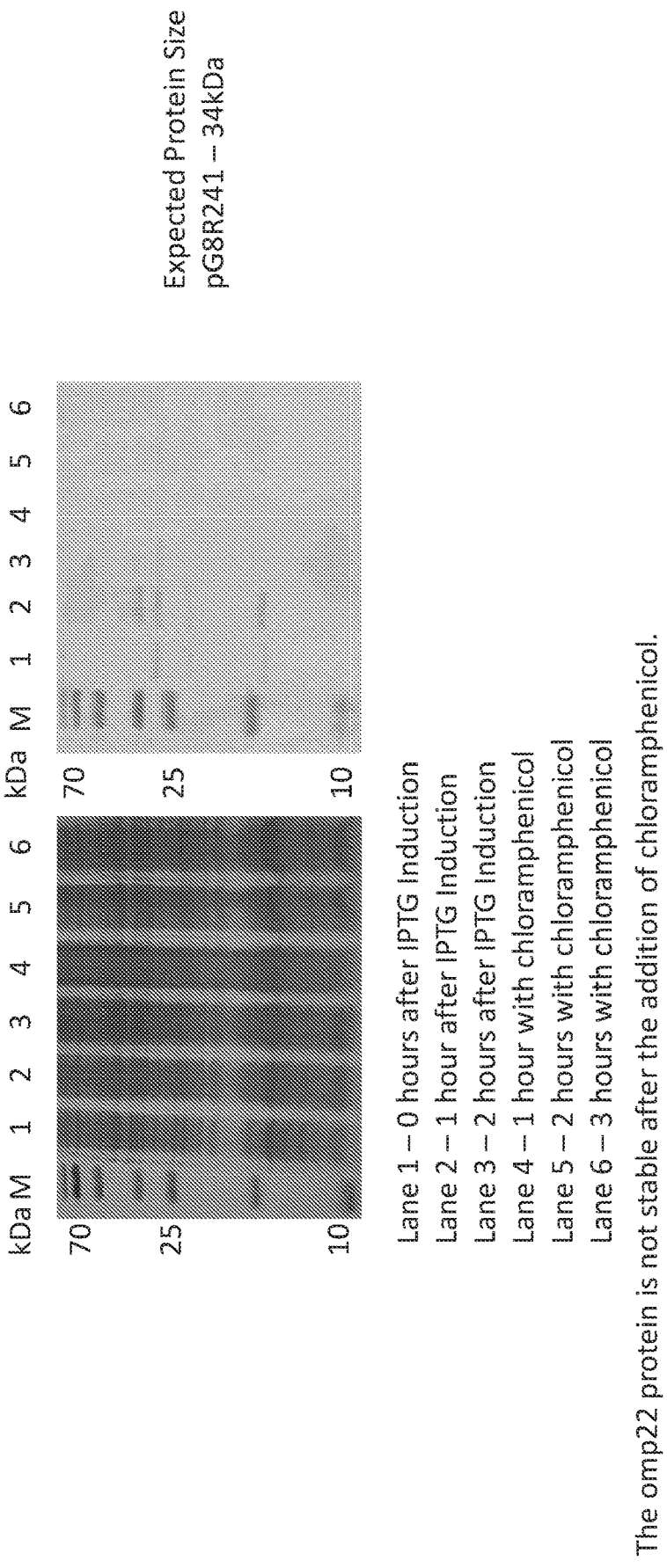
FIG. 10 Antigen Synthesis & Stability – χ12509(pG8R241)
Lane 1 – 0 hours after IPTG Induction
Lane 2 – 1 hour after IPTG Induction
Lane 3 – 2 hours after IPTG Induction
Lane 4 – 1 hour with chloramphenicol
Lane 5 – 2 hours with chloramphenicol
Lane 6 – 3 hours with chloramphenicol
The omp22 protein is not stable after the addition of chloramphenicol.

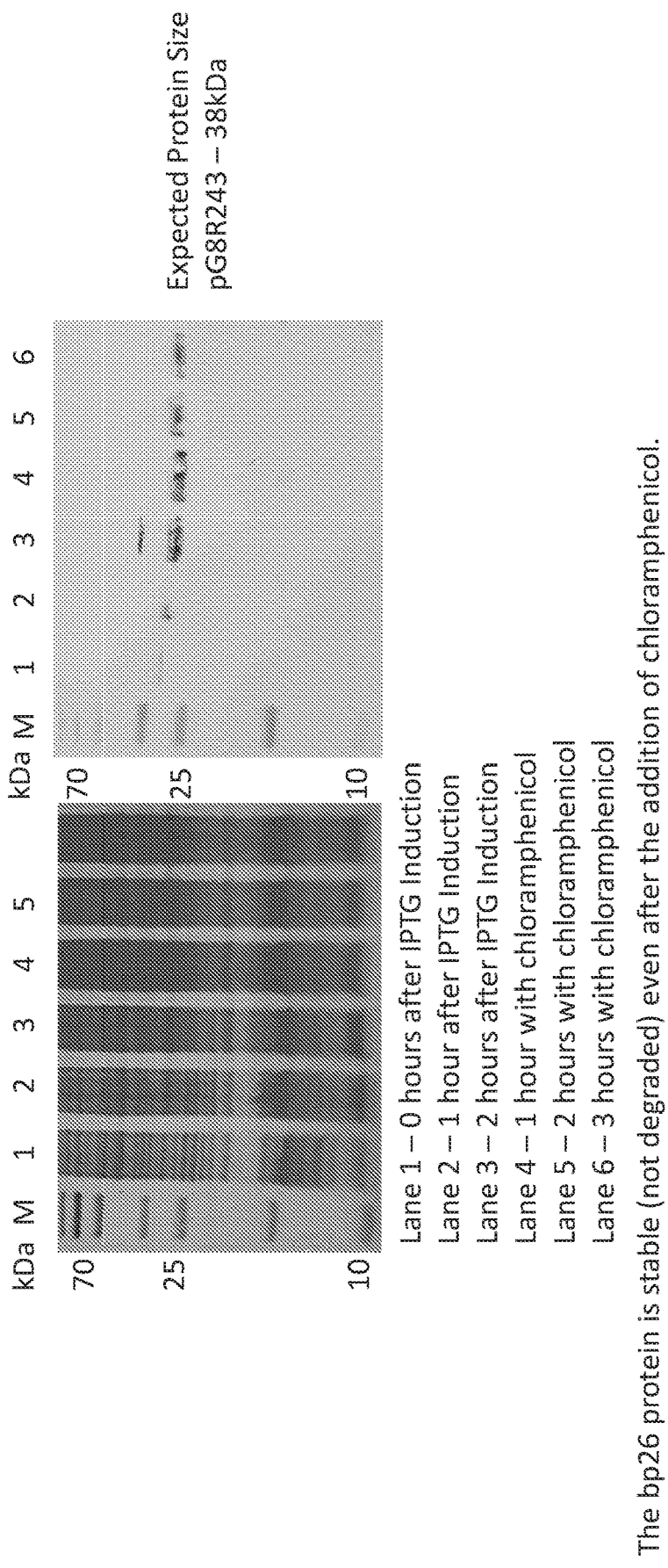
FIG. 11 Antigen Synthesis & Stability – χ12509(pG8R243)
Lane 1 – 0 hours after IPTG Induction
Lane 2 – 1 hour after IPTG Induction
Lane 3 – 2 hours after IPTG Induction
Lane 4 – 1 hour with chloramphenicol
Lane 5 – 2 hours with chloramphenicol
Lane 6 – 3 hours with chloramphenicol
The bp26 protein is stable (not degraded) even after the addition of chloramphenicol.

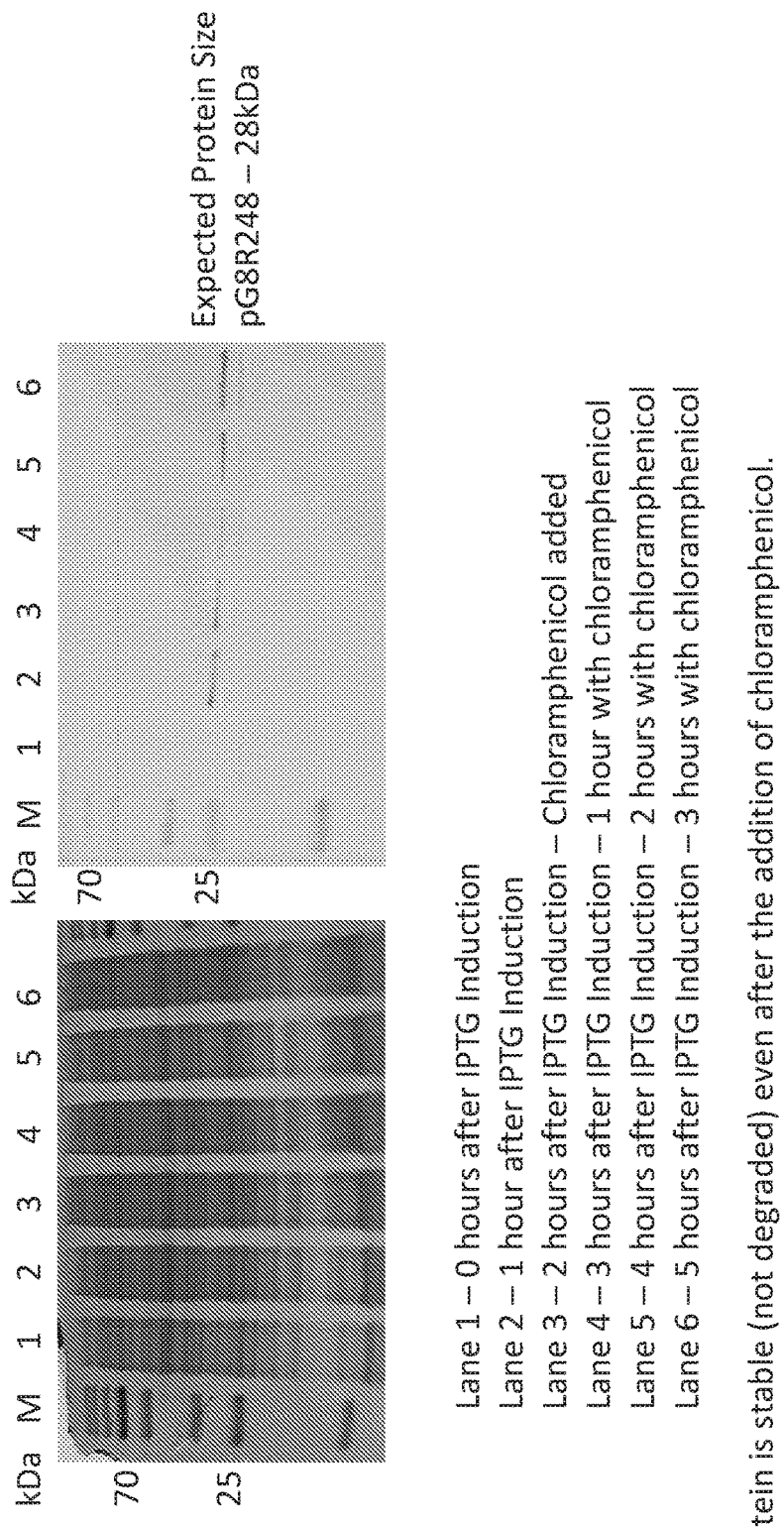

FIG. 12 Antigen Synthesis & Stability – χ12509(pG8R248)

Lane 1 – 0 hours after IPTG Induction
Lane 2 – 1 hour after IPTG Induction
Lane 3 – 2 hours after IPTG Induction – Chloramphenicol added
Lane 4 – 3 hours after IPTG Induction – 1 hour with chloramphenicol
Lane 5 – 4 hours after IPTG Induction – 2 hours with chloramphenicol
Lane 6 – 5 hours after IPTG Induction – 3 hours with chloramphenicol The omp25 protein is stable (not degraded) even after the addition of chloramphenicol.

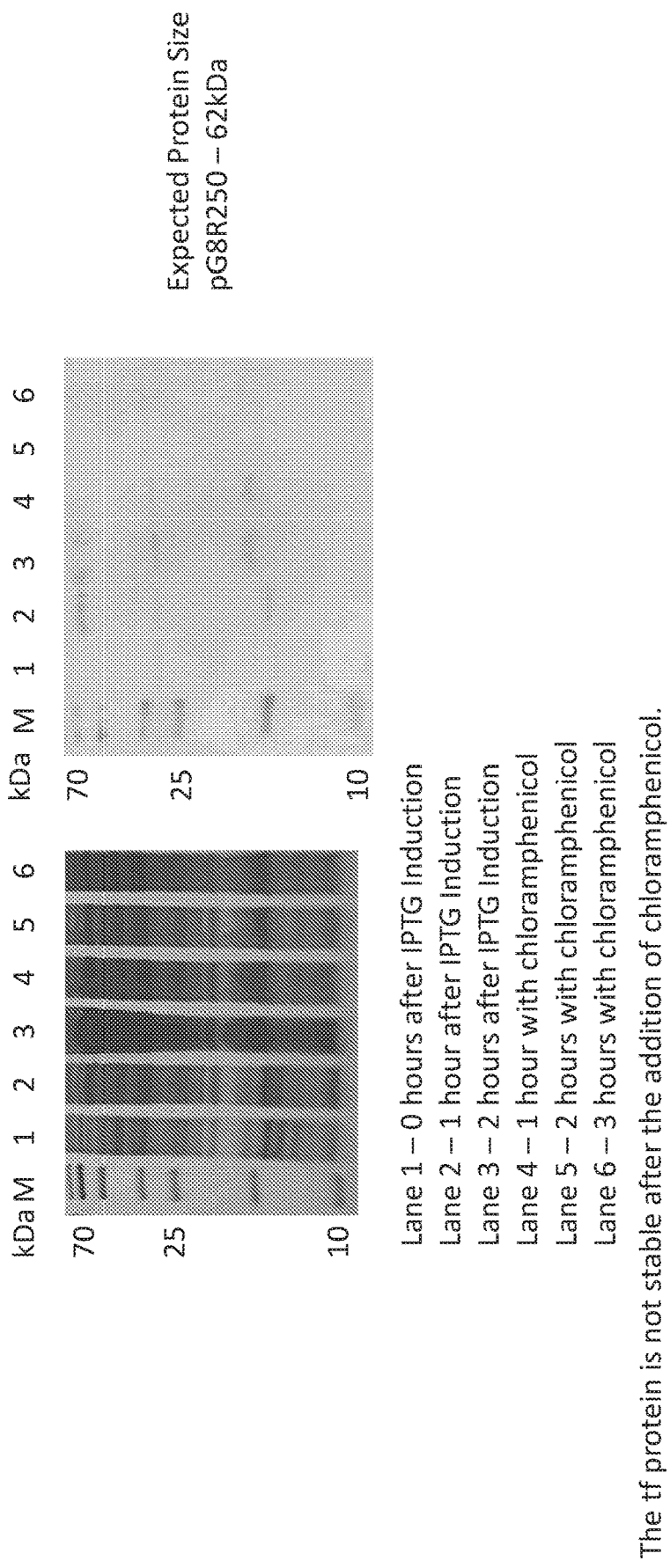
FIG. 13 Antigen Synthesis & Stability – X12509(pG8R250)
Lane 1 – 0 hours after IPTG Induction
Lane 2 – 1 hour after IPTG Induction
Lane 3 – 2 hours after IPTG Induction
Lane 4 – 1 hour with chloramphenicol
Lane 5 – 2 hours with chloramphenicol
Lane 6 – 3 hours with chloramphenicol
The tf protein is not stable after the addition of chloramphenicol.

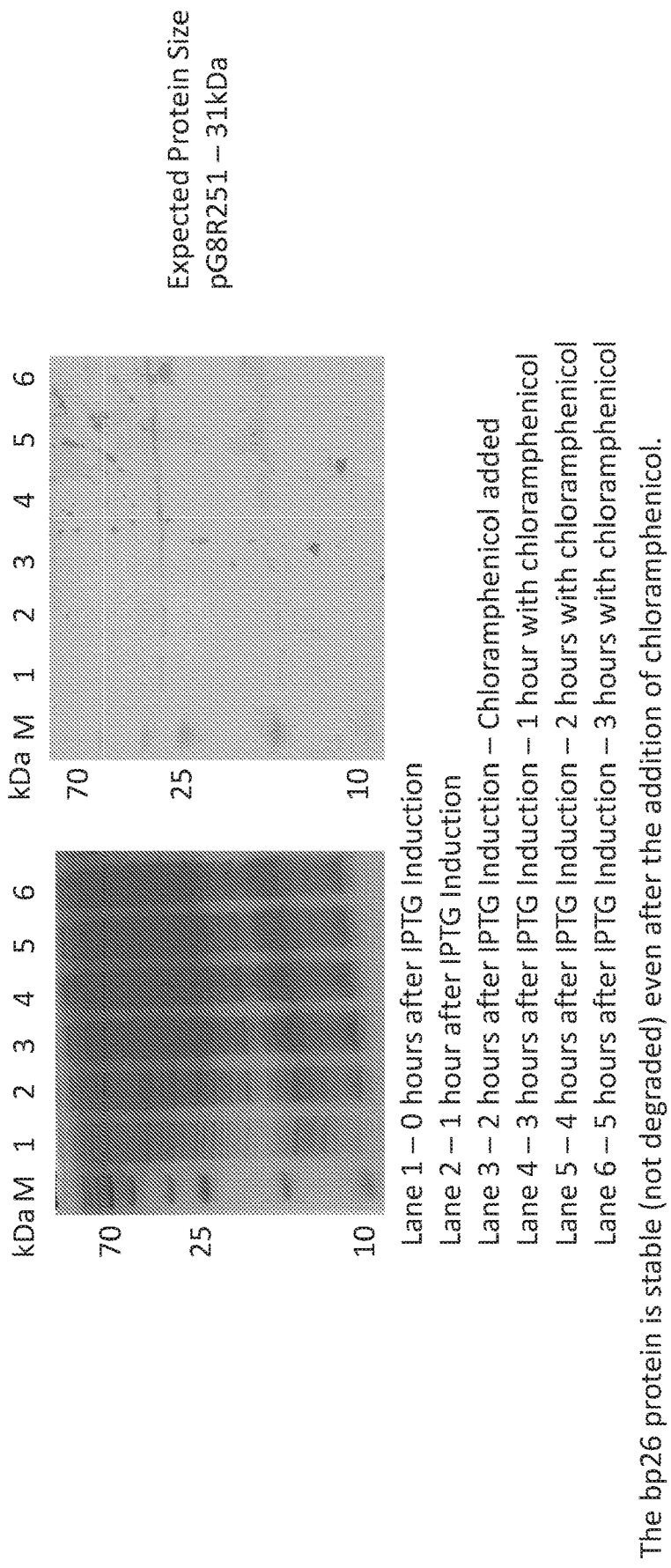

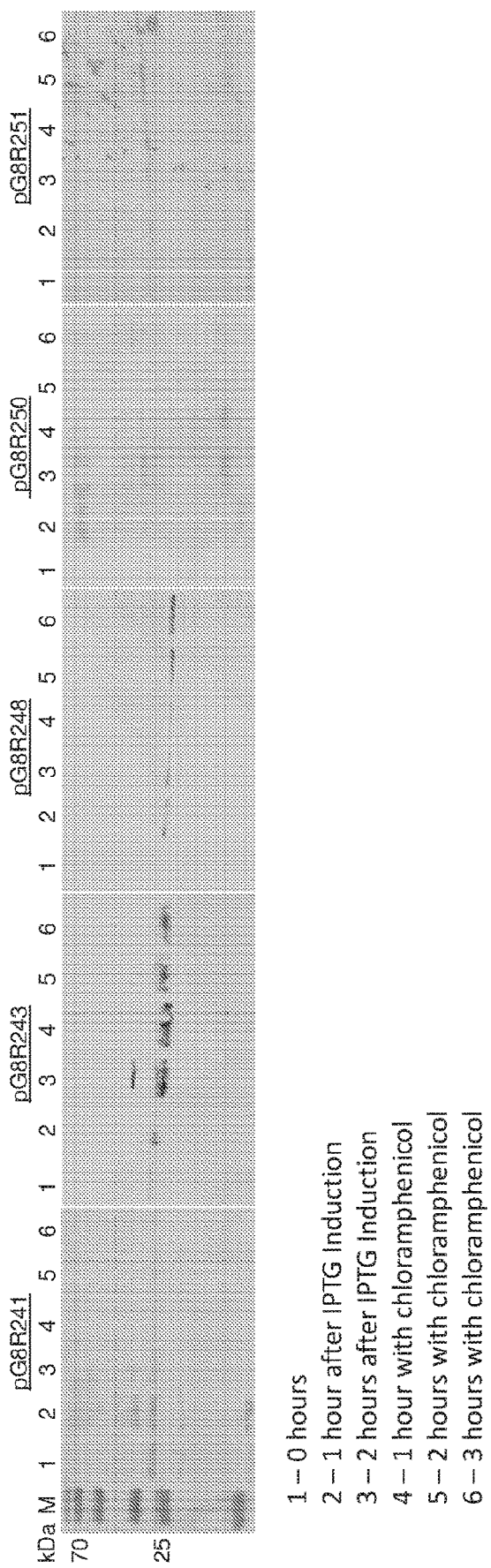

FIG. 15 Antigen Synthesis Stability in χ12509

1 – 0 hours
2 – 1 hour after IPTG Induction
3 – 2 hours after IPTG Induction
4 – 1 hour with chloramphenicol
5 – 2 hours with chloramphenicol
6 – 3 hours with chloramphenicol Results: pG8R241 – The Omp22 protein is not stable after the addition of chloramphenicol. pG8R243 – The bp26 protein is stable (not degraded) even after the addition of chloramphenicol. pG8R248 – The Omp25 protein is stable (not degraded) even after the addition of chloramphenicol. pG8R250 - The tf protein is not stable after the addition of chloramphenicol. pG8R251 - The bp26 protein is stable (not degraded) even after the addition of chloramphenicol.

FIG. 16 Plasmid Stability in χ12509 – pG8R241, pG8R243, pG8R248, pG8R250, pG8R251
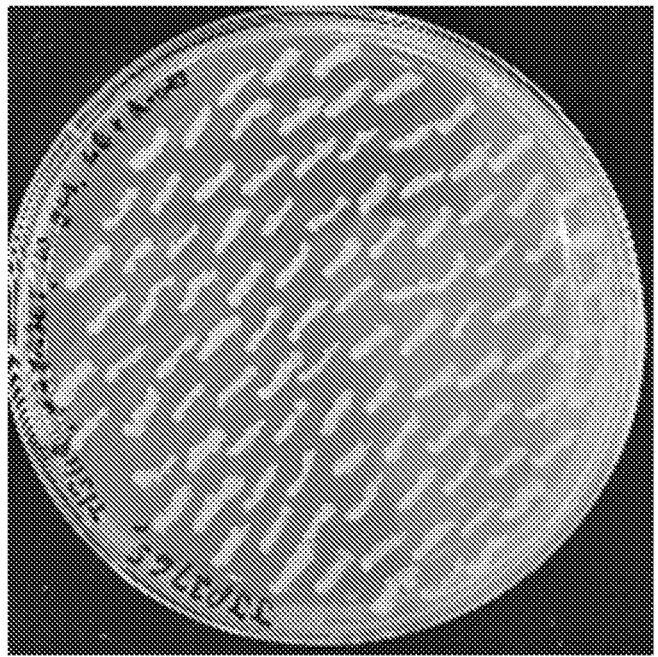
- Plasmids are stably maintained during construct growth under permissive conditions
- Patch plate
  - 100 of 100 colonies grew on LB with 0.2% L-arabinose plates
    - Selective media with no DAP – plasmid must be present for bacteria to grow
  - Tested after 10, 20, 30, 40 & 50 generations of growth FIG. 17 pG8R111-*btuB* in χ12341(pG8R258)
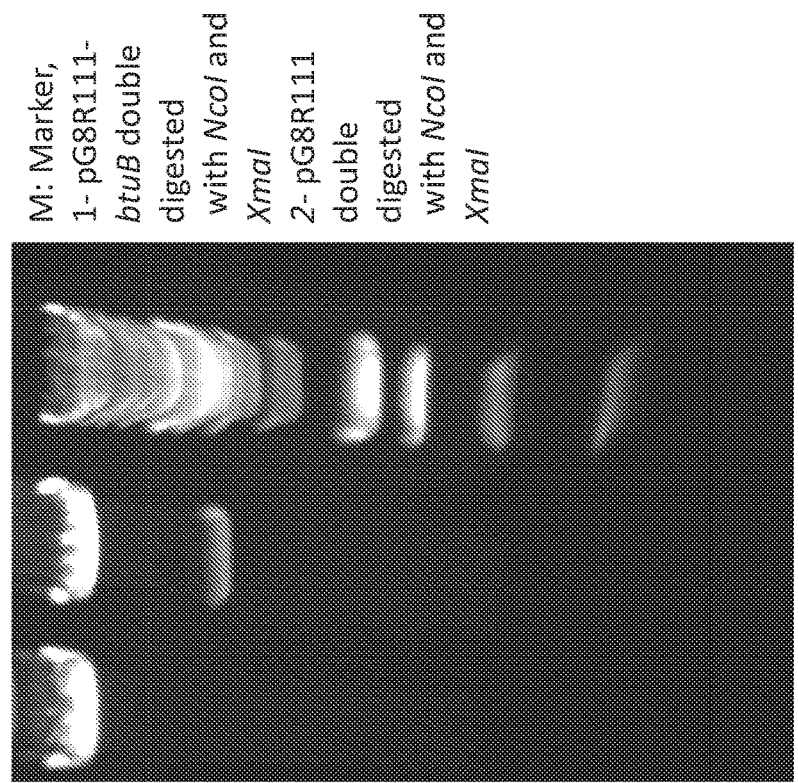
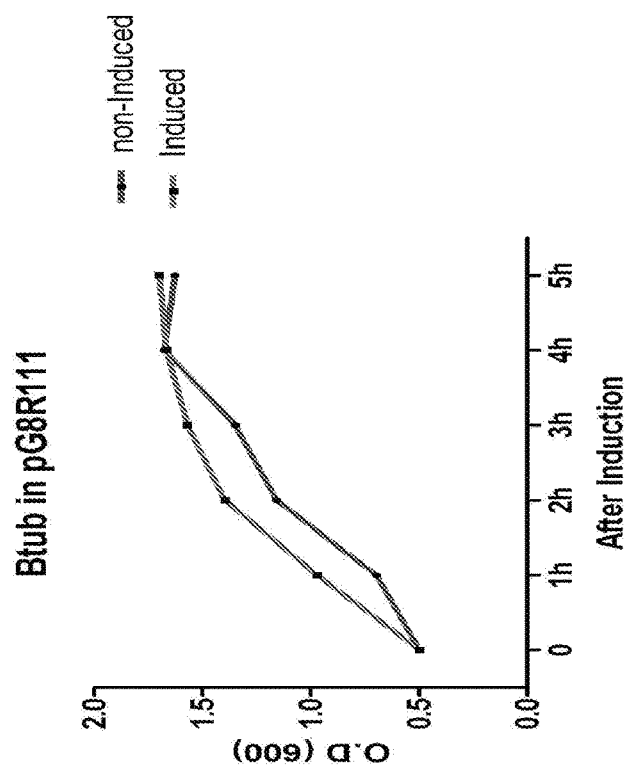

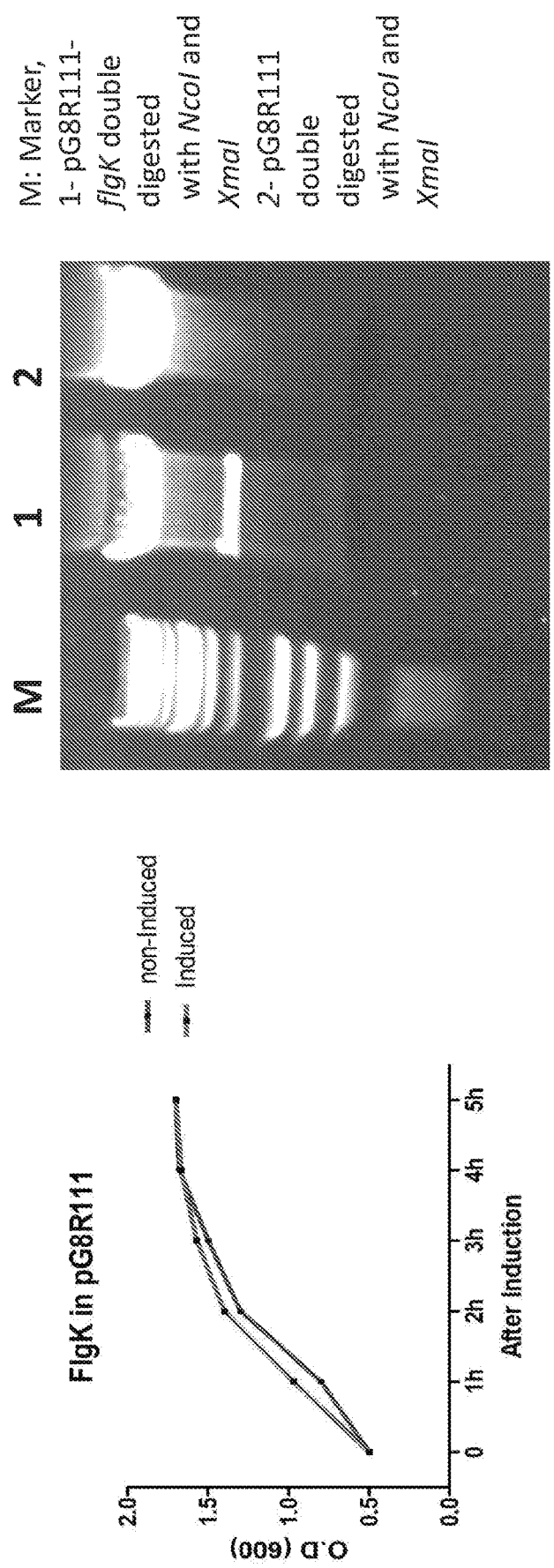
FIG. 18 pG8R111-flgK in χ12341(pG8R260)

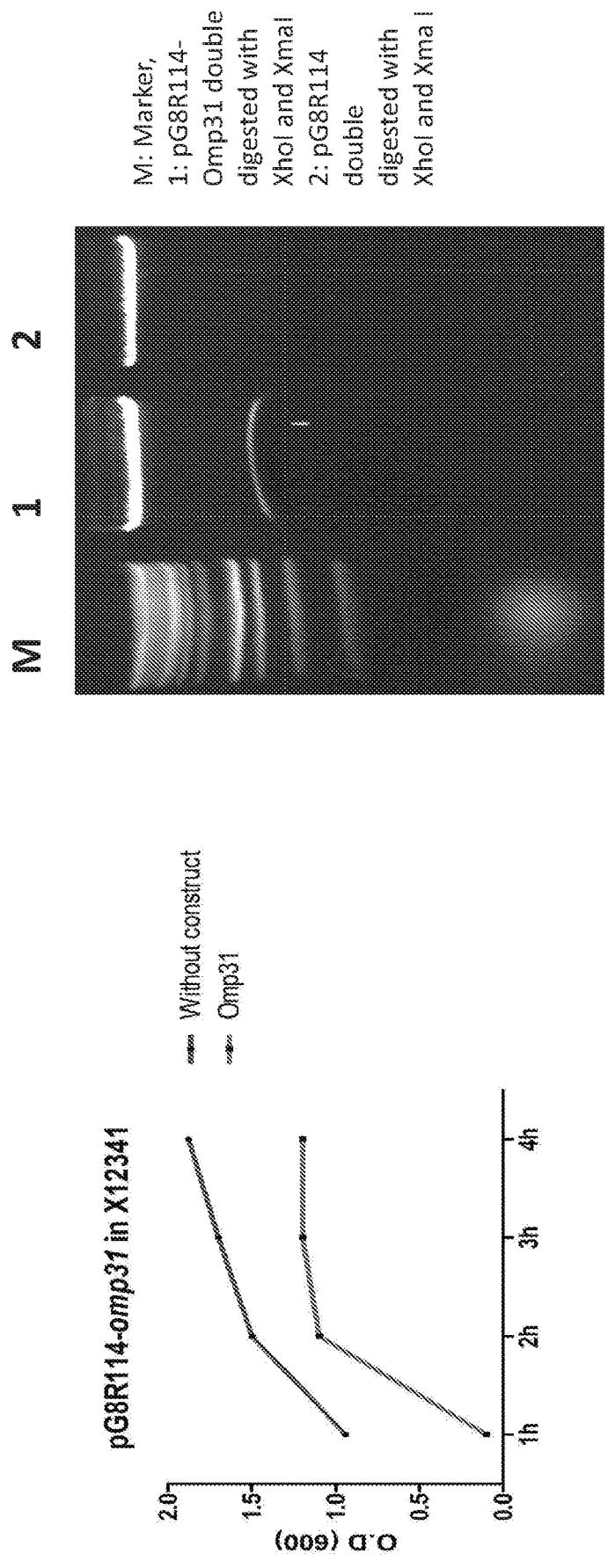
FIG. 19 pG8R114-omp31 in X12341(pG8R261)

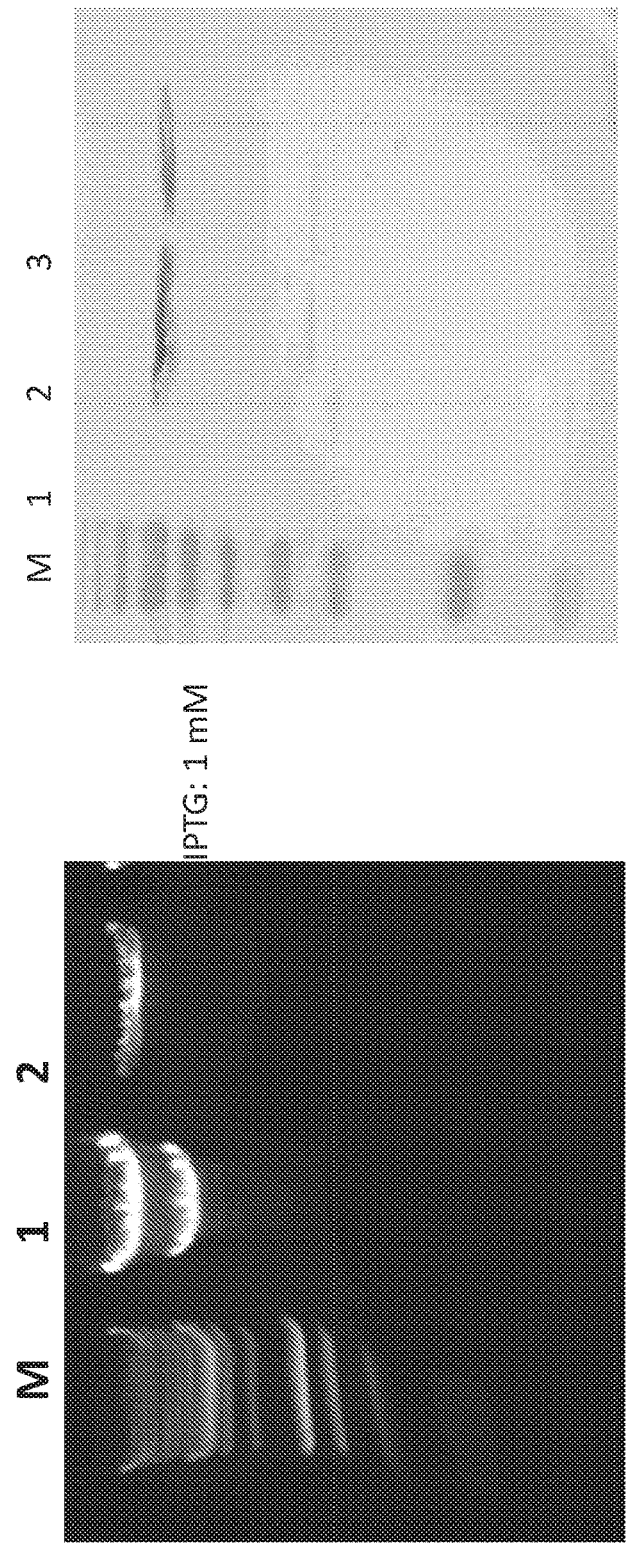
FIG. 20 Chimeric gene expression in pG8R111 vector in *Salmonella* χ12341(pG8R231)

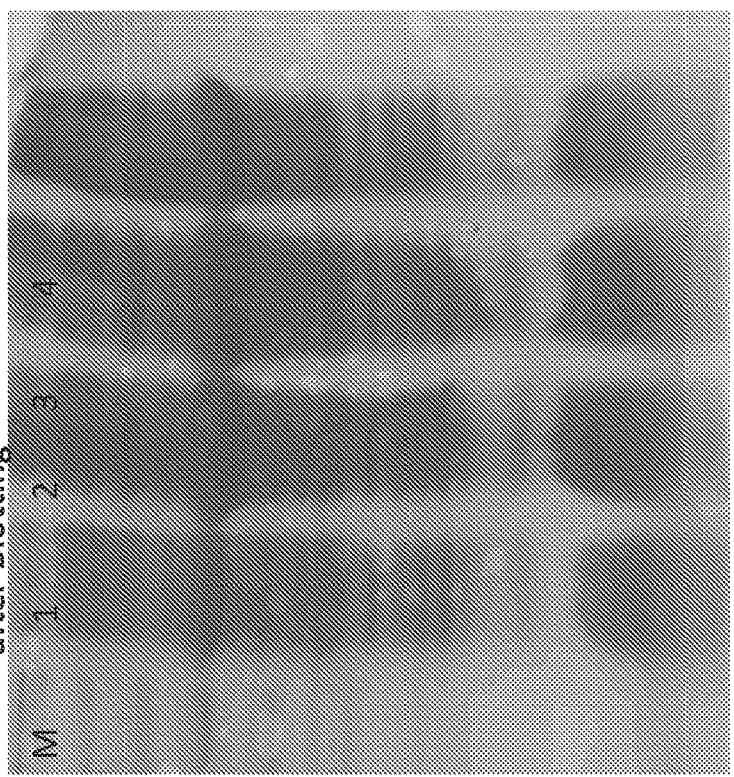
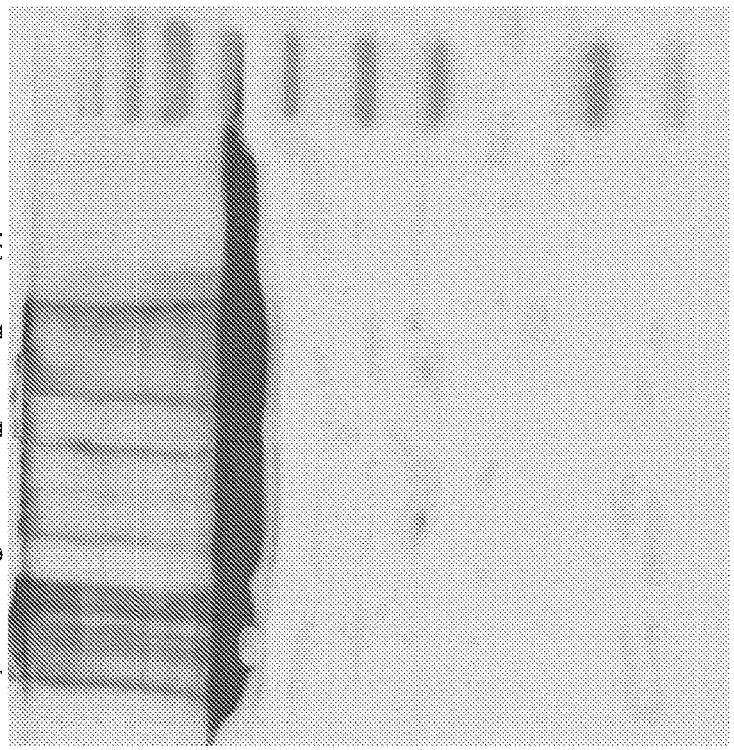
FIG. 21 pGR111-bis-l7/l12-Cu/Zn in X12341(pG8R259)
Coomassie Blue staining after Blotting
M: Marker, 1: Before Induction; 2: 2hrs after induction; 3: 4hrs after induction; 4: 4hrs after induction FIG. 22 pGR111-bls-L7/L12-Cu/Zn in X12341(pG8R259)
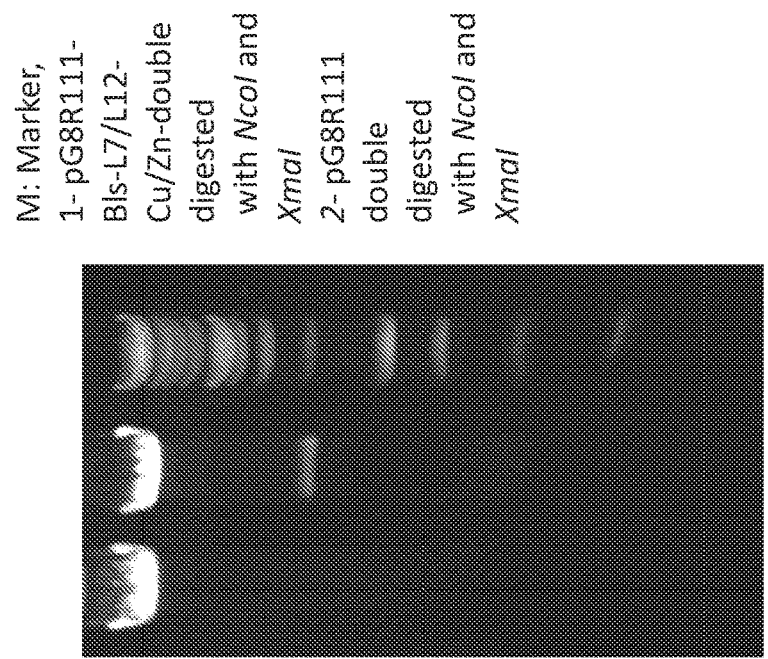
M: Marker,
1- pG8R111-Bls-L7/L12-Cu/Zn-double digested with NcoI and XmaI
2- pG8R111 double digested with NcoI and XmaI
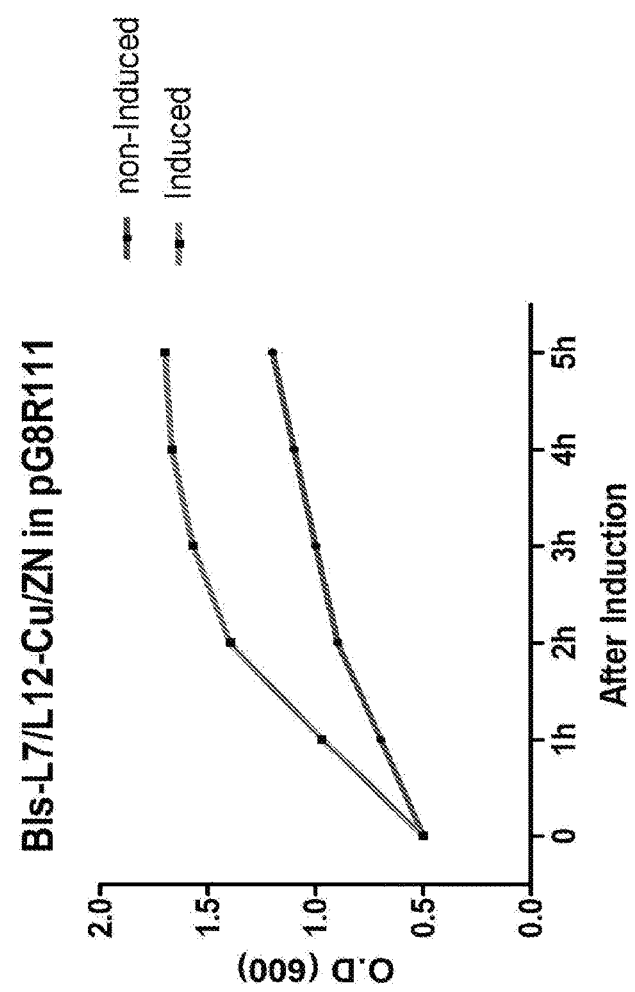

FIG. 23 Results of *B. melitensis* S19 Challenge in Mice

FIG. 24 Testing Vaccine Construct – PIESV-Bm#1

Groups of mice vaccinated

| Group Designation | Vaccine Provided | Route of Vaccinatio n | Dosage (CFU) of Vaccination | Dosage volume (µl) of Vaccination | Challenge Strain | Route of Challenge | Dosage (CFU) of Challenge | Dosage volume (µl) of Challenge |
|---|---|---|---|---|---|---|---|---|
| Group 4 – PIESV-Bm #1 | χ12509 with pG8R251 (pG8R114 with bp26) | Oral | $10^9$ CFU | 20µl | *Brucella abortus* S19 | Intraperitoneal | $10^7$ CFU | 100µl |
| Group 5 – Empty Vector Control | χ12509 with pG8R114 | Oral | $10^9$ CFU | 20µl | *Brucella abortus* S19 | Intraperitoneal | $10^7$ CFU | 100µl |
| Group 6 – Unvaccinated Control | BSG control | Oral | $10^9$ CFU | 20µl | *Brucella abortus* S19 | Intraperitoneal | $10^7$ CFU | 100µl |

Time Table

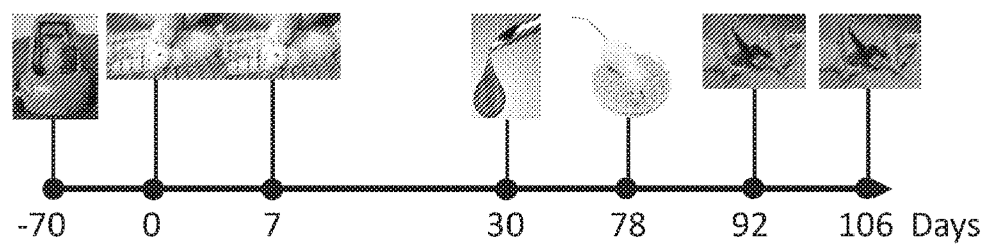

The female mice were 7 weeks old when they arrived at UF and 17 weeks old at first vaccination.

FIG. 25B

FIG. 27: Sequence for pG8R251(pG8R114 with bp26)

ggatcttccggaagaccttccattctgaaatgagctgttgacaattaatcatccggctcgtataatgtgtggaattgtgagcggataacaatttcaca
caggaaacagaccatgaaaaaacaacatttccgtgtcgcccttattccttttttgcggcattttgccttcctgtttttgctcacccagaaacgctggtg
aaagtaaaagatgctgaactcgag CAG GAA AAC CAG ATG ACC ACC CAG CCG GCG CGT ATC GCT GTT ACC
GGT GAA GGT ATG ATG ACC GCT TCT CCG GAC ATG GCT ATC CTG AAC CTG TCT GTT CTG CGT CAG
GCG AAA ACC GCG CGT GAA GCG ATG ACC GCG AAC GAA GCT ATG ACC AAA GTT CTG GAC GCG
ATG AAA AAA GCG GGT ATC GAA GAC CGT GAC CTC CAG ACC GGT GGT ATC AAC ATC CAG CCG ATC
TAC GTT TAC CCG GAC GAC AAA AAC AAC CTG AAA GAA CCG ACC ATC ACC GGT TAC TCT GTT TCT
ACC TCT CTG ACC GTT CGT GTT CGT GAA CTG GCG AAC GTT GGT AAA ATC CTG GAC GAA TCT GTT
ACC CTG GGT GTT AAC CAG GGT GGT GAC CTG AAC CTG GTT AAC GAC AAC CCG TCT GCT GTT ATC
AAC GAA GCG CGT AAA CGT GCT GTT GCT AAC GCT ATC GCT AAA GCG AAA ACC CTG GCT GAC GCT
GCG GGT GTT GGT CTG GGT CGT GTT GTT GAA ATC TCT GAA CTG TCT CGT CCG CCG ATG CCG ATG
CCG ATC GCG CGT GGT CAG TTC CGT ACC ATG CTG GCG GCT GCT CCG GAC AAC TCT GTT CCG ATC
GCT GCT GGT GAA AAC TCT TAC AAC GTT TCT GTT AAC GTT GTT TTC GAA ATC AAA ▓▓▓▓▓▓
▓▓▓▓▓▓▓▓▓▓▓▓▓▓ ▓▓▓▓▓▓ TAA
ctgcagccaagctcccaagcttggctgtttggcggatgagagaagattttcagcctgatacagattaaatcagaacgcagaagcggt
ctgataaaacagaatttgcctggcggcagtagcgcggtggtcccacctgaccccatgccgaactcagaagtgaaacgccgtagcgc
cgatggtagtgtggggtctccccatgcgagagtagggaactgccaggcatcaaataaaacgaaaggctcagtcgaaagactgggc
ctttcgttttatctgttgtttgtcggtgaacgctctcctgagtaggacaaatccgccgggagcggatttgaacgttgcgaagcaacggccc
ggagggtggcgggcaggacgcccgccataaactgccaggcatcaaattaagcagaaggccatcctgacggatggcctttttgcgttt
ctacaaactcttttgttatttttctaaatacattcaaatatgtatccgctcatgagacaataaccctgataaatgcttcaataatggaagatct
tccaacatcacaggtaaacagaaacgtcgggtcgatcgggaaattctttcccggacggcgcggggttgggcaagccgcaggcgcg
tcagtgctttagcgggtgtcggggcgcagccatgacccagtcacgtagcgatagcggagtgtatactggcttaactatgcggcatcag
agcagattgtactgagagtgcaccatatgcggtgtgaaataccgcacagatgcgtaaggagaaaataccgcatcaggcgctcttccg
cttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctgg
cgttttccataggctccgcccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacctgtccgcctttctccctc
gggaagcgtggcgctttctcatagctcacgctgtaggtatctcagttcggtgtaggtcgttcgctccaagctgggctgtgtgcacgaacc
cccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgatctttctacggggtctg
acgctcagtggaacgaaaactcacgttaagggattttggtcatgagattatcaaaaaggatcttcacctagatcctttttaaattaaaaatg
aagttttaaatcaatctaaagtatatatgagtaaacttggtctgacagtctagaagatctagccccgcctaatgagcgggcttttttttaattcg
caattccccgatgcataatgtgcctgtcaaatggacgaagcagggattctgcaaacccatgctactccgtcaagccgtcaattgtctga
ttcgttaccaattatgacaacttgacggctacatcattcactttttcttcacaaccggcacggaactcgctcgggctggccccggtgcatttt
ttaaatacccgcgagaaatagagttgatcgtcaaaaccaacattgcgaccgacggtggcgataggcatccgggtggtgctcaaaag
cagcttcgcctggctgatacgttggtcctcgcgccagcttaagacgctaatccctaactgctggcggaaaagatgtgacagacgcgac
ggcgacaagcaaacatgctgtgcgacgctggcgatatcaaaattgctgtctgccaggtgatcgctgatgtactgacaagcctcgcgta
cccgattatccatcggtggatggagcgactcgttaatcgcttccatgcgccgcagtaacaattgctcaagcagatttatcgccagcagct
ccgaatagcgcccttccccttgccggcgttaatgatttgcccaaacaggtcgctgaaatgcggctggtgcgcttcatccgggcgaaa
gaaccccgtattggcaaatattgacggccagttaagccattcatgccagtaggcgcgcggacgaaagtaaacccactggtgatacc
attcgcgagcctccggatgacgaccgtagtgatgaatctctcctggcgggaacagcaaaatatcacccggtcggcaaacaaattctc
gtccctgattttcaccaccccctgaccgcgaatggtgagattgagaatataaccttcattcccagcggtcggtcgataaaaaaatcga
gataaccgttggcctcaatcggcgttaaacccgccaccagatgggcattaaacgagtatccggcagcaggggatcattttgcgcttc
agccatactttcatactcccgccattcagagaagaaaccaattgtccatattgcatcagacattgccgtcactgcgtctttactggctctt
ctcgctaaccaaaccggtaaccccgcttattaaaagcattctgtaacaaagcgggaccaaagccatgacaaaaacgcgtaacaaa
agtgtctataatcacggcagaaaagtccacattgattatttgcacggcgtcacactttgctatgccatagcattttatccataagattagcg
gatcctacctgacgctttttatcgcaactctctactgtttctccataccgttttttgggctagcgaattctgagaacaaactaagtggataa
atttcgtgttcaggggccaacgaagctccagggcgaagtcacaatttccggcgctaaaaatgctgctctgcctatccttttgccgcacta

FIG. 27 (CONT.)

ctggcggaagaaccggtagagatccagaacgtcccgaaactgaaagacgtcgatacatcaatgaagctgctaagccagctgggtg
cgaaagtagaacgtaatggttctgtgcatattgatgcccgcgacgttaatgtattctgcgcaccttacgatctggttaaaaccatgcgtgct
tctatctgggcgctggggccgctggtagcgcgctttggtcaggggcaagtttcactacctggcggttgtacgatcggtgcgcgtccggtt
gatctacacatttctggcctcgaacaattaggcgcgaccatcaaactggaagaaggttacgttaaagcttccgtcgatggtcgtttgaaa
ggtgcacatatcgtgatggataaagtcagcgttggcgcaacggtgaccatcatgtgtgctgcaaccctggcggaaggcaccacgatt
attgaaaacgcagcgcgtgaaccggaaatcgtcgataccgcgaacttcctgattacgctgggtgcgaaaattagcggtcagggcac
cgatcgtatcgtcatcgaaggtgtggaacgttaggcggcggtgtctatcgcgttctgccggatcgtatcgaaaccggtacttcctggtg
gcggcggcgatttctcgcggcaaaattatctgccgtaacgcgcagccagatactctcgacgccgtgctggcgaaactgcgtgacgct
ggagcggacatcgaagtcggcgaagactggattagcctggatatgcatggcaaacgtccgaaggctgttaacgtacgtaccgcgcc
gcatccggcattcccgaccgatatgcaggcccagttcacgctgttgaacctggtggcagaagggaccgggtttatcaccgaaacggt
ctttgaaaaccgctttatgcatgtgccagagctgagccgtatgggcgcgcacgccgaaatcgaaagcaataccgttatttgtcacggtg
ttgaaaaactttctggcgcacaggttatggcaaccgatctgcgtgcatcagcaagcctggtgctggctggctgtattgcggaagggacg
acggtggttgatcgtatttatcacatcgatcgtggctacgaacgcattgaagacaaactgcgcgctttaggtgcaaatattgagcgtgtg
aaaggcgaataagaattcaaggcaaaaaacgctgtgaaaaatgttggttttatcggctggcgcggaatggtcggctctgttctcatgca
acgcatggtagaggagcgcgatttcgacgctattcgccctgttttcttttctacctcccagtttggacaggcggcgcccaccttcggcgac
acctccaccggcacgctacaggacgcttttgatctggatgcgctaaaagcgctcgatatcatcgtgacctgccagggcggcgattata
ccaacgaaatttatccaaagctgcgcgaaagcggatggcagggttactggattgatgcggcttctacgctgcgcatgaaagatgatg
ccattattattctcgacccggtcaaccaggacgtgattaccgacggcctgaacaatggcgtgaagacctttgtgggcggtaactgtacc
gttagcctgatgttgatgtcgctggcggtctctttgcccataatctcgttgactgggtatccgtcgcgacctatcaggccgcctccggcgg
cggcgcgcgccatatgcgcgagctgttaacccagatgggtcagttgtatggccatgtcgccgatgaactggcgacgccgtcttccgca
attcttgatattgaacgcaaagtacggcattgacccgcagcggcgagctgccggttgataacttggcgtaccgctggcgggaagcct
gatccctggatcgacaaacagctcgataacggccagagccgcgaagagtggaaaggccaggcggaaaccaacaagattctca
atactgcctctgtgattccggttgatggtttgtgtgtgcgcgtcggcgcgctgcgctgtcacagccaggcgttcaccatcaagctgaaaa
aagaggtatccattccgacggtggaagaactgctggcggcacataatccgtgggcgaaagtggtgccgaacgatcgtgatatcact
atgcgcgaattaaccccggcggcggtgaccggcacgttgactacgccggttggtcgtctgcgtaagctgaacatggggccagagttc
ttgtcggcgtttaccgtaggcgaccagttgttatggggcgccgccgagccgctgcgtcgaatgctgcgccagttggcctagtctaggga
cgatgatgcaaccgataccgtcgacggatcacatagactcgctccgaaattaaagaacacttaaattatctactaaaggaatctttagt
caagtttatttaagatgacttaactatgaatacacaattgatgggtgagcgtaggagcatgcttatgcgaaaggccatcctgacggatg
gccttttt FIG. 28 >bp26 - Codon Optimization

```
▓▓▓ ▓▓▓ ▓▓▓▓▓▓▓ CAG GAA AAC CAG ATG ACC ACC CAG CCG GCG CGT ATC GCT GTT ACC GGT GAA
                 Q   E   N   Q   M   T   T   Q   P   A   R   I   A   V   T   G   E

GGT ATG ATG ACC GCT TCT CCG GAC ATG GCT ATC CTG AAC CTG TCT GTT CTG CGT CAG GCG AAA
 G   M   M   T   A   S   P   D   M   A   I   L   N   L   S   V   L   R   Q   A   K

ACC GCG CGT GAA GCG ATG ACC GCG AAC AAC GAA GCT ATG ACC AAA GTT CTG GAC GCG ATG AAA
 T   A   R   E   A   M   T   A   N   N   E   A   M   T   K   V   L   D   A   M   K

AAA GCG GGT ATC GAA GAC CGT GAC CTC CAG ACC GGT GGT ATC AAC ATC CAG CCG ATC TAC GTT
 K   A   G   I   E   D   R   D   L   Q   T   G   G   I   N   I   Q   P   I   Y   V

TAC CCG GAC GAC AAA AAC AAC CTG AAA GAA CCG ACC ATC ACC GGT TAC TCT GTT TCT ACC TCT
 Y   P   D   D   K   N   N   L   K   E   P   T   I   T   G   Y   S   V   S   T   S

CTG ACC GTT CGT GTT CGT GAA CTG GCG AAC GTT GGT AAA ATC CTG GAC GAA TCT GTT ACC CTG
 L   T   V   R   V   R   E   L   A   N   V   G   K   I   L   D   E   S   V   T   L

GGT GTT AAC CAG GGT GGT GAC CTG AAC CTG GTT AAC GAC AAC CCG TCT GCT GTT ATC AAC GAA
 G   V   N   Q   G   G   D   L   N   L   V   N   D   N   P   S   A   V   I   N   E

GCG CGT AAA CGT GCT GTT GCT AAC GCT ATC GCT AAA GCG AAA ACC CTG GCT GAC GCT GCG GGT
 A   R   K   R   A   V   A   N   A   I   A   K   A   K   T   L   A   D   A   A   G

GTT GGT CTG GGT CGT GTT GTT GAA ATC TCT GAA CTG TCT CGT CCG CCG ATG CCG ATG CCG ATC
 V   G   L   G   R   V   V   E   I   S   E   L   S   R   P   P   M   P   M   P   I

GCG CGT GGT CAG TTC CGT ACC ATG CTG GCG GCT GCT CCG GAC AAC TCT GTT CCG ATC GCT GCT
 A   R   G   Q   F   R   T   M   L   A   A   A   P   D   N   S   V   P   I   A   A

GGT GAA AAC TCT TAC AAC GTT TCT GTT AAC GTT GTT TTC GAA ATC AAA ▓▓▓▓▓ ▓▓▓▓▓
 G   E   N   S   Y   N   V   S   V   N   V   V   F   E   I   K

▓▓▓▓▓ ▓▓▓▓▓ TAA ▓▓▓▓
              *
```

FIG. 30: Sequence for pG8R241 (pG8R110 with omp22)
ATCTAGCCCGCCTAATGAGCGGGCTTTTTTTTAATTCGCAATTCCCCGATGCATAATGAaaC
TGCCTGTCAAATGGACGAAGCAGGGATTCTGCAAACCCTATGCTACTCCGTCAAGCCGTCA
ATTGTCTGATTCGTTACCAATTATGACAACTTGACGGCTACATCATTCACTTTTTCTTCACAA
CCGGCACGaAACTCGCTCGGGCTGGCCCCGGTGCATTTTTAAATACtCGCGAGAAATAGA
GTTGATCGTCAAAACCAACATTGCGACCGACGGTGGCGATAGGCATCCGGGTaGTGCTCA
AAAGCAGCTTCGCCTGaCTaATgCGTTGGTCCTCGCGCCAGCTTAAGACGCTAATCCCTAA
CTGCTGGCGGAAAAGATGTGACAGACGCGACGGCGACAAGCAAACATGCTGTGCGACGC
TGGCGATATCAAAATTGCTGTCTGCCAGGTGATCGCTGATGTACTGACAAGCCTCGCGTAC
CCGATTATCCATCGGTGGATGGAGCGACTCGTTAATCGCTTCCATGCGCCGCAGTAACAAT
TGCTCAAGCAGATTTATCGCCAGCAGCTCCGAATAGCGCCCTTCCCCTTGCCCGGCGTTA
ATGATTTGCCCAAACAGGTCGCTGAAATGCGGCTGGTGCGCTTCATCCGGGCGAAAGAAa
CCCGTATTGGCAAATATTGACGGCCAGTTAAGCCATTCATGCCAGTAGGCGCGCGGACGA
AAGTAAACCCACTGGTGATACCATTCGCGAGCCTCCGGATGACGACCGTAGTGATGAATCT
CTCCTGGCGGGAACAGCAAAATATCACCCGGTCGGCAgACAAATTCTCGTCCCTGATTTTT
CACCACCCCTGACCGCGAATGGTGAGATTGAGAATATAACCTTTCATTCCCAGCGGTCG
GTCGATAAAAAAATCGAGATAACCGTTGGCCTCAATCGGCGTTAAACCCGCCACCAGATGG
GCATTAAACGAGTATCCCGGCAGCAGGGGATCATTTTGCGCTTCAGCCATACTTTTCATAC
TCCCGCCATTCAGAGAAGAAACCAATTGTCCATATTGCATCAGACATTGCCGTCACTGCGT
CTTTTACTGGCTCTTCTCGCTAACCAAACCGGTAACCCCGCTTATTAAAAGCATTCTGTAAC
AAAGCGGGACCAAAGCCATGACAAAAACGCGTAACAAAAGTGTCTATAATCACGGCAGAAA
AGTCCACATTGATTATTTGCACGGCGTCACACTTTGCTATGCCATAGCATTTTTATCCATAA
GATTAGCGGATCCTACCTGACGCTTTTTATCGCAACTCTCTACTGTTTCTCCATACCCgtttttt
ggGCTAGCGAATTCTGAGAACAAACTAAatggataaatttcgtgttcaggggccaacgaagctccagggcgaagtc
acaatttccggcgctaaaaatgctgctctgcctatcctttttgccgcactactggcggaagaaccggtagagatccagaacgtcccgaa
actgaaagacgtcgatacatcaatgaagctgctaagccagctgggtgcgaaagtagaacgtaatggttctgtgcatattgatgcccgc
gacgttaatgtatctgcgcaccttacgatctggttaaaaccatgcgtgcttctatctgggcgctggggccgctggtagcgcgctttggtca
ggggcaagtttcactacctggcggttgtacgatggtgcgcgtccggttgatctacacatttctggcctcgaacaattaggcgcgaccat
caaactggaagaaggttacgttaaagcttccgtcgatggtcgtttgaaaggtgcacatatcgtgatggataaagtcagcgttggcgcaa
cggtgaccatcatgtgtgctgcaaccctggcggaaggcaccacgattattgaaaacgcagcgcgtgaaccggaaatcgtcgatacc
gcgaacttcctgattacgctgggtgcgaaaattagcggtcagggcaccgatcgtatcgtcatcgaaggtgtggaacgttaggcggcg
gtgtctatcgcgttctgccggatcgtatcgaaaccggtactttcctggtggcggcggcgatttctcgcggcaaaattatctgccgtaacgc
gcagccagatactctcgacgccgtgctggcgaaactgcgtgacgctggagcggacatcgaagtcggcgaagactggattagcctg
gatatgcatggcaaacgtccgaaggctgttaacgtacgtaccgcgccgcatccggcattcccgaccgatatgcaggcccagttcacg
ctgttgaacctggtggcagaagggaccgggtttatcaccgaaacggtctttgaaaaccgctttatgcatgtgccagagctgagccgtat
gggcgcgcacgccgaaatcgaaagcaataccgttatttgtcacggtgttgaaaaactttctggcgcacaggttatggcaaccgatctg
cgtgcatcagcaagcctggtgctggctggctgtattgcggaagggacgacggtggttgatcgtatttatcacatcgatcgtggctacga
acgcattgaagacaaactgcgcgctttaggtgcaaatattgagcgtgtgaaaggcgaataaGAATTCaggaaaaaaacgctGt
gaaaaatGTTGGTTTTATCGGCTGGCGCGGAATGGTCGGCTCTGTTCTCATGCAACGCATGG
TAGAGGAGCGCGATTTCGACGCTATTCGCCCTGTTTTCTTTTCTACCTCCCAGTTTGGACA
GGCGGCGCCCACCTTCGGCGACACCTCCACCGGCACGCTACAGGACGCTTTTGATCTGG
ATGCGCTAAAAGCGCTCGATATCATCGTGACCTGCCAGGGCGGCGATTATACCAACGAAA
TTTATCCAAAGCTGCGCGAAAGCGGATGGCAGGGTTACTGGATTGATGCGGCTTCTACGC
TGCGCATGAAAGATGATGCCATTATTATTCTCGACCCGGTCAACCAGGACGTGATTACCGA
CGGCCTGAACAATGGCGTGAAGACCTTTGTGGGCGGTAACTGTACCGTTAGCCTGATGTT
GATGTCGCTGGGCGGTCTCTTTGCCCATAATCTCGTTGACTGGGTATCCGTCGCGACCTAT
CAGGCCGCCTCCGGCGGCGGCGCGCGCcatatgcgcgagctgttaacccagatgggTCAGTTGTATGG
CCATGTCGCCGATGAACTGGCGACGCCGTCTTCCGCAATTCTTGATATTGAACGCAAAGTT
ACGGCATTGACCCGCAGCGGCGAGCTGCCGGTTGATAACTTTGGCGTACCGCTGGCGGG
AAGCCTGATCCCCTGGATCGACAAACAGCTCGATAACGGCCAGAGCCGCGAAGAGTGGAA
AGGCCAGGCGGAAACCAACAAGATTCTCAATACTGCCTCTGTGATTCCGGTTGATGGTTTG

FIG. 30 (CONT.)

TGTGTGCGCGTCGGCGCGCTGCGCTGTCACAGCCAGGCGTTCACCATCAAGCTGAAAAAA
GAGGTATCCATTCCGACGGTGGAAGAACTGCTGGCGGCACATAATCCGTGGGCGAAAGTG
GTGCCGAACGATCGTGATATCACTATGCGCGAATTAACCCCGGCGGCGGTGACCGGCAC
GTTGACTACGCCGGTTGGTCGTCTGCGTAAGCTGAACATGGGGCCAGAGTTCTTGTCGGC
GTTTACCGTAGGCGACCAGTTGTTATGGGGCGCCGagCCGAGCCGCTGCGTCGAATGCTG
CGCCAGTTGgcgtagtctagctgcacgataccgtcgacttgtacaTAGACTCGCTCCGAAATTAAAGAACACT
TAAATTATCTACTAAAGGAATCTTTAGTCAAGTTTATTTAAGATGACTTAACTATGAATACAC
AATTGATGGGTGAGCGTAGGAgcatgcTTATGCGAAAGGCCATCCTGACGGATGGCCTTTTT
GGATCTTCCGGAAGACCTTCCATTCTGAAATGAGCTGTTGACAATTAATCATCCGGCTCGT
ATAATGTGTGGAATTGTGAGCGGATAACAATTTCACACAGGAAACAGACCATGGtgacaaaaat
aactttatctccccagaatttagaatccaaaaacaggaaaccacactactaaaagaaaaatcaaccgagaaaaattctttagcaaa
aagtattctcgcagtaaaaaatcacttcatcgaattaaggtcaaaattatcggaacgttttatttcgcataagaacactgagtcttctgcaa
cacactttcaccgaggaagcgcatctgagggccgggcagtgttgacaaatgaattcgttGGATCCGTCGACcccggg
        GCG GAC ATG ATG GGT GGT ACC GAC TAC ACC TAC AAC GAC CCG GTT GCG GCG GGT
CCG CAC GAC TGG TCT GGT AAC TAC GTT GGT GCG CAG GTT GGT GGT TCT TCT TCT AAA
TTC CCG TCT CCG TTC GCG TCT CGT ACC GGT GCG CTG GGT GGT ATC GTT GTT GGT AAA
AAC ATG CAG AAC GGT AAC ATC GTT TTC GGT GCG GAA CTG GAA GGT AAC TTC GCG GAA
GCG GAA CAC CGT ATC GGT CAC GGT GGT ACC CTA CAG CAG TCT TGG AAC GGT AAC GCG
AAA GGT AAA GTT GGT TAC ACC TTC GAC AAA ACC CTG GTT TAC GGT ACC GCG GGT TAC
GGT GTT ACC CGT TTC AAA GCG AAA GAC AAC ACC ACC TCT GCG TCT GGT TGC GAA GGT
GGT GTT CTG ATC GGT GCG GGT GTT GAA CAG GCG CTG TCT GGT CCG CTG TCT GTT AAA
GCG GAA TAC GAC TTC CAG CGT TTC AAC GAC GTT AAA TCT CAG GTT AAC GGT ATC GAA
CAG CGT AAC AAC CTG AAA AAC CAC TCT ATC AAA GCG GGT CTG AAC TAC AAA TTC
                                    TAG
CTGCAGCCAAGCTCCCAAGCTTGGCTGTTTTGGCGGATGAGAGAAGATTTTCAGCTTCTGA
TACAGATTAAATCAGAACGCAGAAGCGGTCTGATAAAACAGAATTTGCCTGGCGGCAGTAG
CGCGGTGGTCCCACCTGACCCCATGCCGAACTCAGAAGTGAAACGCCGTAGCGCCGATG
GTAGTGTGGGGTCTCCCCATGCGAGAGTAGGGAACTGCCAGGCATCAAATAAAACGAAAG
GCTCAGTCGAAAGACTGGGCCTTTCGTTTTATCTGTTGTTTGTCGGTGAACGCTCTCCTGA
GTAGGACAAATCCGCCGGGAGCGGATTTGAACGTTGCGAAGCAACGGCCCGGAGGGTGG
CGGGCAGGACGCCCGCCATAAACTGCCAGGCATCAAATTAAGCAGAAGGCCATCCTGACG
GATGGCCTTTTTGCGTTTCTACAAACTCTTTTGTTTATTTTTCTAAATACATTCAAATATGTAT
CCGCTCATGAGACAATAACCCTGATAAATGCTTCAATAATGGAAGATCTTCCAACATCACAG
GTAAACAGAAACGTCGGGTCGATCGGGAAATTCTTTCCCGGACGGCGCGGGGTTGGGCA
AGCCGCAGGCGCGTCAGTGCTTTTAGCGGGTGTCGGGGCGCAGCCATGACCCAGTCACG
TAGCGCTAGCGGAGTGTATACTGGCTTACTATGTTGGCACTGATGAGGGTGTCAGTGAAGT
GCTTCATGTGGCAGGAGAAAAAAGGCTGCACCGGTGCGTCAGCAGAATATGTGATACAGG
ATATATTCCGCTTCCTCGCTCACTGACTCGCTACGCTCGGTCGTTCGACTGCGGCGAGCG
GAAATGGCTTACGAACGGGGCGGAGATTTCCTGGAAGATGCCAGGAAGATACTTAACAGG
GAAGTGAGAGGGCCGCGGCAAAGCCGTTTTTCCATAGGCTCCGCCCCCTGACAAGCATC
ACGAAATCTGACGCTCAAATCAGTGGTGGCGAAACCCGACAGGACTATAAAGATACCAGG
CGTTTCCCCCTGGCGGCTCCCTCGTGCGCTCTCCTGTTCCTGCCTTTCGGTTTACCGGTGT
CATTCCGCTGTTATGGCCGCGTTTGTCTCATTCCACGCCTGACACTCAGTTCCGGGTAGGC
AGTTCGCTCCAAGCTGGACTGTATGCACGAACCCCCGTTCAGTCCGACCGCTGCGCCTT
ATCCGGTAACTATCGTCTTGAGTCCAACCCGGAAAGACATGCAAAAGCACCACTGGCAGC
AGCCACTGGTAATTGATTTAGAGGAGTTAGTCTTGAAGTCATGCGCCGGTTAAGGCTAAAC
TGAAAGGACAAGTTTTGGTGACTGCGCTCCTCCAAGCCAGTTACCTCGGTTCAAAGAGTTG
GTAGCTCAGAGAACCTTCGAAAAACCGCCCTGCAAGGCGGTTTTTTCGTTTTCAGAGCAAG
AGATTACGCGCAGACCAAAACGATCTCAAGAAGATCATCTTATTAATCAGATAAAATATTTC
TAGATTTCAGTGCAATTTATCTCTTCAAATGTAGCACCTGAAGTCAGCCCCATACGATATAA
GTTGTTGGA FIG. 31: >omp22 -- Codon Optimization

```
CCC GGG ▓▓▓ GCG GAC ATG ATG GGT GGT ACC GAC TAC ACC TAC AAC GAC CCG GTT GCG GCG
            A   D   M   M   G   G   T   D   Y   T   Y   N   D   P   V   A   A

GGT CCG CAC GAC TGG TCT GGT AAC TAC GTT GGT GCG CAG GTT GGT GGT TCT TCT TCT AAA TTC
G   P   H   D   W   S   G   N   Y   V   G   A   Q   V   G   G   S   S   S   K   F

CCG TCT CCG TTC GCG TCT CGT ACC GGT GCG CTG GGT GGT ATC GTT GTT GGT AAA AAC ATG CAG
P   S   P   F   A   S   R   T   G   A   L   G   G   I   V   V   G   K   N   M   Q

AAC GGT AAC ATC GTT TTC GGT GCG GAA CTG GAA GGT AAC TTC GCG GAA GCG GAA CAC CGT ATC
N   G   N   I   V   F   G   A   E   L   E   G   N   F   A   E   A   E   H   R   I

GGT CAC GGT GGT ACC CTA CAG CAG TCT TGG AAC GGT AAC GCG AAA GGT AAA GTT GGT TAC ACC
G   H   G   G   T   L   Q   Q   S   W   N   G   N   A   K   G   K   V   G   Y   T

TTC GAC AAA ACC CTG GTT TAC GGT ACC GCG GGT TAC GGT GTT ACC CGT TTC AAA GCG AAA GAC
F   D   K   T   L   V   Y   G   T   A   G   Y   G   V   T   R   F   K   A   K   D

AAC ACC ACC TCT GCG TCT GGT TGC GAA GGT GGT GTT CTG ATC GGT GCG GGT GTT GAA CAG GCG
N   T   T   S   A   S   G   C   E   G   G   V   L   I   G   A   G   V   E   Q   A

CTG TCT GGT CCG CTG TCT GTT AAA GCG GAA TAC GAC TTC CAG CGT TTC AAC GAC GTT AAA TCT
L   S   G   P   L   S   V   K   A   E   Y   D   F   Q   R   F   N   D   V   K   S

CAG GTT AAC GGT ATC GAA CAG CGT AAC AAC CTG AAA AAC CAC TCT ATC AAA GCG GGT CTG AAC
Q   V   N   G   I   E   Q   R   N   N   L   K   N   H   S   I   K   A   G   L   N

TAC AAA TTC ▓▓▓▓▓▓▓▓▓▓▓▓▓▓▓▓▓▓▓▓▓▓ ▓▓▓ TAA ▓▓▓
Y   K   F                              *
```

FIG. 33: Sequence for pG8R243 (pG8R110 with bp26)
ATCTAGCCCGCCTAATGAGCGGGCTTTTTTTTAATTCGCAATTCCCCGATGCATAATGAaaCTGCCT
GTCAAATGGACGAAGCAGGGATTCTGCAAACCCTATGCTACTCCGTCAAGCCGTCAATTGTCTGAT
TCGTTACCAATTATGACAACTTGACGGCTACATCATTCACTTTTTCTTCACAACCGGCACGaAACTC
GCTCGGGCTGGCCCCGGTGCATTTTTTAAATACtCGCGAGAAATAGAGTTGATCGTCAAAACCAAC
ATTGCGACCGACGGTGGCGATAGGCATCCGGGTaGTGCTCAAAAGCAGCTTCGCCTGaCTaATgC
GTTGGTCCTCGCGCCAGCTTAAGACGCTAATCCCTAACTGCTGGCGGAAAAGATGTGACAGACGC
GACGGCGACAAGCAAACATGCTGTGCGACGCTGGCGATATCAAAATTGCTGTCTGCCAGGTGATC
GCTGATGTACTGACAAGCCTCGCGTACCCGATTATCCATCGGTGGATGGAGCGACTCGTTAATCG
CTTCCATGCGCCGCAGTAACAATTGCTCAAGCAGATTTATCGCCAGCAGCTCCGAATAGCGCCCT
TCCCCTTGCCCGGCGTTAATGATTTGCCCAAACAGGTCGCTGAAATGCGGCTGGTGCGCTTCATC
CGGGCGAAAGAAaCCCGTATTGGCAAATATTGACGGCCAGTTAAGCCATTCATGCCAGTAGGCGC
GCGGACGAAAGTAAACCCACTGGTGATACCATTCGCGAGCCTCCGGATGACGACCGTAGTGATGA
ATCTCTCCTGGCGGGAACAGCAAAATATCACCCGGTCGGCAgACAAATTCTCGTCCCTGATTTTTC
ACCACCCCTGACCGCGAATGGTGAGATTGAGAATATAACCTTTCATTCCCAGCGGTCGGTCGAT
AAAAAAATCGAGATAACCGTTGGCCTCAATCGGCGTTAAACCCGCCACCAGATGGGCATTAAACG
AGTATCCCGGCAGCAGGGGATCATTTTGCGCTTCAGCCATACTTTTCATACTCCCGCCATTCAGAG
AAGAAACCAATTGTCCATATTGCATCAGACATTGCCGTCACTGCGTCTTTTACTGGCTCTTCTCGCT
AACCAAACCGGTAACCCCGCTTATTAAAAGCATTCTGTAACAAAGCGGGACCAAAGCCATGACAAA
AACGCGTAACAAAAGTGTCTATAATCACGGCAGAAAAGTCCACATTGATTATTTGCACGGCGTCAC
ACTTTGCTATGCCATAGCATTTTTATCCATAAGATTAGCGGATCCTACCTGACGCTTTTTATCGCAA
CTCTCTACTGTTTCTCCATACCGttttttggGCTAGCGAATTCTGAGAACAAACTAAatggataaatttcgtgttca
ggggccaacgaagctccagggcgaagtcacaatttccggcgctaaaaatgctgctctgcctatcctttttgccgcactactggcggaagaaccg
gtagagatccagaacgtcccgaaactgaaagacgtcgatacatcaatgaagctgctaagccagctgggtgcgaaagtagaacgtaatggttct
gtgcatattgatgcccgcgacgttaatgtattctgcgcaccttacgatctggttaaaaccatgcgtgcttctatctgggcgctggggccgctggtagc
gcgctttggtcaggggcaagtttcactacctggcggttgtacgatcggtgcgcgtccggttgatctacacatttctggcctcgaacaattaggcgcg
accatcaaactggaagaaggttacgttaaagcttccgtcgatggtcgtttgaaaggtgcacatatcgtgatggataaagtcagcgttggcgcaac
ggtgaccatcatgtgtgctgcaaccctggcggaaggcaccacgattattgaaaacgcagcgcgtgaaccggaaatcgtcgataccgcgaactt
cctgattacgctgggtgcgaaaattagcggtcagggcaccgatcgtatcgtcatcgaaggtgtggaacgttaggcggcggtgtctatcgcgttctg
ccggatcgtatcgaaaccggtactttcctggtggcggcggcgatttctcgcggcaaaaattatctgccgtaacgcgcagccagatactctcgacgc
cgtgctggcgaaactgcgtgacgctggagcggacatcgaagtcggcgaagactggattagcctgatatgcatggcaaacgtccgaaggctgt
taacgtacgtaccgcgccgcatccggcattcccgaccgatatgcaggcccagttcacgctgttgaacctggtggcagaagggaccgggtttatc
accgaaacggtctttgaaaaacgctttatgcatgtgccagagctgagccgtatgggcgcgcacgccgaaatcgaaagcaataccgttattgtca
cggtgttgaaaaactttctggcgcacacaggttatggcaaccgatctgcgtgcatcagcaagcctggtgctggctggctgtattgcggaagggacga
cggtggttgatcgtatttatcacatcgatcgtggctacgaacgcattgaagacaaactgcgcgctttaggtgcaaatattgagcgtgtgaaaggcg
aataaGAATTCaggaaaaaaacgctGtgaaaaatGTTGGTTTTATCGGCTGGCGCGGAATGGTCGGCTCTGT
TCTCATGCAACGCATGGTAGAGGAGCGCGATTTCGACGCTATTCGCCCTGTTTTCTTTTCTACCTC
CCAGTTTGGACAGGCGGCGCCCACCTTCGGCGACACCTCCACCGGCACGCTACAGGACGCTTTT
GATCTGGATGCGCTAAAAGCGCTCGATATCATCGTGACCTGCCAGGGCGGCGATTATACCAACGA
AATTTATCCAAAGCTGCGCGAAAGCGGATGGCAGGGTTACTGGATTGATGCGGCTTCTACGCTGC
GCATGAAAGATGATGCCATTATTATTCTCGACCCGGTCAACCAGGACGTGATTACCGACGGCCTG
AACAATGGCGTGAAGACCTTTGTGGGCGGTAACTGTACCGTTAGCCTGATGTTGATGTCGCTGGG
CGGTCTCTTTGCCCATAATCTCGTTGACTGGGTATCCGTCGCGACCTATCAGGCCGCCTCCGGCG
GCGGCGCGCCcatatgcgcgagctgttaacccagatgggTCAGTTGTATGGCCATGTCGCCGATGAACTGGC
GACGCCGTCTTCCGCAATTCTTGATATTGAACGCAAAGTTACGGCATTGACCCGCAGCGGCGAGC
TGCCGGTTGATAACTTTGGCGTACCGCTGGCGGGAAGCCTGATCCCCTGGATCGACAAACAGCTC
GATAACGGCCAGAGCCGCGAAGAGTGGAAAGGCCAGGCGGAAACCAACAAGATTCTCAATACTG
CCTCTGTGATTCCGGTTGATGGTTTGTGTGTGCGCGTCGGCGCGCTGCGCTGTCACAGCCAGGC
GTTCACCATCAAGCTGAAAAAGAGGTATCCATTCCGACGGTGGAAGAACTGCTGGCGGCACATA
ATCCGTGGGCGAAAGTGGTGCCGAACGATCGTGATATCACTATGCGCGAATTAACCCCGGCGGC
GGTGACCGGCACGTTGACTACGCCGGTTGGTCGTCTGCGTAAGCTGAACATGGGGCCAGAGTTC

FIG. 33 (CONT.)

TTGTCGGCGTTTACCGTAGGCGACCAGTTGTTATGGGGCGCCGagCCGAGCCGCTGCGTCGAATG
CTGCGCCAGTTGgcgtagtctagctgcacgataccgtcgacttgtacaTAGACTCGCTCCGAAATTAAAGAACACTT
AAATTATCTACTAAAGGAATCTTTAGTCAAGTTTATTTAAGATGACTTAACTATGAATACACAATTGA
TGGGTGAGCGTAGGAgcatgcTTATGCGAAAGGCCATCCTGACGGATGGCCTTTTTGGATCTTCCGG
AAGACCTTCCATTCTGAAATGAGCTGTTGACAATTAATCATCCGGCTCGTATAATGTGTGGAATTGT
GAGCGGATAACAATTTCACACAGGAAACAGACCATGGtgacaaaaataactttatctccccagaatttagaatccaaa
aacaggaaaccacactactaaaagaaaaatcaaccgagaaaaattctttagcaaaaagtattctcgcagtaaaaaatcacttcatcgaattaa
ggtcaaaattatcggaacgttttatttcgcataagaacactgagtcttctgcaacacactttcaccgaggaagcgcatctgagggccgggcagtgtt
gacaaatgaattcgttGGATCCGTCGACcccggg▓▓▓▓▓ CAG GAA AAC CAG ATG ACC ACC CAG CCG GCG
CGT ATC GCT GTT ACC GGT GAA GGT ATG ATG ACC GCT TCT CCG GAC ATG GCT ATC CTG AAC CTG
TCT GTT CTG CGT CAG GCG AAA ACC GCG CGT GAA GCG ATG ACC GCG AAC AAC GAA GCT ATG ACC
AAA GTT CTG GAC GCG ATG AAA AAA GCG GGT ATC GAA GAC CGT GAC CTC CAG ACC GGT GGT ATC
AAC ATC CAG CCG ATC TAC GTT TAC CCG GAC GAC AAA AAC AAC CTG AAA GAA CCG ACC ATC ACC
GGT TAC TCT GTT TCT ACC TCT CTG ACC GTT CCT GTT CCT GAA CTG GCG AAC GTT GGT AAA ATC
CTG GAC GAA TCT GTT ACC CTG GGT GTT AAC CAG GGT GGT GAC CTG AAC CTG GTT AAC GAC AAC
CCG TCT GCT GTT ATC AAC GAA GCG CGT AAA CGT GCT GTT GCT AAC GCT ATC GCT AAA GCG AAA
ACC CTG GCT GAC GCT GCG GGT GTT GGT CTG GGT CGT GTT GTT GAA ATC TCT GAA CTG TCT CGT
CCG CCG ATG CCG ATG CCG ATC GCG CGT GGT CAG TTC CGT ACC ATG CTG GCG GCT GCT CCG GAC
AAC TCT GTT CCG ATC GCT GCT GGT GAA AAC TCT TAC AAC GTT TCT GTT AAC GTT GTT TTC GAA
ATC AAA ▓▓▓▓▓▓▓▓▓▓▓▓▓▓▓▓▓▓▓ ▓▓▓▓▓ TAA
TGaCTGCAGCCAAGCTCCCAAGCTTGGCTGTTTTGGCGGATGAGAGAAGATTTTCAGCTTC
TGATACAGATTAAATCAGAACGCAGAAGCGGTCTGATAAAACAGAATTTGCCTGGCGGCAG
TAGCGCGGTGGTCCCACCTGACCCCATGCCGAACTCAGAAGTGAAACGCCGTAGCGCCG
ATGGTAGTGTGGGGTCTCCCCATGCGAGAGTAGGGAACTGCCAGGCATCAAATAAAACGA
AAGGCTCAGTCGAAAGACTGGGCCTTTCGTTTTATCTGTTGTTTGTCGGTGAACGCTCTCC
TGAGTAGGACAAATCCGCCGGGAGCGGATTTGAACGTTGCGAAGCAACGGCCCGGAGGG
TGGCGGGCAGGACGCCCGCCATAAACTGCCAGGCATCAAATTAAGCAGAAGGCCATCCTG
ACGGATGGCCTTTTTGCGTTTCTACAAACTCTTTTGTTTATTTTTCTAAATACATTCAAATAT
GTATCCGCTCATGAGACAATAACCCTGATAAATGCTTCAATAATGGAAGATCTTCCAACATC
ACAGGTAAACAGAAACGTCGGGTCGATCGGGAAATTCTTTCCCGGACGGCGCGGGGTTG
GGCAAGCCGCAGGCGCGTCAGTGCTTTTAGCGGGTGTCGGGGCGCAGCCATGACCCAGT
CACGTAGCGCTAGCGGAGTGTATACTGGCTTACTATGTTGGCACTGATGAGGGTGTCAGT
GAAGTGCTTCATGTGGCAGGAGAAAAAAGGCTGCACCGGTGCGTCAGCAGAATATGTGAT
ACAGGATATATTCCGCTTCCTCGCTCACTGACTCGCTACGCTCGGTCGTTCGACTGCGGC
GAGCGGAAATGGCTTACGAACGGGGCGGAGATTTCCTGGAAGATGCCAGGAAGATACTTA
ACAGGGAAGTGAGAGGGCCGCGGCAAAGCCGTTTTTCCATAGGCTCCGCCCCCCTGACA
AGCATCACGAAATCTGACGCTCAAATCAGTGGTGGCGAAACCCGACAGGACTATAAAGATA
CCAGGCGTTTCCCCCTGGCGGCTCCCTCGTGCGCTCTCCTGTTCCTGCCTTTCGGTTTAC
CGGTGTCATTCCGCTGTTATGGCCGCGTTTGTCTCATTCCACGCCTGACACTCAGTTCCGG
GTAGGCAGTTCGCTCCAAGCTGGACTGTATGCACGAACCCCCGTTCAGTCCGACCGCTG
CGCCTTATCCGGTAACTATCGTCTTGAGTCCAACCCGGAAAGACATGCAAAAGCACCACTG
GCAGCAGCCACTGGTAATTGATTTAGAGGAGTTAGTCTTGAAGTCATGCGCCGGTTAAGGC
TAAACTGAAAGGACAAGTTTTGGTGACTGCGCTCCTCCAAGCCAGTTACCTCGGTTCAAAG
AGTTGGTAGCTCAGAGAACCTTCGAAAAACCGCCCTGCAAGGCGGTTTTTTCGTTTTCAGA
GCAAGAGATTACGCGCAGACCAAAACGATCTCAAGAAGATCATCTTATTAATCAGATAAAAT
ATTTCTAGATTTCAGTGCAATTTATCTCTTCAAATGTAGCACCTGAAGTCAGCCCCATACGA
TATAAGTTGTTGGA FIG. 34 >bp26 - Codon Optimization

```
▓▓▓ ▓▓▓ ▓▓▓▓▓ CAG GAA AAC CAG ATG ACC ACC CAG CCG GCG CGT ATC GCT GTT ACC GGT GAA
              Q   E   N   Q   M   T   T   Q   P   A   R   I   A   V   T   G   E

GGT ATG ATG ACC GCT TCT CCG GAC ATG GCT ATC CTG AAC CTG TCT GTT CTG CGT CAG GCG AAA
 G   M   M   T   A   S   P   D   M   A   I   L   N   L   S   V   L   R   Q   A   K

ACC GCG CGT GAA GCG ATG ACC GCG AAC AAC GAA GCT ATG ACC AAA GTT CTG GAC GCG ATG AAA
 T   A   R   E   A   M   T   A   N   N   E   A   M   T   K   V   L   D   A   M   K

AAA GCG GGT ATC GAA GAC CGT GAC CTC CAG ACC GGT GGT ATC AAC ATC CAG CCG ATC TAC GTT
 K   A   G   I   E   D   R   D   L   Q   T   G   G   I   N   I   Q   P   I   Y   V

TAC CCG GAC GAC AAA AAC AAC CTG AAA GAA CCG ACC ATC ACC GGT TAC TCT GTT TCT ACC TCT
 Y   P   D   D   K   N   N   L   K   E   P   T   I   T   G   Y   S   V   S   T   S

CTG ACC GTT CGT GTT CGT GAA CTG GCG AAC GTT GGT AAA ATC CTG GAC GAA TCT GTT ACC CTG
 L   T   V   R   V   R   E   L   A   N   V   G   K   I   L   D   E   S   V   T   L

GGT GTT AAC CAG GGT GGT GAC CTG AAC CTG GTT AAC GAC AAC CCG TCT GCT GTT ATC AAC GAA
 G   V   N   Q   G   G   D   L   N   L   V   N   D   N   P   S   A   V   I   N   E

GCG CGT AAA CGT GCT GTT GCT AAC GCT ATC GCT AAA GCG AAA ACC CTG GCT GAC GCT GCG GGT
 A   R   K   R   A   V   A   N   A   I   A   K   A   K   T   L   A   D   A   A   G

GTT GGT CTG GGT CGT GTT GTT GAA ATC TCT GAA CTG TCT CGT CCG CCG ATG CCG ATG CCG ATC
 V   G   L   G   R   V   V   E   I   S   E   L   S   R   P   P   M   P   M   P   I

GCG CGT GGT CAG TTC CGT ACC ATG CTG GCG GCT GCT CCG GAC AAC TCT GTT CCG ATC GCT GCT
 A   R   G   Q   F   R   T   M   L   A   A   A   P   D   N   S   V   P   I   A   A

GGT GAA AAC TCT TAC AAC GTT TCT GTT AAC GTT GTT TTC GAA ATC AAA ▓▓▓▓ ▓▓▓▓▓
 G   E   N   S   Y   N   V   S   V   N   V   V   F   E   I   K

▓▓▓▓▓ ▓▓▓ ▓▓▓ TAA ▓▓▓▓
               *
```

FIG. 36: Sequence for pG8R250 (pG8R114 with tf)
ggatcttccggaagaccttccattctgaaatgagctgttgacaattaatcatccggctcgtataatgtgtggaattgtgagcggataacaatttcaca
caggaaacagaccatgaaaaaacaacatttccgtgtcgcccttattcccttttttgcggcatttgccttcctgttttttgctcacccagaaacgctggtg
aaagtaaaagatgctgaactcgag ATG ACC CGT TCT GAA GGT CTG AAC ATG CAG GTT ACC GAA ACC CTG
AAC GAA GGT CTG AAA CGT GAA ATC AAA GTT GTT GTT CCG GCG GGT GAC CTG GAA GCG AAA CTG
GCG GAA CGT CTG GAA ACC GCG CGT GGT CGT GCG CGT ATC AAC GGT TTC CGT CCG GGT AAA GTT
CCG ACC GCG CAC CTG CGT AAA ATG TAC GGT AAA TCT TTC ATG GCG GAA ATC GTT AAC GAA ATC
CTG AAC
GAC TCT TCT CGT TCT ATC CTG GCG GAA CGT AAC GAA AAA TCT GCG ACC CAG CCG GAA
GTT ATC ATG TCT GAA GAC GAA AAA GAA GCG GAA AAA GTT CTG GAC GGT AAA GCG GAC
TTC GTT TTC TCT CTG AAC TAC GAA GTT CTG CCG GCG ATC GAA GTT AAA GAC TTC TCT
AAA ATC GCG GTT ACC CGT GAA GTT GTT GAC ATC TCT GAC GAA GAA GTT GAC GAA CAG
GTT AAA CGT ATC GCG TCT TCT ACC CGT ACC TTT GAA ACC AAA AAA GGT AAA GCG GAA
AAC GAA GAT CGT GTT ACC ATC GAC TAC CTG GGT AAA CTG GAC GGT GAA CCG TTC GAA
GGT GGT GCG GAC AAC GAC GCG CAG CTG GTT CTG GGT TCT GGT CAG TTC ATT CCG GGT
TTC GAA GAA CAG CTG ATC GGT CTG AAA GCG GGT GAC GAA AAA GTT ATC ACC GTT ACG
TTC CCG GCG GAA TAC GGT GCG GCG CAC CTG GCG GGT AAA GAA GCG ACC TTC GAC ATC
AAA GTT AAA GAA GTT GCG AAA CCG AAC GAA CTG GTT CTG GAC GAC GAA ACC GCG AAA
AAA CTG GGT ATC GAA TCT CTG GAA CGT CTG CGT CAG GTT GTT CGT GAA CAG ATC GAA
TCT CAG TAC GGT CAG ATC ACC CGT CAG AAA GTT AAA CGT CAG ATC CTG GAC GCG CTG
GAC GGT GAC TAC CAG TTC GAA ACC CCG CAG AAA CTG GTT GAC GCG GAA TTC AAC AAC
ATC TGG CAG CAG ATC AAC TTC GAC CTC CAG CAG GCG GGT CGT ACC TTC GAA GAC GAA
GAA ACC ACC GAA GAA GCG GCG CGT GAA GAA TAC CGT AAA CTG GCG GAA CGT CGT GTT
CGT CTG GGT CTG GTT CTG TCT GAA ATC GGT GAA AAA GCG GGT GTT GAA GTT ACC GAA
GAA GAA CTC CAG CGT GCG GTT TAC GAC CAG GTT CGT CGT TAT CCG GGT CAG GAA AAA
GAA ATC TAC GAC TTC CTG CGT CGT ACC CCG GAC GCG GTT GCG AAC CTG CGT GCG CCG
ATC TTC GAA GAA AAA GTT GTT GAC CAC CTG CTG GCG AAC ATC AAC GTT ACC GAC AAA
AAA GTT TCT AAA GAA GAA CTG ACC GCG GAA GAC GAA GAC GCG GCG TCT GAA GCG AAA
CCG GCG AAA AAA GCG GCG GCG AAA AAA AAA GCG GCG CCG AAA AAA AAA GCG GAA GAA
GGT AAA TCT GAA GAA GCG ░░░ ░░░ ░░░░░░░░░░░░░░ ░░░ ░░░ TGA
ctgcagccaagctcccaagctggctgtttggcggatgagagaagatttcagcctgatacagattaaatcagaacgcagaagcggt
ctgataaaacagaaatttgcctggcggcagtagcgcggtggtcccacctgaccccatgccgaactcagaagtgaaacgccgtagcgc
cgatggtagtgtgggtctccccatgcgagagtagggaactgccaggcatcaaatataaaacgaaaggctcagtcgaaagactgggc
ctttcgttttatctgttgtttgtcggtgaacgctctcctgagtaggacaaatccgccgggagcggatttgaacgttgcgaagcaacggccc
ggagggtggcgggcaggacgcccgccataaactgccaggcatcaaattaagcagaaggccatcctgacggatggcctttttgcgtttt
ctacaaactcttttgtttatttttctaaatacattcaaatatgtatccgctcatgagacaataaccctgataaatgcttcaataatggaagatct
tccaacatcacaggtaaacagaaacgtcgggtcgatcgggaaattctttcccggacggcgcgggtttgggcaagccgcaggcgcg
tcagtgcttttagcgggtgtcggggcgcagccatgacccagtcacgtagcgatagcggagtgtatactggcttaactatgcggcatcag
agcagattgtactgagagtgcaccatatgcggtgtgaaataccgcacagatgcgtaaggagaaaataccgcatcaggcgctcttccg
cttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctgg
cgttttccataggctccgccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacctgtccgcctttctccctc
gggaagcgtggcgctttctcatagctcacgctgtaggtatctcagttcggtgtaggtcgttcgctccaagctgggctgtgtgcacgaacc
ccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgatcttttctacggggtctg
acgctcagtggaacgaaaactcacgttaagggattttggtcatgagattatcaaaaaggatcttcacctagatccttttaaattaaaaatg
aagttttaaatcaatctaaagtatatatgagtaaacttggtctgacagtctagaagatctagcccgcctaatgagcgggcttttttttaattcg
caattcccgatgcataatgtgcctgtcaaatggacgaagcagggattctgcaaaccctatgctactccgtcaagccgtcaattgtctga
ttcgttaccaattatgacaacttgacggctacatcattcactttttcttcacaaccggcacggaactcgctcgggctggccccggtcatttt
ttaaatacccgcgagaaatagagttgatcgtcaaaaccaacattgcgaccgacggtggcgataggcatccggggtggtgctcaaaag

FIG. 36 (CONT.)

cagcttcgcctggctgatacgttggtcctcgcgccagcttaagacgctaatccctaactgctggcggaaaagatgtgacagacgcgac
ggcgacaagcaaacatgctgtgcgacgctggcgatatcaaaattgctgtctgccaggtgatcgctgatgtactgacaagcctcgcgta
cccgattatccatcggtggatggagcgactcgttaatcgcttccatgcgccgcagtaacaattgctcaagcagatttatcgccagcagct
ccgaatagcgcccttcccctttgccggcgttaatgattgcccaaacaggtcgctgaaatgcggctggtgcgcttcatccgggcgaaa
gaaccccgtattggcaaatattgacggccagttaagccattcatgccagtaggcgcgcggacgaaagtaaacccactggtgatacc
attcgcgagcctccggatgacgaccgtagtgatgaatctctcctggcgggaacagcaaaatatcacccggtcggcaaacaaattctc
gtccctgattttcaccaccccctgaccgcgaatggtgagattgagaatataaccttcattcccagcggtcggtcgataaaaaaatcga
gataaccgttggcctcaatcggcgttaaacccgccaccagatgggcattaaacgagtatcccggcagcaggggatcattttgcgcttc
agccatacttttcatactcccgccattcagagaagaaaccaattgtccatattgcatcagacattgccgtcactgcgtctttactggctctt
ctcgctaaccaaaccggtaaccccgcttattaaaagcattctgtaacaaagcgggaccaaagccatgacaaaaacgcgtaacaaa
agtgtctataatcacggcagaaaagtccacattgattatttgcacggcgtcacactttgctatgccatagcattttatccataagattagcg
gatcctacctgacgcttttatcgcaactctctactgtttctccatacccgttttttgggctagcgaattctgagaacaaactaagtggataa
atttcgtgttcaggggccaacgaagctccagggcgaagtcacaatttccggcgctaaaaatgctgtctgcctatcctttttgccgcacta
ctggcggaagaaccggtagagatccagaacgtcccgaaactgaaagacgtcgatacatcaatgaagctgctaagccagctgggtg
cgaaagtagaacgtaatggttctgtgcatattgatgcccgcgacgttaatgtattctgcgcaccttacgatctggttaaaaccatgcgtgct
tctatctgggcgctggggccgctggtagcgcgctttggtcaggggcaagtttcactacctggcggttgtacgatcggtgcgcgtccggtt
gatctacacattctggcctcgaacaattaggcgcgaccatcaaactggaagaaggttacgttaaagcttccgtcgatggtcgtttgaaa
ggtgcacatatcgtgatggataaagtcagcgttggcgcaacggtgaccatcatgtgtgctgcaaccctggcggaaggcaccacgatt
attgaaaacgcagcgcgtgaaccggaaatcgtcgataccgcgaacttcctgattacgctgggtgcgaaaattagcggtcagggcac
cgatcgtatcgtcatcgaaggtgtggaacgttaggcggcggtgtctatcgcgttctgccggatcgtatcgaaaccggtacttcctggtg
gcggcggcgatttctcgcggcaaaattatctgccgtaacgcgcagccagatactctcgacgccgtgctggcgaaactgcgtgacgct
ggagcggacatcgaagtcggcgaagactggattagcctggatatgcatggcaaacgtccgaaggctgttaacgtacgtaccgcgcc
gcatccggcattcccgaccgatatgcaggcccagttcacgctgttgaacctggtggcagaagggaccgggtttatcaccgaaacggt
ctttgaaaaccgctttatgcatgtgccagagctgagccgtatgggcgcgcacgccgaaatcgaaagcaataccgttatttgtcacggtg
ttgaaaaactttctggcgcacaggttatggcaaccgatctgcgtgcatcagcaagcctggtgctggctggctgtattgcggaagggacg
acggtggttgatcgtatttatcacatcgatcgtggctacgaacgcattgaagacaaactgcgcgcttaggtgcaaatattgagcgtgtg
aaaggcgaataagaattcaaggcaaaaaacgctgtgaaaaatgttggttttatcggctggcgcggaatggtcggctctgttctcatgca
acgcatggtagaggagcgcgatttcgacgctattcgccctgttttcttttctacctcccagtttggacaggcggcgcccaccttcggcgac
acctccaccggcacgctacaggacgcttttgatctggatgcgctaaaagcgctcgatatcatcgtgacctgccagggcggcgattata
ccaacgaaatttatccaaagctgcgcgaaagcggatggcagggttactggattgatgcggcttctacgctgcgcatgaaagatgatg
ccattattattctcgacccggtcaaccaggacgtgattaccgacggcctgaacaatggcgtgaagacctttgtgggcggtaactgtacc
gttagcctgatgttgatgtcgctgggcggtctctttgcccataatctcgttgactgggtatccgtcgcgacctatcaggccgcctccggcgg
cggcgcgcgccatatgcgcgagctgttaacccagatgggtcagttgtatggccatgtcgccgatgaactggcgacgccgtcttccgca
attcttgatattgaacgcaaagttacggcattgaccgcagcggcgagctgccggttgataacttggcgtaccgctggcgggaagcct
gatccctggatcgacaaacagctcgataacggccagagccgcgaagagtggaaaggccaggcggaaaccaacaagattctca
atactgcctctgtgattccggttgatggtttgtgtgcgcgtcggcgcgctgcgctgtcacagccaggcgttcaccatcaagctgaaaa
aagaggtatccattccgacggtggaagaactgctggcggcacataatccgtgggcgaaagtggtgccgaacgatcgtgatatcact
atgcgcgaattaaccccggcggcggtgaccggcacgttgactacgccggttggtcgtctgcgtaagctgaacatgggccagagttc
ttgtcggcgtttaccgtaggcgaccagttgttatggggcgccgccgagccgctgcgtcgaatgctgcgccagttggcctagtctaggga
cgatgatgcaaccgataccgtcgacggatcacatagactcgctccgaaattaaagaacacttaaattatctactaaaggaatctttagt
caagtttatttaagatgacttaactatgaatacacaattgatgggtgagcgtaggagcatgcttatgcgaaaggccatcctgacggatg
gccttttt FIG. 37: >Tf – Codon optimization

```
░░░ ░░░ ATG ACC CGT TCT GAA GGT CTG AAC ATG CAG GTT ACC GAA ACC CTG AAC GAA
        M   T   R   S   E   G   L   N   M   Q   V   T   E   T   L   N   E

GGT CTG AAA CGT GAA ATC AAA GTT GTT GTT CCG GCG GGT GAC CTG GAA GCG AAA CTG GCG GAA
G   L   K   R   E   I   K   V   V   V   P   A   G   D   L   E   A   K   L   A   E

CGT CTG GAA ACC GCG CGT GGT CGT GCG CGT ATC AAC GGT TTC CGT CCG GGT AAA GTT CCG ACC
R   L   E   T   A   R   G   R   A   R   I   N   G   F   R   P   G   K   V   P   T

GCG CAC CTG CGT AAA ATG TAC GGT AAA TCT TTC ATG GCG GAA ATC GTT AAC GAA ATC CTG AAC
A   H   L   R   K   M   Y   G   K   S   F   M   A   E   I   V   N   E   I   L   N

GAC TCT TCT CGT TCT ATC CTG GCG GAA CGT AAC GAA AAA TCT GCG ACC CAG CCG GAA GTT ATC
D   S   S   R   S   I   L   A   E   R   N   E   K   S   A   T   Q   P   E   V   I

ATG TCT GAA GAC GAA AAA GAA GCG GAA AAA GTT CTG GAC GGT AAA GCG GAC TTC GTT TTC TCT
M   S   E   D   E   K   E   A   E   K   V   L   D   G   K   A   D   F   V   F   S

CTG AAC TAC GAA GTT CTG CCG GCG ATC GAA GTT AAA GAC TTC TCT AAA ATC GCG GTT ACC CGT
L   N   Y   E   V   L   P   A   I   E   V   K   D   F   S   K   I   A   V   T   R

GAA GTT GTT GAC ATC TCT GAC GAA GAA GTT GAC GAA CAG GTT AAA CGT ATC GCG TCT TCT ACC
E   V   V   D   I   S   D   E   E   V   D   E   Q   V   K   R   I   A   S   S   T

CGT ACC TTT GAA ACC AAA AAA GGT AAA GCG GAA AAC GAA GAT CGT GTT ACC ATC GAC TAC CTG
R   T   F   E   T   K   K   G   K   A   E   N   E   D   R   V   T   I   D   Y   L

GGT AAA CTG GAC GGT GAA CCG TTC GAA GGT GGT GCG GAC AAC GAC GCG CAG CTG GTT CTG GGT
G   K   L   D   G   E   P   F   E   G   G   A   D   N   D   A   Q   L   V   L   G

TCT GGT CAG TTC ATT CCG GGT TTC GAA GAA CAG CTG ATC GGT CTG AAA GCG GGT GAC GAA AAA
S   G   Q   F   I   P   G   F   E   E   Q   L   I   G   L   K   A   G   D   E   K

GTT ATC ACC GTT ACG TTC CCG GCG GAA TAC GGT GCG GCG CAC CTG GCG GGT AAA GAA GCG ACC
V   I   T   V   T   F   P   A   E   Y   G   A   A   H   L   A   G   K   E   A   T

TTC GAC ATC AAA GTT AAA GAA GTT GCG AAA CCG AAC GAA CTG GTT CTG GAC GAC GAA ACC GCG
F   D   I   K   V   K   E   V   A   K   P   N   E   L   V   L   D   D   E   T   A

AAA AAA CTG GGT ATC GAA TCT CTG GAA CGT CTG CGT CAG GTT GTT CGT GAA CAG ATC GAA TCT
K   K   L   G   I   E   S   L   E   R   L   R   Q   V   V   R   E   Q   I   E   S

CAG TAC GGT CAG ATC ACC CGT CAG AAA GTT AAA CGT CAG ATC CTG GAC GCG CTG GAC GGT GAC
Q   Y   G   Q   I   T   R   Q   K   V   K   R   Q   I   L   D   A   L   D   G   D

TAC CAG TTC GAA ACC CCG CAG AAA CTG GTT GAC GCG GAA TTC AAC AAC ATC TGG CAG CAG ATC
Y   Q   F   E   T   P   Q   K   L   V   D   A   E   F   N   N   I   W   Q   Q   I

AAC TTC GAC CTC CAG CAG GCG GGT CGT ACC TTC GAA GAC GAA GAA ACC ACC GAA GAA GCG GCG
N   F   D   L   Q   Q   A   G   R   T   F   E   D   E   E   T   T   E   E   A   A

CGT GAA GAA TAC CGT AAA CTG GCG GAA CGT CGT GTT CGT CTG GGT CTG GTT CTG TCT GAA ATC
R   E   E   Y   R   K   L   A   E   R   R   V   R   L   G   L   V   L   S   E   I
```

FIG. 37 (CONT.)

```
GGT GAA AAA GCG GGT GTT GAA GTT ACC GAA GAA GAA CTC CAG CGT GCG GTT TAC GAC CAG GTT
 G   E   K   A   G   V   E   V   T   E   E   E   L   Q   R   A   V   Y   D   Q   V

CGT CGT TAT CCG GGT CAG GAA AAA GAA ATC TAC GAC TTC CTG CGT CGT ACC CCG GAC GCG GTT
 R   R   Y   P   G   Q   E   K   E   I   Y   D   F   L   R   R   T   P   D   A   V

GCG AAC CTG CGT GCG CCG ATC TTC GAA GAA AAA GTT GTT GAC CAC CTG CTG GCG AAC ATC AAC
 A   N   L   R   A   P   I   F   E   E   K   V   V   D   H   L   L   A   N   I   N

GTT ACC GAC AAA AAA GTT TCT AAA GAA GAA CTG ACC GCG GAA GAC GAA GAC GCG GCG TCT GAA
 V   T   D   K   K   V   S   K   E   E   L   T   A   E   D   E   D   A   A   S   E

GCG AAA CCG GCG AAA AAA GCG GCG GCG AAA AAA AAA GCG GCG CCG AAA AAA AAA GCG GAA GAA
 A   K   P   A   K   K   A   A   A   K   K   K   A   A   P   K   K   K   A   E   E

GGT AAA TCT GAA GAA GCG ▓▓▓▓▓▓ ▓▓▓▓▓▓▓▓▓▓▓▓▓▓▓▓▓▓ ▓▓▓▓▓▓ TAA ▓▓▓▓▓▓
 G   K   S   E   E   A                                          *
```

FIG. 39: Sequence for pG8R248 (pG8R114 with omp25)
ggatcttccggaagaccttccattctgaaatgagctgttgacaattaatcatccggctcgtataatgtgtggaattgtgagcggataacaa
tttcacacaggaaacagaccatgaaaaaacaacatttccgtgtcgccccttattcccttttttgcggcattttgccttcctgttttttgctcaccca
gaaacgctggtgaaagtaaaagatgctgaactcgag GCG GAC GCG ATC CAG GAA CAG CCG CCG GTT CCG
GCT CCG GTT GAA GTT GCT CCG CAG TAC TCT TGG GCT GGT GGG TAC ACC GGT CTG TAC
CTG GGT TAC GGT TGG AAC AAA GCG AAA ACC TCT ACC GTT GGT TCT ATC AAA CCG GAC
GAC TGG AAA GCT GGT GCT TTC GCT GGT TGG AAC TTC CAG CAG GAC CAG ATC GTT TAC
GGT GTT GAA GGT GAC GCG GGT TAC TCT TGG GCT AAA AAA TCT AAA GAC GGT CTG GAA
GTT AAA CAG GGT TTC GAA GGT TCT CTG CGT GCG CGT GTT GGT TAC GAC CTG AAC CCG
GTT ATG CCG TAC CTG ACC GCT GGT ATC GCG GGT TCT CAG ATC AAA CTG AAC AAC GGT
CTG GAC GAC GAA TCT AAA TTC CGT GTT GGT TGG ACC GCT GGT GCT GGT CTG GAA GCT
AAA CTG ACC GAC AAC ATC CTG GGT CGT GTT GAA TAC CGT TAC ACC CAG TAC GGT AAC
AAA AAC TAC GAC CTG GCT GGT ACC ACC GTT CGT AAC AAA CTG GAC ACC CAG GAC TTC
CGT GTT GGT ATC GGT TAC AAA TTC ▓▓▓▓▓▓▓▓▓▓▓▓▓▓▓▓▓▓▓▓▓▓▓▓▓▓ ▓▓▓▓▓▓ TAA
ctgcagccaagctcccaagcttggctgttttggcggatgagagaagattttcagcctgatacagattaaatcagaacgcagaagcggt
ctgataaaacagaatttgcctggcggcagtagcgcggtggtcccacctgaccccatgccgaactcagaagtgaaacgccgtagcgc
cgatggtagtgtgggtctcccccatgcgagagtagggaactgccaggcatcaaataaaacgaaaggctcagtcgaaagactgggc
ctttcgttttatctgttgtttgtcggtgaacgctctcctgagtaggacaaatccgccgggagcggatttgaacgttgcgaagcaacggccc
ggagggtggcggcaggacgcccgccataaactgccaggcatcaaattaagcagaaggccatcctgacggatggcctttttgcgttt
ctacaaactcttttgtttattttttctaaatacattcaaatatgtatccgctcatgagacaataaccctgataaatgcttcaataatggaagatct
tccaacatcacaggtaaacagaaacgtcgggtcgatcgggaaattcttccggacggcgcggggttgggcaagccgcaggcgcg
tcagtgcttttagcgggtgtcggggcgcagccatgacccagtcacgtagcgatagcggagtgtatactggcttaactatgcggcatcag
agcagattgtactgagagtgcaccatatgcggtgtgaaataccgcacagatgcgtaaggagaaaataccgcatcaggcgctcttccg
cttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctgg
cgtttttccataggctccgcccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacctgtccgcctttctcccttc
gggaagcgtggcgctttctcatagctcacgctgtaggtatctcagttcggtgtaggtcgttcgctccaagctgggctgtgtgcacgaacc
ccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgatcttttctacggggtctg
acgctcagtggaacgaaaactcacgttaagggattttggtcatgagattatcaaaaaggatcttcacctagatccttttaaattaaaaatg
aagttttaaatcaatctaaagtatatatgagtaaacttggtctgacagtctagaagatctagcccgcctaatgagcgggcttttttttaattcg
caattccccgatgcataatgtgcctgtcaaatggacgaagcagggattctgcaaaccctatgctactccgtcaagccgtcaattgtctga
ttcgttaccaattatgacaacttgacggctacatcattcacttttttcttcacaaccggcacggaactcgctcgggctggccccggtgcatttt
ttaaataccccgcgagaaatagagttgatcgtcaaaaccaacatgcgaccgacggtggcgataggcatccgggtggtgctcaaaag
cagcttcgcctggctgatacgttggtcctcgcgccagcttaagacgctaatccctaactgctggcggaaaagatgtgacagacgcgac
ggcgacaagcaaacatgctgtgcgacgctggcgatatcaaaattgctgtctgccaggtgatcgctgatgtactgacaagcctcgcgta
cccgattatccatcggtggatggagcgactcgttaatcgcttccatgcgccgcagtaacaattgctcaagcagatttatcgccagcagct
ccgaatagcgcccttccccttgcccggcgttaatgatttgcccaaacaggtcgctgaaatgcggctggtgcgcttcatccgggcgaaa
gaaccccgtattggcaaatattgacggccagttaagccattcatgccagtaggcgcgcggacgaaagtaaacccactggtgatacc
attcgcgagcctccggatgacgaccgtagtgatgaatctctcctggcgggaacagcaaaatatcacccggtcggcaaacaaattctc
gtccctgattttcaccaccccctgaccgcgaatggtgagattgagaatataaccttcattcccagcggtcggtcgataaaaaaatcga
gataaccgttggcctcaatcggcgttaaacccgccaccagatgggcattaaacgagtatcccggcagcaggggatcattttgcgcttc
agccatactttcatactcccgccattcagagaagaaaccaattgtccatattgcatcagacattgccgtcactgcgtctttactggctctt
ctcgctaaccaaaccggtaaccccgcttattaaaagcattctgtaacaaagcgggaccaaagccatgacaaaaacgcgtaacaaa
agtgtctataatcacggcagaaaagtccacattgattattgcacggcgtcacactttgctatgccatagcatttttatccataagattagcg
gatcctacctgacgctttttatcgcaactctctactgtttctccataccgtttttttgggctagcgaattctgagaacaaactaagtggataa
atttcgtgttcaggggccaacgaagctccaggggcgaagtcacaatttccggcgctaaaaatgctgtctgcctatccttttgccgcacta
ctggcggaagaaccggtagagatccagaacgtcccgaaactgaaagacgtcgatacatcaatgaagctgctaagccagcgggtg
cgaaagtagaacgtaatggttctgtgcatattgatgcccgcgacgttaatgtattctgcgcaccttacgatctggttaaaaccatgcgtgct

FIG. 39 (CONT.)

tctatctgggcgctggggccgctggtagcgcgctttggtcaggggcaagtttcactacctggcggttgtacgatcggtgcgcgtccggtt
gatctacacatttctggcctcgaacaattaggcgcgaccatcaaactggaagaaggttacgttaaagcttccgtcgatggtcgtttgaaa
ggtgcacatatcgtgatggataaagtcagcgttggcgcaacggtgaccatcatgtgtgctgcaaccctggcggaaggcaccacgatt
attgaaaacgcagcgcgtgaaccggaaatcgtcgataccgcgaacttcctgattacgctgggtgcgaaaattagcggtcagggcac
cgatcgtatcgtcatcgaaggtgtggaacgtttaggcggcggtgtctatcgcgttctgccggatcgtatcgaaaccggtacttcctggtg
gcggcggcgatttctcgcggcaaaattatctgccgtaacgcgcagccagatactctcgacgccgtgctggcgaaactgcgtgacgct
ggagcggacatcgaagtcggcgaagactggattagcctggatatgcatggcaaacgtccgaaggctgttaacgtacgtaccgcgcc
gcatccggcattcccgaccgatatgcaggcccagttcacgctgttgaacctggtggcagaagggaccgggtttatcaccgaaacggt
ctttgaaaaccgctttatgcatgtgccagagctgagccgtatgggcgcgcacgccgaaatcgaaagcaataccgttatttgtcacggtg
ttgaaaaacttctggcgcacaggttatggcaaccgatctgcgtgcatcagcaagcctggtgctggctggctgtattgcggaagggacg
acggtggttgatcgtatttatcacatcgatcgtggctacgaacgcattgaagacaaactgcgcgctttaggtgcaaatattgagcgtgtg
aaaggcgaataagaattcaaggcaaaaaacgctgtgaaaaatgttggttttatcggctggcgcggaatggtcggctctgttctcatgca
acgcatggtagaggagcgcgatttcgacgctattcgccctgttttctttctacctcccagtttggacaggcggcgcccaccttcggcgac
acctccaccggcacgctacaggacgcttttgatctggatgcgctaaaagcgctcgatatcatcgtgacctgccagggcggcgattata
ccaacgaaattatccaaagctgcgcgaaagcggatggcagggttactggattgatgcggcttctacgctgcgcatgaaagatgatg
ccattattattctcgacccggtcaaccaggacgtgattaccgacggcctgaacaatggcgtgaagacctttgtgggcggtaactgtacc
gttagcctgatgttgatgtcgctgggcggtctctttgcccataatctcgttgactgggtatccgtcgcgacctatcaggccgcctccggcgg
cggcgcgcgccatatgcgcgagctgttaacccagatgggtcagttgtatggccatgtcgccgatgaactggcgacgccgtcttccgca
attcttgatattgaacgcaaagttacggcattgacccgcagcggcgagctgccggttgataactttggcgtaccgctggcgggaagcct
gatccctggatcgacaaacagctcgataacggccagagccgcgaagagtggaaaggccaggcggaaaccaacaagattctca
atactgcctctgtgattccggttgatggttgtgtgtgcgcgtcggcgcgctgcgctgtcacagccaggcgttcaccatcaagctgaaaa
aagaggtatccattccgacggtggaagaactgctggcggcacataatccgtgggcgaaagtggtgccgaacgatcgtgatatcact
atgcgcgaattaaccccggcggcggtgaccggcacgttgactacgccggttggtcgtctgcgtaagctgaacatggggccagagttc
ttgtcggcgtttaccgtaggcgaccagttgttatggggcgccgccgagccgctgcgtcgaatgctgcgccagttggcctagtctaggga
cgatgatgcaaccgataccgtcgacggatcacatagactcgctccgaaattaaagaacacttaaattatctactaaaggaatctttagt
caagtttatttaagatgacttaactatgaatacacaattgatgggtgagcgtaggagcatgcttatgcgaaaggccatcctgacggatg
gccttttt

FIG. 40: >omp25

| CCC GGG | ▓▓▓ | GCG | GAC | GCG | ATC | CAG | GAA | CAG | CCG | CCG | GTT | CCG | GCT | CCG | GTT | GAA | GTT | GCT |
|---|---|---|---|---|---|---|---|---|---|---|---|---|---|---|---|---|---|---|
| | | A | D | A | I | Q | E | Q | P | P | V | P | A | P | V | E | V | A |

```
CCG CAG TAC TCT TGG GCT GGT GGG TAC ACC GGT CTG TAC CTG GGT TAC GGT TGG AAC AAA GCG
 P   Q   Y   S   W   A   G   G   Y   T   L   Y   L   G   Y   G   W   N   K   A

AAA ACC TCT ACC GTT GGT TCT ATC AAA CCG GAC GAC TGG AAA GCT GGT GCT TTC GCT GGT TGG
 K   T   S   T   V   G   S   I   K   P   D   D   W   K   A   G   A   F   A   G   W

AAC TTC CAG CAG GAC CAG ATC GTT TAC GGT GTT GAA GGT GAC GCG GGT TAC TCT TGG GCT AAA
 N   F   Q   Q   D   Q   I   V   Y   G   V   E   G   D   A   G   Y   S   W   A   K

AAA TCT AAA GAC GGT CTG GAA GTT AAA CAG GGT TTC GAA GGT TCT CTG CGT GCG CGT GTT GGT
 K   S   K   D   G   L   E   V   K   Q   G   F   E   G   S   L   R   A   R   V   G

TAC GAC CTG AAC CCG GTT ATG CCG TAC CTG ACC GCT GGT ATC GCG GGT TCT CAG ATC AAA CTG
 Y   D   L   N   P   V   M   P   Y   L   T   A   G   I   A   G   S   Q   I   K   L

AAC AAC GGT CTG GAC GAC GAA TCT AAA TTC CGT GTT GGT TGG ACC GCT GGT GCT GGT CTG GAA
 N   N   G   L   D   D   E   S   K   F   R   V   G   W   T   A   G   A   G   L   E

GCT AAA CTG ACC GAC AAC ATC CTG GGT CGT GTT GAA TAC CGT TAC ACC CAG TAC GGT AAC AAA
 A   K   L   T   D   N   I   L   G   R   V   E   Y   R   Y   T   Q   Y   G   N   K

AAC TAC GAC CTG GCT GGT ACC ACC GTT CGT AAC AAA CTG GAC ACC CAG GAC TTC CGT GTT GGT
 N   Y   D   L   A   G   T   T   V   R   N   K   L   D   T   Q   D   F   R   V   G

ATC GGT TAC AAA TTC ▓▓▓▓▓▓▓▓▓▓▓▓▓▓▓▓▓▓▓▓▓▓▓▓ ▓▓▓▓▓▓ TAA ▓▓▓▓▓
 I   G   Y   K   F                                        *
```

FIG. 47: Chimeric gene synthesis by pG8R111 in Salmonella x12341 (pG8R231)

FIG. 49: pG8R114-*omp31* in X12341(pG8R261)

Fig. 51: pG8R111-*figk* in x12341(pG8R260)

FIG. 53: pG8R111-*btub* x12341(pG8R258)
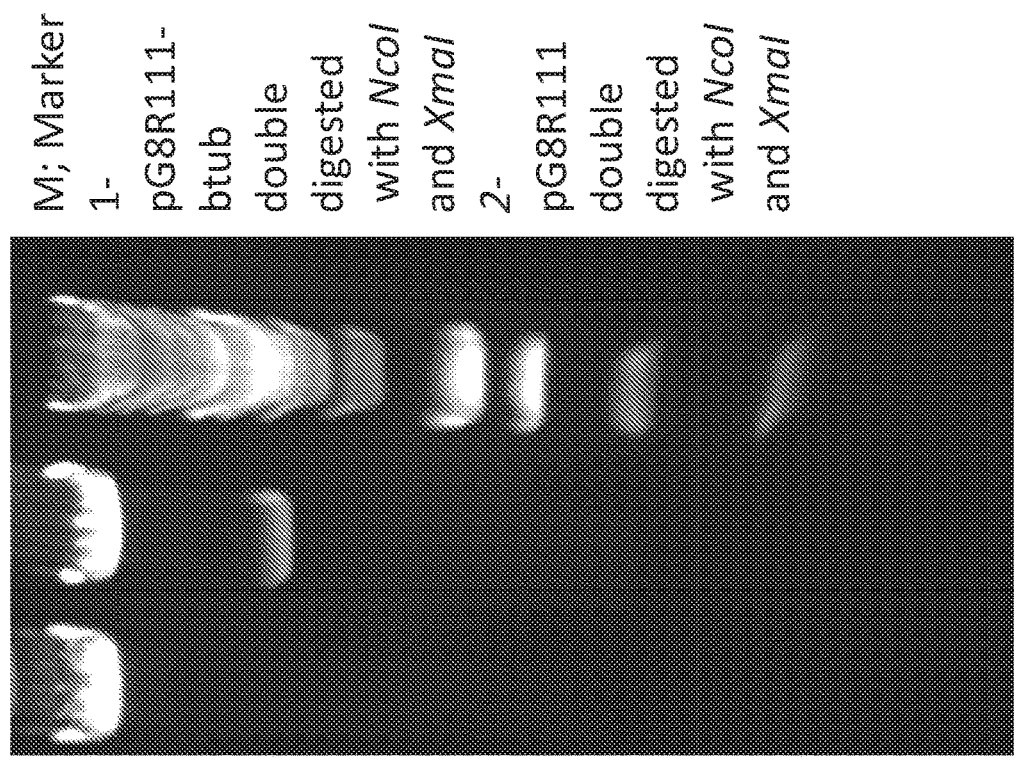
M; Marker
1- pG8R111-btub double digested with NcoI and XmaI
2- pG8R111 double digested with NcoI and XmaI
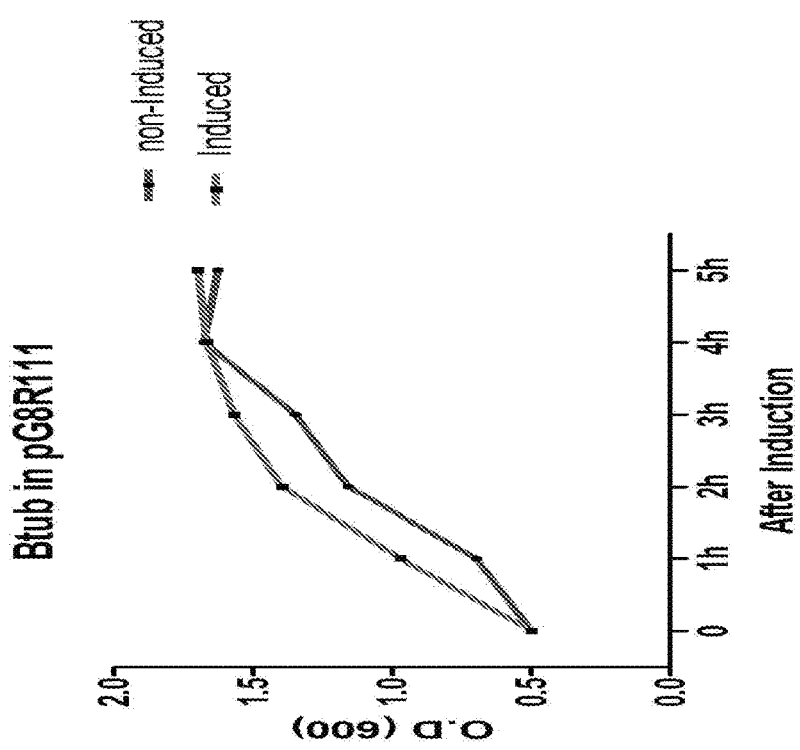

FIG. 55: pGR111-bls-l7/l12-cu/zn in X1234 (pG8R259)
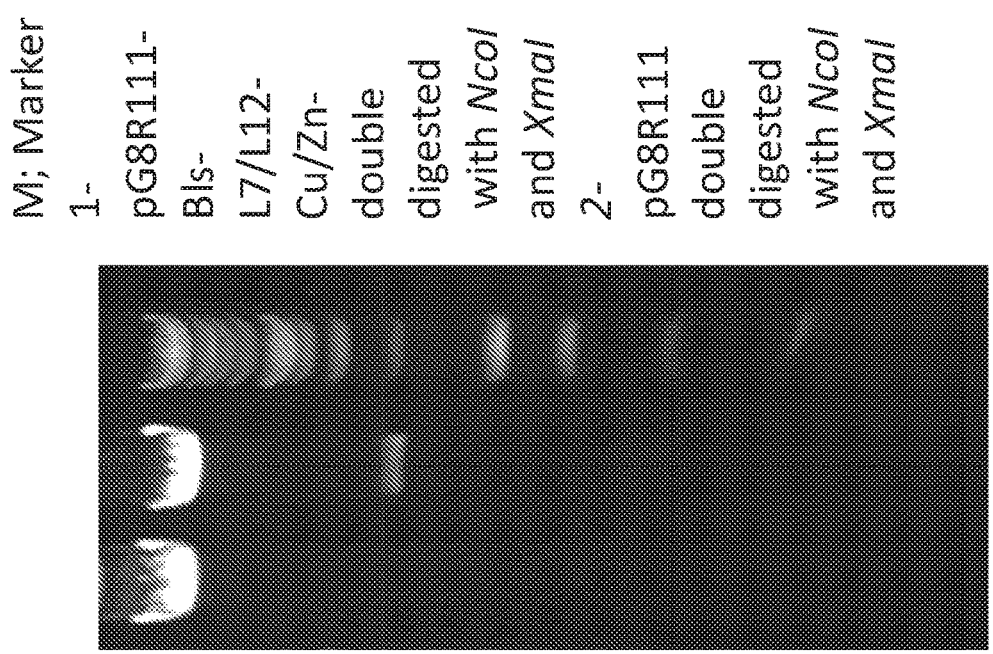
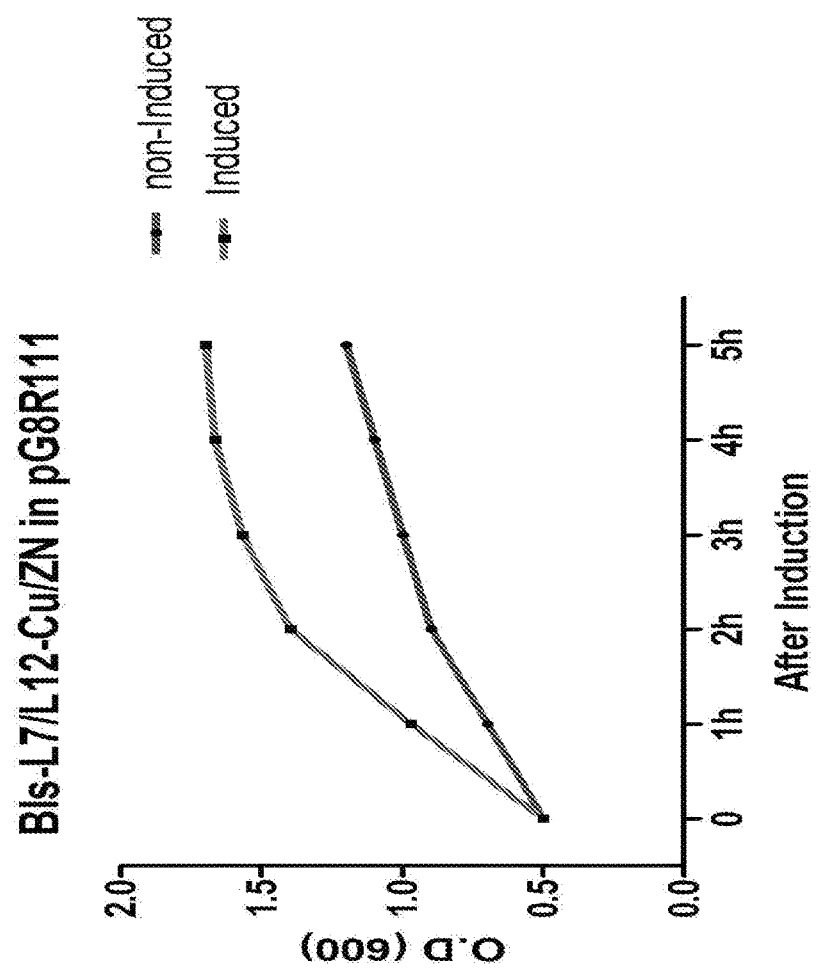

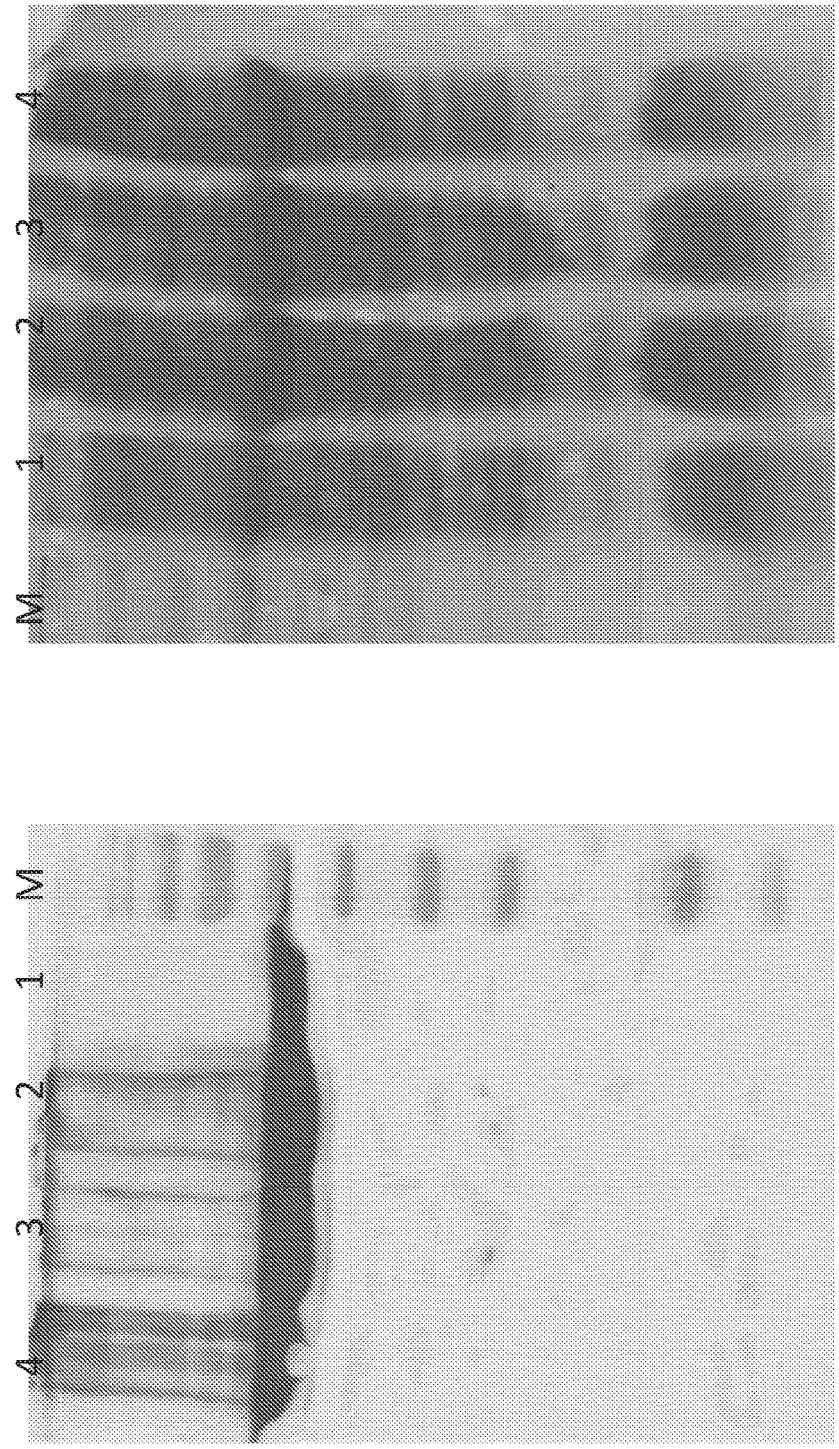
FIG. 56: pGR111-bls-l7/l12-cu/zn in X1234 (pG8R259)
M: Marker; 1: Before Induction; 2: 2hrs after induction; 3: 4hrs after induction; 4: 4hrs after induction

PROTECTIVE IMMUNITY ENHANCED SALMONELLA VACCINE (PIESV) AGAINST BRUCELLA SPP

STATEMENT OF GOVERNMENT SUPPORT

This invention was made with government support under grant No. 2017-67017-26179 awarded by The United States Department of Agriculture, National Institutes of Food & Agriculture and Grant No. AI056289 awarded by the National Institutes of Health. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "10457-372US1_ST25.txt" created on Oct. 4, 2021 and is 105,476 size bytes in size. The sequence listing contained in this .txt file is part of the specification and is hereby incorporated by reference herein in its entirety.

BACKGROUND

Brucellae are facultative, intracellular Gram-negative proteobacteria that are highly infectious pathogens that cause abortions and infertility in domestic and wild mammals and severe and debilitating disease in humans (1, 2). Brucellosis, caused mainly by B. abortus (cattle), B. melitensis (sheep and goats) and B. suis (swine), occurs worldwide with the highest prevalence in the Middle East, Asia, Africa, tropical America and the Mediterranean region (2, 3). Zoonotic reservoirs also exist in U.S. wildlife animals (4). B. abortus, B. melitensis, and B. suis are potential biological warfare agents, and are serious concerns because there is presently no human vaccine (5) and livestock vaccines are ineffective (6).

The annual incidence of human Brucella infections is estimated at 500,000 cases but the disease is widely acknowledged to be underreported (7). Control of brucellosis relies principally on surveillance, testing, removal of infected animals, control provisions for import/export of animals and animal products, and vaccination. Antibiotic treatment of animals is regulated and discouraged due to the large doses and long treatment required and concern about selection for increased resistance to antibiotics.

BRIEF DESCRIPTION OF DRAWINGS

FIG. 1. Plasmid maps.

FIG. 3. Triple-sugar regulated Salmonella vaccine χ12341 induces better protection against C. perfringens challenge than double-sugar regulated strain χ11802. NV/NCh: nonmedicated, no challenge group; NV/Ch: nonmedicated, C. perfringens challenge group; Vac 1/Ch: χ11802(pG8R220), Cp challenge group; Vac 2/ch: χ12341 (pG8R220), Cp challenge group; Vector/Ch: χ12341 (pYA3681), Cp challenge group; BMD/Ch: Bacitracin Methylene Disalicylate, Cp challenge group. FIG. 3A shows average lesion score. FIG. 3B shows percent mortality. FIG. 3C shows weight gain. FIG. 3D shows feed conversion ratio.

FIG. 7 shows western blot results for χ12509.

FIG. 10 provides antigen synthesis and stability results for χ12509(pG8R241).

FIG. 11 provides antigen synthesis and stability results for χ12509(pG8R243).

FIG. 12 provides antigen synthesis and stability results for χ12509(pG8R248).

FIG. 13 provides antigen synthesis and stability results for χ12509(pG8R250).

FIG. 14 provides antigen synthesis and stability results for χ12509(pG8R251).

FIG. 15 provides antigen synthesis and stability results for χ12509.

FIG. 16 provides a photograph of a culture showing plasmid stability of pG8R241, pG8R243, pG8R248, pG8R250, pG8R251.

FIG. 17 shows that pG8R258 encoding BtuB when placed in χ12341 had rapid degradation of synthesized antigen.

FIG. 18 shows that pG8R260 encoding FIgK in pG8R111 when placed in χ12341 had rapid degradation of synthesized antigen.

FIG. 19 shows that pG8R261 encoding Omp31 in pG8R111 when placed in χ12341 showed that the antigen synthesized was very toxic and inhibited growth of the construct.

FIG. 20 shows Chimeric gene expression in pG8R111 vector in Salmonella χ12341(pG8R231).

FIG. 21 provides photographs of gels showing expression of fusion construct of BLS, the L7/L12 ribosome proteins and the Cu/Zn super oxide dismutase in pG8R259.

FIG. 22 provides results showing that the fusion construct of BLS, the L7/L12 ribosome proteins and the Cu/Zn super oxide dismutase in pG8R259 displayed instability.

FIG. 23 provides graphs showing results of B. melitensis S19 challenge in mice. FIG. 23A shows colonization titers per spleen. FIG. 23B shows colonization titers per time point.

FIG. 24 provides a diagram showing vaccination scheme.

FIG. 25 Spleen Protection Analysis. FIG. 25B shows a time curve of splenic CFUs post i.p. immunization.

FIG. 27 (SEQ ID NO: 1) shows the sequence for pG8R251 with bp26.

FIG. 28 (SEQ ID NOS: 2 and 3) shows the codon optimization for bp26.

FIG. 30 (SEQ ID NO: 4) shows the sequence for pG8R241 with opm22.

FIG. 31 (SEQ ID NOS: 5 and 6) shows the codon optimization of omp22.

FIG. 33 (SEQ ID NO: 7) shows the sequence of pG8R243 with bp26

FIG. 34 (SEQ ID NOS: 8 and 9) shows the codon optimization for bp26

FIG. 36 (SEQ ID NO: 10) shows the sequence for pG8R250 with tf.

FIG. 37 (SEQ ID NOS: 11 and 12) shows the codon optimization for tf.

FIG. 39 (SEQ ID NO: 13) shows the sequence of pG8R248 with omp25.

FIG. 40 (SEQ ID NOS: 14 and 15) shows the plasmid sequence of omp25.

FIG. 53 shows the data related to the plasmid shown in FIG. 52.

FIG. 55 shows the data related to the plasmid shown in FIG. 54.

FIG. 56 shows gel data for pGR111-bls-I7/I12-cu/zn in X1234 (pG8R259).

DETAILED DESCRIPTION

Figures 1A, 1B, 1C:
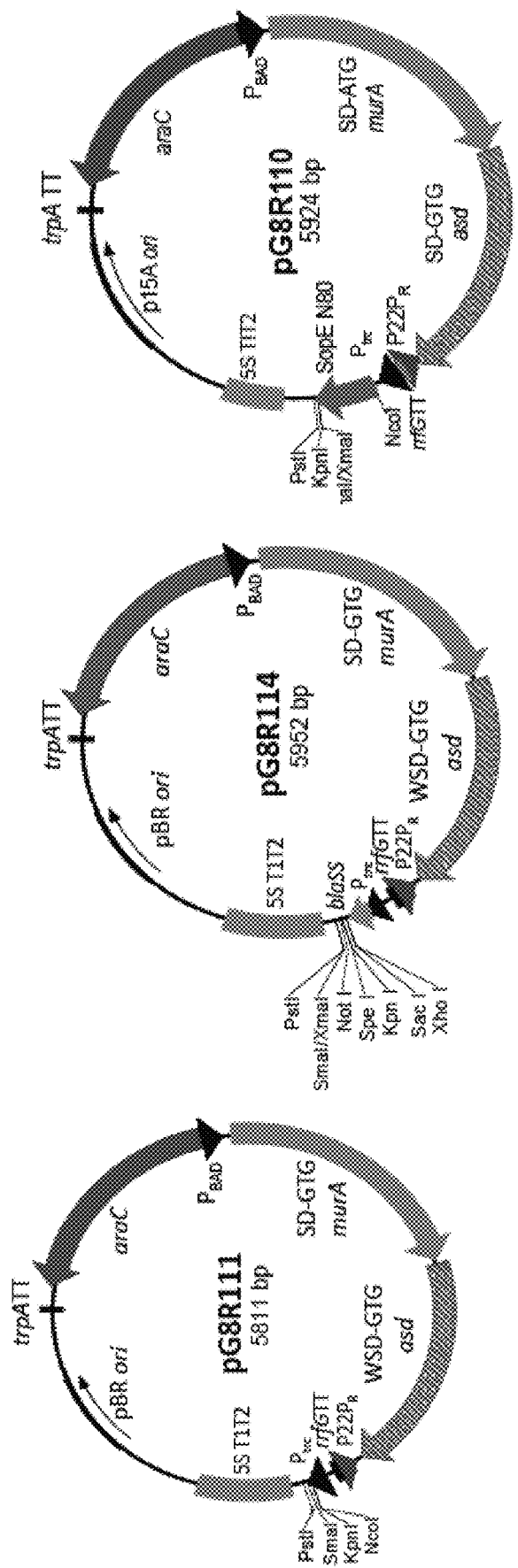
FIG. 1A pertains to lysis vector pG8R111, pBR ori; p15A ori, pYA4589 and pSC101 ori, pYA4595.
FIG. 1B pertains to lysis vectors with improved bla SS pG8R112, pSC101 ori; pG8R113, p15A ori, and pG8R114, pBR ori.
FIG. 1C pertains to lysis vector with T3SS SopE N-80 pG8R110, p15A ori.

Bacterial pathogens have evolved means to succeed as pathogens by infecting without recognition by receptors triggering innate immunity, by suppressing induction of immunity and by inducing immune responses to antigens that confer no protective immunity. Embodiments described herein circumvent these abilities in *Salmonella* so as to provide a vector system that induces maximal protective immune responses. Another major problem in using live attenuated bacterial vaccine vectors is the accumulation of attenuating mutations that confer avirulence and safety but which decrease the ability of the vaccine to contend with natural host defenses and to invade cells in the MALT to colonize and persist in internal effector lymphoid tissues, which collectively decrease the ability of the vaccine to induce protective immune responses. The embodiments disclosed herein solve this problem in multiple ways by using regulated delayed in vivo shut off of virulence genes, regulated delayed synthesis of recombinant protective antigens and regulated delayed lysis in vivo to confer biological containment with no persistence of vaccine cells and no survival if excreted. This enables the improved vaccine, at the time of vaccination, to exhibit the same or better abilities of the wild-type virulent parent to colonize internal lymphoid tissues to maximize induction of protective immune responses.

These innovative technologies plus other genetic modifications enhance early induction of innate immunity and also favor induction of specific humoral or cellular immune responses. In specific embodiments, these approaches are used in conjunction with the selection of known and putative protective antigens to construct Protective Immunity Enhanced *Salmonella* Vaccine (PIESV) strains to synthesize and deliver multiple *Brucella melitensis* antigens to generate a vaccine to prevent infection and abortion caused by *B. melitensis* and *B. abortus*. The techniques provided herein may be adapted to generate vaccines against *Brucella* species.

Definitions

The "attenuated" as used herein refers to the process of rendering certain pathogen virulence attributes needed to cause diseases less able to cause such disease symptoms.

The term "codon optimized" or "codon optimization" as used herein refers to enhancing the ability of the antigen encoding sequence to be expressed in the *Salmonella* vaccine strain by selecting codons that are used for highly expressed genes in *Salmonella*. Such codon optimization also includes changing the GC content of the antigen encoding sequence to be similar to that used for *Salmonella* (i.e., ~52% GC). In addition, the codon optimization can also be used to enhance the stability of the mRNA encoded by the antigen encoding sequence so as to be less likely to be degraded by RNases.

The term "delayed attenuation" as used herein refers to a means of gene regulation such that the attenuation attribute is not expressed during growth of the vaccine strain or during it administration to an animal host but is not expressed after the vaccine enters the animal host and is manifest as a consequence of vaccine cell division in vivo with gradual dilution of the virulence gene product by at least half at each cell division in vivo.

The term "high level synthesis" refers to a means of synthesizing a protein antigen at a level that exceeds that level of synthesis that would be synthesized by a chromosomal gene encoding that antigen and can be achieved by encoding the antigen gene on a multi-copy plasmid and/or by placing the antigen encoding sequence under the control of a promoter known to cause gene product synthesis at an elevated level greater than would be caused by using the native promoter for that antigen encoding gene.

The term "balanced-lethal plasmid-host" is the design of the plasmid-host composition such that survival of the host is dependent on the maintenance of the plasmid such that loss of the plasmid results in death of the host. (See Nakayama et al. 1988 Nat Biotech or Galan et al. 1990 Gene, whose teachings are incorporated by reference).

The term "secretory signal" as used herein means a sequence that enables a protein fused to it to be secreted out of the bacterial cell cytoplasm.

Overview

The embodiments described herein address the priority to develop vaccines and vaccine delivery systems to prevent *Brucella* caused diseases of domestic farm animals and wildlife zoonotic reservoirs that are a concern to public health.

Although *Brucella* infection in U.S. livestock is now rare, the increasing prevalence in bison, elk, deer and feral swine leads to infection of domestic farm animals. In addition, last year hunters of wild boar in Florida contracted *B. suis* that may be present in half the feral swine population. *Brucella* species also represent a biothreat and humans, who are self-centered, often forget that the most potent bioweapons attack the food supply.

Subunit vaccines seldom induce long-term protective immunity to prevent infection and the live attenuated *B. abortus* S19 and RB51 and *B. melitensis* Rev1 vaccines do not induce sterilizing immunity such that persistence of strains continue to cause abortion in subsequent pregnancies. The new innovative vaccine vector system provided herein is efficacious in inducing protective immunity against *Brucella* infection and induced abortion. Although designed for livestock, the vaccine construct embodiments may be administered to wildlife species and will have the potential to confer protective immunity to humans. This is important since no available vaccines are safe to use in humans. An added benefit to embodiments is the provision of an inexpensive vaccine that can be manufactured as a thermostable lyophilized product that can be reconstituted at the time and place of easy mucosal administration. This is particularly important in the developing world where *Brucella* infections are much more prevalent than in the U.S. and with devastating adverse health and economic consequences.

Currently, three live attenuated *Brucella* strains have been used as vaccines for brucellosis prevention, *B. abortus* S19 and RB51 for cattle and *B. melitensis* Rev1 for small ruminants (8). Although the smooth strains S19 from *B. abortus* and Rev1 from *B. melitensis* are able to induce effective levels of protection in cattle, goats and sheep, respectively, these vaccines sometimes cause abortion in pregnant cows (9, 10), are pathogenic to humans and the rough *B. abortus* strain RB51 confers resistance to rifampicin, which is the first-line antibiotic for human brucellosis treatment (11). Therefore, the development of safe and effective vaccines that completely prevent *Brucella* infection and abortion and protect different animal host species are necessary for eradication of brucellosis in endemic countries.

As stated above, most successful pathogens have evolved means to circumvent host immune defense systems and traditional means of attenuation following the pioneering work of Pasteur to render them suitable as vaccines while enhancing safety have decreased their immunogenicity. These problems have traditionally been compensated for by increasing vaccine dose and number of vaccinations to achieve adequate levels of protective immunity to infection. In contrast, embodiments disclosed herein address and largely eliminate these problems in the continuing development and improvement of *Salmonella* strains to use as vaccines and recombinant vaccine vectors as described herein. Since extracellular capsular materials are immunosuppressive and also promote long-term persistence of *Salmonella*, we eliminated means by which our *Salmonella* vaccine strains synthesize these polymers (13-15). Since about 50 percent of all serum antibodies in *Salmonella*-immunized animals are to the OmpA protein and since immune responses to the OmpA protein confer no protection against *Salmonella* infection, we have deleted the ompA gene to eliminate the synthesis of this subterfuge antigen (see Preliminary Results). In so doing, immune responses to other OMPs are increased with enhanced induction of protective immunity.

Our current *Salmonella* vectors are now designed to effectively colonize internal lymphoid tissues after mucosal administration almost as efficiently as the wild-type virulent *Salmonella* parent strain (16). We achieve this in several ways. Our vaccines synthesize LPS O-antigen during in vitro growth but cease to synthesize LPS in vivo. Thus, vaccine cells become increasingly sensitive to complement-mediated cytotoxicity and phagocytosis after 8 to 10 cell divisions in the absence of the sugar-required for LPS synthesis (17). It should be noted that cell division in vivo varies from 10 to 30 hours. Another means of regulated delayed attenuation (16) results in lysis of vaccine cells by inability to synthesize the essential peptidoglycan precursors diaminopimelic acid (DAP) and muramic acid whose syntheses are dependent on supply of arabinose during in vitro growth (18). In vivo, arabinose is absent and vaccine cells lyse after 8 to 12 cell divisions. This releases peptidoglycan components and DNA to enhance recruitment of innate immunity in infected host cells via activation of Nod1, Nod2 and TLR9 receptors. Protective antigen delivery by regulated delayed lysis has given superior immune responses compared to delivery without programmed lysis in five different studies (19).

Since synthesis of protective antigens in *Salmonella* vectored vaccines is a metabolic load that decreases colonizing ability, we eliminated this problem by developing regulated delayed synthesis of recombinant antigens by plasmid-encoded codon-optimized sequences (20). This has increased the induced levels of protective immunity to multiple pathogens (21).

As additional means to further enhance induction of protective immunity, we observed that secretion of protective antigens using Type 2 secretion systems (T2SSs) very much enhanced induced protective immunity (22) and later learned that this was most likely due to overproduction of protective antigen-containing outer membrane vesicles (23, 49). We recently further improved means for type 2 secretion (24). We have also used the type 3 secretion system (T3SS) to deliver protective antigens to the cytosol of host cells to enhance induction of CD8-dependent immunities (25). Often both T2SS and T3SS are used in conjunction with regulated delayed lysis to maximize induction of protective immunity (17).

The type of immune response induced can also be altered by inclusion of appropriate deletion mutations. The ΔsopB mutation decreases intestinal inflammation (26), eliminates a means of immunosuppression and importantly increases induction of mucosal immune responses (27). The ΔsifA mutation also eliminates a means of immunosuppression (25) and enables *Salmonella* to escape the *Salmonella*-containing vesicle (SCV) so that vaccine strains with the regulated delayed lysis attribute lyse in the cytosol. Synthesized protective antigens are then delivered to the proteasome for presentation by Class I to elicit CD8-dependent immune responses(25).

Plasmid

An attenuated microorganism as described herein that is capable of the regulated expression of at least one nucleic acid sequence encoding a *Brucella* antigen may also comprise, in part, a plasmid vector. The plasmid vector comprises a nucleic acid sequence encoding at least one *Brucella* antigen operably linked to a promoter. The promoter is regulated by the chromosomally encoded repressor, such that the expression of the nucleic acid sequence encoding an antigen is repressed during in vitro growth of the microorganism, but the microorganism is capable of high-level synthesis of the antigen in an animal or human host.

As used herein, "plasmid vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses or mucosal immune responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

A vector may comprise one or more than one nucleic acid sequence encoding a *Brucella* antigen, whether regulated or not, as detailed above.

Attenuation of the Recombinant Bacterium

In each of the above embodiments, the microorganism capable of regulated expression of *Brucella* antigens also is attenuated. "Attenuated" refers to the state of the microorganism (e.g., bacterium) wherein the microorganism has been weakened from its wild-type fitness by some form of recombinant or physical manipulation. This may include altering the genotype of the microorganism to reduce its ability to cause disease. However, the bacterium's ability to colonize the gut (in the case of *Salmonella*) and induce immune responses is, preferably, not substantially compromised. For instance, in one embodiment, regulated attenuation allows the recombinant microorganism to express one or more nucleic acids encoding products important for the microorganism to withstand stresses encountered in the host after immunization. This allows efficient invasion and colonization of lymphoid tissues before the recombinant microorganism is regulated to display the attenuated phenotype.

In one embodiment, a microorganism may be attenuated by regulating LPS O-antigen synthesis. In another embodiment, a recombinant microorganism may be attenuated as described below. In which case, both regulated attenuation and regulated expression of a *Brucella* antigen encoding sequence may be dependent upon an arabinose regulatable system. Consequently, the concentration of arabinose needed for optimal expression of the regulated enteric antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences encoding the virulence protein, so that the production levels of the virulence protein are optimal for both the regulated attenuation phenotype and the regulated expression when growing strains with a given concentration of arabinose. In addition, these attenuating nucleic acid sequences may be regulated by other systems using well-established protocols known to one of skill in the art. For example, they may be regulated using promoters dependent on addition of maltose, rhamnose, or xylose rather than arabinose.

Other methods of attenuation are known in the art. For instance, attenuation may be accomplished by altering (e.g., deleting) native nucleic acid sequences found in the wild-type bacterium. For instance, if the microorganism is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant microorganism to induce disease symptoms.

The microorganism may also be modified to create a balanced-lethal host-vector system, although other types of systems may also be used (e.g., creating complementation heterozygotes). For the balanced-lethal host-vector system, the microorganism may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the microorganism is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall.

Yet another balanced-lethal host-vector system comprises modifying the microorganism such that the synthesis of an essential constituent of the rigid layer of the bacterial cell wall is dependent on a nutrient (e.g., arabinose) that can be supplied during the growth of the microorganism. For example, a microorganism may—comprise the $\Delta P_{murA}$::TT araC $P_{araBAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the microorganism in vitro.

When arabinose is absent, however, as it is in an animal or human host, the essential constituent of the peptidoglycan layer of the cell wall is not synthesized. This mutation represents an arabinose dependent lethal mutation. In the absence of arabinose, synthesis of muramic acid ceases and lysis of the microorganism occurs because the peptidoglycan layer of the cell wall is not synthesized. It is not possible to generate ΔmurA mutations because they are lethal. The necessary nutrient, a phosphorylated muramic acid, cannot be exogenously supplied because enteric bacteria cannot take the nutrient up from the media. Recombinant bacteria with a $\Delta P_{murA}$::TT araC $P_{araBAD}$ murA deletion-insertion mutation grown in the presence of arabinose exhibit effective colonization of effector lymphoid tissues after oral vaccination prior to undergoing lysis due to the inability to synthesize muramic acid.

Similarly, various embodiments may comprise the araC $P_{araBAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced-lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above.

In one embodiment, ΔasdA27::TT araC $P_{araBAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{araBAD}$ c2 has the 1104 base-pair asd nucleic acid sequence deleted (1 to 1104, but not including the TAG stop codon) and the 1989 base-pair fragment containing T4 ipIII TT araC $P_{araBAD}$ c2 inserted. The c2 nucleic acid sequence in ΔasdA27::TT araC $P_{araBAD}$ c2 has a SD sequence that was optimized to TAAGGAGGT. It also has an improved $P_{araBAD}$ promoter such that the −10 sequence is improved from TACTGT to TATAAT. Furthermore, it has a codon optimized c2 nucleic acid sequence, in which the second codon was modified from AAT to AAA.

In further embodiments, the microorganism may be attenuated by regulating the murA nucleic acid sequence encoding the first enzyme in muramic acid synthesis and the asd nucleic acid sequence essential for DAP synthesis. These embodiments may comprise the chromosomal deletion-insertion mutations ΔasdA27::TT araC $P_{araBAD}$ c2 and $\Delta P_{murA25}$::TT araC $P_{araBAD}$ murA. This host-vector grows in LB broth with 0.1% L-arabinose, but is unable to grow in or on media devoid of arabinose since it undergoes cell wall-less death by lysis. In some embodiments of the invention, the recombinant microorganism may comprise araBAD mutations to preclude breakdown of internalized arabinose such that asd and murA nucleic acid sequence expression continues for a cell division or two after oral immunization into an environment that is devoid of external arabinose. (For example a strain with a $\Delta P_{murA}$::TT araC $P_{sraBAD}$ murA deletion-insertion mutation undergoes about two cell divisions and then commences to lyse in media made of mouse or chicken feed or chicken breast meat, unless they are supplemented with arabinose). Either GTG or TTG start codons for the murA and asd nucleic acid sequences are important to decrease translation efficiency on multi-copy plasmids. For instance plasmid vector pG8R114 contains the murA nucleic acid sequence (with altered start codon sequences to decrease translation efficiency) under the control of an araC $P_{araBAD}$ promoter. Also, the second nucleic acid sequence under the direction of this promoter is the asd nucleic acid sequence (with altered start codon sequences to decrease translation efficiency). The P22 $P_R$ promoter is in the anti-sense direction of both the asd nucleic acid sequence and the murA nucleic acid sequence. The P22 $P_R$ is repressed by the C2 repressor made during growth of the strain in media with arabinose (due to the ΔasdA27::TT araC $P_{araBAD}$ c2 deletion-insertion). However, C2 concentration decreases due to cell division in vivo to cause $P_R$ directed synthesis of anti-sense mRNA to further block translation of asd and murA mRNA. The araC $P_{araBAD}$ sequence is also not from *E. coli* B/r as originally described but represents a sequence derived from *E. coli* K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asd nucleic acid sequence does not replace the chromosomal asd mutation since they have a deleted sequence in common, consequently, the *E. coli* murA nucleic acid sequence was used in the plasmid instead of using the *Salmonella* murA nucleic acid sequence. The recombinant microorganism of this embodiment is avirulent at oral doses in excess of $10^9$ CFU to BALB/c mice. In addition to being fully attenuated, this construction exhibits complete biological containment with no in vivo recombinant bacteria survivors detectable after 21 days and no recombinant bacteria survivors during or after excretion. This property enhances vaccine safety and minimizes potential for immunization of those not intended to be immunized or in humans not elected to be immunized.

Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the microorganism in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

B. melitensis Antigens

Various B. melitensis antigens and sequences may be implemented in the vaccine system and microorganism disclosed herein. Examples of B. melitensis antigens that may be included but are not limited to Omp22 (28), Omp25 (29), Omp31 (30, 31), BtuB (28), Tf (31, 32), Bp26 (32, 33), FlgK (28), BLS (34, 35), L7/L12 (36) and Cu/ZN SOD (37) antigens. The sequences of these antigens are known and provided in the cited literature. In preparation for vector construction we do a complete bioinformatic analysis of all structural properties of each protein, analyze the structure of the transcribed mRNA and then modify DNA codons to enhance stability of mRNA and efficiency of translation in Salmonella. We sometimes do protein engineering to delete sequences that interfere with stability or synthesis by the PIESV vector strain that impair growth and that are not likely important for immunogenicity.

For non-secreted B. melitensis antigens without native signal sequences, the commercially synthesized DNA sequences are inserted into pG8R111 (pBR on) and pYA4589 (p15A on). For those proteins with a native signal sequence, the codon-optimized sequence lacking the native SS is inserted into the pG8R114 (pBR on) and pG8R113 (p15A on) vectors with the improved bla SS (38) to maximize antigen synthesis levels and secretion to enhance production of immunogenic outer membrane vesicles. We also insert sequences without their native signal peptides into the T3SS vector pG8R110 (p15A on).

Secretory Signals

As taught herein, secretory signal sequences may be included in the plasmid vectors to direct delivery of the expressed sequence out of the cell. These include secretory signal sequences for the type 2 and type 3 secretory systems. The improved bla SS used in pG8R114 and other plasmid vectors is described in Jiang et al. (38) and the sequence for the T3SS with fusion to the N-terminal 80 amino acids of the SopE protein as used in pG8R110 is given in Juarez et al. (39).

Biological Containment

Under certain embodiments, a live attenuated microorganism may possess the potential to survive and multiply if excreted from a host. This leads to the possibility that individuals not electing to be immunized may be exposed to the attenuated microorganism. Consequently, in certain embodiments, an attenuated microorganism of the invention may comprise one or more mutations that decrease, if not preclude, the ability of Salmonella vaccines to persist in the GI tract of animals.

In some embodiments, the attenuated microorganism may comprise a method of regulated delayed lysis in vivo that prevents bacterial persistence in vivo and survival if excreted. These mutations include: Δ(wza-wcaM)-8 that prevents synthesis of colanic acid and other polysaccharide capsules that protect lysing cells from display of complete lysis and thus enhances the level of biological containment afforded by using the regulated delayed lysis in vivo attribute. ΔasdA27::TT araC $P_{araBAD}$ c2 insertion-deletion mutation to impose a requirement for the peptidoglycan constituent DAP and $\Delta P_{murA25}$::TT araC $P_{araBAD}$ murA insertion-deletion mutation as a conditional-lethal mutation blocking synthesis of the peptidoglycan constituent muramic acid. The latter two mutations are typically complemented by a regulated delayed lysis plasmid vector such as pG8R110, pG8R111 and pG8R114 (FIG. 1) that have an arabinose-dependent expression of asdA and murA genes. An attenuated microorganism comprising such mutations grows normally in the presence of arabinose. In vivo, however, the bacterium ceases to express any nucleic acids encoding the AsdA and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring complete biological containment.

Vaccine Compositions and Administration

An attenuated microorganism of the invention has been modified to enhance its ability to synthesize and deliver antigens that would induce protective immunity to infections caused by other pathogens, in this case from Brucella. As such this recombinant attenuated microorganism may be particularly suited for use as a vaccine. Infection of a host with a Salmonella strain typically leads to colonization of the gut-associated lymphoid tissue (GALT) or Peyer's patches, which leads to the induction of a generalized mucosal immune response to the attenuated microorganism. Further penetration of the bacterium into the mesenteric lymph nodes, liver and spleen augments the induction of systemic and cellular immune responses directed against the bacterium. Thus, the use of recombinant Salmonella for oral immunization stimulates all three branches of the immune system, which is particularly important for immunizing against infectious disease agents that colonize on and/or invade through mucosal surfaces.

An attenuated microorganism of the invention may be administered to a host as a vaccine composition. As used herein, a vaccine composition is a composition designed to elicit an immune response to the attenuated microorganism, including any antigens that may be expressed by the bacterium. In an exemplary embodiment, the immune response is protective. As used herein, "protective" means that the immune response contributes to the lessening of any symptoms associated with infection of a host with the pathogen the antigen was derived from or designed to elicit a response against. For example, a protective antigen from a pathogen, such as Brucella spp, may induce an immune response that helps to ameliorate symptoms associated with Brucella infection or reduce the morbidity and mortality associated with infection with the pathogen. The use of the term "protective" in this invention does not necessarily require that the host is completely protected from the effects of the pathogen.

Immune responses to antigens are well studied and widely reported. A survey of immunology is given by Paul, W E, Stites D et. al. and Ogra P L. et. al. (11-13). Mucosal immunity is also described by Ogra P L et. al. (14).

Vaccine compositions of the present invention may be administered to any host capable of mounting an immune response. Such hosts may include all vertebrates, for example, mammals. In a specific embodiment, the mammal is a ruminant such as cow, horse, pig, goat, or sheep. The vaccine can be administered as a prophylactic or for treatment purposes.

In exemplary embodiments, the attenuated microorganism is alive when administered to a host in a vaccine composition. Suitable vaccine composition formulations and methods of administration are detailed below.

Vaccine Composition

The *Salmonella* vaccines discussed herein are typically lyophilized after production and may be reconstituted in a pharmaceutically acceptable carrier prior to administration. Such a carrier may be any solvent or solid material for encapsulation that is non-toxic to the inoculated host and compatible with the attenuated microorganism. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the respiratory tract, the vaccine is preferably presented in the form of an aerosol.

The dosages of a vaccine or vaccine composition disclosed herein can and will vary depending on the attenuated microorganism, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the attenuated microorganism, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

In an exemplary embodiment, attenuated microorganisms may be administered orally. Oral administration of a composition comprising an attenuated microorganism allows for greater ease in disseminating vaccine compositions for infectious agents to a large number of people in need thereof, for example, in Third World countries or during times of biological warfare. In addition, oral administration allows for attachment of the bacterium to, and invasion of, the gut-associated lymphoid tissues (GALT or Peyer's patches) and/or effective colonization of the mesenteric lymph nodes, liver, and spleen. This route of administration thus enhances the induction of mucosal immune responses as well as systemic and cellular immune responses.

In another embodiment, attenuated microorganisms 12341 may be administered by coarse spray. The vaccines are administered by this whole-body spray route in an amount that is effective in eliciting an immune response, i.e. antibody and/or cellular immunity. Whole-body spray administration is surprisingly effective for vaccines comprising a live avirulent derivative of an enteropathogenic bacteria such as attenuated *Salmonella*. The effective doses, which elicit an immune response, are roughly comparable to doses that are effective by the oral route of administration, such as administration in the drinking water.

Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

Methods of Use

A further aspect of the invention encompasses methods of using an attenuated microorganism of the invention. For instance, in one embodiment the invention provides a method for modulating a host's immune system. The method comprises administering to the host an effective amount of a composition comprising an attenuated microorganism of the invention. One of skill in the art will appreciate that an effective amount of a composition is an amount that will generate the desired immune response (e.g., mucosal, humoral or cellular). Methods of monitoring a host's immune response are well-known to physicians, veterinarians, and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against a *Brucella* antigen in a host. The method comprises administering to the host an effective amount of a composition comprising an attenuated microorganism of the invention.

In still another embodiment, an attenuated microorganism of the invention may be used in a method for eliciting an immune response against *Brucella* in a host in need thereof. The method comprises administrating to the host an effective amount of a composition comprising an attenuated microorganism as described herein. In a further embodiment, an attenuated microorganism described herein may be used in a method for ameliorating one or more symptoms of *Brucella* infection in a host in need thereof. The method comprises administering an effective amount of a composition comprising an attenuated microorganism as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, there-

EXAMPLES

Example 1

Bacterial strains. The starting parental PIESV vector strain is the *S.* Typhimurium χ12495 with the ΔP$_{murA25}$::TT araC P$_{araBAD}$ murA ΔasdA27::TT araC P$_{araBAD}$ c2 ΔwaaL46 ΔpagL64::TT rhaRS P$_{rhaBAD}$ waaL Δ(wza-wcaM)-8 ΔrelA197::araC P$_{araBAD}$ lacI TT ΔrecF126 ΔsifA26 genotype or its parent χ12341 that has the pmi-2416 mutation. Derivatives of χ12495 were generated with the ΔaraBAD65::TT (=χ12509) and with ΔaraBAD65::TT and ΔrhaBADSR515 (=χ12527) to preclude metabolism of arabinose and rhamnose (to reduce acid production during growth and improve arabinose and rhamnose regulation of sugar-regulated genes). Another important benefit from inclusion of the ΔaraBAD65::TT and ΔrhaBADSR515 mutations is that the inability to metabolize (breakdown) the arabinose and rhamnose taken up by vaccine cells during growth prior to introducing an immunized animal host is the delayed cessation of peptidoglycan and LPS synthesis and assembly. This results in another few cell divisions prior to onset of lysis and this in turn increases the immunogenicity of the vaccine construct. In addition, other derivatives have been constructed with ΔompA11 to eliminate induction of an irrelevant immune response; with ΔsopB1925 to enhance induction of mucosal antibody immunity; and with SifA+ restored (to enhance CD4 rather than CD8 responses). For ultimate use of vaccine constructs to immunize ruminant species that are much more sensitive to LPS lipid A endotoxin than are chickens and mice, the ΔpagP81::P$_{lpp}$ lpxE deletion-insertion mutation is added to cause synthesis of mono-phosphoryl lipid A that is the adjuvant non-toxic form of lipid A to recruit TLR4 innate immunity in a non-inflammatory manner (27). All strains have both arabinose- and rhamnose-regulated gene expression. Since non-phosphorylated arabinose and rhamnose are unavailable in vivo, all these strains cease to synthesize MurA, Asd and WaaL enzymes in vivo that are diluted by at least half at every in vivo cell division. However, as noted above, the inclusion of the ΔaraBAD65::TT and ΔrhaBADSR515 mutations enables retention of arabinose and rhamnose within vaccine cells to delay the cessation in expression of arabinose- and rhamnose-regulated genes to prolong the vaccine in vivo persistence for a few added cell divisions. Collectively these programmed events lead to ultimate absence of LPS O-antigen to cause complement sensitivity and enhanced ability to be phagocytized while also losing the ability to synthesize the peptidoglycan layer of the cell wall to result in PIESV cell lysis after some 8 to 12 cell divisions in vivo. ΔrelA197::araC P$_{araBAD}$ lacI TT confers regulated delayed synthesis of protective antigens encoded by the lysis plasmids described below due to the arabinose-induced synthesis of the LacI repressor that is gradually diluted by cell division to enable synthesis of antigens encoded on the plasmid vector under Ptrc promoter control (39). ΔrelA (40) and Δ(wza-wcaM)-8 (15) enhance complete lysis of the PIESVs (17) and this lysis in situ releases peptidoglycan constituents to activate Nod1 and Nod2 and DNA to activate TLR9 to significantly enhance immunogenicity. ΔsifA26 allows the RASVs to escape the SCV (41) so that some cells lyse in the cytosol to deliver protective antigens to the proteasome for class I presentation to lead to CD8-dependent immune responses. ΔrecF126 decreases inter- and intra-plasmidic recombination to enhance stability of plasmid vectors (42). ΔsopB1925 decreases immunosuppression and inflammation but increases mucosal immune responses (43). The dependence on two different sugars to enable expression of full virulence constitutes an important additional safety feature. The χ12341 progenitor of χ12495 has been used to successfully immunize chickens in addition to mice and is the improved PIESV vector strain in a vaccine against *Clostridium perfringens* that causes necrotic enteritis in poultry (38). *S.* Typhimurium strains with very similar genotype and phenotype to χ12495 and its derivatives are also being used as vector strains in development of vaccines against *Campylobacter jejuni*, *Escherichia coli* (APEC) and *Eimeria* in poultry.

Plasmid vectors. All plasmids confer the regulated delayed lysis in vivo phenotype (17, 25, 39, 41, 44) and employ the balanced-lethal vector-host concept for stable plasmid maintenance (45) to ensure that live PIESVs are sensitive to all antibiotics and thus unable to disseminate antibiotic resistance when PIESVs are used in non-enclosed environments. The regulated lysis vectors depicted in FIG. 1 all have P$_{trc}$-regulated synthesis of protective antigens for delivery by cell lysis and araC P$_{araBAD}$-regulated murA and asd genes with GTG start codons to decrease translation efficiency. The P22 P$_R$ located with opposite orientation to the transcription of the araC P$_{araBAD}$ GTG-murA GTG-asd genes is repressed by the C2 repressor made during growth of the PIESV vector strains with arabinose (due to the ΔasdA27::TT araC P$_{araBAD}$ c2 mutation). However, C2 concentration decreases due to cell division in vivo to cause P$_R$-directed anti-sense mRNA synthesis to block translation of residual asdA and murA mRNA. Transcription terminators (TT) flank all plasmid domains for controlled lysis, replication and gene expression so that expression in one domain does not affect activities of another domain. Levels of induced cellular immunities are often highest with lower levels of delivered antigen whereas induction of antibody responses are better with delivery of higher amounts of antigen (46, 47). FIG. 1 depicts the regulated delayed lysis vectors to be used for antigen synthesis and delivery in the studies described in this application. Vectors have been produced with low (pSC101 on), moderate (p15A on) and high (pBR on) copy numbers both without and with the much-improved optimized β-lactamase signal sequence (48). Recombinant antigen delivery is achieved during lysis of the RASV or by action of host phagocytic cells breaking down PIESV cells in the case of using non-secretion vectors such as pG8R111 (FIG. 1A).

However, use of the pG8R114 (FIG. 1B) vector with fusion of antigens to the bla SS (T2SS) leads to delivery of antigens to the periplasm that results in increased production of outer membrane vesicles (OMVs) that enhance immunogenicity and antibody production against delivered antigens (23, 49). The pG8R110 vector (p15A on) (FIG. 1C) has an improved T3SS for delivery of synthesized protective antigens to the cytosol to enhance CD8-dependent immunities prior to the lysis of PIESV cells. In addition, as shown many years ago (prior to developing the regulated lysis attribute), use of type 2 secretion for protective antigen delivery also leads to protective antigen released into the supernatant fluid surrounding PIESV cells to also enhance the level of induced immune responses (23, 49, 50).

Accordingly, the underlying strategy of the vaccine system described herein achieves certain desired attributes [after eliminating the means by which *Salmonella* suppresses and subverts induction of immunity or uses subterfuge strategies to divert immune response to non-protective antigens]: 1) regulated delayed attenuation (e.g. regulated shut off of LPS O-antigen, 2) regulated delayed synthesis of protective antigens encoded by codon-optimized sequences; and 3) regulated delayed lysis in vivo. Regulated delayed synthesis of protective antigens is achieved by regulating the synthesis of protective antigens by use of LacI regulatable promoters such as $P_{trc}$, $P_{tac}$, $P_{lac}$, $P_{lpp\ lacO}$, $P_{ompA\ lacO}$, etc. (the lacO sequence that is recognized by LacI, which binds to it is present on $P_{trc}$, etc.) that are present on the plasmids depicted in FIG. 1 and include in the chromosome the ΔrelA197::araC $P_{araBAD}$ lacI TT deletion-insertion mutation. This makes synthesis of LacI dependent on growth in the presence of arabinose, which is absent in vivo. Thus as cell division occurs in vivo, the concentration of LacI decreases by half at each cell division and one begins to get expression of Ptrc (for example) regulated genes.

Certification of current PIESV vector systems delivering protective antigens for use and testing under Level 1 containment. Based off the complete safety of the recombinant PIESV strains administered to newborn, pregnant, malnourished and immunodeficient mice and safety when $10^{10}$ CFU were administered to humans, the NIH and UF IBC have approved use of all new PIESV constructs with the regulated delayed lysis attribute to be evaluated under level I containment and under conditions representative of commercial production for farm animals and in human outpatients in vaccine trials.

Figure 2:
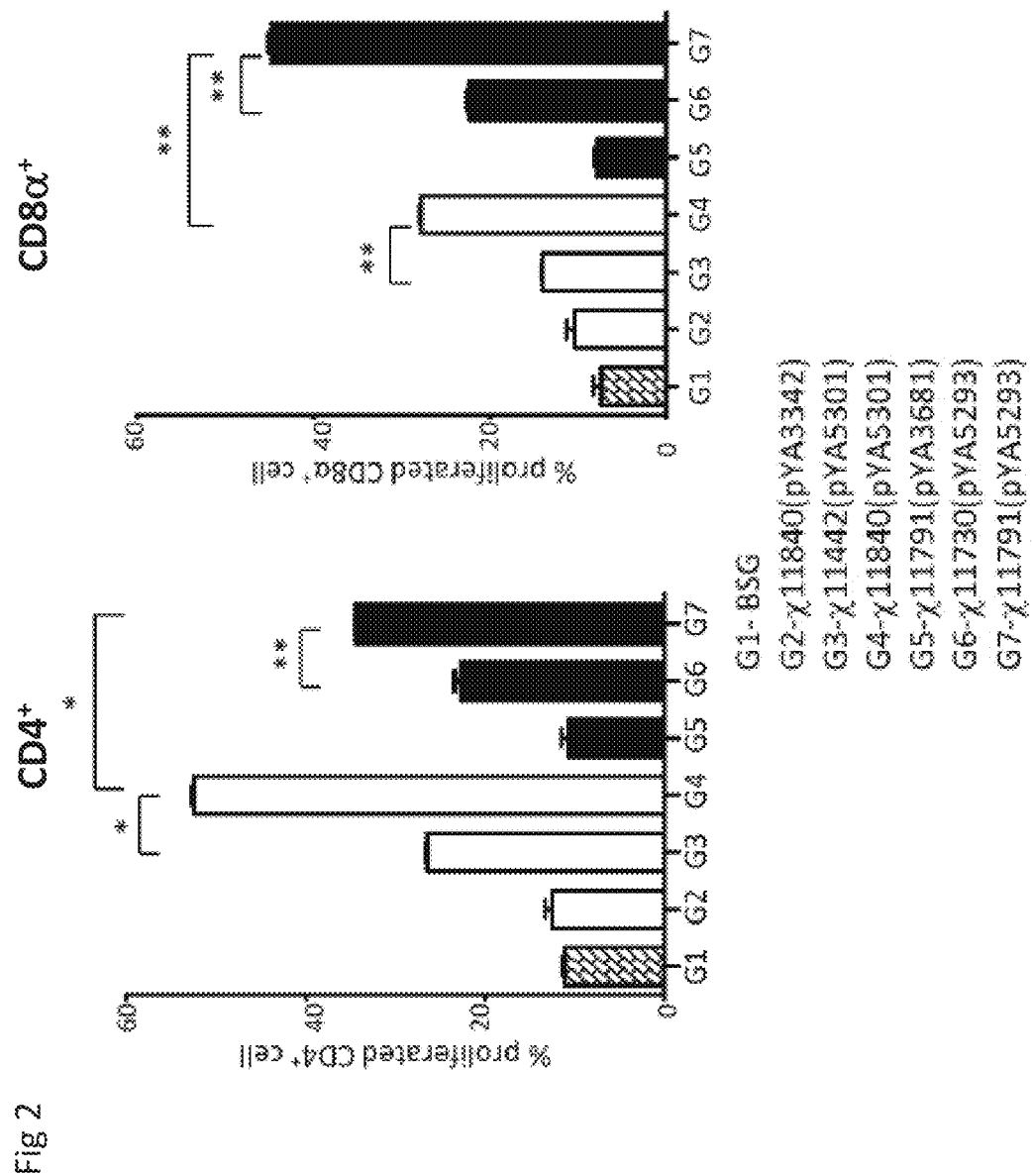
FIG. 2. SO7-specific CD4 and CD8 proliferation analysis in non-lysis versus lysis RASVs without and with escape from SCV due to ΔsifA mutation.

Results validating use of PIESV vector systems to induce protective immunities. A comparative study of PIESV vectors was conducted that did or did not have the regulated delayed lysis in vivo attribute and with and without the ability to escape the SCV due to the ΔsifA26 mutation. In these studies, we delivered the SO7 antigen of *Eimeria tenella* and demonstrated protective immunity to challenge with *E. tenella* sporozoites including normal weight gain and absence of disease symptoms. FIG. 2 depicts the levels of antigen-specific CD4 and CD8 cells induced in immunized SPAFAS white leghorns. Birds immunized with strains having the ΔsifA26 mutation with or without lysis induced the highest levels of CD4 and CD8 cells but the ΔsifA26 strain with regulated delayed lysis gave the highest level of SO7-dependent CD8 cell titers and also had weight gains and feed conversion efficiencies equal to or better than the non-immunized non-challenged controls.

A study has been conducted comparing the delivery of the *C. perfringens* PlcC and GST-NetB operon fusion protective antigens in the regulated lysis strain reported on by Jiang et al. (36) versus the three-sugar dependent regulated lysis stain χ12341 (closely related to the strains to be used in constructing PIESV strains to deliver *B. melitensis* antigens). As demonstrated by the data in FIG. 3, broiler birds vaccinated with the χ12341 construct had the lowest lesion scores and mortality after *C. perfringens* challenge. They also had the best feed conversion efficiency and weight gain. This vaccine with a minor improvement of the original pYA5112 vector is now proceeding through the evaluations to secure an APHIS license for commercial production and distribution.

Example 2

Selection of *B. melitensis* antigens and construction of recombinant plasmid constructs encoding their synthesis and delivery. Table 1 lists the *B. melitensis* antigens initially selected to be delivered by the PIESV vector strains. These were selected based on previous results implicating these proteins as likely protective antigens as well as our own bioinformatic searches for homologs of protein antigens in other pathogens shown to induce potentially protective immune responses. The amino acid sequences of each of these proteins was analyzed bioinformatically to ascertain structural attributes including defining whether the proteins were or were not secreted via presence of signal secretion sequences. We then analyzed the nucleotide sequences and codon optimized these to enable efficient transcription and translation of the *Brucella* antigens absent their *Brucella* signal peptide (if any) in *Salmonella*. We also modified some codons to enhance stability of mRNA synthesized. We then specified placement of specific restriction enzyme cleavage sites at the end of sequences that also specified a C-terminal His-tag sequence prior to having the sequences commercially synthesized. In two cases, we also designed sequences to specify fusions for three *Brucella* antigens. These commercially synthesized codon-optimized sequences were then inserted into the pG8R111, pG8R114 and pG8R110 (FIG. 1) vectors. The C-terminal His tag enables monitoring of synthesis using western blots using an anti-His tag MAb. This C-terminal His tag also enables purification of the antigen for use in immunological studies. The constructed plasmids were introduced into the *E. coli* host χ6212 containing the pSC101 ori pYA232 encoding the lacI$^q$ gene to overproduce the LacI repressor to cause *B. melitensis* antigen synthesis to be dependent on IPTG induction.

TABLE 1

List of antigens from *B. melitensis* that will be used in the PIESV against *B. melitensis*.

| Antigen name | Gene/ Gene ID | Function | Signal peptide/ aa cut site | bp/aa (after deletion of signal sequence) | GC content before/after codon optimization | Percent Identity compared to *Brucella abortus* homologs | Reference |
|---|---|---|---|---|---|---|---|
| Omp22 | omp22/ 29593520 | Porin family protein. | Between aa 24 and 25 | 567/189 | 58.2/52.7 | 99% | (28) |
| Omp25 | omp25/ 29594100 | Membrane protein. | Between aa 23 and 24 | 573/191 | 57.8/52.7 | 99% | (29) |

TABLE 1-continued

List of antigens from *B. melitensis* that will be used in the PIESV against *B. melitensis*.

| Antigen name | Gene/Gene ID | Function | Signal peptide/aa cut site | bp/aa (after deletion of signal sequence) | GC content before/after codon optimization | Percent Identity compared to *Brucella abortus* homologs | Reference |
|---|---|---|---|---|---|---|---|
| Omp31 | omp31/ 29595531 | Outer Membrane Protein | Between aa 19 and 20 | 666/222 | 56.2/48 | 65% | (30, 31) |
| Trigger factor | tf/ 29593902 | Cytosolic chaperone protein. | No/N/A | 1458/486 | 56.2/51.1 | 99% | (31, 32) |
| Bp26 | bp26/ 29593322 | Periplasmic, protein. | Between aa 28 and 29 | 669/223 | 55.6/52.8 | 100% | (32, 33) |
| BtuB | btuB/ 29593454 | TonB-dependent receptor | Between aa 23 and 24 | 1794/598 | 56.3/Not yet optimized | 99% | (28) |
| FlgK | flgK/ 29595162 | Flagellar hook-associated protein FlgK | NO | 1455/485 | 58.1/Not yet optimized | 99% | (28) |
| BLS | KJ401344.1 | lumazine synthase | NO | 477bp/158aa | 57/49 | 100% | (34, 35) |
| L7/L12 | L27819.1 | ribosomal protein | NO | 468bp/124aa | 55.3/49 | 100% | (36) |
| Cu/Zn | AGZ13506.1 | superoxide dismutase | NO | 522/172aa | 53/49 | 100% | (37) |

```
Codon Optimized genes with Restriction digest on sites, and His tags
XmaI = CCC GGG-amino acids = P G XhoI = CTC GAG-amino acids = L E PstI = CTG CAG-amino acids = L Q AvrII = CCT AGG-amino acids = P R HIS Tag = CAC CAC CAC CAC CAC CAC (SEQ ID NO: 16)- amino acids = H H H H H H (SEQ ID NO: 17)

TAA = STOP

>omp22
                                                          (SEQ ID NOS: 5 and 6)
CCC GGG CTC GAG CCG GAC ATG ATG GGT GGT ACC GAC TAC ACC TAC AAC GAC CCG GTT GCG GCG
              A   D   M   M   G   G   T   D   Y   T   Y   N   D   P   V   A   A GGT CCG CAC GAC TGG TCT GGT AAC TAC GTT GGT GCG CAG GTT GGT GGT TCT TCT TCT AAA TTC
 G   P   H   D   W   S   G   N   Y   V   G   A   Q   V   G   G   S   S   S   K   F CCG TCT CCG TTC GCG TCT CGT ACC GGT GCG CTG GGT GGT ATC GTT GTT GGT AAA AAC ATG CAG
 P   S   P   F   A   S   R   T   G   A   L   G   G   I   V   V   G   K   N   M   Q AAC GGT AAC ATC GTT TTC GGT GCG GAA CTG GAA GGT AAC TTC GCG GAA GCG GAA CAC CGT ATC
 N   G   N   I   V   F   G   A   E   L   E   G   N   F   A   E   A   E   H   R   I GGT CAC GGT GGT ACC CTA CAG CAG TCT TGG AAC GGT AAC GCG AAA GGT AAA GTT GGT TAC ACC
 G   H   G   G   T   L   Q   Q   S   W   N   G   N   A   K   G   K   V   G   Y   T TTC GAC AAA ACC CTG GTT TAC GGT ACC GCG GGT TAC GGT GTT ACC CGT TTC AAA GCG AAA GAC
 F   D   K   T   L   V   Y   G   T   A   G   Y   G   V   T   R   F   K   A   K   D AAC ACC ACC TCT GCG TCT GGT TGC GAA GGT GGT GTT CTG ATC GGT GCG GGT GTT GAA CAG GCG
 N   T   T   S   A   S   G   C   E   G   G   V   L   I   G   A   G   V   E   Q   A CTG TCT GGT CCG CTG TCT GTT AAA GCG GAA TAC GAC TTC CAG CGT TTC AAC GAC GTT AAA TCT
 L   S   G   P   L   S   V   K   A   E   Y   D   F   Q   R   F   N   D   V   K   S
```

```
CAG GTT AAC GGT ATC GAA CAG CGT AAC AAC CTG AAA AAC CAC TCT ATC AAA GCG GGT CTG AAC
 Q   V   N   G   I   E   Q   R   N   N   L   K   N   H   S   I   K   A   G   L   N

TAC AAA TTC CCT AGG CAC CAC CAC CAC CAC CAC CCT AGG TAA CTG CAG
    (SEQ ID NO: 5)
 Y   K   F      (SEQ ID NO: 6)                              *

>omp25
                                                    (SEQ ID NOS: 14 and 15)
CCC GGG CTC GAG GCG GAC GCG ATC CAG GAA CAG CCG CCG GTT CCG GCT CCG GTT GAA GTT GCT
                 A   D   A   I   Q   E   Q   P   P   V   P   A   P   V   E   V   A CCG CAG TAC TCT TGG GCT GGT GGG TAC ACC GGT CTG TAC CTG GGT TAC GGT TGG AAC AAA GCG
 P   Q   Y   S   W   A   G   G   Y   T   G   L   Y   L   G   Y   G   W   N   K   A AAA ACC TCT ACC GTT GGT TCT ATC AAA CCG GAC GAC TGG AAA GCT GGT GCT TTC GCT GGT TGG
 K   T   S   T   V   G   S   I   K   P   D   D   W   K   A   G   A   F   A   G   W AAC TTC CAG CAG GAC CAG ATC GTT TAC GGT GTT GAA GGT GAC GCG GGT TAC TCT TGG GCT AAA
 N   F   Q   Q   D   Q   I   V   Y   G   V   E   G   D   A   G   Y   S   W   A   K AAA TCT AAA GAC GGT CTG GAA GTT AAA CAG GGT TTC GAA GGT TCT CTG CGT GCG CGT GTT GGT
 K   S   K   D   G   L   E   V   K   Q   G   F   E   G   S   L   R   A   R   V   G TAC GAC CTG AAC CCG GTT ATG CCG TAC CTG ACC GCT GGT ATC GCG GGT TCT CAG ATC AAA CTG
 Y   D   L   N   P   V   M   P   Y   L   T   A   G   I   A   G   S   Q   I   K   L AAC AAC GGT CTG GAC GAC GAA TCT AAA TTC CGT GTT GGT TGG ACC GCT GGT GCT GGT CTG GAA
 N   N   G   L   D   D   E   S   K   F   R   V   G   W   T   A   G   A   G   L   E GCT AAA CTG ACC GAC AAC ATC CTG GGT CGT GTT GAA TAC CGT TAC ACC CAG TAC GGT AAC AAA
 A   K   L   T   D   N   I   L   G   R   V   E   Y   R   Y   T   Q   Y   G   N   K AAC TAC GAC CTG GCT GGT ACC ACC GTT CGT AAC AAA CTG GAC ACC CAG GAC TTC CGT GTT GGT
 N   Y   D   L   A   G   T   T   V   R   N   K   L   D   T   Q   D   F   R   V   G ATC GGT TAC AAA TTC CCT AGG CAC CAC CAC CAC CAC CAC CCT AGG TAA CTG CAG
                                                                    *

(SEQ ID NO: 14)
 I   G   Y   K   F
(SEQ ID NO: 15)

>tf
                                                    (SEQ ID NOS: 11 and 12)
CCC GGG CTC GAG ATG ACC CGT TCT GAA GGT CTG AAC ATG CAG GTT ACC GAA ACC CTG AAC GAA
                 M   T   R   S   E   G   L   N   M   Q   V   T   E   T   L   N   E GGT CTG AAA CGT GAA ATC AAA GTT GTT GTT CCG GCG GGT GAC CTG GAA GCG AAA CTG GCG GAA
 G   L   K   R   E   I   K   V   V   V   P   A   G   D   L   E   A   K   L   A   E CGT CTG GAA ACC GCG CGT GGT CGT GCG CGT ATC AAC GGT TTC CGT CCG GGT AAA GTT CCG ACC
 R   L   E   T   A   R   G   R   A   R   I   N   G   F   R   P   G   K   V   P   T GCG CAC CTG CGT AAA ATG TAC GGT AAA TCT TTC ATG GCG GAA ATC GTT AAC GAA ATC CTG AAC
 A   H   L   R   K   M   Y   G   K   S   F   M   A   E   I   V   N   E   I   L   N GAC TCT TCT CGT TCT ATC CTG GCG GAA CGT AAC GAA AAA TCT GCG ACC CAG CCG GAA GTT ATC
 D   S   S   R   S   I   L   A   E   R   N   E   K   S   A   T   Q   P   E   V   I ATG TCT GAA GAC GAA AAA GAA GCG GAA AAA GTT CTG GAC GGT AAA GCG GAC TTC GTT TTC TCT
 M   S   E   D   E   K   E   A   E   K   V   L   D   G   K   A   D   F   V   F   S CTG AAC TAC GAA GTT CTG CCG GCG ATC GAA GTT AAA GAC TTC TCT AAA ATC GCG GTT ACC CGT
 L   N   Y   E   V   L   P   A   I   E   V   K   D   F   S   K   I   A   V   T   R GAA GTT GTT GAC ATC TCT GAC GAA GAA GTT GAC GAA CAG GTT AAA CGT ATC GCG TCT TCT ACC
 E   V   V   D   I   S   D   E   E   V   D   E   Q   V   K   R   I   A   S   S   T CGT ACC TTT GAA ACC AAA AAA GGT AAA GCG GAA AAC GAA GAT CGT GTT ACC ATC GAC TAC CTG
 R   T   F   E   T   K   K   G   K   A   E   N   E   D   R   V   T   I   D   Y   L GGT AAA CTG GAC GGT GAA CCG TTC GAA GGT GGT GCG GAC AAC GAC GCG CAG CTG GTT CTG GGT
 G   K   L   D   G   E   P   F   E   G   G   A   D   N   D   A   Q   L   V   L   G TCT GGT CAG TTC ATT CCG GGT TTC GAA GAA CAG CTG ATC GGT CTG AAA GCG GGT GAC GAA AAA
 S   G   Q   F   I   P   G   F   E   E   Q   L   I   G   L   K   A   G   D   E   K
```

```
GTT ATC ACC GTT ACG TTC CCG GCG GAA TAC GGT GCG GCG CAC CTG GCG GGT AAA GAA GCG ACC
 V   I   T   V   T   F   P   A   E   Y   G   A   A   H   L   A   G   K   E   A   T

TTC GAC ATC AAA GTT AAA GAA GTT GCG AAA CCG AAC GAA CTG GTT CTG GAC GAC GAA ACC GCG
 F   D   I   K   V   K   E   V   A   K   P   N   E   L   V   L   D   D   E   T   A

AAA AAA CTG GGT ATC GAA TCT CTG GAA CGT CTG CGT CAG GTT GTT CGT GAA CAG ATC GAA TCT
 K   K   L   G   I   E   S   L   E   R   L   R   Q   V   V   R   E   Q   I   E   S

CAG TAC GGT CAG ATC ACC CGT CAG AAA GTT AAA CGT CAG ATC CTG GAC GCG CTG GAC GGT GAC
 Q   Y   G   Q   I   T   R   Q   K   V   K   R   Q   I   L   D   A   L   D   G   D

TAC CAG TTC GAA ACC CCG CAG AAA CTG GTT GAC GCG GAA TTC AAC AAC ATC TGG CAG CAG ATC
 Y   Q   F   E   T   P   Q   K   L   V   D   A   E   F   N   N   I   W   Q   Q   I

AAC TTC GAC CTC CAG CAG GCG GGT CGT ACC TTC GAA GAC GAA GAA ACC ACC GAA GAA GCG GCG
 N   F   D   L   Q   Q   A   G   R   T   F   E   D   E   E   T   T   E   E   A   A

CGT GAA GAA TAC CGT AAA CTG GCG GAA CGT CGT GTT CGT CTG GGT CTG GTT CTG TCT GAA ATC
 R   E   E   Y   R   K   L   A   E   R   R   V   R   L   G   L   V   L   S   E   I

GGT GAA AAA GCG GGT GTT GAA GTT ACC GAA GAA GAA CTC CAG CGT GCG GTT TAC GAC CAG GTT
 G   E   K   A   G   V   E   V   T   E   E   E   L   Q   R   A   V   Y   D   Q   V

CGT CGT TAT CCG GGT CAG GAA AAA GAA ATC TAC GAC TTC CTG CGT CGT ACC CCG GAC GCG GTT
 R   R   Y   P   G   Q   E   K   E   I   Y   D   F   L   R   R   T   P   D   A   V

GCG AAC CTG CGT GCG CCG ATC TTC GAA GAA AAA GTT GTT GAC CAC CTG CTG GCG AAC ATC AAC
 A   N   L   R   A   P   I   F   E   E   K   V   V   D   H   L   L   A   N   I   N

GTT ACC GAC AAA AAA GTT TCT AAA GAA GAA CTG ACC GCG GAA GAC GAA GAC GCG GCG TCT GAA
 V   T   D   K   K   V   S   K   E   E   L   T   A   E   D   E   D   A   A   S   E

GCG AAA CCG GCG AAA AAA GCG GCG GCG AAA AAA AAA GCG GCG CCG AAA AAA AAA GCG GAA GAA
 A   K   P   A   K   K   A   A   A   K   K   K   A   A   P   K   K   K   A   E   E

GGT AAA TCT GAA GAA GCG CCT AGG CAC CAC CAC CAC CAC CAC CCT AGG TAA CTG CAG (SEQ ID NO: 11)
 G   K   S   E   E   A                                                 *
(SEQ ID NO: 12)

>bp26
                                                         (SEQ ID NOS: 8 and 9)
CCC GGG CTC GAG CAG GAA AAC CAG ATG ACC ACC CAG CCG GCG CGT ATC GCT GTT ACC GGT GAA
                 Q   E   N   Q   M   T   T   Q   P   A   R   I   A   V   T   G   E GGT ATG ATG ACC GCT TCT CCG GAC ATG GCT ATC CTG AAC CTG TCT GTT CTG CGT CAG GCG AAA
 G   M   M   T   A   S   P   D   M   A   I   L   N   L   S   V   L   R   Q   A   K ACC GCG CGT GAA GCG ATG ACC GCG AAC AAC GAA GCT ATG ACC AAA GTT CTG GAC GCG ATG AAA
 T   A   R   E   A   M   T   A   N   N   E   A   M   T   K   V   L   D   A   M   K AAA GCG GGT ATC GAA GAC CGT GAC CTC CAG ACC GGT GGT ATC AAC ATC CAG CCG ATC TAC GTT
 K   A   G   I   E   D   R   D   L   Q   T   G   G   I   N   I   Q   P   I   Y   V TAC CCG GAC GAC AAA AAC AAC CTG AAA GAA CCG ACC ATC ACC GGT TAC TCT GTT TCT ACC TCT
 Y   P   D   D   K   N   N   L   K   E   P   T   I   T   G   Y   S   V   S   T   S CTG ACC GTT CGT GTT CGT GAA CTG GCG AAC GTT GGT AAA ATC CTG GAC GAA TCT GTT ACC CTG
 L   T   V   R   V   R   E   L   A   N   V   G   K   I   L   D   E   S   V   T   L GGT GTT AAC CAG GGT GGT GAC CTG AAC CTG GTT AAC GAC AAC CCG TCT GCT GTT ATC AAC GAA
 G   V   N   Q   G   G   D   L   N   L   V   N   D   N   P   S   A   V   I   N   E GCG CGT AAA CGT GCT GTT GCT AAC GCT ATC GCT AAA GCG AAA ACC CTG GCT GAC GCT GCG GGT
 A   R   K   R   A   V   A   N   A   I   A   K   A   K   T   L   A   D   A   A   G GTT GGT CTG GGT CGT GTT GTT GAA ATC TCT GAA CTG TCT CGT CCG CCG ATG CCG ATG CCG ATC
 V   G   L   G   R   V   V   E   I   S   E   L   S   R   P   P   M   P   M   P   I
```

-continued

```
GCG CGT GGT CAG TTC CGT ACC ATG CTG GCG GCT GCT CCG GAC AAC TCT GTT CCG ATC GCT GCT
 A   R   G   Q   F   R   T   M   L   A   A   A   P   D   N   S   V   P   I   A   A

GGT GAA AAC TCT TAC AAC GTT TCT GTT AAC GTT GTT TTC GAA ATC AAA CCT AGG CAC CAC CAC
 G   E   N   S   Y   N   V   S   V   N   V   V   F   E   I   K   (SEQ ID NO: 9)

CAC CAC CAC CCT AGG TAA CTG CAG (SEQ ID NO: 8)
                          *
```

Plasmids:
Plasmid: pG8R260 Genus/Species: *Brucella melitensis*
Host: *E. coli* χ6212(pYA232) Replicon: pBR ori
Size: 1811 bp Gene cloned: fIgK *Brucella melitensis*
Marker(s): pYA232 with Tc resistance needs DAP because plasmid does not complement host's Δasd mutation.
Tests:
Description: fIgK sequence was optimized according to be expressed in *S. Typhimurium*. His-tag was added at the C-terminal end of each fragment before the stop codon.

Then by using the XhoI site at the N-terminal and the XmaI site at the C-terminal ends, the fragment was introduced into pG8R111.

Host genotype: χ6212=φ80d lacZΔM15 deoR Δ(lacZYA-argF)U169 supE44 λ$^-$ gyrA96 recA1 relA1 endA1 Δasd Δzhf-2::Tn10 hsdR17 (R$^-$ M$^+$)

Host phenotype: χ6212=Rec$^-$(UV$^s$) Asd$^-$ Lac$^-$ Nal$^r$ Tet$^s$
Plasmid Derivation:
FigK (SEQ ID NOS: 18, 19 and 20)

```
ATG T-- TCA CTT AGT TCT GCT CTT CTG ACG GCC AAA AGT TCA CTT GCG GCA ACG TCC AAG CAG ACG TCC GTG GTT
ATG GAA TCT CTG TCT TCT GCG CTG CTG ACC GCG AAA TCT TCT CTG GCG GCG ACC TCT AAA CAG ACC TCT GTT GTT
 M   E   S   L   S   S   A   L   L   T   A   K   S   S   L   A   A   T   S   K   Q   T   S   V   V

TCC CGC AAT ATT TCA GGG GCG AAA GAT GCG GAT TAT TCC CGG CGC ACG GCC TCC CTT GTA TCG GGC CCC TAT GGC
TCT CGT AAC ATC TCT GGT GCG AAA GAC GCG GAC TAC TCT CGT CGT ACC GCG TCT CTG GTT TCT GGT CCG TAC GGT
 S   R   N   I   S   G   A   K   D   A   D   Y   S   R   R   T   A   S   L   V   S   G   P   Y   G

TCC CTT TAT GTG GGG ATC AGC CGG TCG GCG GAT GAA GCG ATG TTC AAT CGC TAT ATC CAG TCG AAC AGC GCC GCT
TCT CTG TAC GTT GGT ATC TCT CGT TCT GCG GAA GAA GCG ATG TTC AAC CGT TAC ATC CAG TCT AAC TCT GCG GCG
 S   L   Y   V   G   I   S   R   S   A   D   E   A   M   F   N   R   Y   I   Q   S   N   S   A   A

TCC GCA TCG TCC ACT CTC GCA GAC GGT CTG GAC CGC CTT TCC GCG CTT TAT TCG GCG GAT AAT TAT TCC GGC TCC
TCT GCG TCT TCT ACC CTG GCG GAC GGT CTG GAC CGT CTG TCT GCG CTG TAC TCT GCG GAC AAC TAC TCT GGT TCT
 S   A   S   S   T   L   A   D   G   L   D   R   L   S   A   L   Y   S   A   D   N   Y   S   G   S

CCT TCC GGC CTT ATC GGC GAT CTG CGC GAC GCA CTC CAG ACC TAT GTC GCT TCG CCT TCC AAC AGC GCG CTT GGC
CCG TCT GGT CTG ATC GGT GAC CTG CGT GAC GCG CTG CAG ACC TAC GTT GCG TCT CCG TCT AAC TCT GCG CTG GGT
 P   S   G   L   I   G   D   L   R   D   A   L   Q   T   Y   V   A   S   P   S   N   S   A   L   G

GAT AGC GTG GTC TCG GTT GCG CAG TCG CTT GCC AAT GCG TTG AAT GAC TGT ACG CGG CAG GTG CAG TCG CTG CGC
GAC TCT GTT GTT TCT GTT GCG CAG TCT CTG GCG AAC GCG CTG AAC GAC TGC ACC CGT CAG GTT CAG TCT CTG CGT
 D   S   V   V   S   V   A   Q   S   L   A   N   A   L   N   D   C   T   R   Q   V   Q   S   L   R

AAC GAT GCC GAC CGG GAA ATT GCG GAT TCC GTC GCC AAT ATC AAC GAT CTT CTG GCA AAA TTC GAG AAG GCC AAT
AAC GAC GCG GAC CGT GAA ATC GCG GAC TCT GTT GCG AAC ATC AAC GAC CTG CTG GCG AAA TTC GAA AAA GTT AAC
 N   D   A   D   R   E   I   A   D   S   V   A   N   I   N   D   L   L   A   K   F   E   K   V   N

CAG AAC GTG GTT GGT GGC ACC CGC ATG GGG CGG GAC GTG TCG GAT TAT CTC GAT CAG CGC GAT GCA TTG CTG AAA
CAG AAC GTT GTT GGT GGT ACC CGT ATG GGT CGT GAC GTT TCT GAC TAC CTG GAC CAG CGT GAC GCG CTG CTG AAA
 Q   N   V   V   G   G   T   R   M   G   R   D   V   S   D   Y   L   D   Q   R   D   A   L   L   K

CAG CTT TCA GGC GAG ATC GGC ATC ACA ACC ATG ATG CGC GGT GAC AAC GAC ATG GTT ATT TTC GCC GAA AAC GGC
CAG CTG TCT GGT GAA ATC GGT ATC ACC ACC ATG ATG CGT GGT GAC AAC GAC ATG GTT ATC TTC GCG GAA AAC GGT
 Q   L   S   G   E   I   G   I   T   T   M   M   R   G   D   N   D   M   V   I   F   A   E   N   G

GTC ACC CTG TTT GAG ACG ACG GCA CGC AAG GTC ACT TTC GAG CAA TCC GCC GTT CTG ACG CCG GGC GTG GCG GGC
GTT ACC CTG TTC GAA ACC ACC GCG CGT AAA GTT ACC TTC GAA CAG TCT GCG GTT CTG ACT CCT GGC GTT GCG GGT
 V   T   L   F   E   T   T   A   R   K   V   T   F   E   Q   S   A   V   L   T   P   G   V   A   G

AAG GCG GTG ACG GTC GAT GGC GTG CCG CTC AGC CAT GAT ACG TTC GAC CAG CCT TTT GGT ACG GGC CGC TTG AGC
AAA GCG GTT ACC GTT GAC GGT GTT CCG CTG TCT CAC GAC ACC TTC GAC CAG CCG TTC GGT ACC GGT CGT CTG TCT
 K   A   V   T   V   D   G   V   P   L   S   H   D   T   F   D   Q   P   F   G   T   G   R   L   S

GGG CTT TTG CAA TTG CGC GAC CAG ATC GCA CCG CAA TAC CAG ATG CAG CTT GAT GAA ATC GCA CGC GGG CTG GTG
GGT CTG CTG CAG CTG CGT GAC CAG ATC GCG CCG CAG TAC CAG ATG CAG CTG GAC GAA ATC GCG CGT GGT CTG GTT
 G   L   L   Q   L   R   D   Q   I   A   P   Q   Y   Q   M   Q   L   D   E   I   A   R   G   L   V

ACG GTG TTT GCC GAA AGC GAC CAG ACG GGT TCT AGC CCG GAC CAG ACC GGG CTT TTC AGC TGG AGC GGC TCG CCC
ACC GTT TTC GCG GAA TCT GAC CAG ACC GGT TCT TCT CCG GAC CAG ACC GGT CTG TTC TCT TGG TCT GGT TCT CCG
 T   V   F   A   E   S   D   Q   T   G   S   S   P   D   Q   T   G   L   F   S   W   S   G   S   P
```

-continued

```
GCC ATA CCG GGT GCA GGC CTT TCT GCC GGT ATC GCC GGA ACG ATC GAG GTG TCC GTG CCG TTC ATT GCT TCT GAA
GCG ATT CCT GGC GCG GGT CTG TCT GCG GGT ATC GCG GGT ACC ATC GAA GTT TCT GTT CCG TTC ATC GCG TCT GAA
 A   I   P   G   A   G   L   S   A   G   I   A   G   T   I   E   V   S   V   P   F   I   A   S   E

GGC GGC AGC GCG CTT CTT CTG CGC GAC GGC GGG GCC AAT GGC GCG AAT TAT AAG TAT AAT GTG CAA GGC GCT GCC
GGT GGT TVT GCG CTG CTG CTG CGT GAC GGT GGT GCG AAC GGT GCG AAC TAC AAA TAC AAC GTT CAG GGT GCG GCG
 G   G   S   A   L   L   L   R   D   G   G   A   N   G   A   N   Y   K   Y   N   V   Q   G   A   A

GGG TTT AGT GAT CGC CTG CGC GCG CTG AAC GAA GCC TTT TCC GAA CCC ATG GTT TTT GAT GCA GCG GCG GGG ATT
GGT TTC TCT GAC CGT CTG CGT GCG CTG AAC GAA GCG TTC TCT GAA CCG ATG GTT TTC GAC GCG GCG GCG GGT ATC
 G F S   D  RLRA IN EA FSE PMVF DA  A  AG I

TCC TCC AGT TCA AGC GGT ATC GGC TAC AGC GCC TCG TCT CTG GGC TGG CTT GAA GGC AAG CGC CAG AAA GCC AAT
TCT TCT TCT TCT TCT CTG ATC GGT TAC TCT GCG TCT TCT CTG GGT TGG CTG GAA GGT AAA CGT CAG AAA GCG AAC
 S   S   S   S   S   L   I   G   Y   S   A   S   S   L   G   W   L   E   G   K   R   Q   K   A   N

AGC GAA TTT ACC TAT AAT GGG ACG GTC GCC AGC CAG GCC GAT TTT GCT CTT TCC AAC GCC ACT GGC GTC GAT ATC
TCT GAA TTC ACC TAC AAC GGT ACC GTT GCG TCT CAG GCG GAC TTC GCG CTG TCT AAC GCC GGT GTT GAC ATC
 S   E   F   T   Y   N   G   T   V   A   S   Q   A   D   F   A   L   S   N   A   T   G   V   D   I

GAC ACT GAA ATG CGC TGC TTC TCG GAC TTG GAA CAT TCC TAT CAG GCA TCA AGC CGG GTG CTG ACG ACG GTT AGC
GAC ACC GAA ATG GCG CTG CTG CTG GAC CTG GAA CAC TCT TAC CAG GCG TCT TCT CGT GTT CTG ACC ACC GTT TCT
 D   T   E   M   A   L   L   L   D   L   E   H   S   Y   Q   A   S   S   R   V   L   T   T   V   S

GCA ATG CTT GAT GAT CTT CTT AAC GCG GTG                                              (SEQ ID NO: 19)
GCG ATG CTG GAC GAC CTG CTG AAC GCG GTT                                              (SEQ ID NO: 20)
 A   M   L   D   D   L   L   N   A   V                                               (SEQ ID NO: 18)
```

Plasmid: pG8R261 Genus/Species: *Brucella melitensis*
Host: *E. coli* χ6212(pYA232) Replicon: pBR ori
Size: 801 bp Gene cloned: omp31 *Brucella melitensis*
Marker(s):): pYA232 with Tc resistance needs DAP because plasmid does not complement host's Δasd mutation
Tests:
Description: omp31 sequence was optimized according to be expressed in *S. Typhimurium*. His-tag was added at the C-terminal end of each fragment before the stop codon.

Then by using the XhoI site at the N-terminal and the XmaI site at the C-terminal ends, the fragment was introduced into pG8R114.

Host genotype: χ6212=φ80d lacZΔM15 deoR Δ(lacZYA-argF)U169 supE44 λ⁻ gyrA96 recA1 relA1 endA1 Δasd Δzhf-2::Tn10 hsdR17 (R⁻ M⁺)

Host phenotype: χ6212=Rec⁻(UV$^s$) Asd⁻ Lac⁻ Nal$^r$ Tet$^s$
omp31 (SEQ ID NOS: 21, 22 and 23)

```
ATGAAATCCG TAATTTTGGC GTCCATCGCC GCTATGTTCG CCACGTCCGC TATGGCT (Signal Peptide is removed)
GCC GAC GTG GTT GTT TCT GAA CCT TCC GCC CCC ACT GCT GCT CCT GTT GAC ACC TTC TCG TGG ACC GGC
GCG GAC GTT GTT GTT TCT GAA CCG TCT GCG CCG ACC GCG GCG CCG GTT GAC ACC TTC TCT TGG ACC GGT
 A   D   V   V   V   S   E   P   S   A   P   T   A   A   P   V   D   T   F   S   W   T   G GGC TAT ATC GGT ATC AAC GCC GGT TAC GCA GGC GGC AAG TTC AAG CAT CCA TTT TCT AGC TTT GAC AAG GAA GAC
GGT TAC ATC GGT ATC AAC GCG GGT TAC GCG GGT GGT AAA TTC AAA CAC CCG TTC TCT TCT TTC GAC AAA GAA GAC
 G   Y   I   G   I   N   A   G   Y   A   G   G   K   F   K   H   P   F   S   S   F   D   K   E   D AAC GAA CAG GTT TCC GGT TCG CTC GAC GTA ACA GCT GGC GGC TTC GTC GGT GGT GTT CAG GCC GGT TAC AAC TGG
AAC GAA CAG GTT TCT GGT TCT CTG GAC GTT ACC GCG GGT GGT TTC GTT GGT GGT GTT CAG GCG GGT TAC AAC TGG
 N   E   Q   V   S   G   S   L   D   V   T   A   G   G   F   V   G   G   V   Q   A   G   Y   N   W CAG CTC GAC AAC GGC GTC GTG CTC GGC GCG GAA ACC GAC TTC CAG GGA TCG AGC GTT ACG GGT TCG ATT TCA GCC
CAG CTG GAC AAC GGT GTT GTT CTG GGT GCG GAA ACC GAC TTC CAG GGT TCT TCT GTT ACC GGT TCT ATC TCT GCG
 Q   L   D   N   G   V   V   L   G   A   E   T   D   F   Q   G   S   S   V   T   G   S   I   S   A GGT GCC AGC GGT CTC GAA GGC AAA GCT GAA ACC AAG GTC GAG TGG TTC GGC ACA GTT CGT GCC CGT CTT GGC TAC
GGT GCG TCT GGT CTG GAA GGT AAA GCG GAA ACC AAA GTT GAA TGG TTC GGT ACC GTT CGT GCG CGT CTG GGT TAC
 G   A   S   G   L   E   G   K   A   E   T   K   V   E   W   F   G   T   V   R   A   R   L   G   Y ACG GCT ACC GAA CGC CTC ATG GTT TAT GGT ACC GGC GGT CTG GCC TAT GGT AAG GTC AAG TCT GCG TTC AAC CTG
ACC GCG ACC GAA CGT CTG ATG GTT TAC GGT ACC GGT GGT CTG GCG TAC GGT AAA GTT AAA TCT GCG TTC AAC CTG
 T   A   T   E   R   L   M   V   Y   G   T   G   G   L   A   Y   G   K   V   K   S   A   F   N   L GGT GAT GAT GCA AGT GCC CTG CAC ACG TGG TCC GAC AAG ACG AAA GCT GGC TGG ACC CTC GGC GCT GGT GCT GAA
GGT GAC GAC GCG TCT GCG CTG CAC ACC TGG TCT GAC AAA ACC AAA GCG GGT TGG ACC CTG GGT GCG GGT GCG GAA
 G   D   D   A   S   A   L   H   T   W   S   D   K   T   K   A   G   W   T   L   G   A   G   A   E TAT GCC ATC AAC AAC AAC TGG ACG CTC AAG TCG GAA TAC CTC TAC ACC GAC CTC GGC AAG CGC AAC CTC GTC GAC
TAC GCG ATC AAC AAC AAC TGG ACC CTG AAA TCT GAA TAC CTG TAC ACC GAC CTG GGT AAA CGT AAC CTG GTT GAC
 Y   A   I   N   N   N   W   T   L   K   S   E   Y   L   Y   T   D   L   G   K   R   N   L   V   D GTT GAC AAT AGC TTC CTT GAG AGC AAG GTC AAT TTC CAC ACT GTT CGC GTC GGT CTG AAC TAC AAG TTC
(SEQ ID NO: 21)
GTT GAC AAC TCT TTC CTG GAA TCT AAA GTT AAC TTC CAC ACC GTT CGT GTT GGT CTG AAC TAC AAA TTC
(SEQ ID NO: 22)
 V   D   N   S   F   L   E   S   K   V   N   F   H   T   V   R   V   G   L   N   Y   K   F
(SEQ ID NO: 23)
```

Plasmid: pG8R258 Genus/Species: *Brucella melitensis*
Host: *E. coli* χ6212(pYA232) Replicon: pBR ori
Size: 1818 bp Gene cloned: btuB *Brucella melitensis*
Marker(s): pYA232 with Tc resistance needs DAP because plasmid does not complement host's Δasd mutation
Description: btuB sequence was optimized according to be expressed in *S. Typhimurium*. His-tag was added at the C-terminal end of the fragment before the stop codon. Then by using the XhoI site at the N-terminal and the XmaI site at the C-terminal ends, the fragment was introduced into pG8R111.

Host genotype: χ6212=ϕ80d lacZΔM15 deoR Δ(lacZYA-argF)U169 supE44 $\lambda^-$ gyrA96 recA1 relA1 endA1 Δasd Δzhf-2::Tn10 hsdR17 ($R^-$ $M^+$)

Host phenotype: χ6212=$Rec^-$($UV^s$) $Asd^-$ $Lac^-$ $Nal^r$ $Tet^s$ btuB (SEQ ID NOS: 24, 25 and 26)

```
ATG GCG CAG GAT GGC GGG GAT AAG GAT GAT GGT GTC ACA CTT GAT ACT ATC GTG GTG ACA CCG CTC CGC CGG GCC
ATG GAA CAA GAT GGT GGT GAT AAA GAT GAT GGT GTT ACA CTG GAC ACT ATC GTA GTA ACT CCT CTG CGT CGT GCA
M   E   Q   D   G   G   D   K   D   D   G   V   T   L   D   T   I   V   V   T   P   L   R   R   A

TCG TCG CTT CAG CGA TCC ACG TCC TCG GTG AGC GTT ATT GAC GCT GCC GAT ATC GAA CGG TCC GCC GCG CCC GAT
TCT TCT CTG CAG CGT TCT ACC TCT TCT GTT TCT GTT ATC GAC GCG GCG GAC ATC GAA CGT TCT GCG GCG CCG GAC
 S   S   L   Q   R   S   T   S   S   V   S   V   I   D   A   A   D   I   E   R   S   A   A   P   D

CTG CAA TCC TTG CTG CAA ACC TAT AGC GGC ATT TCG GTC AAG ACG AAT GGT GGG CAG GGG TCT TCC GCC GAT ATC
CTG CAG TCT CTG CTG CAG ACC TAC TCT GGT ATC TCT GTT AAA ACC AAC GGT GGT CAG GGT TCT TCT GCG GAG ATC
 L   Q   S   L   L   Q   T   Y   S   G   I   S   V   K   T   N   G   G   Q   G   S   S   A   D   I

TAT ATG CGC GGC ATG TCG TCG AAG CAG ACG GTC GTG CTG GTC AAT GGG GTG CGC ACG GCT TCG GCA ACG AGT GGA
TAC ATG CGT GGT ATG TCT TCT AAA CAG ACC GTT GTT CTG GTT AAC GGT GTT CGT ACC GCG TCT GCG ACC TCT GGT
 Y   M   R   G   M   S   S   K   Q   T   V   V   L   V   N   G   V   R   T   A   S   A   T   S   G

TCG ACC GCG CTT GCC AAT ATT CCG CTG ACC TCC ATC GAA CGT ATC GAG ATT GCC AGG GGC GCG CAT TCC TCG CAA
TCT ACC GCG CTG GCG AAC ATC CCG CTG ACC TCT ATC GAA CGT ATC GAA ATC GCG CGT GGT GCG CAC TCT TCT CAG
 S   T   A   L   A   N   I   P   L   T   S   I   E   R   I   E   I   A   R   G   A   H   S   S   Q

TAT GGC GCG GAT GCA ATC GGC GGT GTC ATC AAT ATC ATC ACC AAA CAG GGC GGG GCC TGC GGC GAA CGC GCA TGG
TAC GGT GCG GAC GCG ATC GGT GGT GTT ATC AAC ATC ATC ACC AAA CAG GGT GGT GCG TGC GGT GAA CGT GCG TGG
 Y   G   A   D   A   I   G   G   V   I   N   I   I   T   K   Q   G   G   A   C   G   E   R   A   W

TGC GGC AGC GTT TCA ACA GGC GTG TCG CAT CCA TGG GGC GGT TAT GCA TCG GGT TCG TTA CAA GGC CGC AGC AGC
TGC GGT TCT GTT TCT ACC GGT GTT TCT CAC CCG TGG GGT GGT TAC GCG TCT GGT TCT CTG CAG GGT CGT TCT TCT
 C   G   S   V   S   T   G   V   S   H   P   W   G   G   Y   A   S   G   S   L   Q   G   R   S   S

GAC GGT ATC GAT TAT GCC GTA GGG GCA GCG TTT ACC GGC ACT CAA GGC TAT GAT TTC ACC ACG CCG GAA GCA TTC
GAC GGT ATC GAC TAC GCG GTT GGT GCG GCG TTC ACC GGT ACC CAG GGT TAC GAC TTC ACC ACC CCG GAA GCG TTC
 D   G   I   D   Y   A   V   G   A   A   F   T   G   T   Q   G   Y   D   F   T   T   P   E   A   F

GGC CAC GAG CCG GAC GAT GAT GGT TTC CTG CAG GGC TCG TTC AAT TTT GCG CTG TCG AAA GAT TTC GAC TGG GGC
GGT CAC GAA CCG GAC GAC GAC GGT TTC CTG CAG GGT TCT TTC AAC TTC GCG CTG TCT AAA GAC TTC GAC TGG GGT
 G   H   E   P   D   D   D   G   F   L   Q   G   S   F   N   F   A   L   S   K   D   F   D   W   G

AAA ATC TAT GCG GAC GGC CTC TTC AGC CGT GGG CGC AAC CAG TAT GAT GCG ACC GCA CCC GCA TTC AAC GAA GCG
AAA ATC TAC GCG GAC GGT CTG TTC TCT CGT GGT CGT AAC CAG TAC GAC GCG ACC GCG CCG GCG TTC AAC GAA GCG
 K   I   Y   A   D   G   L   F   S   R   G   R   N   Q   Y   D   A   T   A   P   A   F   N   E   A

GAT AGT ACG GCC TTT ACC GGC AAG GTC GGC ACA CGG ATC GAC CAT ACG GCC GAC TGG TCC TCG ACG GTG GAA TTC
GAC TCT ACC GCG TTC ACC GGT AAA GTT GGT ACC CGT ATC GAC CAC ACC GCG GAC TGG TCT TCT ACC GTT GAA TTC
 D   S   T   A   F   T   G   K   V   G   T   R   I   D   H   T   A   D   W   S   S   T   V   E   F

AGC ACC GGG ATC GAC AAT AGC CGG AAT TTC CGC AAG GGG ATC GAA GGT TCG GAC TGG TTC GAG ACC AGG CGT TAC
TCT ACC GGT ATC GAC AAC TCT CGT AAC TTC CGT AAA GGT ATC GAA GGT TCT GAC TGG TTC GAA ACC CGT CGT TAC
 S   T   G   I   D   N   S   R   N   F   R   K   G   I   E   G   S   D   W   F   E   T   R   R   Y

GGG GTG TTC GCC TCG ACC GAA AAA AGC TTC GAT ACC GGC AAG GTC TCG CAT GTT GTG ACT GGC GGC GTT GAA GCC
GGT GTT TTC GCG TCT ACC GAA AAA TCT TTC GAC ACC GGT AAA GTT TCT CAT GTT GTT ACC GGT GGT GTT GAA GCG
  G   V   F   A   S   T   E   K   S   F  D   T   G   K   V   S   H   V   V   T   G   G   V   E   A

TAT CGG GAA AAA ATC AAT ACG ACC ATC GAT TAT GAC GAG ACA GGC CGC GAT CTT GCC GCC GTG TTC GGG CAA TAT
TAC CGT GAA AAA ATC AAC ACC ACC ATC GAC TAC GAC GAA ACC GGT CGT GAC CTG GCG GCG GTT TTC GGT CAG TAC
 Y   R   E   K   I   N   T   T   I   D   Y   D   E   T   G   R   D   L   A   A   V   F   G   Q   Y

TCG CTG GAA TAT GAT GCA TTG CGT TTC GAT GGC GGC ATT CGC TAC GAC CAT AAT GGC CAG TTC GGC AAT GTG ACC
TCT CTG GAA TAC GAC GCG CTG CGT TTC GAC GGT GGT ATC CGT TAC GAC CAC AAC GGT CAG TTC GGT AAC GTT ACC
 S   L   E   Y   D   A   L   R   F   D   G   G   I   R   Y   D   H   N   G   Q   F   G   N   V   T

ACC TAT AAT CTT GGC GCG AGC TAT GAA ATC CTG CCT GAT CTG GTG CTG CGT TCA TCC TAT GCG ACG GGT TTC CGC
ACC TAC AAC CTG GGT GCG TCT TAC GAA ATC CTG CCG GAC CTG GTT CTG CGT TCT TCT TAC GCG ACC GGT TTC CGT
 T   Y   N   L   G   A   S   Y   E   I   L   P   D   L   V   L   R   S   S   Y   A   T   G   F   R

GCC CCG ACT TTC AAC GAG CTT TAT TAT CCG GGC TTT GCC AAT CCC GAC CTG CAA CCC GAA AAA TCC CGT TCT GTG
GCG CCG ACC TTC AAC GAA CTG TAC TAT CCT GGC TTC GCG AAC CCG GAC CTG CAG CCG GAA AAA TCT CGT TCT GTT
 A   P   T   F   N   E   L   Y   Y   P   G   F   A   N   P   D   L   Q   P   E   K   S   R   S   V
```

```
GAA GTC GGG CTG AAC TGG CAG GCG ACG GCT TCG ACA AGC CTC GAC ATG GCA CTC TAT CAG ACC CGG CTC AGC GAT
GAA GTT GGT CTG AAC TGG CAG GCG ACC GCG TCT ACC TCT CTG GAC ATG GCG CTG TAC CAG ACC CGT CTG TCT GAC
 E   V   G   L   N   W   Q   A   T   A   S   T   S   L   D   M   A   L   Y   Q   T   R   L   S   D

GCA ATC ATG AGC ACT GCG CCG TCC TAT ATT CCG TAT AAT ATT GCA AGC GCG AAG GTG ACC GGC CTT GAA GCG ACA
GCG ATC ATG TCT ACC GCG CCG TCT TAC ATC CCG TAC AAC ATC GCG TCT GCG AAA GTT ACC GGT CTG GAA GCG ACC
 A   I   M   S   T   A   P   S   Y   I   P   Y   N   I   A   S   A   K   V   T   G   L   E   A   T

CTC AGC CAT AGC TTC AAC GAA CAA TGG GGC ATC AAG GGA ATG GTG GAC CTC AAG CGG CCT GTC GAT GAA GAT AGC
CTG TCT CAC TCT TTC AAC GAA CAG TGG GGT ATC AAA GGT ATG GTT GAC CTG AAA CGT CCG GTT GAC GAA GAC TCT
 L   S   H   S   F   N   E   Q   W   G   I   K   G   M   V   D   L   K   R   P   V   D   E   D   S

GGG AAT GAT CTT CCC TAT CGC GAA CGT TTC AAG GCG GCC GCC GAA GTG AAC TTC AAG CCG GTG GAA AAG CTC GAT
GGT AAC GAC CTG CCG TAC CGT GAA CGT TTC AAA GCG GCG GCG GAA GTT AAC TTC AAA CCG GTT GAA AAA CTG GAC
 G   N   D   L   P   Y   R   E   R   F   K   A   A   A   E   V   N   F   K   P   V   E   K   L   D

CTG ACG GCA CGG GTG CTC TAT GGC GGT TCG CGC TAT ACC AAT GCG AAA AAT ACG AAG AAA CTC GGC GAT TAT GTC
CTG ACC GCG CGT GTT CTG TAC GGT GGT TCT CGT TAC ACC AAC GCG AAA AAC ACC AAA AAA CTG GGT GAC TAC GTT
 L T   A R V L Y G G S R Y T N A K N T K K L   G D Y V

ACC GCG GAT TTT GTG GCG CTC TAT TCG ATC GAC AAA CAA TCG CAG TTG AAG TTC TCG GTG GAG AAT ATC TTC GAC
ACC GCG GAC TTC GTT GCG CTG TAC TCT ATC GAC AAA CAG TCT CAG CTG AAA TTC TCT GTT GAA AAC ATC TTC GAC
 T   A   D   F   V   A   L   Y   S   I   D   K   Q   S   Q   L   K   F   S   V   E   N   I   F   D

AAG GAT TAC GAG ACG AGT TCC GGC TAT GTT GCG CCG GGC CGC ACC ATC ACT ATC GGG CTG ACC CGT AAT TTC (SEQ ID
                                                                                              NO: 24)
AAG GAC TAC GAA ACC TCT TCT GGT TAC GTT GCG CCG GGT CGT ACC ATC ACC ATC GGT CTG ACC CGT AAC TTC (SEQ ID
                                                                                              NO: 25)
 K   D   Y   E   T   S   S   G   Y   V   A   P   G   R   T   I   T   I   G   L   T   R   N   F (SEQ ID
                                                                                              NO: 26)
```

Chimeric Antigens:
Plasmid: pG8R231 Genus/Species: *Brucella melitensis*
Host: *E. coli* χ6212(pYA232) Replicon: pBR ori
Size: 1692 bp Gene cloned: tf-bp26-omp31 of *Brucella melitensis* (chimeric TBO)
Marker(s): pYA232 with Tc resistance needs DAP because plasmid does not complement host's Δasd mutation
Description: Antigenic parts of omp31, bp21 and tf sequences were optimized according to be expressed in *S. Typhimurium*. His-tag was added at the C-terminal end of the fusion fragment before the stop codon. Then by using the NcoI site at the N-terminal and the XmaI site at the C-terminal ends, the fusion fragment was introduced into pG8R111.

Host genotype: χ6212=φ80d lacZΔM15 deoR Δ(lacZYA-argF)U169 supE44 λ− gyrA96 recA1 relA1 endA1 Δasd Δzhf-2::Tn10 hsdR17 (R− M+)

Host phenotype: χ6212=Rec−(UV$^s$) Asd− Lac− Nal$^r$ Tet$^s$

Chimeric construct including TF, BP26[93-111] and Omp31[48-74] (SEQ ID NOS: 27, 28, and 29)

```
TF
ATG ACA AGA AGT GAA GGT TTG AAC ATG CAG GTT ACC GAA ACG CTC AAT GAA GGG CTG AAG CGC GAG

ATG ACT CGT TCC GAG GGC CTG AAC ATG CAG GTT ACC GAA ACC CTG AAC GAA GGT CTG AAA CGC GAA

M    T    R    S    E    G    L    N    M    Q    V    T    E T    L    N    E    G    L    K    R    E

ATC AAA GTC GTG GTT CCG GCC GGG GAT CTT GAA GCC AAG CTC GCT GAG CGG CTC GAA ACC GCG CGC GGC CGC GCC

ATT AAG GTT GTG GTT CCG GCA GGC GAT CTG GAA GCA AAA CTG GCT GAA CGC CTG GAG ACT GCG CGT GGT CGC GCA

I    K    V    V    V    P    A    G    D    L    E    A    K    L    A    E    R    L    E    T    A    R    G    R    A

CGC ATC AAC GGC TTC CGT CCG GGC AAG GTG CCG ACG GCTCAC CTG CGC AAG ATG TAC GGC AAG TCC TTC ATG GCC GAG

CGC ATT AAC GGT TTC CGT CCG GGC AAA GTT CCG ACC GCT CAT CTG CGC AAA ATG TAC GGT AAG TCT TTC ATG GCG GAA

R    I    N    G    F    R    P    G    K    V    P    T    A    H    L    R    K    M    Y    G    K    S    F    M    A    E

ATC GTC AAC GAA ATC CTC AAC GAT TCG TCG CGT TCC ATC CTT GCC GAA GCG AAC GAA AAG TCG GCG ACC CAG CCT GAA

ATT GTT AAC GAG ATT CTG AAC GAT TCT AGC CGT TCT ATC CTG GCA GAG CGC AAC GAA AAA TCC GCG ACT CAG CCG GAA

I    V    N    E    I    L    N    D    S    S    R    S    I    L    A    E    R    N    E    K    S    A    T    Q    P    E

GTC ATC ATG TCG GAA GAC GAA AAA GAA GCC GAG AAG GTT CTC GAC GGC AAG GCC GAT TTC GTT TTC TCG CTG AAC TAT

GTG ATC ATG TCT GAA GAC GAG AAA GAG GCG GAG AAA GTT CTG GAT GGT AAA GCA GAC TTT GTT TTC TCT CTG AAC TAC

V    I    M    S    E    D    E    K    E    A    E    K    V    L    D    G    K    A    D    F    V    F    S    L    N    Y
```

```
GAA GTG CTG CCG GCA ATC GAG GTC AAG GAC TTC TCC AAG ATC GCC GTG ACC CGT GAA GTC GTC GAC ATT TCC GAT GAG
GAG GTT CTG CCG GCT ATC GAG GTG AAA GAT TTC TCT AAA ATC GCG GTG ACC CGT GAA GTT GTG GAT ATT TCC GAC GAG
 E   V   L   P   A   I   E   V   K   D   F   S   K   I   A   V   T   R   E   V   V   D   I   S   D   E
GAA GTC GAT GAA CAG GTC AAG CGC ATT GCG TCG TCG ACC CGC ACC TTT GAA ACC AAG AAG GGC AAG GCC GAA AAC
GAG GTG GAT GAA CAG GTT AAA CGT ATC GCG TCT TCT ACC CGC ACC TTC GAG ACC AAG AAA GGT AAG GCT GAA AAC
 E   V   D   E   Q   V   K   R   I   A   S   S   T   R   T   F   E   T   K   K   G   K   A   E   N
GAA GAT CGC GTC ACG ATC GAC TAT CTG GGC AAG CTC GAC GGC GAG CCG TTT GAA GGC GGT GCA GAC AAT GAC GCA
GAG GAT CGC GTT ACC ATT GAC TAC CTG GGT AAA CTG GAC GGC GAG CCG TTT GAG GGT GGT GCA GAC AAC GAT GCA
 E   D   R   V   T   I   D   Y   L   G   K   L   D   G   E   P   F   E   G   G   A   D   N   D   A
CAG CTC GTT CTC GGT TCC GGC CAG TTC ATT CCG GGC TTT GAA GAA CAG CTC ATT GGC TTG AAG GCT GGC GAC GAG
CAG CTG GTT CTG GGC TCC GGT CAG TTC ATT CCG GGC TTT GAA GAG CAG CTG ATC GGC CTG AAG GCT GGC GAC GAA
 Q   L   V   L   G   S   G   Q   F   I   P   G   F   E   E   Q   L   I   G   L   K   A   G   D   E
AAG GTC ATC ACC GTA ACG TTC CCG GCT GAA TAC GGC GCT GCG CAT CTG GCT GGC AAG GAA GCA ACC TTC GAC ATC AAG
AAG GTT ATT ACT GTG ACC TTT CCG GCG GAA TAC GGT GCG GCA CAT CTG GCT GGT AAG GAG GCG ACC TTT GAC ATC AAA
 K   V   I   T   V   T   F   P   A   E   Y   G   A   A   H   L   A   G   K   E   A   T   F   D   I   K
GTG AAG GAA GTT GCC AAG CCG AAC GAA CTC GTT CTC GAT GAC GAA ACC GCA AAG AAG CTC GGC ATT GAG TCG CTT
GTG AAG GAG GTT GCG AAA CCG AAC GAA CTG GTG CTG GAT GAT GAG ACC GCA AAG AAG CTG GGC ATC GAA TCT CTG
 V   K   E   V   A   K   P   N   E   L   V   L   D   D   E   T   A   K   K   L   G   I   E   S   L
GAG CGT CTG CGT CAG GTT GTG CGC GAA CAG ATC GAA AGC CAG TAC GGC CAG ATC ACC CGC CAG AAA GTG AAG CGT
GAA CGT CTG CGT CAG GTT GTT CGT GAA CAG ATC GAG TCT CAG TAC GGT CAG ATT ACC CGT CAG AAG GTT AAG CGC
 E   R   L   R   Q   V   V   R   E   Q   I   E   S   Q   Y   G   Q   I   T   R   Q   K   V   K   R
CAG ATT CTC GAC GCC CTT GAT GGT GAT TAT CAG TTT GAA ACC CCG CAG AAG CTG GTT GAC GCC GAG TTC AAC AAC ATC
CAG ATC CTG GAC GCT CTG GAC GGT GAC TAT CAG TTT GAA ACC CCG CAG AAA CTG GTT GAC GCG GAG TTT AAC AAC ATT
 Q   I   L   D   A   L   D   G   D   Y   Q   F   E   T   P   Q   K   L   V   D   A   E   F   N   N   I
TGG CAG CAG ATC AAC TTC GAC CTG CAG CAG GCT GGC CGC ACC TTT GAA GAC GAG GAA ACG ACG GAA GAA CGT GCT
TGG CAG CAG ATC AAC TTC GAC CTG CAG CAG GCT GGT CGT ACT TTC GAG GAT GAA GAG ACC ACT GAA GAA GCA GCG
 W   Q   Q   I   N   F   D   L   Q   Q   A   G   R   T   F   E   D   E   E   T   T   E   E   A   A
CGC GAA GAA TAT CGC AAG CTT GCA GAA CGC CGC GTT CGT CTT GGC CTC GTT CTC TCC GAA ATC GGC GAG AAG GCA
CGT GAA GAA TAC CGT AAG CTG GCG GAG CGT CGT GTG CGC CTG GGT CTG GTT CTG TCT GAG ATC GGT GAG AAA GCG
 R   E   E   Y   R   K   L   A   E   R   R   V   R   L   G   L   V   L   S   E   I   G   E   K   A
GGC GTG GAA GTG ACC GAA GAA GAA CTG CAG CGC GCT GTT TAC GAT CAG GTT CGC CGC TAT CCG GGT CAG GAA AAG
GGC GTT GAG GTG ACT GAG GAA GAA CTG CAG CGT GCG GTG TAT GAC CAG GTG CGC CGT TAT CCG GGC CAG GAG AAG
 G   V   E   V   T   E   E   E   L   Q   R   A   V   Y   D   Q   V   R   R   Y   P   G   Q   E   K
```

Omp31[48-]

```
GAA ATC TAC GAC TTC CTG CGC CGT ACG CCG GAT GCC GTC GCC AAT CTG CGC GCG CCG ATC TTT GAA GAA AAG GTC GTC
GAA ATT TAC GAC TTC CTG CGT CGC ACT CCG GAC GCG GTG GCG AAC CTG CGT GCA CCG ATT TTT GAG GAA AAA GTT GTT
 E   I   Y   D   F   L   R   R   T   P   D   A   V   A   N   L   R   A   P   I   F   E   E   K   V   V
GAT CAT CTG CTG GCC AAC ATC AAT GTG ACC GAC AAG AAG GTC TCG AAG GAA GAG CTG ACG GCT GAA GAC GAA GAT
GAC CAC CTG CTG GCT AAC ATC AAC GTT ACT GAC AAA AAG GTG TCT AAA GAG GAG CTG ACT GCA GAA GAT GAG GAC
 D   H   L   L   A   N   I   N   V   T   D   K   K   V   S   K   E   E   L   T   A   E   D   E   D
```

```
GCA GCT TCG GAA GCA AAG CCT GCC AAG AAG GCG GCT GCG AAG AAG AAG GCT GCG CCG AAG AAG AAG GCC GAA GAA
GCT GCG AGC GAG GCA AAA CCG GCT AAA AAA GCT GCT GCG AAG AAG AAG GCA GCA CCG AAA AAG AAA GCT GAA GAG
 A   A   S   E   A   K   P   A   K   K   A   A   A   K   K   K   A   P   K   K   K   A   E   E

GGC AAG TCC GAA GAG GCT ------------Linker----- -----Linker------ -----Linker-------------- CGC GAT
GGC AAG AGC GAA GAG GCA GAA GCG GCT GCT AAG GAA GCT GCG GCT AAG AAA AAG GCA GGC ATT GAA GAC CGT GAC
 G   K   S   E   E   A   E   A   A   A   K   E   A   A   A   K   K   K   A   G   I   E   D   R   D CTC CAG ACA GGC GGC ATC AAT ATC CAG CCG ATT TAT GTC TAT CCT GAC ----------Linker----AAC GCC GGT TAC
BP26^93-111
CTG CAG ACT GGT GGC ATC AAC ATT CAG CCG ATC TAC GTG TAC CCG GAT GAG GCG GCA GCG AAA AAC GCT GGT TAC L   Q   T   G   G   I   N   I   Q   P   I   Y   V   Y   P   D   E   A   A   A   K   N   A   G   Y GCA GGC GGC AAG TTC AAG CAT CCA TTT TCT AGC TTT GAC AAG GAA GAC AAC GAA CAG GTT TCC GGT TCG AAG CTC
(SEQ ID NO: 27)

GCG GGT GGC AAG TTT AAG CAC CCG TTC TCT TCT TTC GAC AAG GAA GAT AAC GAG CAG GTT TCT GGT AGC AAG CTT
(SEQ ID NO: 28)

A   G   G   K   F   K   H   P   F   S   S   F   D   K   E   D   N   E   Q   V   S   G   S   K   L (SEQ ID NO: 29)
```

Plasmid: pG8R259 Genus/Species: *Brucella melitensis*
Host: *E. coli* χ6212(pYA232) Replicon: pBR ori
Size: 1351 bp Gene cloned: BLS-I7/I12-Cu/Zn *Brucella melitensis*
Marker(s): pYA232 with Tc resistance needs DAP because plasmid does not complement host's Δasd mutation
Tests:
Description: Antigenic parts of BLS, L7/L12 and Cu/Zn sequences were optimized according to be expressed in *S. Typhimurium*. His-tag was added at the C terminal of each fragment before stop codon. Then by using the NcoI site at the N-terminal and XmaI site at the C-terminal ends, the fragment was introduced into pG8R111.
Parent: Depositor: Ghasemi, A. Date: Dec. 16, 2018
Host genotype: χ6212=ϕ80d lacZΔM15 deoR Δ(lacZYA-argF)U169 supE44 λ$^-$ gyrA96 recA1 relA1 endA1 Δasd Δzhf-2::Tn10 hsdR17 (R$^-$ M$^+$)
Host phenotype: χ6212=Rec$^-$(UV$^s$) Asd$^-$ Lac$^-$ Nal$^r$ Tet$^s$
Chimeric Including BLS, Ribosomal Protein L7/L12 and Cu/Zn Superoxide Dismutase (SEQ ID NOS: 30, 31 and 32)

```
BLS
ATG AAC CAA AGC TGT CCG AAC AAG ACA TCC TTT AAA ATC GCA TTC ATT CAG GCC CGC TGG CAC GCC GAC ATC GTT
ATG AAT CAA TCA TGT CCT AAT AAA ACA TCA TTT AAA ATA GCA TTT ATT CAA GCA CGT TGG CAT GCA GAT ATA GTT
 M   N   Q   S   C   P   N   K   T   S   F   K   I   A   F   I   Q   A   R   W   H   A   D   I   V

GAC GAA GCG CGC AAA AGC TTT GTC GCC GAA CTG GCC GCA AAG ACG GGT GGC AGC GTC GAG GTA GAG ATA TTC GAC
GAC GAA GCG CGT AAA TCT TTC GTT GCG GAA CTG GCG GCG AAA ACC GGT GGT TCT GTT GAA GTT GAA ATC TTC GAC
 D   E   A   R   K   S   F   V   A   E   L   A   A   K   T   G   G   S   V   E   V   E   I   F   D

GTG CCG GGT GCA TAT GAA ATT CCC CTT CAC GCC AAG ACA TTG GCC AGA ACC GGG CGC TAT GCA GCC ATC GTC GGT
GTT CCG GGT GCG TAC GAA ATC CCG CTG CAC GCG AAA ACC CTG GCG CGT ACC GGT CGT TAC GCG GCG ATC GTT GGT
 V   P   G   A   Y   E   I   P   L   H   A   K   T   L   A   R   T   G   R   Y   A   A   I   V   G

GCG GCC TTC GTG ATC GAC GGC GGC ATC TAT CGT CAT GAT TTC GTG GCG ACG GCC GTT ATC AAC GGC ATG ATG CAG
GCG GCG TTC GTT ATC GAC GGT GGT ATC TAC CGT CAC GAC TTC GTT GCG ACC GCG GTT ATC AAC GGT ATG ATG CAG
 A   A   F   V   I   D   G   G   I   Y   R   H   D   F   V   A   T   A   V   I   N   G   M   M   Q

GTG CAG CTT GAA ACG GAA GTG CCG GTG CTG AGC GTC GTG CTG ACG CCG CAC CAT TTC CAT GAA AGC AAG GAG CAT
GTT CAG CTG GAA ACC GAA GTT CCG GTT CTG TCT GTT GTT CTG ACC CCG CAC CAC TTC CAC GAA TCT AAA GAA CAC
 V   Q   L   E   T   E   V   P   V   L   S   V   V   L   T   P   H   H   F   H   E   S   K   E   H

CAC GAC TTC TTC CAT GCT CAT TTC AAG GTG AAG GGC GTG GAA GCG GCC CAT GCC GCC TTG CAG ATC GTG AGC GAG
CAC GAC TTC TTC CAC GCG CAC TTC AAA GTT AAA GGT GTT GAA GCG GCA CAC GCA GCA CTC CAG ATC GTT TCT GAA
 H   D F F H A H F K V   K G V E   A A   F I A A L Q   I VS   E

CGC AGC CGC ATC GCC GCG CTT GTC -----Linker------- GCT GAT CTC GCA AAG ATC GTT GAA GAC CTT TCG GCC
CGT TCT CGT ATC GCG GCA CTG GTT                      GAA GCG GCA GCA AAA GCG GAC CTG GCG AAA ATC GTT GAA GAC CTG TCT GCG
 R   S   R   I   A   A   L   V                          E   A   A   A   K   A   D   L   A   K   I   V   E   D   L   S   A L7L12
CTG ACC GTT CTG GAA GCC GCT GAG CTG TCC AAG CTT CTC GAA GAG AAG TGG GGC GTT TCG GCT GCT GCT CCG GTC
CTG ACC GTT CTG GAA GCG GCG GAA CTG TCT AAA CTG CTG GAA GAA AAA TGG GGT GTT TCT GCG GCA GCG CCG GTT
 L   T   V   L   E   A   A   E   L   S   K   L   L   E   E   K   W   G   V   S   A   A   A   P   V
```

-continued

```
GCT GTT GCT GCT GCC GGT GGC GCT GCC CCT GCT GCT GCC GCA GAA GAA AAG ACC GAA TTC GAC GTC GTT CTC GCT
GCG GTT GCG GCA GCA GGT GGT GCA GCA CCG GCA GCA GCA GCA GAA GAA AAA ACC GAA TTT GAC GTT GTT CTG GCG
 A   V   A   A   A   G   G   A   A   P   A   A   A   A   E   E   K   T   E   F   D   V   V   L   A

GAC GGC GGC GCT AAC AAG ATC AAC GTG ATC AAG GAA GTG CGC GCA CTC ACC GGT CTC GGC CTC AAG GAA GCC AAG
GAC GGT GGT GCA AAC AAA ATC AAC GTT ATC AAA GAA GTT CGT GCA CTG ACC GGT CTG GGT CTG AAA GAA GCA AAA
 D   G   G   A   N   K   I   N   V   I   K   E   V   R   A   L   T   G   L   G   L   K   E   A   K

GAC CTG GTC GAA GGC GCT CCG AAG GCT GTC AAG GAA GGC GCC TCG AAG GAC GAA GCT GAG AAG ATC AAG GCA CAG
GAC CTG GTT GAA GGT GCG CCG AAA GCG GTT AAA GAA GGT GCG TCT AAA GAC GAA GCG GAA AAA ATC AAA GCG CAG
 D   L   V   E   G   A   P   K   A   V   K   E   G   A   S   K   D   E   A   E   K   I   K   A   Q

CTC GAA GCT GCT GGC GCC AAG GTT GAA CTC AAG --------Linker--------- AGC ACG ACG GTA AAA ATG TAT GAG
CTG GAA GCG GCG GGT GCG AAA GTT GAA CTG AAA GCG GCG AAA GAA TCT ACC ACC GTT AAA ATG TAC GAA
 L   E   A   A   G   A   K   V   E   L   K   E   A   A   A   K   E   S   T   T   V   K   M   Y   E GCG CTG CCG ACC GGA CCG GGT AAA GAA GTT GGC ACC GTG GTC ATT TCC GAA GCC CCG GGC GGG CTG CAC TTC AAG
GCG CTG CCG ACC GGT CCG GGT AAA GAA GTT GGT ACC GTT GTT ATC TCT GAA GCG CCG GGT GGT CTG CAC TTC AAA
Cu/Zn
 A   L   P   T   G   P   G   K   E   V   G   T   V   V   I   S   E   A   P   G   G   L   H   F   K GTG AAT ATG GAG AAG CTG ACG CCG GGC TAT CAT GGC TTT CAT GTT CAC GAA AAT CCA AGC TGC GCT CCG GGA GAA
GTT AAC ATG GAA AAA CTG ACT CCT GGT TAC CAC GGT TTC CAC GTT CAC GAA AAC CCG TCT TGC GCG CCG GGT GAA
 V   N   M   E   K   L   T   P   G   Y   H   G   F   H   V   H   E   N   P   S   C   A   P   G   E AAA GAC GGC AAG ATC GTA CCG GCT CTT GCT GCC GGC GGG CAT TAT GAT CCG GGT AAT ACC CAT CAC CAT TTA GGG
AAA GAC GGC AAG ATT GTT CCG GCG CTG GCG GCG GGT GGT CAC TAC GAT CCG GGT AAC ACC CAC CAC CAC CTG GGT
 K   D   G   K   I   V   P   A   L   A   A   G   H   Y   D   P   G   N   T   H   H   H   L   G CCT GAA GGT GAT GGA CAT ATG GGC GAT TTG CCA CGC CTG AGC GCC AAT GCT GAC GGC AAG GTG AGT GAA ACC GTT
CCG GAA GGT GAC GGT CAC ATG GGT GAC CTG CCG CGT CTG TCT GCG AAC GCG GAC GGT AAA GTT TCT GAA ACC GTT
 P   E   G   D   G   H   M   G   D   L   P   R   L   S   A   N   A   D   G   K   V   S   E   T   V GTC GCT CCA CAT CTC AAG AAA TTG GCG GAA ATC AAG CAG CGT TCT TTG ATG GTC CAT GTC GGA GGG GAT AAT TAT
GTT GCG CCG CAC CTG AAA AAA CTG GCG GAA ATC AAA CAG CGT TCT CTG ATG GTT CAC GTT GGT GGT GAC AAC TAC
 V   A   P   H   L   K   K   L   A   E   I   K   Q   R   S   L   M   V   H   V   G   G   D   N   Y TCC GAT AAG CCT GAG CCG CTT GGT GGC GGT GGT GCC CGT TTT GCC TGC GGC GTG ATC GAA       (SEQ ID NO: 30)
TCT GAC AAA CCG GAA CCG CTG GGT GGT GGT GGT GCG CGT TTC GCG TGC GGT GTT ATC GAA       (SEQ ID NO: 31)
 S   D   K   P   E   P   L   G   G   G   G   A   R   F   A   C   G   V   I   E       (SEQ ID NO: 32)
```

Example 3

Construction and Characterization of PIESV Constructs Encoding Synthesis and Delivery of the *B. melitensis* Omp22, Omp25, Tf and Bp26 Protein Antigens.

Since the objective is to construct PIESV strains that synthesize and deliver protective antigens to maximize induction or protective immune responses, it follows that the construct must grow well, invade and colonize effector lymphoid tissues efficiently and stably maintain the plasmid vector with stability in the ability to specify synthesis of the protective antigen. The amount of antigen synthesized by the construct is also important with higher levels of antigen synthesis favoring mucosal and systemic antibody production and lower levels enhancing induction of cellular immunities. To achieve our objectives the codon-optimized sequences were cloned into the three regulated lysis plasmid vectors (FIG. 1) and introduced into *E. coli* χ6212(pYA232) for initial screening for antigen synthesis and stability prior to transferring to *S. Typhimurium* χ12509. Table 2 lists the 12 plasmids specifying synthesis of Omp22, Omp25, Tf and Bp26.

Figure 4:
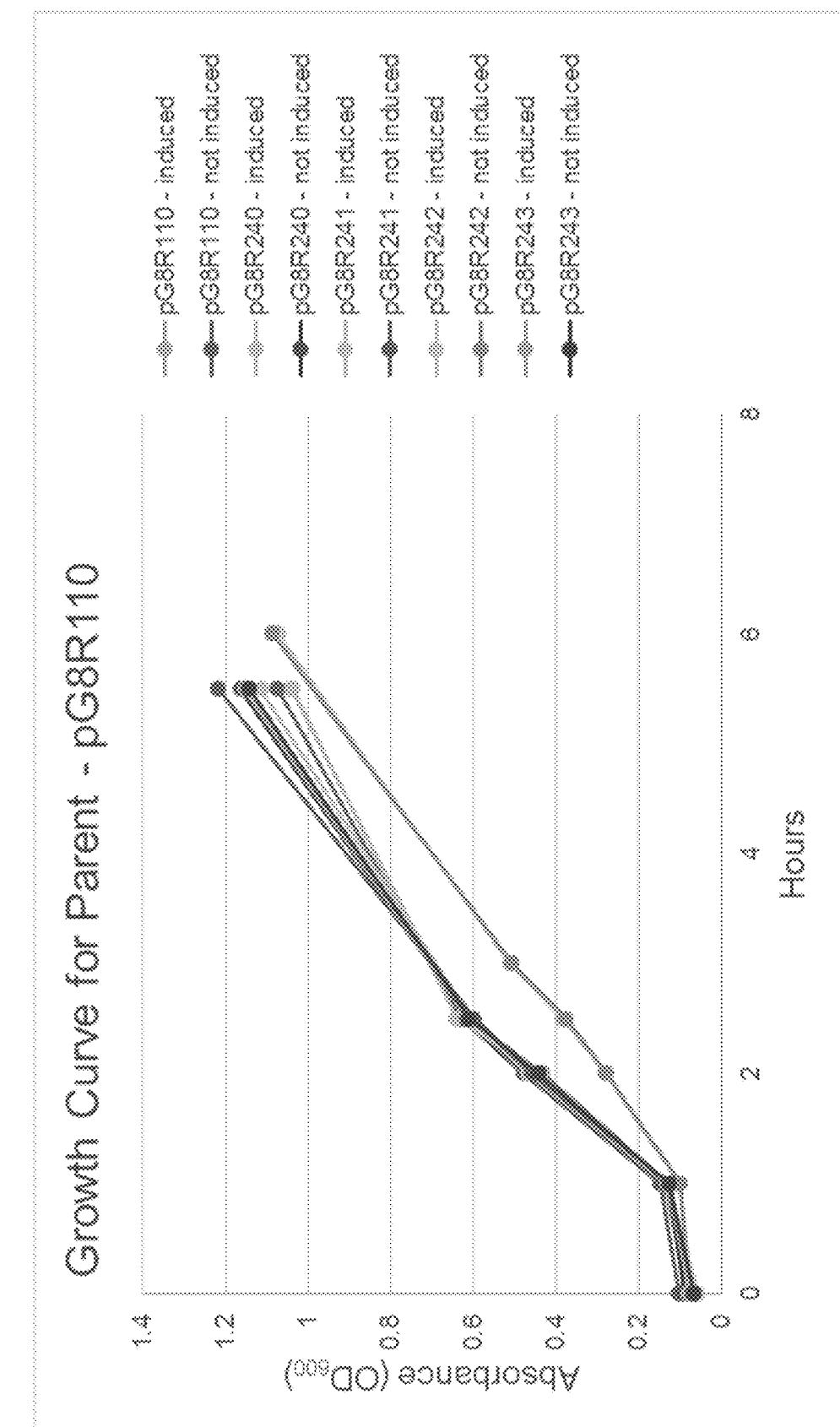
FIG. 4 shows χ6212(pYA232) growth curves.
Figure 4:
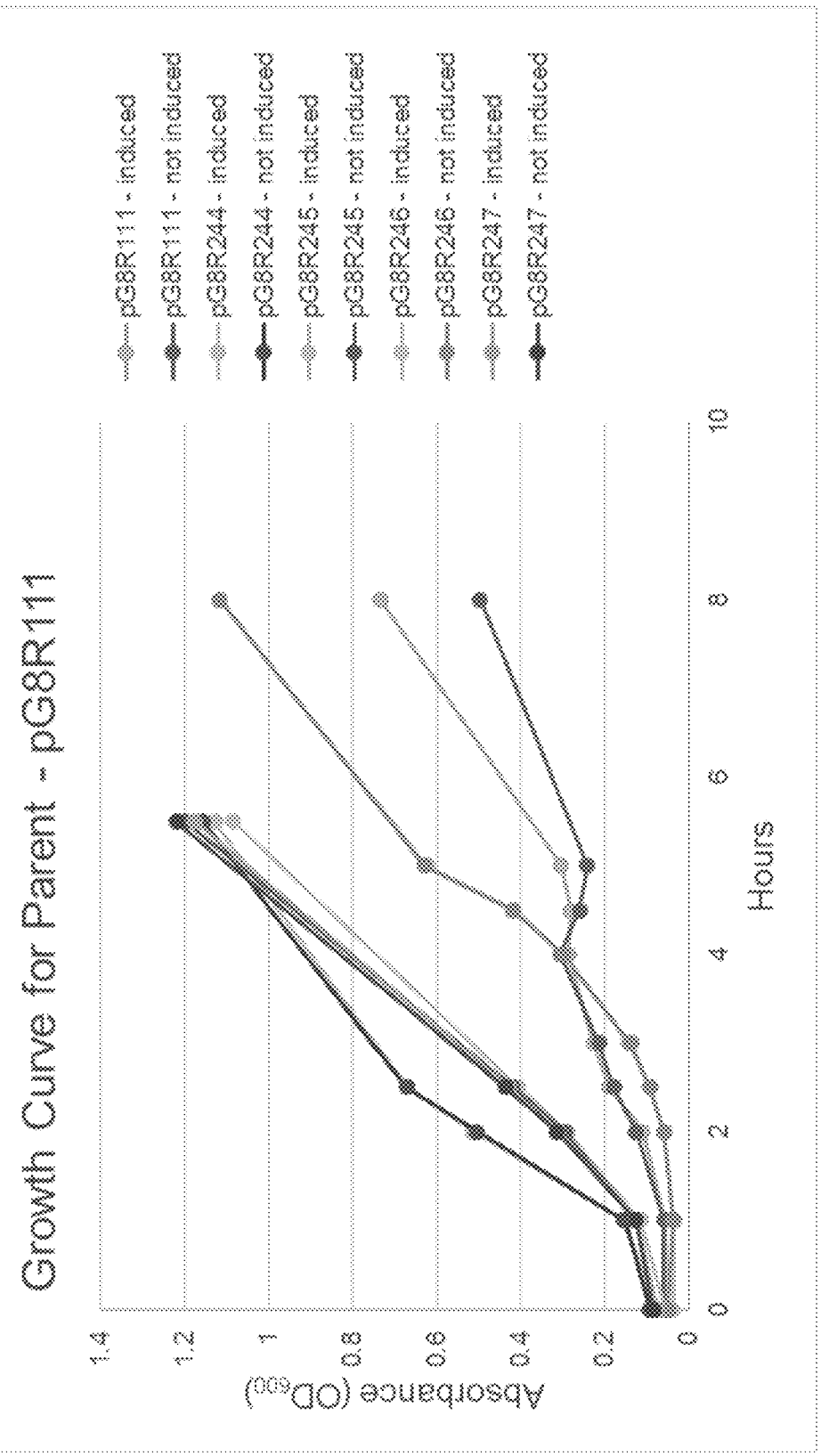
Figure 4:
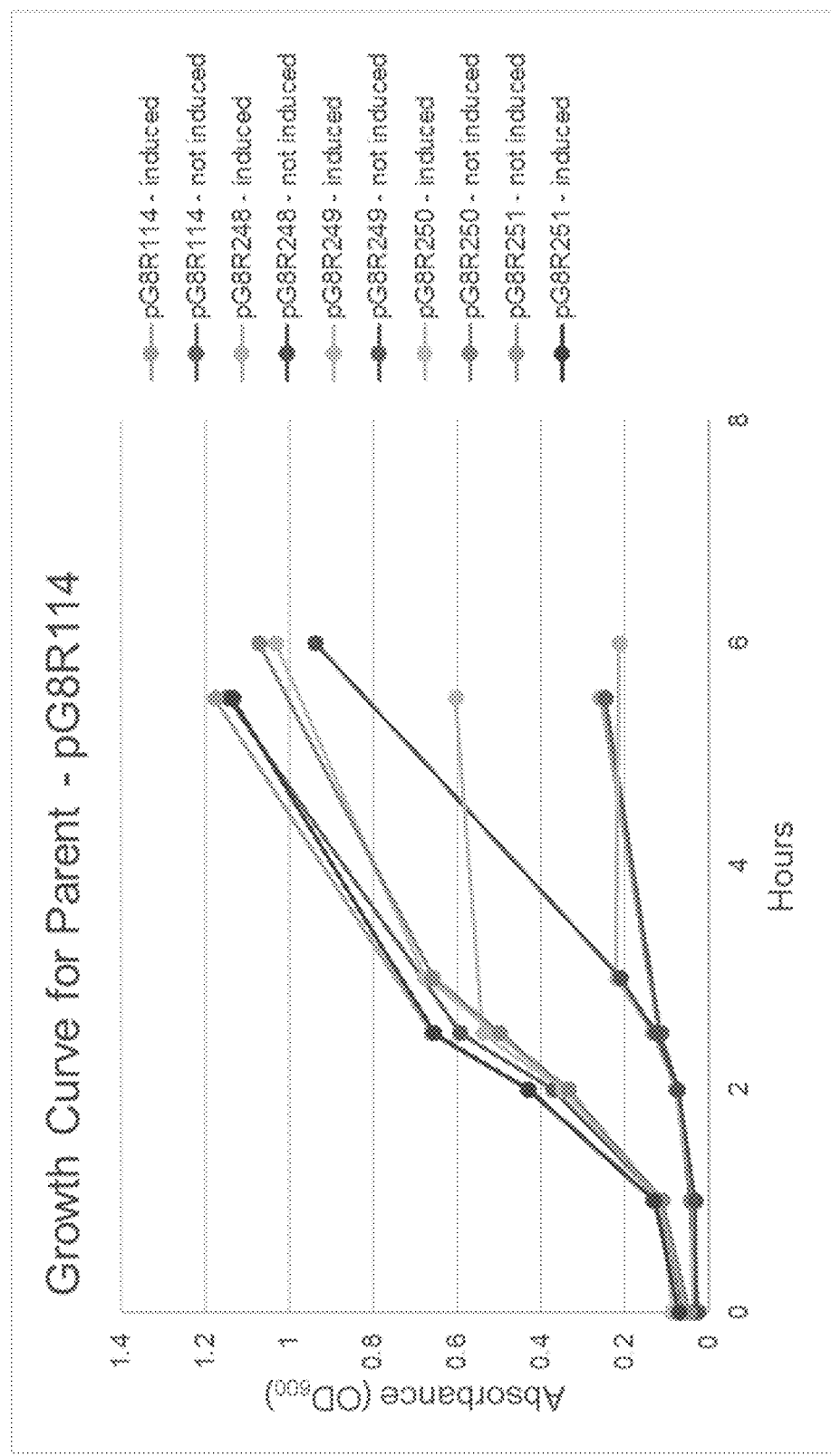
Figure 5:
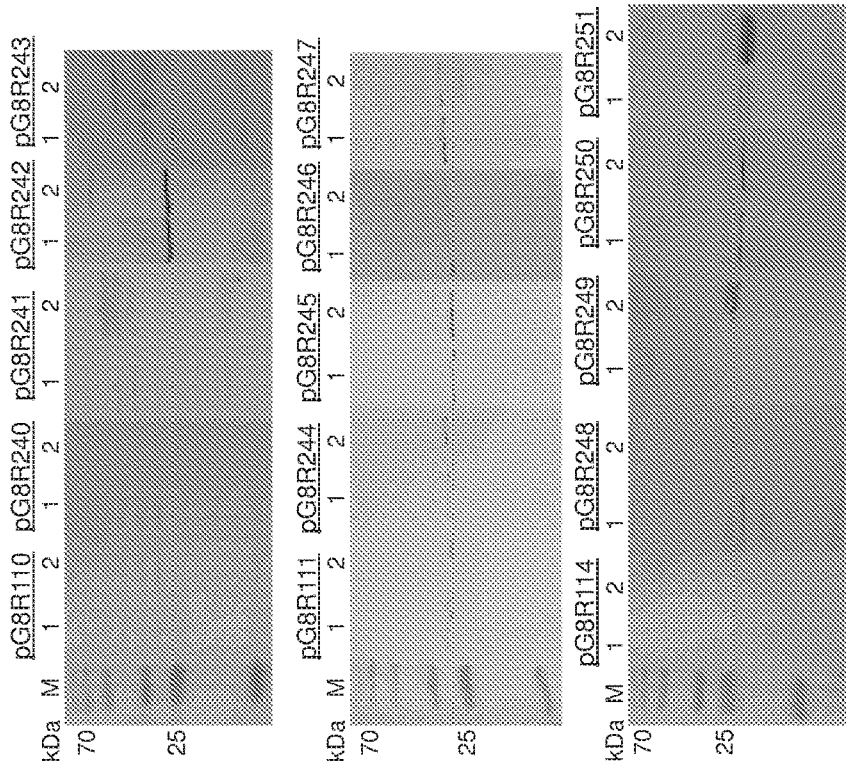
FIG. 5 shows western Blot Results for χ6212(pYA232).
Figure 6:
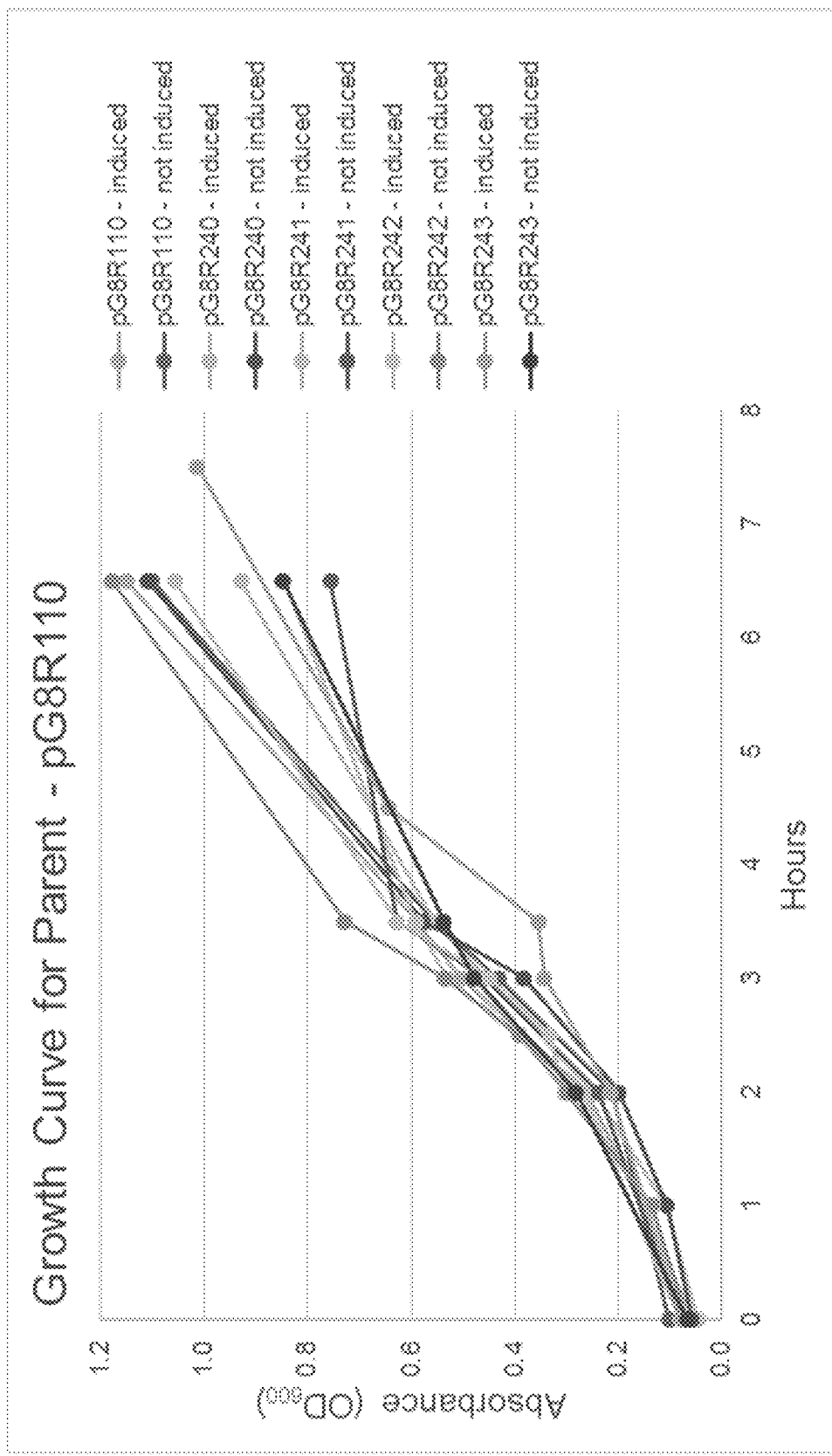
FIG. 6. shows χ12509 growth curves.
Figure 6:
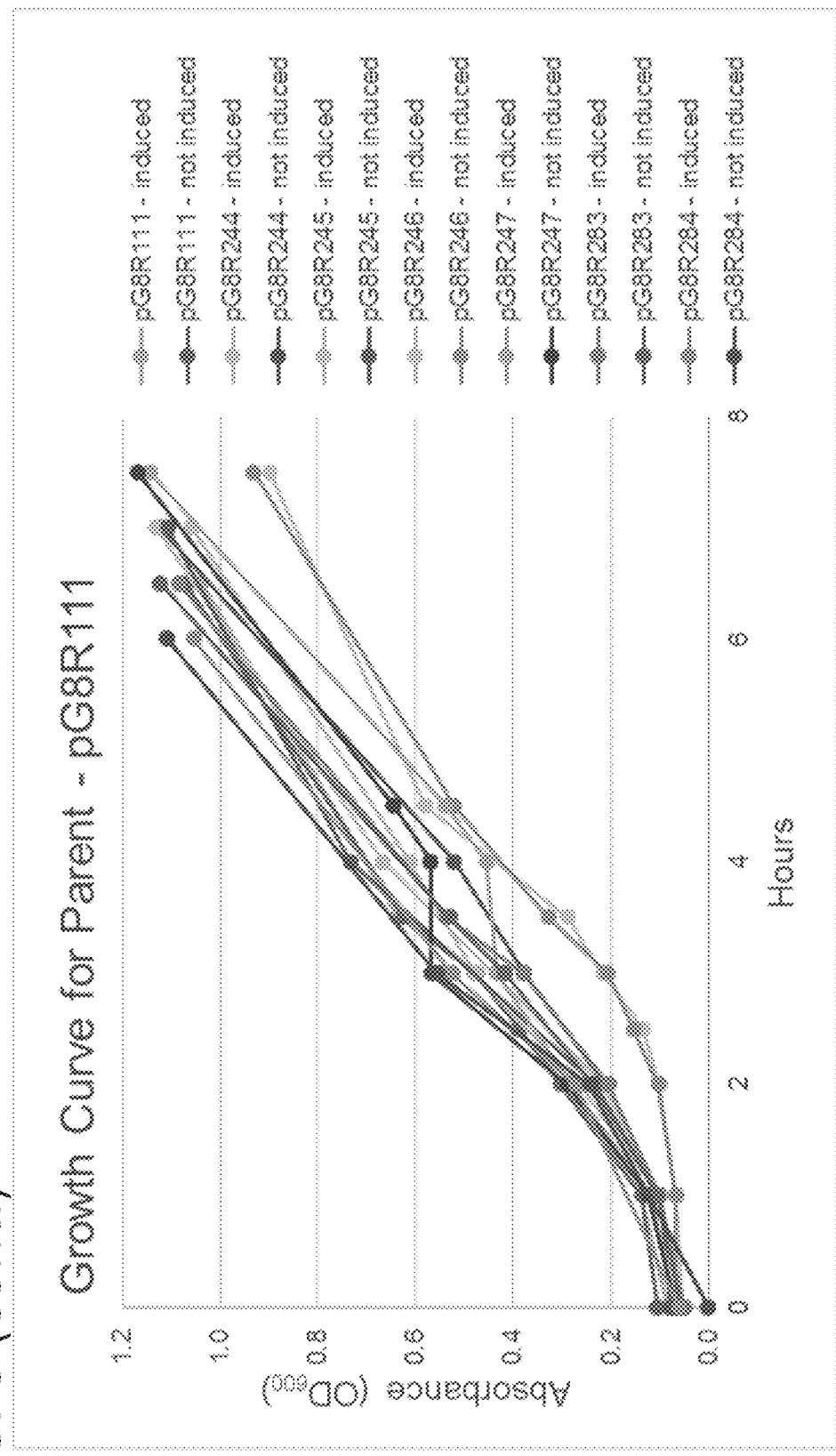
Figure 6:
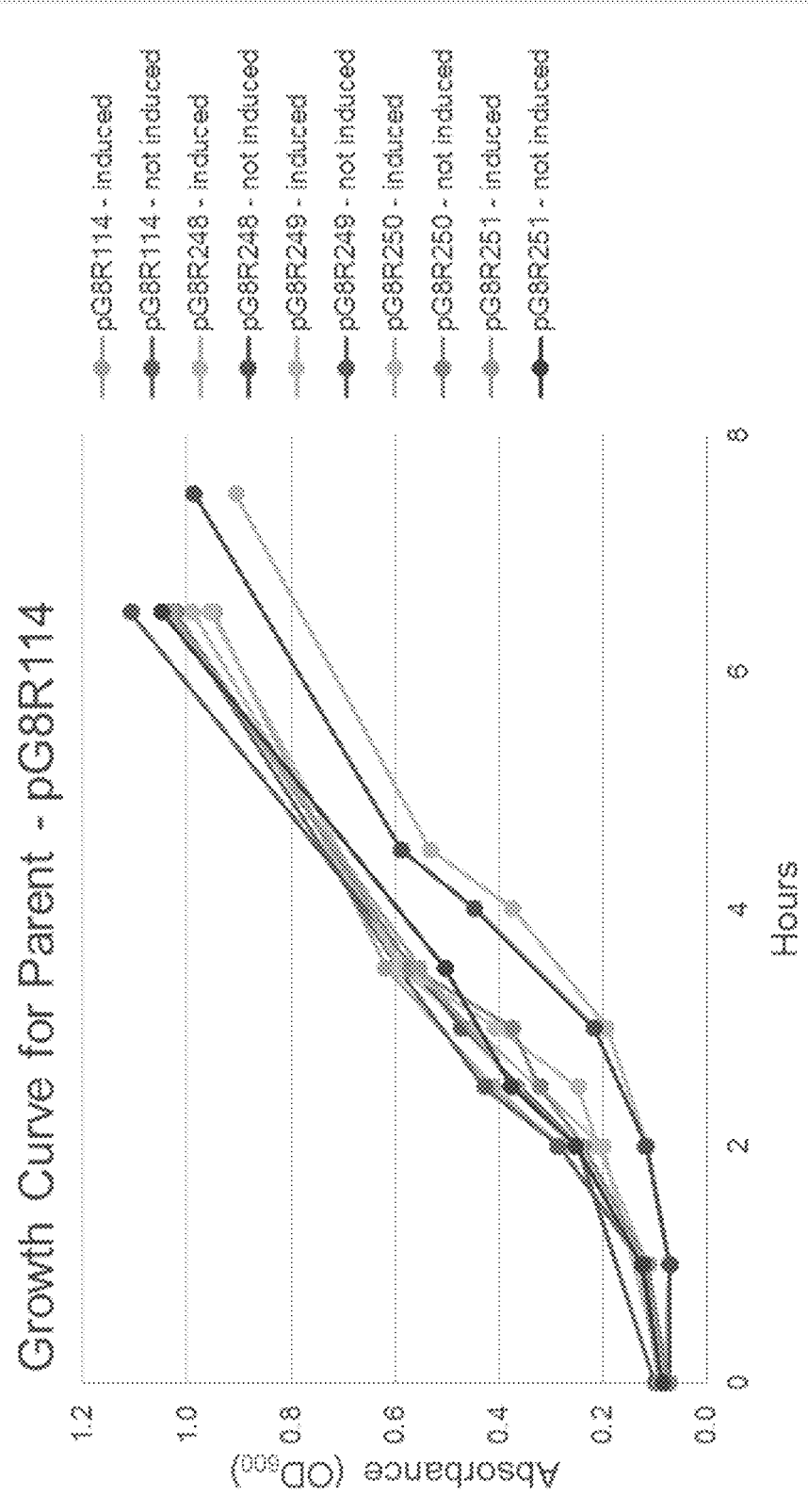
Figure 8A:
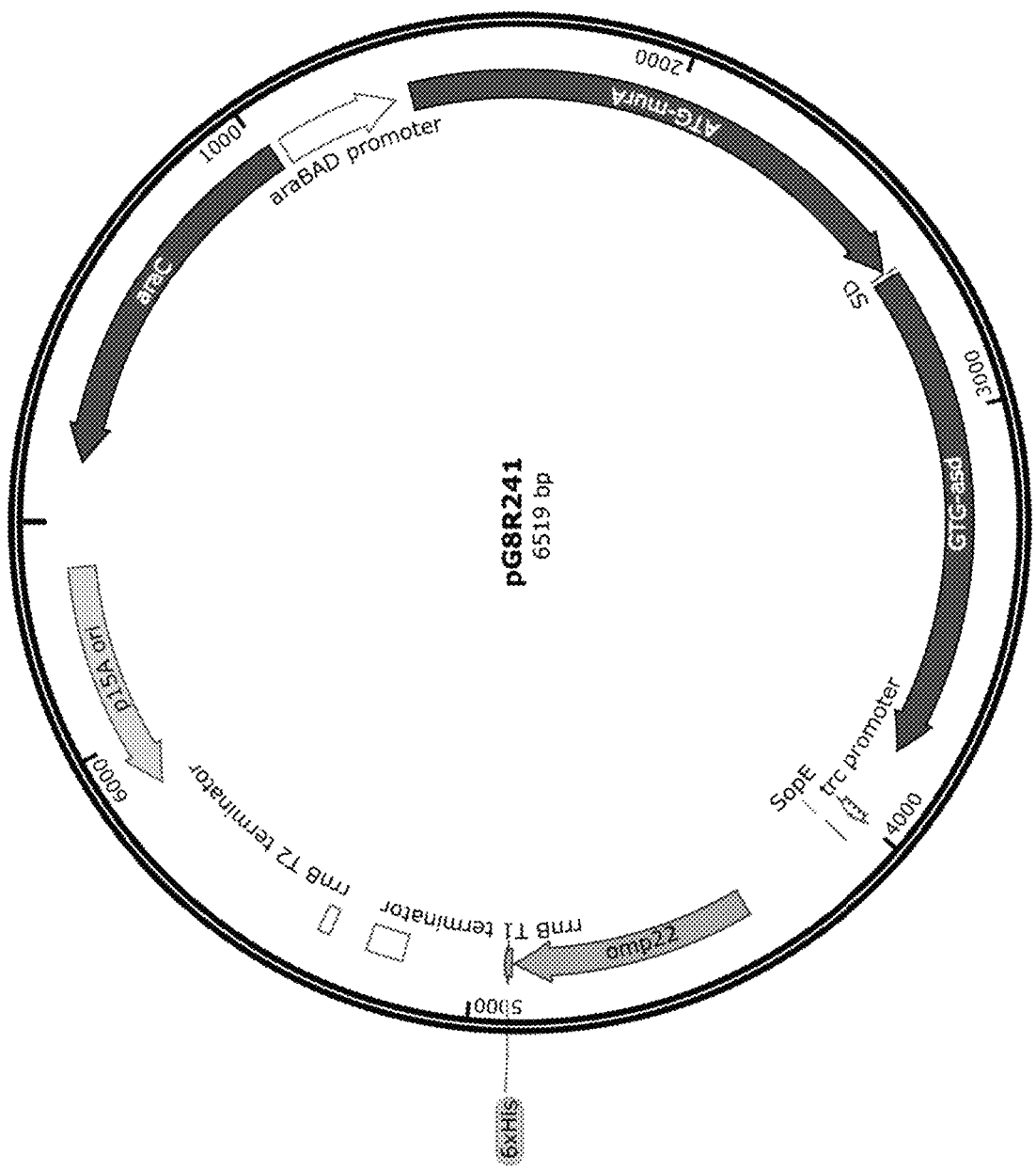
FIG. 8 provides plasmid maps for pG8R241 (FIG. 8A), pG8R243 (FIG. 8B), pG8R248 (FIG. 8C), pG8R250 (FIG. 8D), and pG8R251 (FIG. 8E).
Figure 8B:
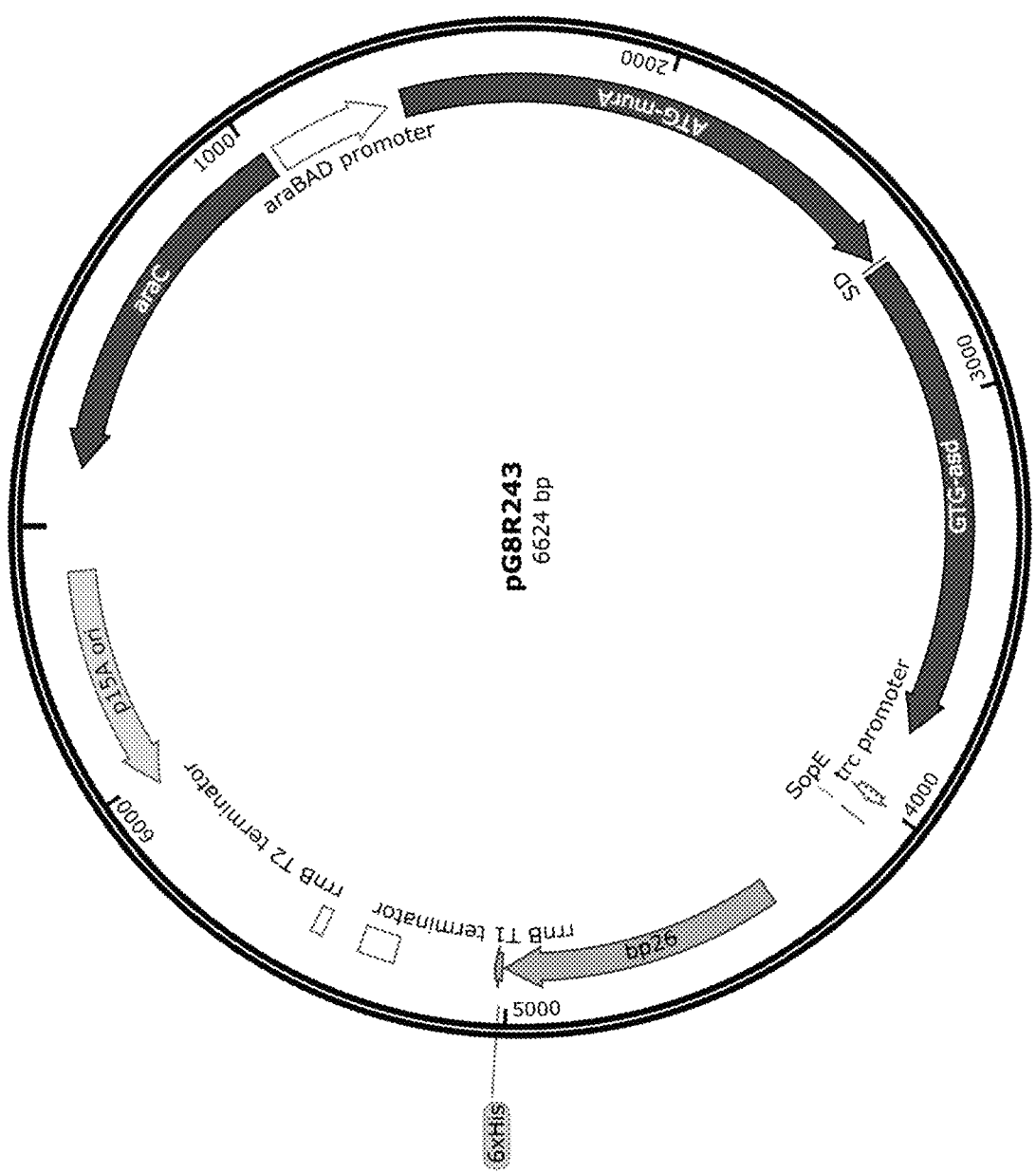
Figure 8C:
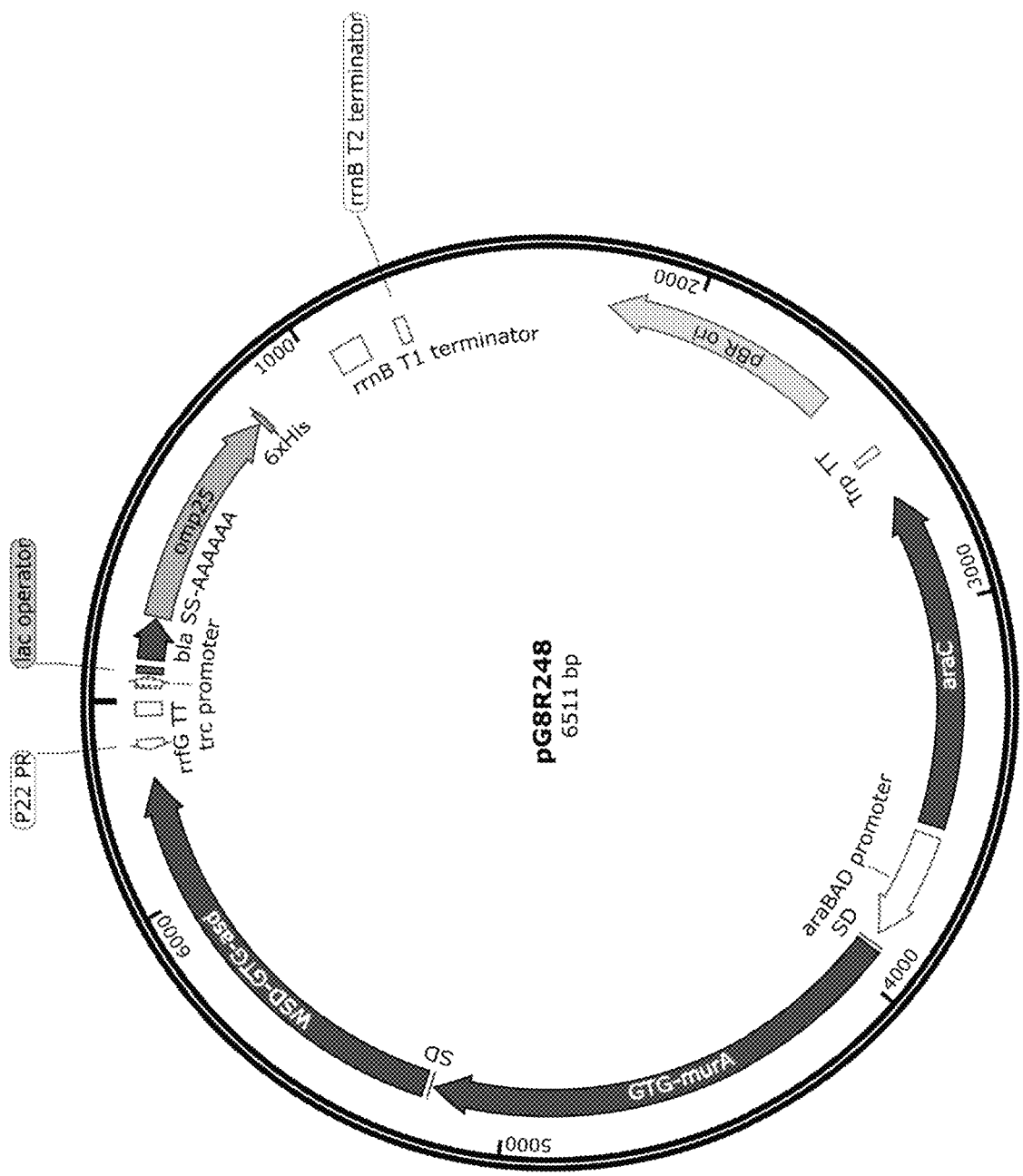
Figure 8D:
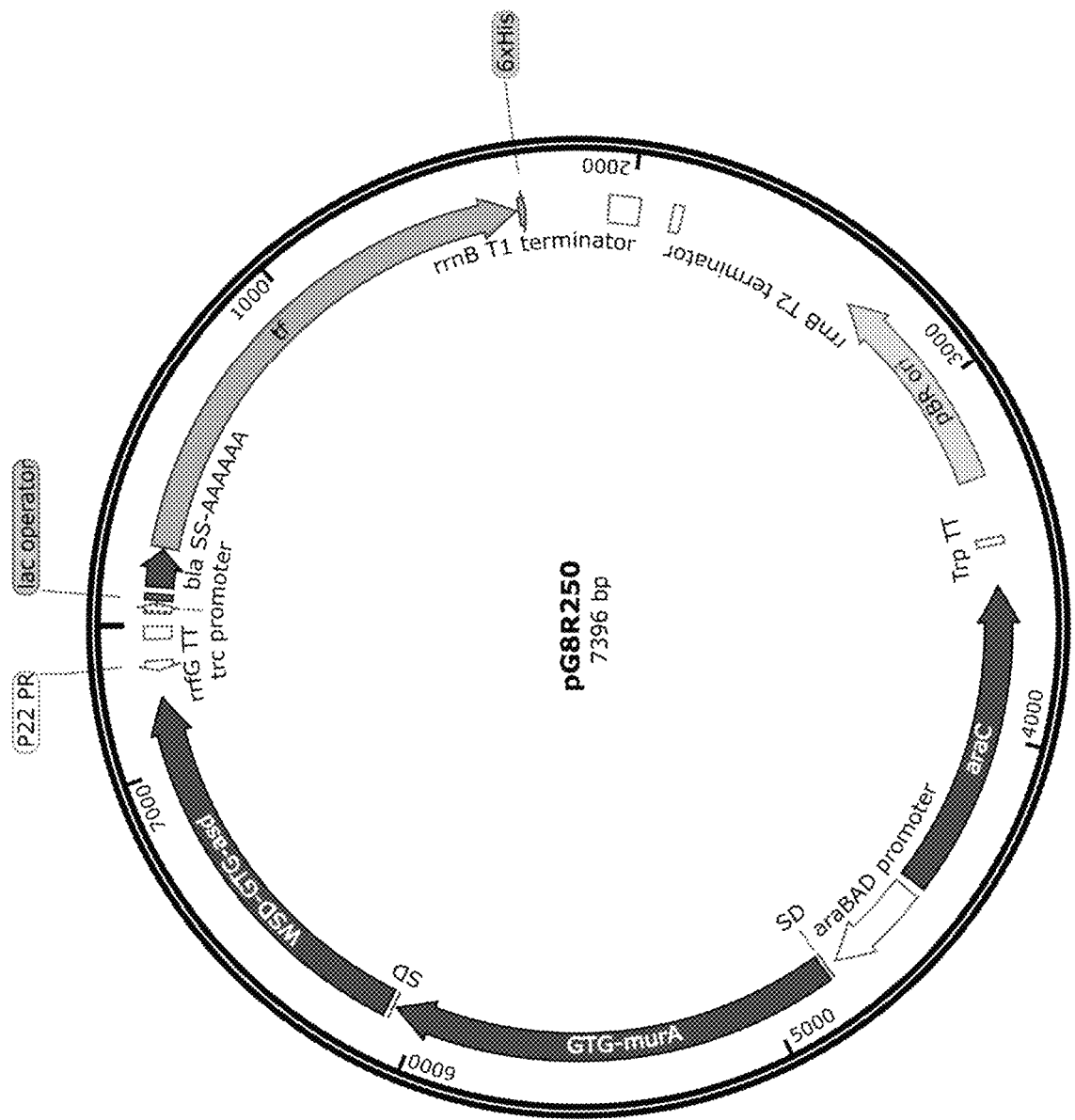
Figure 8E:
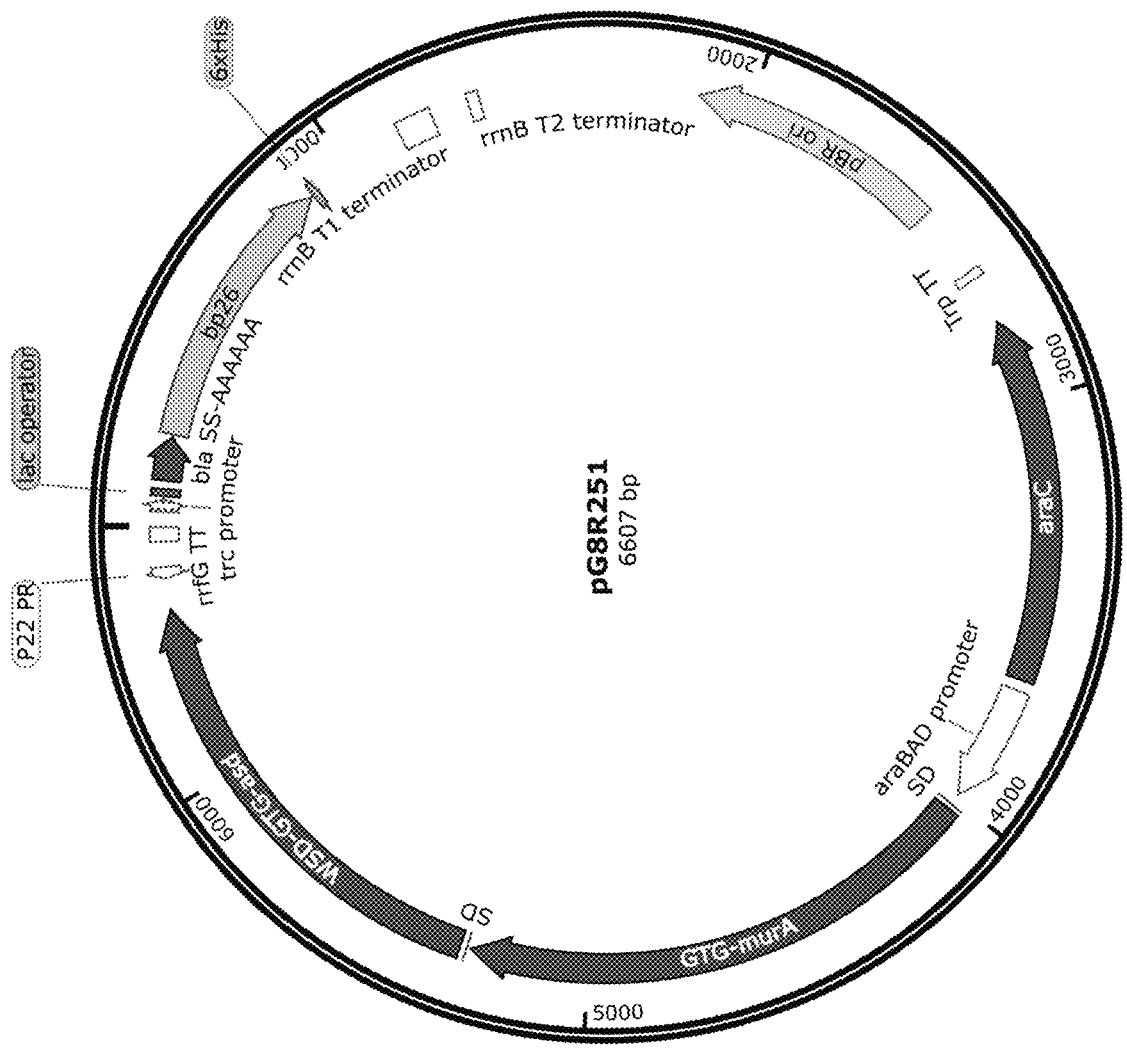
Figure 9:
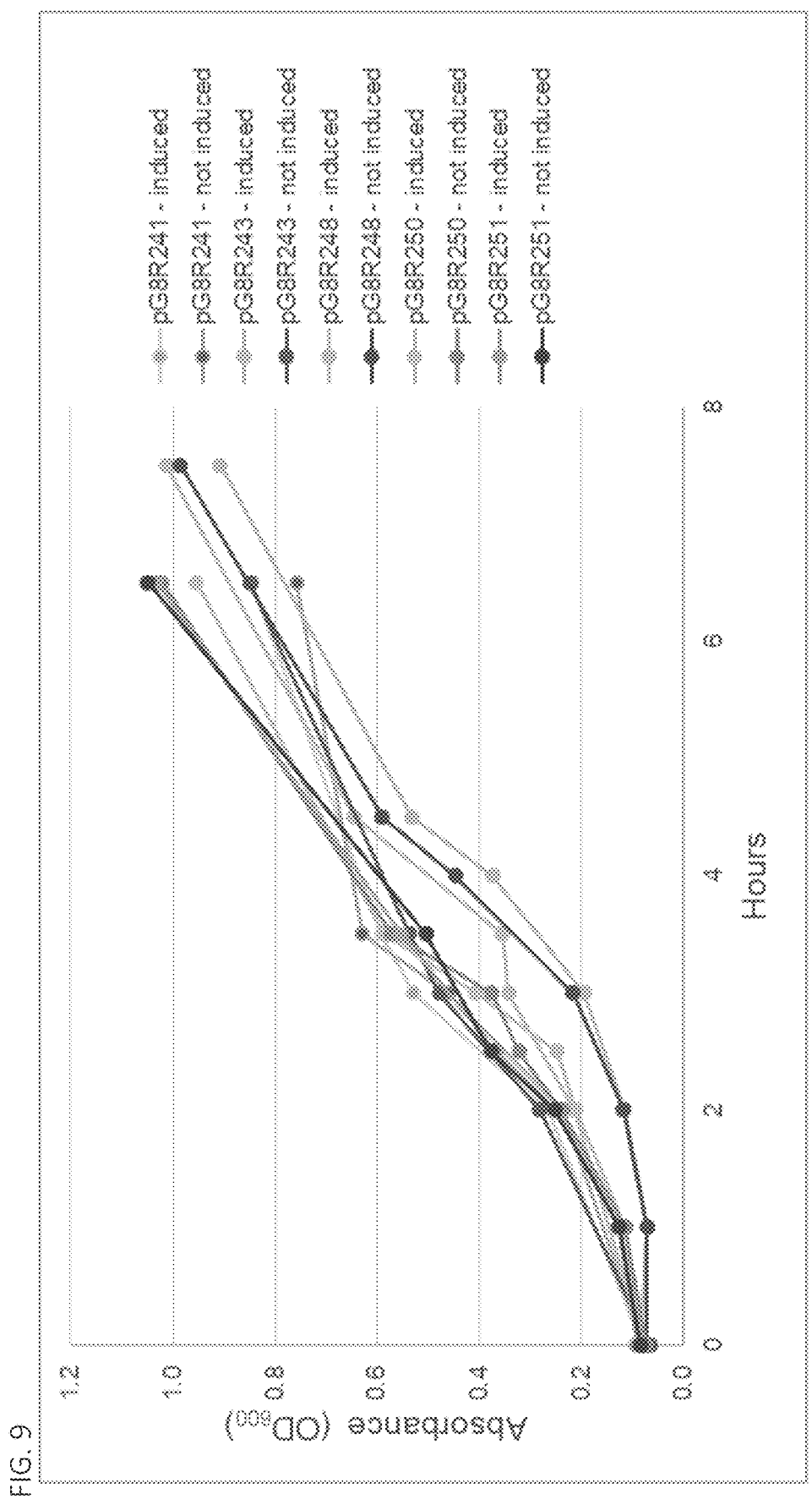
FIG. 9 shows growth curve for χ12509.

FIG. 4 provides data on growth of χ6212(pYA232) with the 12 plasmid constructs with and without induction of antigen synthesis induced by growth with IPTG. FIG. 5 displays western blot analyses of these same 12 constructs. FIGS. 6 and 7 provide the same analyses when the 12 plasmid constructs were introduced into *S. Typhimurium* χ12509. As summarized in Table 2, some proteins such as trigger factor (Tf) were sometimes synthesized by *E. coli* but not *S. Typhimurium* when encoded by pG8R110, by neither bacterial host when encoded by pG8R111 and by both bacterial hosts when encoded by pG8R114. Based on these collective observations, we chose to continue working with five *S. Typhimurium*-plasmid constructs that displayed IPTG-induced antigen synthesis. FIG. 8 depicts 5 of the plasmid maps described herein. FIG. 9 shows data for a comparison of growth rates of the PIESV-Bm constructs made in χ12509 with the plasmids diagrammed in FIG. 8 selected for detailed study. Strains were grown in LB broth supplemented with 0.1% arabinose and 0.1% rhamnose without and with 1 mm IPTG. In all cases, growth rates and final yields were essentially the same whether the plasmid-encoded antigen was or was not being synthesized. However, the χ12509(pG8R248) strain specifying synthesis of the Omp25 antigen demonstrated a lag in initiation of growth independent of synthesis although Omp25 synthesis and delivery did slightly reduce the final yield. Based on these results, it can be concluded that synthesis and delivery of the five antigens selected for further study would not be expected to interfere with vaccine cell growth in vivo, when arabinose is absent to lead to derepression of the Ptrc driven expression of the codon-optimized sequences encoding the five antigens selected for further study.

FIGS. 10 to 14 show Coomassie Blue stained gels of non-induced and induced cultures followed by up to 3 h incubation in the presence of chloramphenicol and the western blot analyses showing induction of antigen synthesis and stability after further protein synthesis was inhibited. These results show that the Omp22 and Tf proteins were degraded in *Salmonella* following their synthesis. Such results often indicate the presence of a protease cleavage site(s) that can be eliminated by subsequent DNA sequence modification. However, since our objective is to generate a PIESV construct to protect against *Brucella* infections, we deferred resolving such problems of non-synthesis or instability of encoded antigens to work with those constructs giving satisfactory results. In this regard, we decided to pursue studies with PIESV delivery of the Bp26 antigen since it gave superior results when encoded on the pG8R114 vector (pBR on) causing T2 secretion and adequate levels of regulated synthesis when encoded on the lower copy number pG8R110 (p15A on) (FIG. 15) that would favor induction of cellular immunities.

FIG. 16 shows that the five selected χ12509 constructs are also stably maintained in χ12509 when cultures are grown under permissive conditions. All other construct characterizations are described in the Materials and Methods described in Example 7

Example 4

Construction and Characterization of PIESV Constructs Encoding Synthesis and Delivery of the *B. melitensis* FlgK, Omp31 and BtuB Protein Antigens and Fusions Encoding Synthesis of Determinants from Three Antigens.

The pG8R258, pG8R260 and pG8R261 encoding BtuB, FlgK and Omp31, respectively, in pG8R111 when placed in χ12341 had rapid degradation of synthesized antigen (BtuB and FlgK) or the antigen synthesized was very toxic and inhibited growth of the construct (Omp31) (FIGS. 17, 18 and 19, respectively). In past studies (Jiang et al. 2015), we have often succeeded in obtaining high-level stable antigen synthesis by constructing fusions. We therefore designed and constructed two fusion constructs. One with a fusion of tf, bp26 and omp31 sequences in pG8R231 gave stable high-level antigen synthesis in χ12341 (FIG. 20). The other fusion of the sequences encoding BLS, the L7/L12 ribosome proteins and the Cu/Zn super oxide dismutase in pG8R259 was overproduced to such an extent (FIG. 21) such that it displayed instability (FIG. 22). This indicates that this fusion will be better specified on a lower copy number plasmid such as pYA4589 (p15A on) or pYA4595 (pSC101 on). The epitopes in these chimeric proteins are likely to induce both B-cell and T-cell mediated immune responses and this was a consideration in selecting the sequences included in the fusions. The plasmid maps and gel data related to the above constructs is provided in FIGS. 46-56, and Table 4.

Example 5

Demonstration of Protective Immunity to *Brucella* Challenge.

Figure 25A:
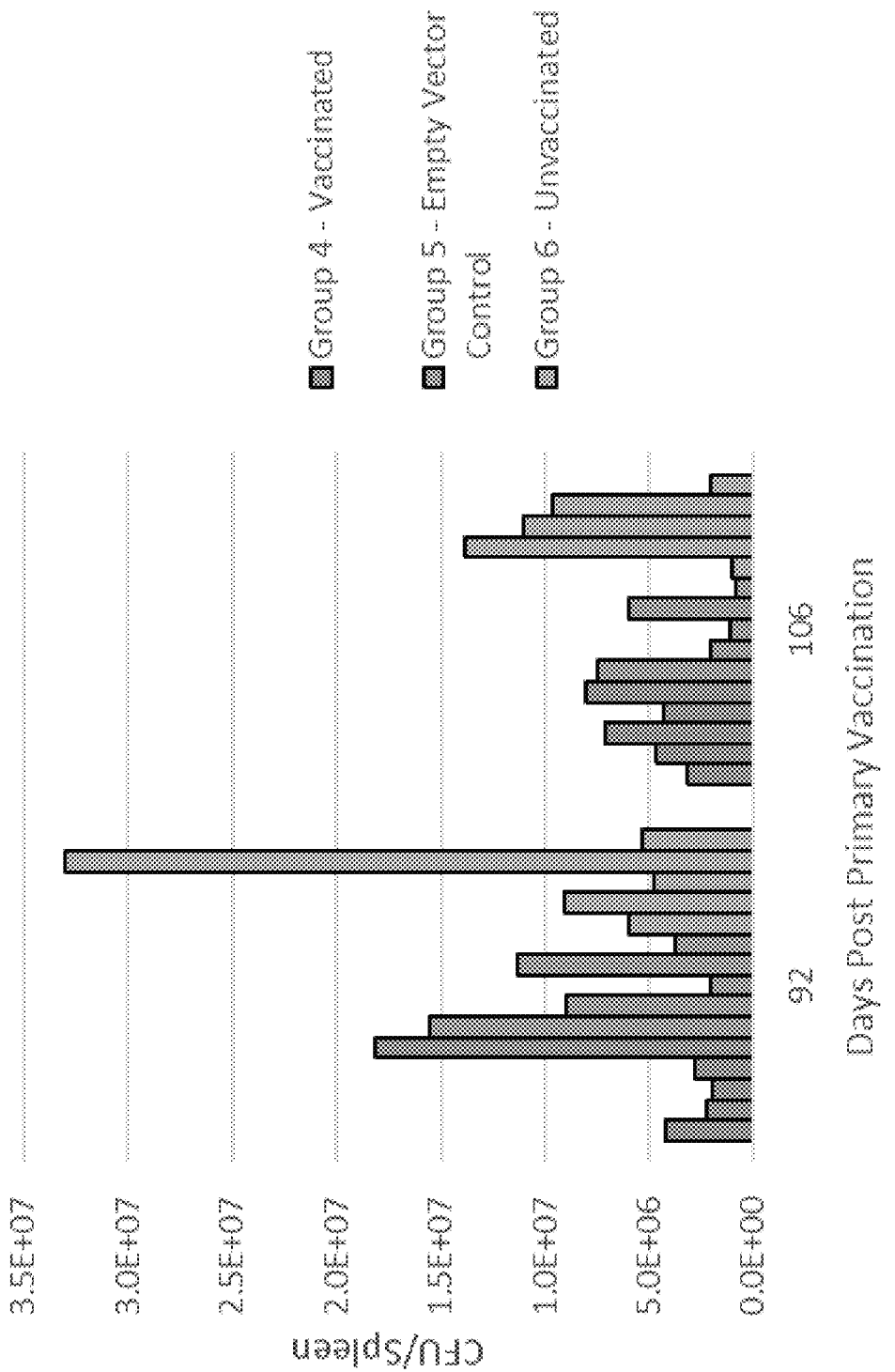
FIG. 25A shows splenic CFUs per mouse per time point.
Figure 25B:
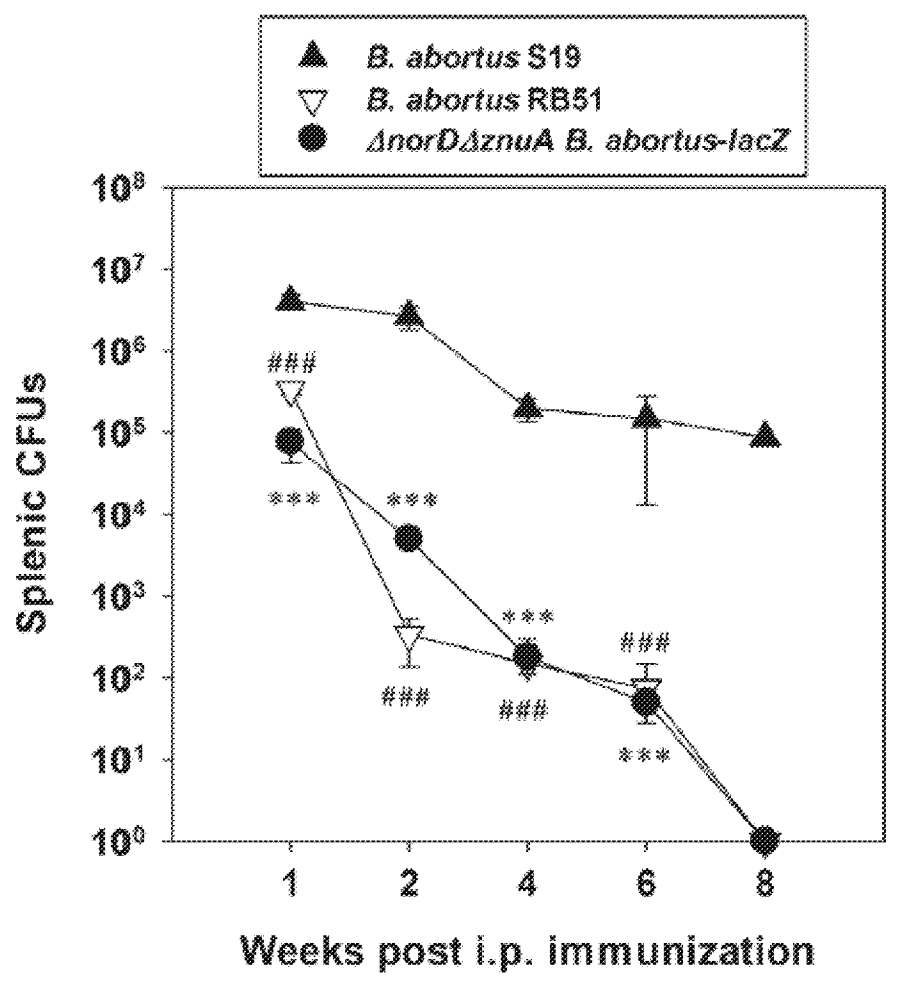
Figure 25C:
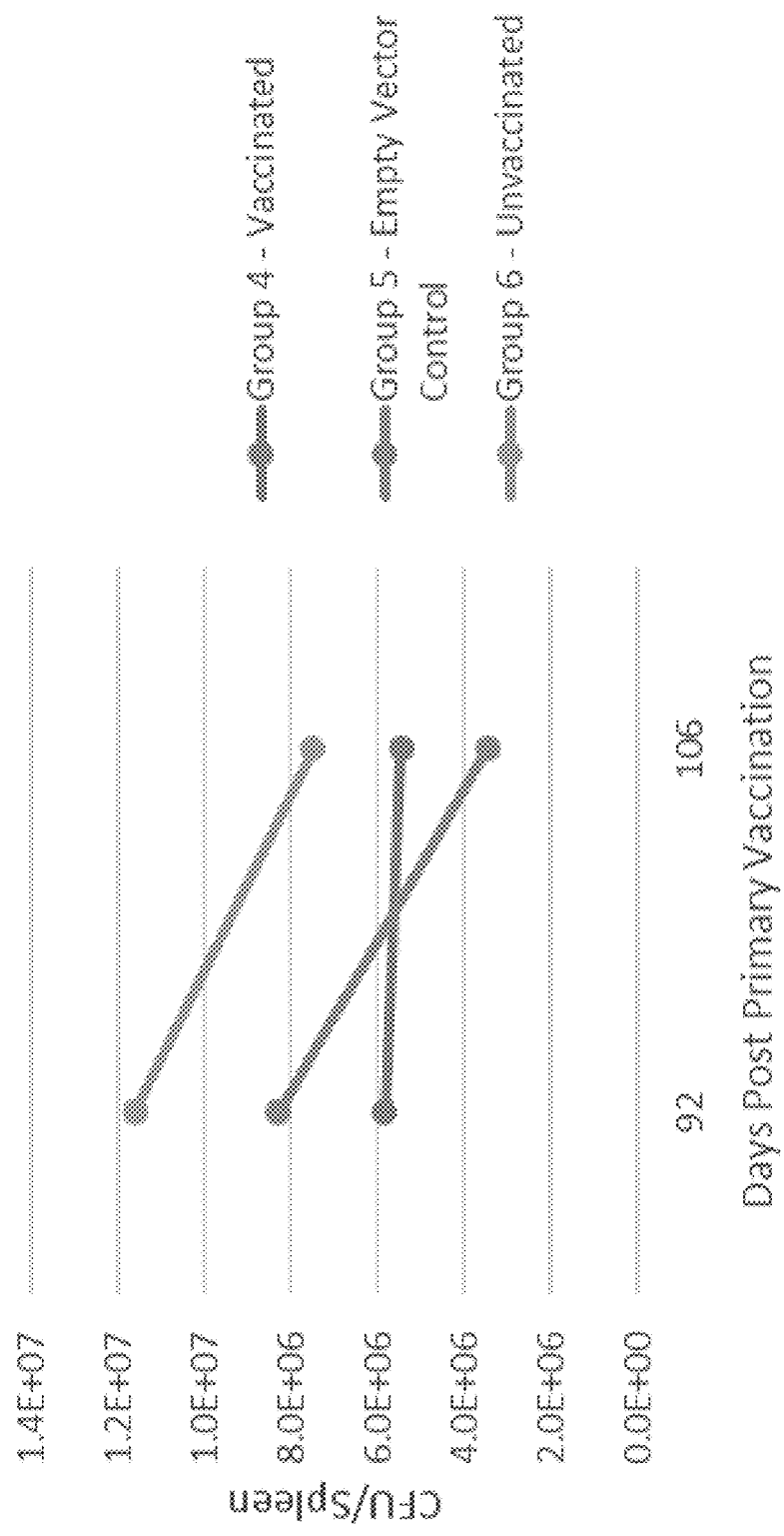
FIG. 25C shows average splenic CFUs per group per time point.
Figure 26:
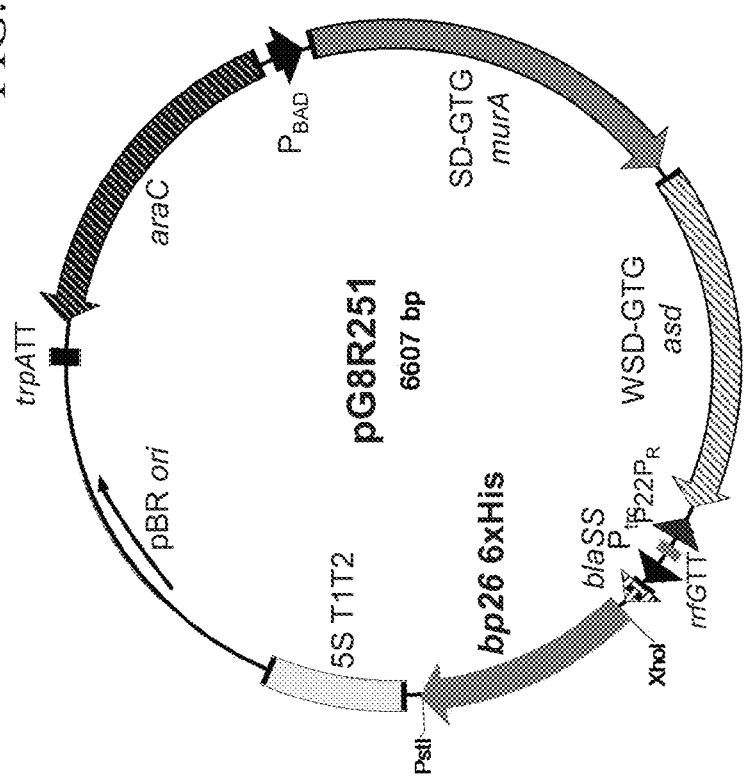
FIG. 26 shows a plasmid map relating to pG8R251.

Since wild-type *B. abortus* and *B. melitensis* are select agents requiring BSL3 and ABSL3 containment for experiments and animal studies, we chose to determine whether our PIESV constructs could inhibit the growth and persistence of the attenuated *B. abortus* vaccine strain S19. *B. abortus* and *B. melitensis* are very closely related and the *B. melitensis* antigens we are having synthesized and delivered by the PIESV constructs have over 99% amino acid sequence identity (except for the Omp31 protein). The S19 strain can infect mice without disease and declines in titer over an 8- to 10-week period (Yang et al. 2016). To verify this, we inoculated mice with $10^7$ CFU of S19 by the i.p., i.n. and s.c. routes and followed titers for 8 weeks. The data is presented in FIG. 23. Based on these results, an experimental design was worked out as depicted in FIG. 24. There were IACUC imposed delays during the vaccine evaluation experiment such that test times to measure S19 titers in spleens were significantly delayed. Nevertheless, a decline in S19 spleen titers was observed for the χ12509(pG8R251) vaccinated mice (FIG. 25) and this was accompanied by an increased titer of antibodies against the Bp26 antigen. Of interest, we also noted that the vector control *S. Typhimurium* also reduced S19 titers, an observation in accord with many other studies that reveal that *Salmonella* with the regulated delayed lysis attribute stimulate significant innate immune responses that are also partially protective.

Upon validating that any of the identified protective antigens listed in Table 1 do indeed induce protection of mice to infection with the *Brucella* strain S19, we construct operon fusions in the appropriate plasmid vector (FIG. 1) to specify synthesis of two or more *Brucella* antigens. In all cases, expression of sequences encoding the antigens is regulated by Ptrc control and each gene is separated by a linker sequence specifying a ribosome binding (SD) sequence as was used to generate the operon fusion for specifying synthesis of the two *C. perfringens* protective antigens PlcC and GST-NetB used to obtain the data shown in FIG. 3 (Jiang et al., Ref 36). Alternatively, all or segments or *B. melitensis* protein antigens possessing immunogenic sequences can be arranged as fusions with appropriate amino acid linkers as has been done for fusions of the Tf, Bp26 and Omp31 proteins and the BLS, L7/L12 and Cu/Zn SOD proteins.

Example 6

Plasmid Map Examples and Sequences

FIGS. 26-40 Provide plasmid information for 5 plasmids that are used to make protective immunity enhanced *Salmonella* vaccines against *Brucella melitensis*. Namely, these relate to pG8R241, pG8R243, pG8R248, pG8R250, pG8R251

Each plasmid is stocked in the Curtiss collection as a plasmid in χ6212(pYA232) *Escherichia coli*. Additionally, each plasmid is stocked in the *Salmonella* collection in χ12509 *S. Typhimurium* UK-1 to make the actual vaccine.

The stocking information for the plasmid and the *Salmonella* collections is provided for each plasmid. In addition, the entire plasmid sequence and the information for the codon optimization for each *Brucella melitensis* gene is provided.

Below is the color coding scheme provided in the figures pertaining to full sequence of the plasmid with the inserted noted gene, codon optimized versions, restriction digest sites and HIS tags:

XmaI = CCC GGG-amino acids = P G

XhoI = CTC GAG-amino acids = L E

PstI = CTG CAG-amino acids = L Q

AvrII = CCT AGG-amino acids = P R

HIS Tag = CAC CAC CAC CAC CAC CAC (SEQ ID NO: 16)- amino acids = H H H H H H (SEQ ID NO: 17)

TAA = STOP

A. pG8R251 with bp26 (FIGS. 26-28)
Chi Number(pG8R/pYA number): χ12509(pG8R251)
Genus: *Salmonella* Species: *S. Typhimurium* UK-1
chi Genotype: ΔP$_{murA25}$::TT araC P$_{araBAD}$ murA ΔasdA27::TT araC P$_{araBAD}$ c2 Δ(wza-wcaM)-8 ΔrelA197::

araC P*araBAD* lacI TT ΔrecF126 ΔsifA26 ΔP*crp*⁺ ΔwaaL46 ΔpagL64::TT rhaRS P*rhaBAD* waaL pmi⁺ ΔaraBAD65::TT Phenotype: Grows in L broth with 0.1% arabinose. DAP not required, asd complemented by plasmid. Needs 0.1% rhamnose for LPS. Expresses *Brucella melitensis* bp26 gene when induced with IPTG.

Description: pG8R251 was electroporated into χ12509 and grown on LB with 0.2% arabinose. Plasmid verified using PCR and sequencing. Western blot for Bp26 verified expression with proper regulation. Smooth LPS verified using LPS gel with 0.1% rhamnose. Plasmid is stable for >50 generations.

| | |
|---|---|
| Plasmid Parent: pG8R114 | |
| Chi Parent: χ12495 | Source: RCIII Lab |
| Depositor: Jessica Jacob | |
| Plasmid: pG8R251 | Genus/Species: *Escherichia coli* |
| Host: χ6212 | Replicon: pBR ori |
| Size: 6607 bp | Gene cloned: bp26 |
| Marker(s): Asd⁺:MurA⁺ | |
| Tests: PCR & Sequencing | |

Description: Restriction Digestion (XhoI and PstI) and ligation used to insert *Brucella melitensis* bp26 gene from pG8R213 into parent pG8R114 plasmid.

Parent: pG8R114 Depositor: Jessica Jacob

Host genotype: 80d lacZ M15 deoR (lacZYA-argF)U169 supE44 gyrA96 recA1 relA1 endA1 asdA4 zhf-2::Tn10 hsdR17 (r⁻ m⁺)

Host phenotype: Rec⁻(UV*ˢ*) Asd⁻ Lac⁻ Nal*ʳ* Tet*ˢ*

Plasmid Derivation:

Source: Reference/Duplicates:

```
Primer sequences:
pG8R_consensus_F-
                              (SEQ ID NO: 33)
    5' CAATTGATGGGTGAGCGTAGG 3' pG8R_consensus_R-
                              (SEQ ID NO: 34)
    5' TCTCTCATCCGCCAAAACAG 3' bp26_CO_F
                              (SEQ ID NO: 35)
    5' CAGGAAAACCAGATGACCAC 3' bp26_CO_R
                              (SEQ ID NO: 36)
    5' AGCGATCGGAACAGAGTTGT 3'
```

Figure 29:
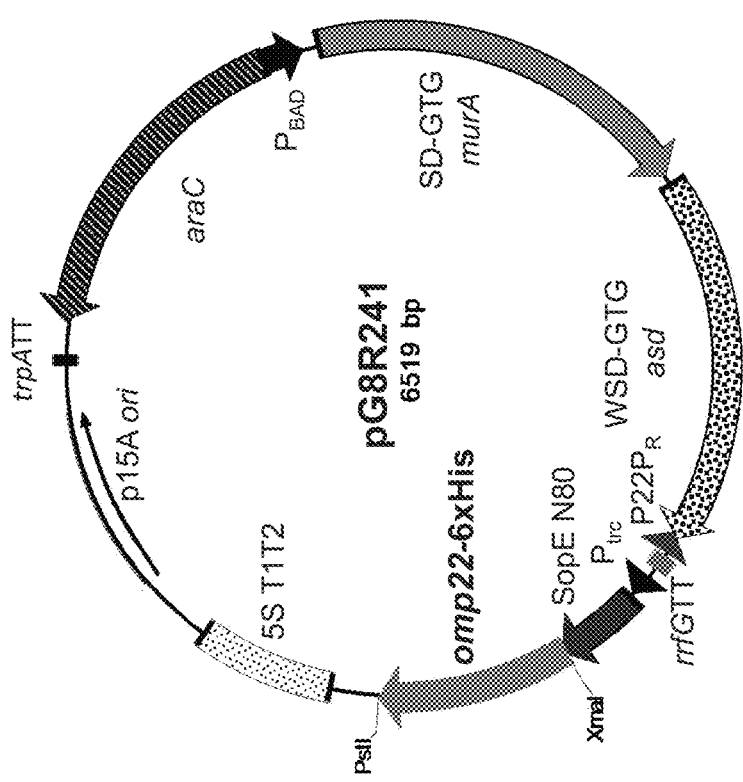
FIG. 29 shows a plasmid map relating to pG8R241.

B. pG8R241 with omp22 (FIGS. 29-31)

Chi Number(pYA number): χ12509 (pG8R241)

Genus: *Salmonella* Species: *S. Typhimurium* UK-1

Chi Genotype: ΔP*murA25*::TT araC P*araBAD* murA ΔasdA27::TT araC P*araBAD* c2 Δ(wza-wcaM)-8 ΔrelA197:: araC P*araBAD* lacI TT ΔrecF126 ΔsifA26 ΔP*crp*⁺ ΔwaaL46 ΔpagL64::TT rhaRS P*rhaBAD* waaL pmi⁺ ΔaraBAD65::TT Phenotype: Grows in L broth with 0.1% arabinose. DAP not required, asd complemented by plasmid. Needs 0.1% rhamnose for LPS. Expresses *Brucella melitensis* omp22 gene when induced with IPTG.

Description: pG8R241 was electroporated into χ12509 and grown on LB with 0.2% arabinose. Plasmid verified using PCR and sequencing. Western blot for Omp22 verified expression with proper regulation. Smooth LPS verified using LPS gel with 0.1% rhamnose. Plasmid is stable for >50 generations.

| | |
|---|---|
| Plasmid Parent: pG8R110 | |
| Chi Parent: χ12495 | Source: RCIII Lab |
| Depositor: Jessica Jacob | |
| Plasmid: pG8R241 | Genus/Species: *Escherichia coli* |
| Host: χ6212 | Replicon: p15A ori |
| Size: 6513 bp | Gene cloned: omp22 |
| Marker(s): Asd⁺:MurA⁺ | |
| Tests: PCR & Sequencing | |

Description: Restriction Digestion (XmaI and PstI) and ligation used to insert *Brucella melitensis* omp22 gene from pG8R214 into parent pG8R110 plasmid.

Parent: pG8R110 Depositor: Jessica Jacob

Host genotype: 80d lacZ M15 deoR (lacZYA-argF)U169 supE44 gyrA96 recA1 relA1 endA1 asdA4 zhf-2::Tn10 hsdR17(r⁻ m⁺)

Host phenotype: Rec⁻(UV*ˢ*) Asd⁻ Lac⁻ Nal*ʳ* Tet*ˢ*

Plasmid Derivation:

Source: Reference/Duplicates:

```
Primer sequences:
pG8R_consensus_F-
                              (SEQ ID NO: 33)
    5' CAATTGATGGGTGAGCGTAGG 3' pG8R_consensus_R-
                              (SEQ ID NO: 34)
    5' TCTCTCATCCGCCAAAACAG 3'

Omp22_CO_F
                              (SEQ ID NO: 37)
    5' GGGTGGTACCGACTACACCT 3'

Omp22_CO_R
                              (SEQ ID NO: 38)
    5' TCAGGTTGTTACGCTGTTCG 3'
```

Figure 32:
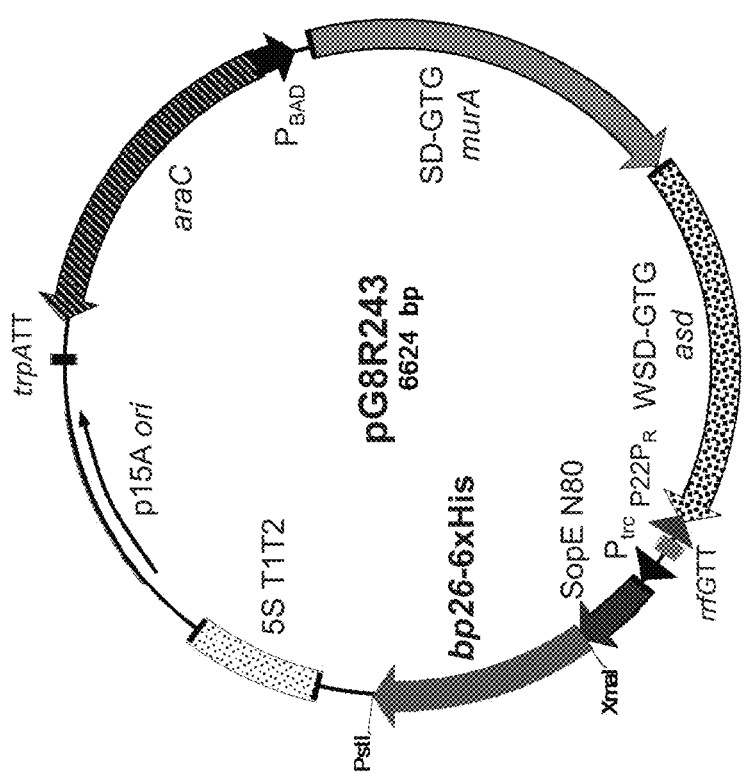
FIG. 32 shows the plasmid map for pG8R243.
Figure 35:
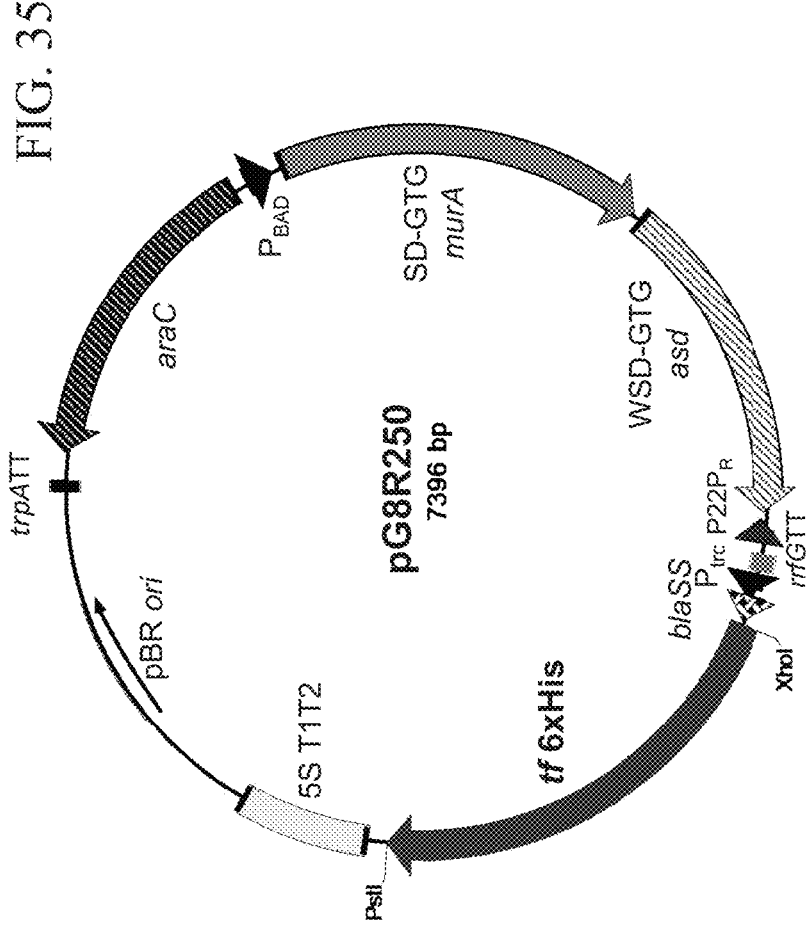
FIG. 35 shows a plasmid map relating to pG8R250.
Figure 38:
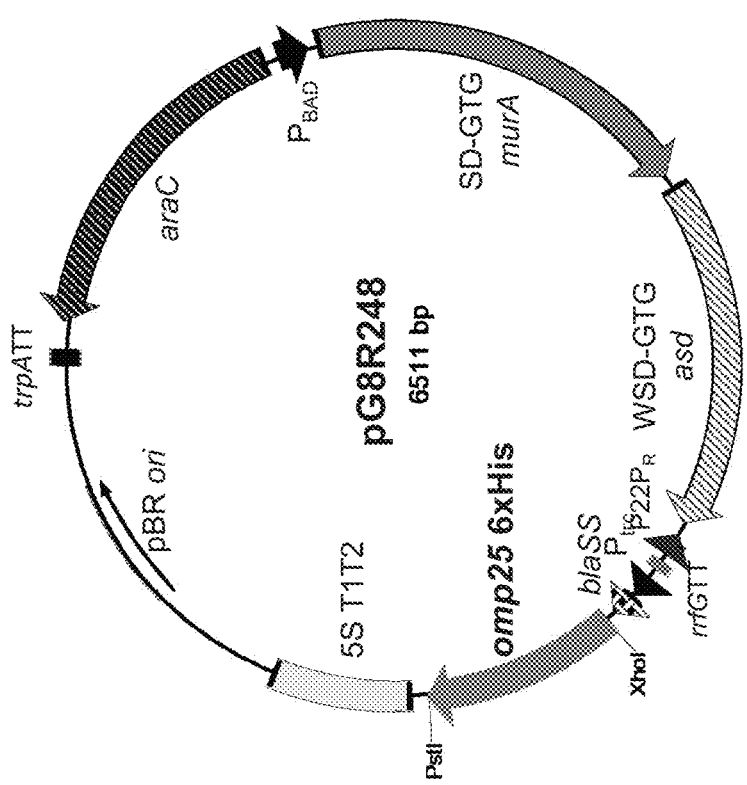
FIG. 38 shows the plasmid map for pG8R248.
Figure 41:
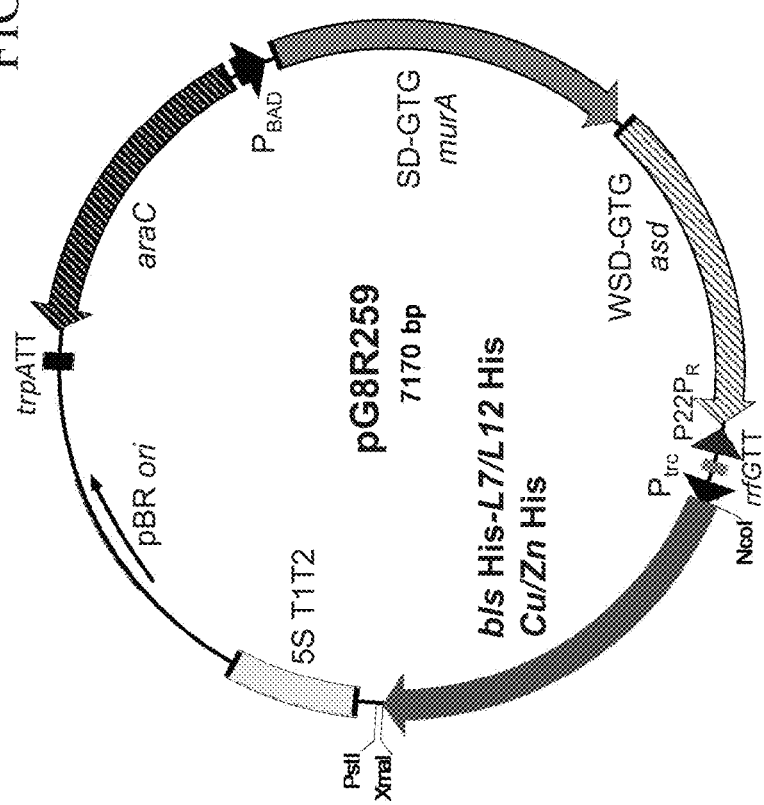
FIG. 41 shows the plasmid map of pG8R259 with chimeric construct.
Figure 42:
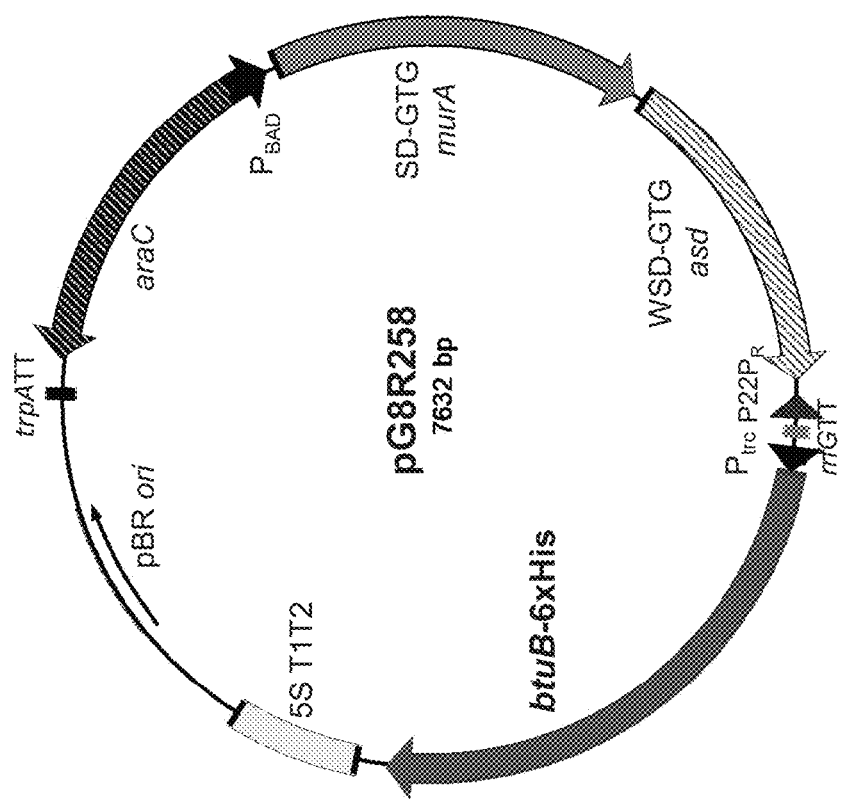
FIG. 42 shows the plasmid map of pG8R258 with ButB.
Figure 43:
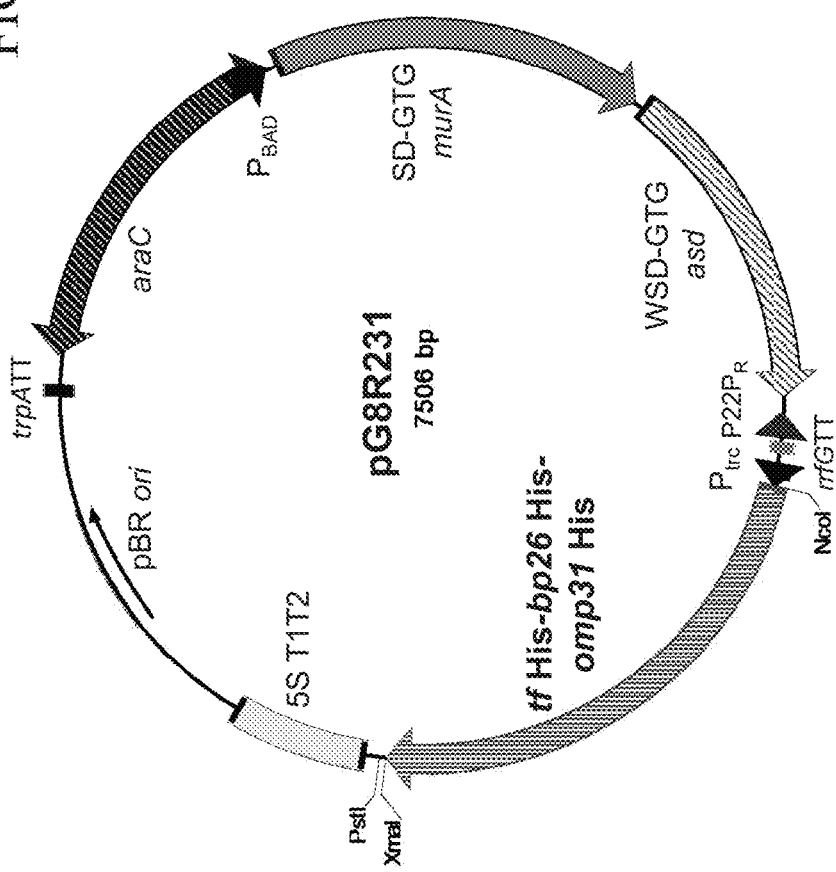
FIG. 43 shows the plasmid map of pG8R231 with chimeric construct.
Figure 44:
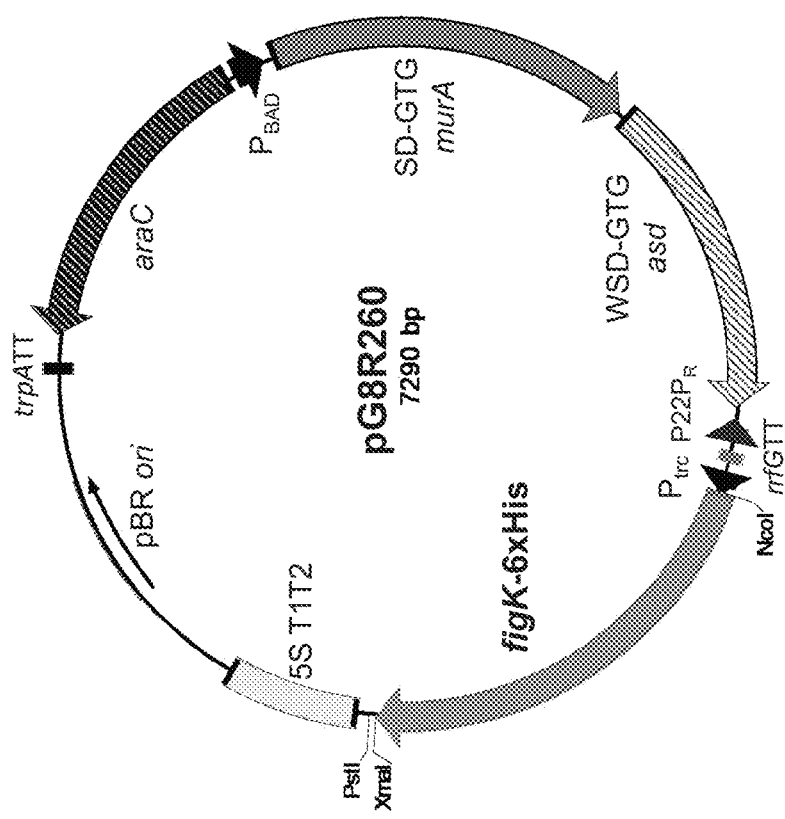
FIG. 44 shows the plasmid map of pG8R260 with FigK.
Figure 45:
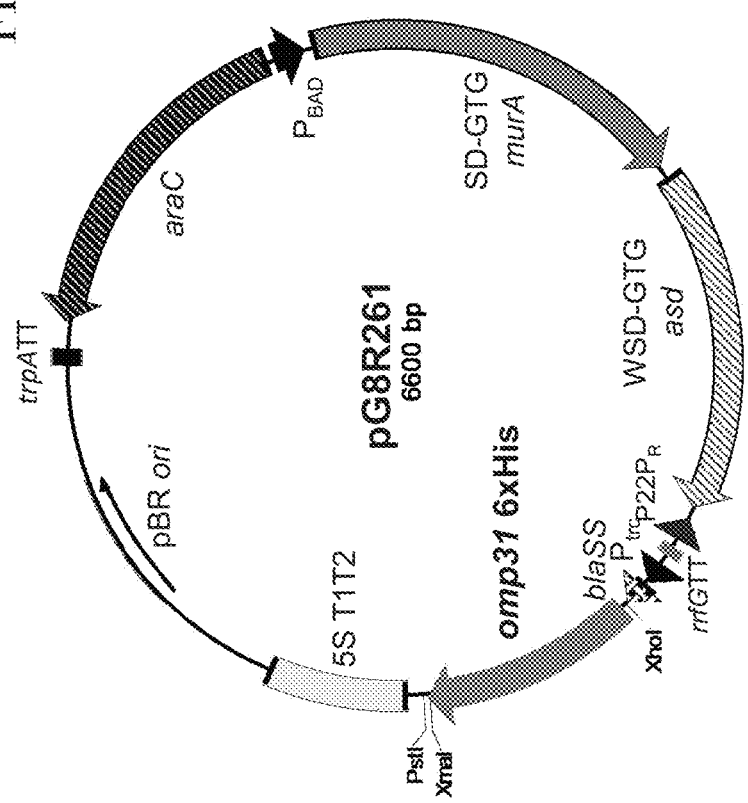
FIG. 45 shows the plasmid map of pG8R261 with omp31.
Figure 46:
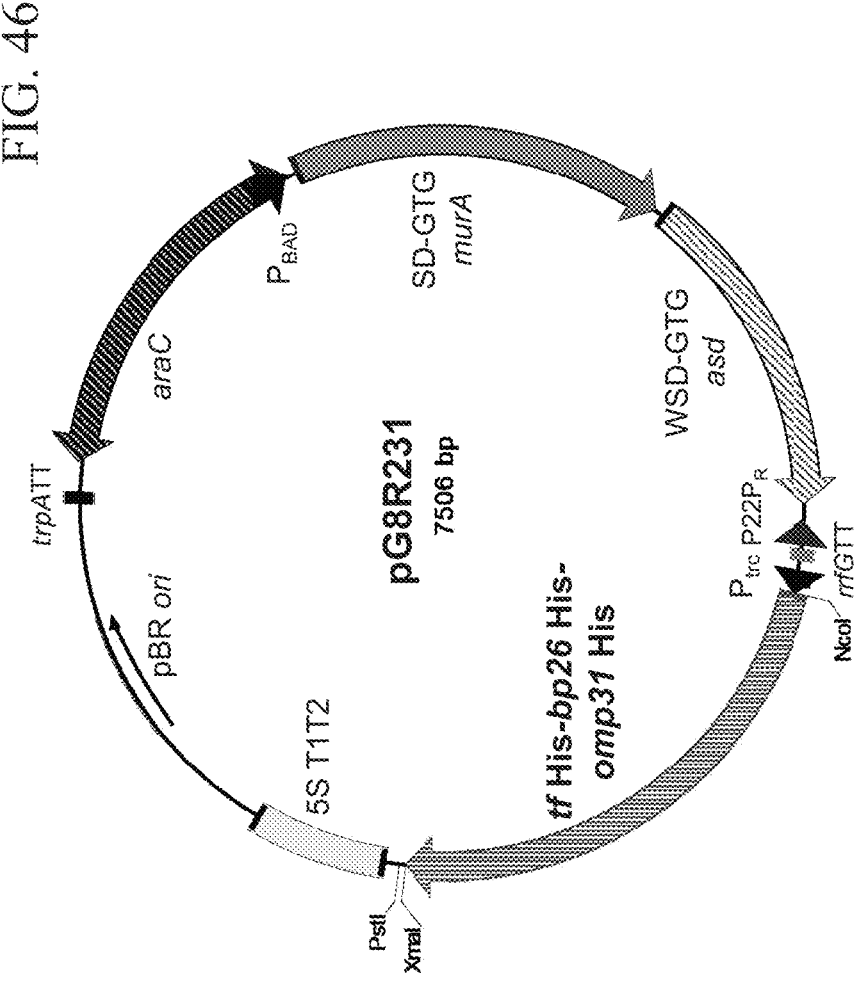
FIG. 46 shows the plasmid map of pGR111-bls-I7/I12-cu/zn in X1234 (pG8R259).
Figure 47:
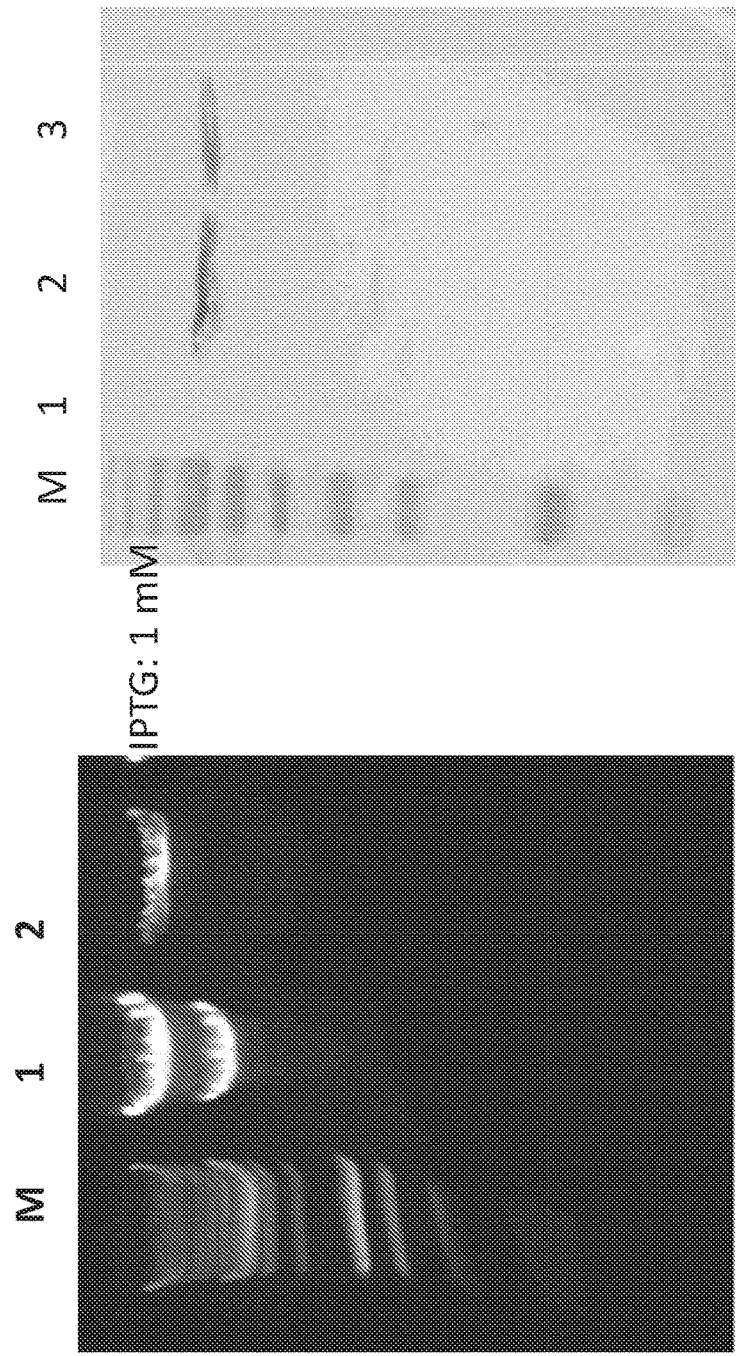
FIG. 47 shows the data related to the plasmid shown in FIG. 46.
Figure 48:
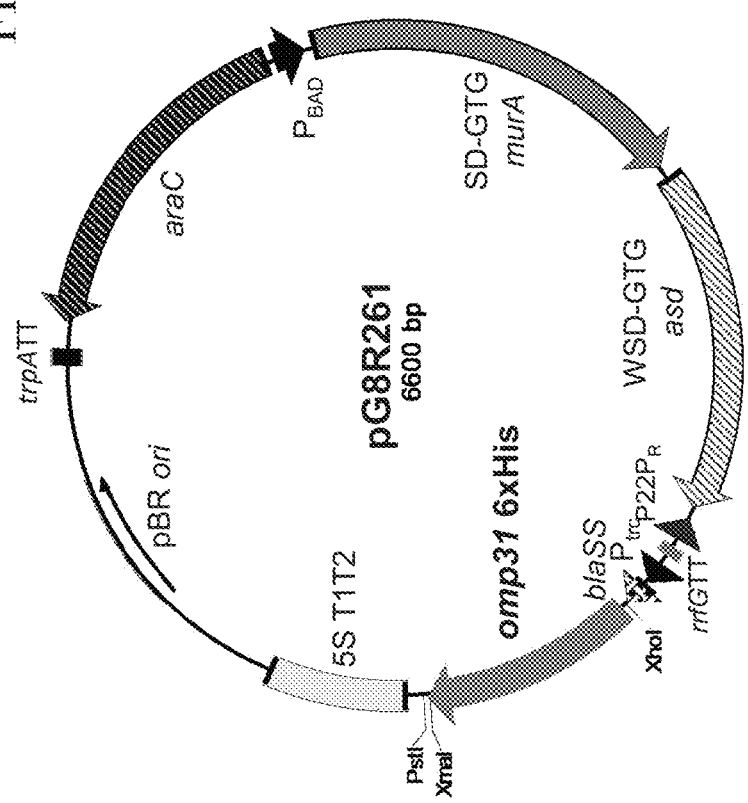
FIG. 48 shows the plasmid map of pG8R114-omp31 in X12341(pG8R261).
Figure 49:
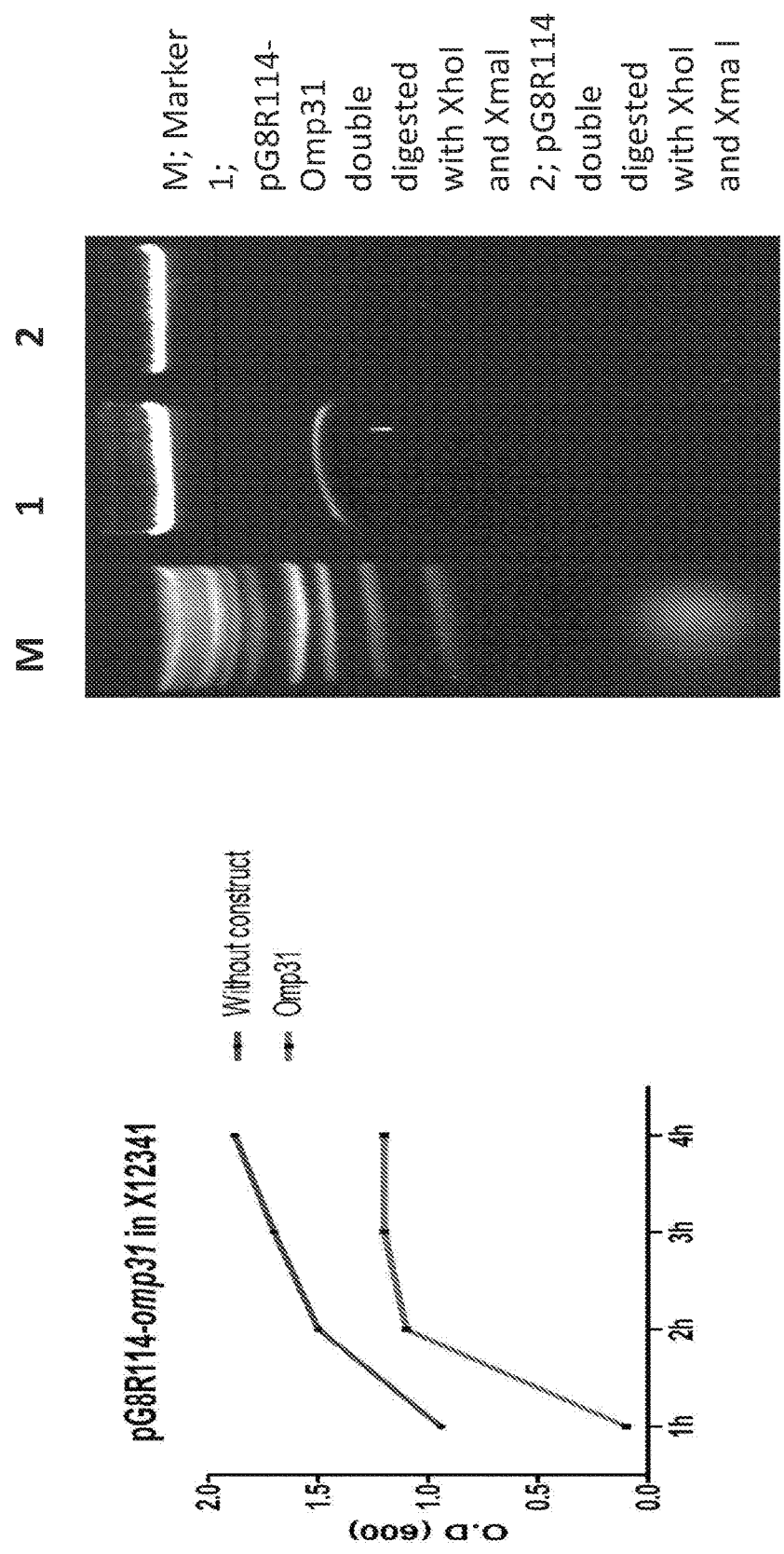
FIG. 49 shows data related to the plasmid shown in FIG. 47.
Figure 50:
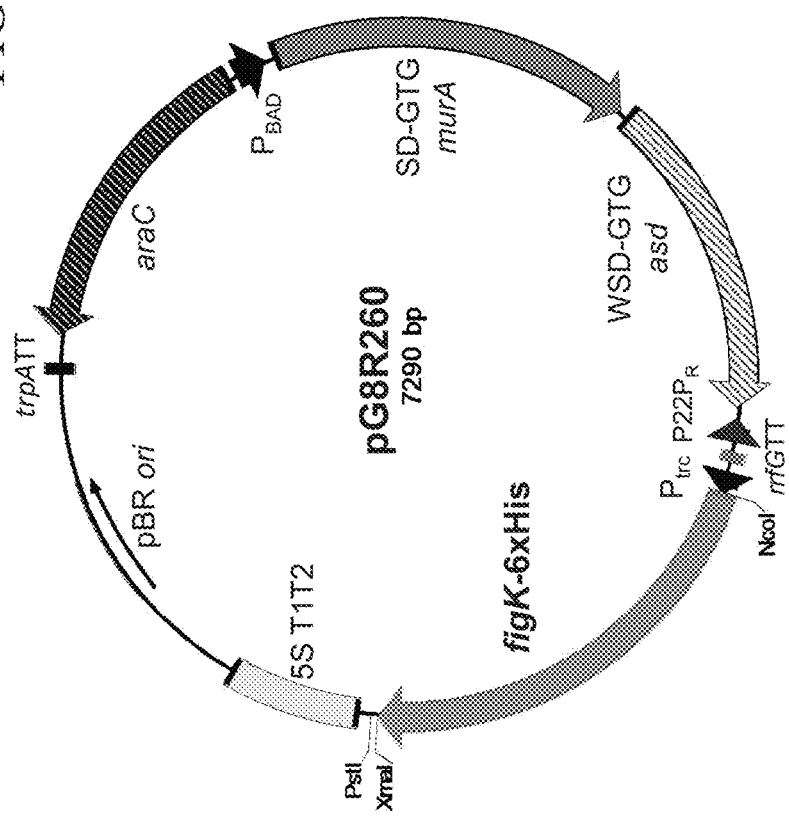
FIG. 50 shows the plasmid map of pG8R111-figk in x12341(pG8R260).
Figure 51:
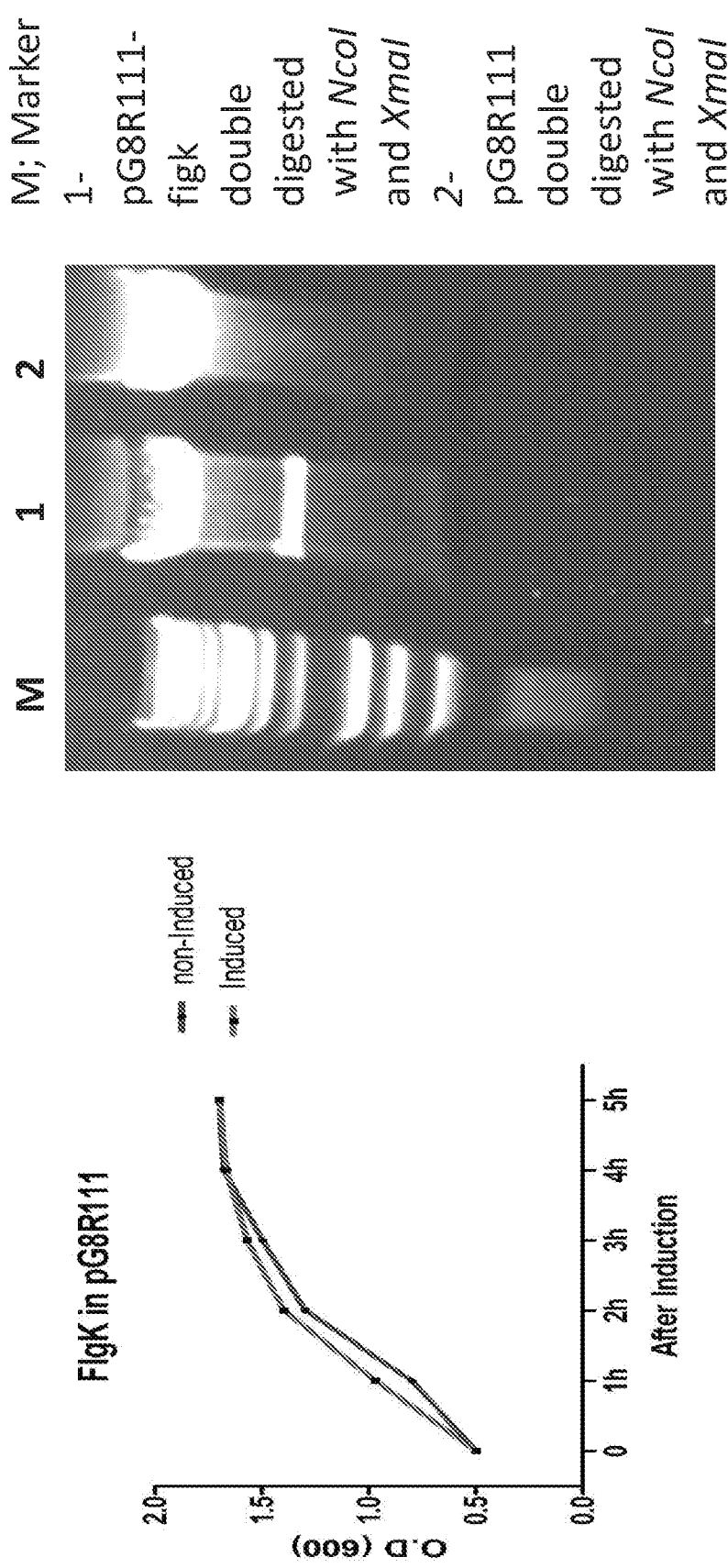
FIG. 51 shows data related to the plasmid shown in FIG. 50.
Figure 52:
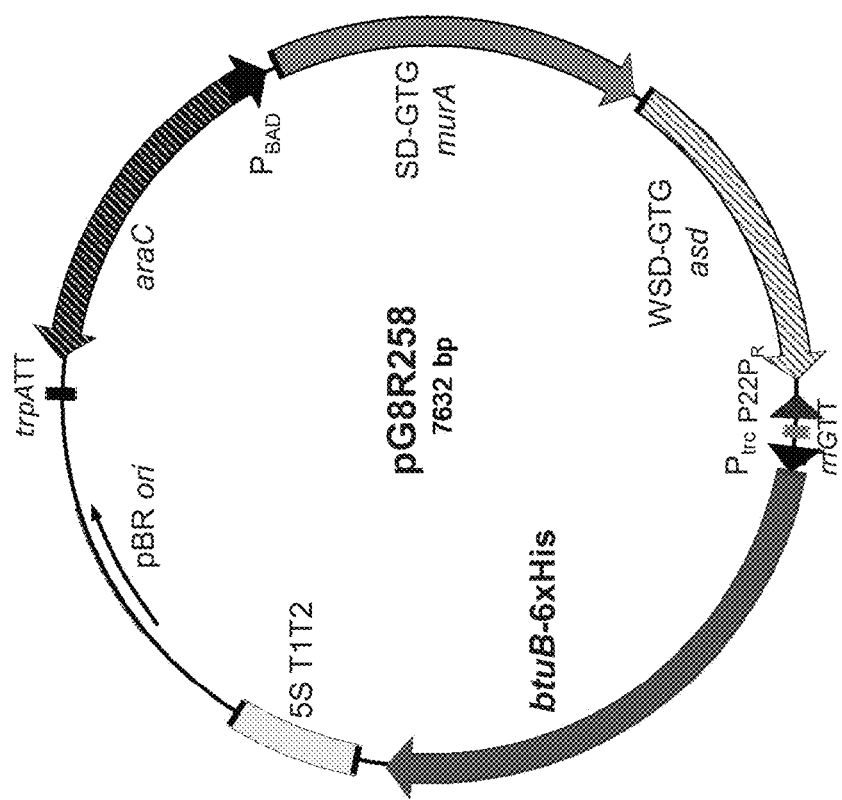
FIG. 52 shows the plasmid map of pG8R111-btub x12341 (pG8R258).
Figure 54:
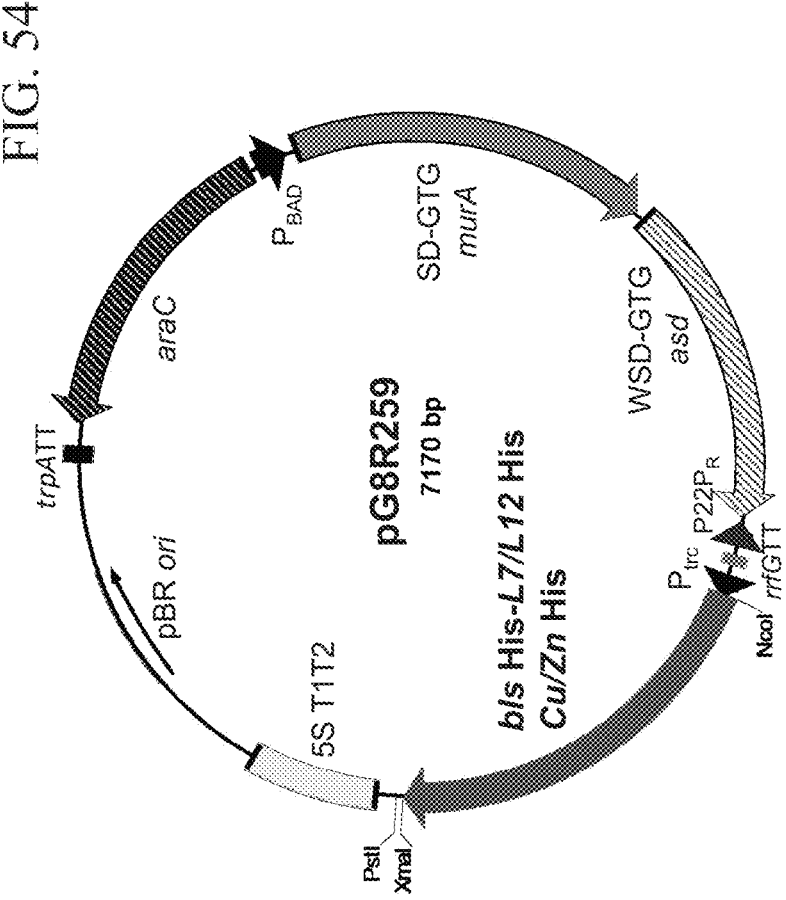
FIG. 54 shows the plasmid map of pGR111-bls-I7/I12-cu/zn in X1234 (pG8R259).

C. pG8R243 (with bp26) FIGS. 32-34

Chi Number(pG8R/pYA number): χ12509(pG8R243)

Genus: *Salmonella* Species: *S. Typhimurium* UK-1

Chi Genotype: ΔP*murA25*::TT araC P*araBAD* murA ΔasdA27::TT araC P*araBAD* c2 Δ(wza-wcaM)-8 ΔrelA197:: araC P*araBAD* lacI TT ΔrecF126 ΔsifA26 ΔP*crp*⁺ ΔwaaL46 ΔpagL64::TT rhaRS P*rhaBAD* waaL pmi⁺ ΔaraBAD65::TT Phenotype: Grows in L broth with 0.1% arabinose. DAP not required, asd complemented by plasmid. Needs 0.1% rhamnose for LPS. Expresses *Brucella melitensis* bp26 gene when induced with IPTG.

Description: pG8R243 was electroporated into χ12509 and grown on LB with 0.2% arabinose. Plasmid verified using PCR and sequencing. Western blot for Bp26 verified expression with proper regulation. Smooth LPS verified using LPS gel with 0.1% rhamnose. Plasmid is stable for >50 generations.

| | |
|---|---|
| Plasmid Parent: pG8R110 | |
| Chi Parent: χ12495 | Source: RCIII Lab |
| Depositor: Jessica Jacob | |
| Plasmid: pG8R243 | Genus/Species: *Escherichia coli* |
| Host: χ6212 | Replicon: p15A ori |
| Size: 6618 bp | Gene cloned: bp26 |
| Marker(s): Asd⁺:MurA⁺ | |
| Tests: PCR & Sequencing | |

Description: Restriction Digestion (XmaI and PstI) and ligation used to insert *Brucella melitensis* bp26 gene from pG8R213 into parent pG8R110 plasmid.

Parent: pG8R110 Depositor: Jessica Jacob

Host genotype: 80d lacZ M15 deoR (lacZYA-argF)U169 supE44 gyrA96 recA1 relA1 endA1 asdA4 zhf-2::Tn10 hsdR17 (r⁻ m⁺)

Host phenotype: Rec⁻(UVˢ) Asd⁻ Lac⁻ Nalʳ Tetˢ
Plasmid Derivation:
Source: Reference/Duplicates:

```
Primer sequences:
pG8R_consensus_F-
                                  (SEQ ID NO: 33)
5' CAATTGATGGGTGAGCGTAGG 3' pG8R_consensus_R-
                                  (SEQ ID NO: 34)
5' TCTCTCATCCGCCAAAACAG 3' bp26_CO_F
                                  (SEQ ID NO: 35)
5' CAGGAAAACCAGATGACCAC 3' bp26_CO_R
                                  (SEQ ID NO: 36)
5' AGCGATCGGAACAGAGTTGT 3'
```

D. pG8R250 with tf (FIGS. 35-37)
Chi Number(pYA number): χ12509 (pG8R250)
Genus: *Salmonella* Species: *S. Typhimurium* UK-1
Chi Genotype: ΔP$_{murA25}$::TT araC P$_{araBAD}$ murA ΔasdA27::TT araC P$_{araBAD}$ c2 Δ(wza-wcaM)-8 ΔrelA197:: araC P$_{araBAD}$ lacI TT ΔrecF126 ΔsifA26 ΔP$_{crp}^{+}$ ΔwaaL46 ΔpagL64::TT rhaRS P$_{rhaBAD}$ waaL pmi⁺ ΔaraBAD65::TT
Phenotype: Grows in L broth with 0.1% arabinose. DAP not required, asd complemented by plasmid. Needs 0.1% rhamnose for LPS. Expresses *Brucella melitensis* tf gene when induced with IPTG.
Description: pG8R250 was electroporated into χ12509 and grown on LB with 0.2% arabinose. Plasmid verified using PCR and sequencing. Western blot for tf verified expression with proper regulation. Smooth LPS verified using LPS gel with 0.1% rhamnose. Plasmid is stable for >50 generations.

| | |
|---|---|
| Plasmid Parent: pG8R114 | |
| Chi Parent: χ12495 | Source: RCIII Lab |
| Depositor: Jessica Jacob | |
| Plasmid: pG8R250 | Genus/Species: *Escherichia coli* |
| Host: χ6212 | Replicon: pBR ori |
| Size: 7396 bp | Gene cloned: tf |
| Marker(s): Asd$^+$:MurA$^+$ | |
| Tests: PCR & Sequencing | |

Description: Restriction Digestion (XhoI and PstI) and ligation used to insert *Brucella melitensis* tf gene from pG8R212 into parent pG8R114 plasmid.

Parent: pG8R114 Depositor: Jessica Jacob

Host genotype: 80d lacZ M15 deoR (lacZYA-argF)U169 supE44 gyrA96 recA1 relA1 endA1 asdA4 zhf-2::Tn10 hsdR17 (r m$^+$)

Host phenotype: Rec$^-$(UV$^s$) Asd$^-$ Lac$^-$ Nal$^r$ Tet$^s$

Plasmid Derivation:

Source: Reference/Duplicates:

```
Primer sequences:
pG8R_consensus_F-
                                  (SEQ ID NO: 33)
5' CAATTGATGGGTGAGCGTAGG 3' pG8R_consensus_R-
                                  (SEQ ID NO: 34)
5' TCTCTCATCCGCCAAAACAG 3'
```

-continued

```
tf_CO_F
                                  (SEQ ID NO: 39)
5' CCCTGAACGAAGGTCTGAAA 3' tf_CO_R
                                  (SEQ ID NO: 40)
5' CAGATTTACCTTCTTCCGCTTT 3'
```

E. pG8R248 with omp25 (FIGS. 38-40)

chi Number(pYA number): χ12509 (pG8R248)

Genus: *Salmonella* Species: *S. Typhimurium* UK-1

Chi Genotype: ΔP$_{murA25}$::TT araC P$_{araBAD}$ murA ΔasdA27::TT araC P$_{araBAD}$ c2 Δ(wza-wcaM)-8 ΔrelA197::araC P$_{araBAD}$ lacI TT ΔrecF126 ΔsifA26 ΔP$_{crp}$$^+$ ΔwaaL46 ΔpagL64::TT rhaRS P$_{rhaBAD}$ waaL pmi$^+$ ΔaraBAD65::TT Phenotype: Grows in L broth with 0.1% arabinose. DAP not required, asd complemented by plasmid. Needs 0.1% rhamnose for LPS. Expresses *Brucella melitensis* omp25 gene when induced with IPTG.

Description: pG8R248 was electroporated into χ12509 and grown on LB with 0.2% arabinose. Plasmid verified using PCR and sequencing. Western blot for omp25 verified expression with proper regulation. Smooth LPS verified using LPS gel with 0.1% rhamnose. Plasmid is stable for >50 generations.

| | |
|---|---|
| Plasmid Parent: pG8R114 | |
| Chi Parent: χ12495 | Source: RCIII Lab |
| Depositor: Jessica Jacob | |
| Plasmid: pG8R248 | Genus/Species: *Escherichia coli* |
| Host: χ6212 | Replicon: pBR ori |
| Size: 6511 bp | Gene cloned: omp25 |
| Marker(s): Asd$^+$:MurA$^+$ | |
| Tests: PCR & Sequencing | |

Description: Restriction Digestion (XhoI and PstI) and ligation used to insert *Brucella melitensis* omp25 gene from pG8R215 into parent pG8R114 plasmid.

Parent: pG8R114 Depositor: Jessica Jacob

Host genotype: 80d lacZ M15 deoR (lacZYA-argF)U169 supE44 gyrA96 recA1 relA1 endA1 asdA4 zhf-2::Tn10 hsdR17 (r$^-$ m$^+$)

Host phenotype: Rec$^-$(UV$^s$) Asd$^-$ Lac$^-$ Nal$^r$ Tet$^s$

Plasmid Derivation:

Source: Reference/Duplicates:

```
Primer sequences:
pG8R_consensus_F-
                                  (SEQ ID NO: 33)
5' CAATTGATGGGTGAGCGTAGG 3' pG8R_consensus_R-
                                  (SEQ ID NO: 34)
5' TCTCTCATCCGCCAAAACAG 3' omp25_CO_F
                                  (SEQ ID NO: 41)
5' TACTCTTGGGCTGGTGGGTA 3' omp25_CO_R
                                  (SEQ ID NO: 42)
5' CCGATACCAACACGGAAGTC 3'
```

Example 7

General Materials and Methods.

Bacterial strains, media and culture conditions. All PIESVs are derived from the highly virulent *S. Typhimurium* UK-1 strain (51). LB broth and agar (52) are used as complex media for propagation and plating of *Salmonella* strains. Purple broth (PB) (Difco), which is devoid of arabinose, mannose and rhamnose, is also used since LB but not PB contains low levels of these sugars. MacConkey agar with 0.5% lactose (Lac) and 0.1% arabinose (Ara) is used to enumerate PIESVs. Bacterial growth is monitored spectrophotometrically and by plating for colony counts. *B. melitensis* and *B. abortus* strains are grown in *Brucella* Broth (BB) and agar media in a 5% $CO_2$ atmosphere. Potato infusion agar (PIA) is used for determination of challenge strain titers in animal studies.

Molecular and genetic procedures. Methods for DNA isolation, restriction enzyme digestion, DNA cloning and use of PCR and real-time PCR for construction and verification of vectors and mutations are standard (53). All oligonucleotide and/or gene segment syntheses are done commercially with codon optimization to enhance translational efficiency in *Salmonella* and stabilize mRNA to "destroy" RNase E cleavage sites (54-56) to prolong mRNA half-life. Plasmid constructs are evaluated by DNA sequencing and for ability of sugar-regulated sequences to specify synthesis of proteins using gel electrophoresis and western blot analyses (57).

In vitro characterizations of PIESV-Bm strains. PIESVs encoding *B. melitensis* antigens are compared with empty vector controls for stability of plasmid maintenance, integrity and antigen synthesis ability when strains are grown in the presence of arabinose and DAP for 50 generations. In other cases, strains are grown in the presence of IPTG for constitutive synthesis of *B. melitensis* antigens to determine whether that results in instability or reduced growth rates. If observed, protein engineering is conducted to rectify the problem to achieve stable synthesis and good growth. Genetic attributes are confirmed by methods described above. Measurement of LPS core and O-antigen are performed after electrophoresis using silver-stained gels (58). The complete sensitivity of PIESVs to all antibiotics are evaluated that might ever be used to treat *Salmonella* infections. Metabolic attributes of bacterial strains are evaluated using API-20E tests.

Animal experimentation. Mice are used to evaluate attenuation, safety and immunogenicity of PIESVs delivering candidate *B. melitensis* protective antigens. Since animal studies at the ABSL3 containment level are very costly ($10/cage of mice/day), determination of whether PIESV constructs can prevent infection of mice from infection by the *B. abortus* S19 or RB51 strain or can increase the rate of clearance of these strains are tested in mice under ABSL2 containment. Based on the high degree of homology of the *B. melitensis* antigens to those in *B. abortus* (see Table 1) being evaluated for inducing protective immunity (~99%), protective immunity against these *B. abortus* strains should be observable. However, those skilled in the art will appreciate that the techniques disclosed herein support the construction of microorganisms engineered to express antigens to other *Brucella* species such as *B. abortus, B. suis* and *B. canis*. However, if necessary challenge studies of vaccinated mice are conducted with either the *B. melitensis* vaccine Rev1 or the wild-type 16M strain under ABSL3 containment. Equal numbers of female and male BALB/c mice, ages 6-8 weeks, are used in each experiment in the current study to obtain data from both genders. Mice are typically held in quarantine one-week for acclimation prior to immunization. PIESV strains are grown in LB broth with necessary supplements to an $OD_{600}$ of ~0.9, sedimented by centrifugation at room temperature and suspended in PBS at densities of $5 \times 10^{10}$ CFU/ml to enable i.n. doses of up to $1 \times 10^9$ CFU to be administered in 20 μl per mouse. Generally, doses of $10^6$ to $10^7$ CFU are adequate to induce maximum immune responses after i.n. vaccination. Animals are housed at the appropriate containment level in ventilated micro-isolator caging for immunization and challenge studies. When desired, sera and mucosal fluids are collected for quantitation of specific IgG and SIgA antibodies at two-week intervals. In other studies, measurement of increases in intracellular IFN-γ by peripheral blood TCRβ$^+$ CD4 or CD8$^+$ T cells harvested in gradient-isolated mononuclear cells three weeks after immunization is conducted. Immunized mice are i.n. challenged at 4 weeks after immunization with doses of vaccine strains S19 or RB51 (or, if necessary, with *B. melitensis* Rev1 of 16M-LacZ as previously described (59)). Spleens and lungs are harvested from $CO_2$ euthanized mice, weighed, and homogenized in water to compare the extent of tissue colonization and persistence of the challenge strain and the vaccine strain (if any) by plating lysate dilutions on PIA plates at 37° C. under 5% $CO_2$ (59).

An evaluation will be conducted of the ability of the most efficacious PIESV strains in preventing *Brucella* infections in immunized mice tested for ability to prevent *Brucella*-induced abortion in pregnant guinea pigs. It should be noted that *Brucella* are unable to induce abortion in mice. Dunkin-Hartley guinea pigs (mostly females for pregnancy studies and a few males for breeding) weighing 250-300 g from Charles River are used for this purpose. Guinea pigs are acclimated for one week prior to being immunized subcutaneously in the inguinal region (60, 61) with candidate vaccine strains grown and prepared as described above.

Monitoring Immune Responses.
  i. Antigen preparation: *B. melitensis* enzymes and antigens synthesized by PIESVs as His-tagged proteins from recombinant *E. coli* BL21 are purified. *Salmonella* B group LPS O-antigen are obtained commercially. An *S. Typhimurium* outer membrane protein (SOMP) fraction (isolated from a mutant strain χ9698 that is deficient in making LPS O-antigen and outer core, synthesis of nine fimbrial antigens synthesized in vitro and flagella and has a modified lipid A that is non-inflammatory) has been prepared. Extracts (heat-killed) are generated of S19, RB51, Rev1 and wild-type *S. Typhimurium* UK-1. These antigens are used as controls in western blots and for immunoassays as described below.
  ii. ELISA: Serum antibodies are measured in blood collected by submandibular bleeding and mucosal antibodies as extracted from nasal, intestinal and vaginal secretions. Sera and secretions are monitored in individual mice. A doubling dilution method is employed with the end point titer being the dilution giving an $OD_{450}$ three times that for the reagent or unimmunized animal control. SIgA titers against the various antigens will are also monitored by ELISA (62, 63). To distinguish between Th1 and Th2 responses, titers of IgG1 and IgG2a are determined. These methods have been described previously (43, 64). Also employed is a fluorescent covalent microsphere immunoassay (FCMIA) technology to analyze the immune responses as a replacement for using ELISA. This assay can measure numerous analytes by using uniquely dually stained microspheres for the measurement of up to 50 analytes simultaneously (65). This assay is useful for immunophenotyping and for measuring levels of relevant cytokines induced in immunized mice. Immune sera are also tested for reaction with extracts of different *Brucella* species separated by PAGE by western blot analyses.

iii. Cellular immune responses: Spleens of immunized mice are removed from euthanized animals in a sterile condition. To assess cellular immune responses, spleens are minced and homogenized with a syringe in 10 ml cold PBS containing 5 mM ethylene diamine tetraacetic acid (PBS-EDTA). The cells are washed twice with PBS-EDTA and mononuclear cells (MNCs) are isolated by Ficoll-Paque (GE Healthcare, Uppsala, Sweden) discontinuous gradient centrifugation. The cells are harvested in complete medium (RPMI 1640) supplemented with 2 mM L-glutamine, 100 U/ml penicillin, 100 µg/ml streptomycin and 10% heat inactivated FBS. The cell concentration is adjusted to $2 \times 10^6$ in 2 ml of complete RPMI 1640 medium and then plated in 24-well flat-bottom plates. Cells are then be treated with a specific relevant antigen or a heat-killed Rev 1 extract and incubated at 37° C. in 5% $CO_2$ for 48 h. Control wells receive PBS instead of the antigen. Supernatants are collected after 48 h and stored at −70° C. Levels of IFN-γ, IL-17, TNFα and IL-4 is measured.

iv. Flow cytometry analyses: Flow cytometry is used to simultaneously detect production of intracellular IFN-γ, TNF-α, IL-10, IL-17, IL-22, and Foxp3 by CD4+ and CD8+ T cells. For staining of intracellular IFN-γ, $1.5 \times 10^6$ splenocytes from immunized animals are seeded into a 24-well tissue culture plate. All samples are re-stimulated with 4 µg/ml of antigen. Three days after the addition of stimuli, Golgi plug (BD Pharmingen) is added for 6 h to stop cytokine secretion. Splenocytes are stained with fluorochrome-conjugated monoclonal antibodies specific for cell surface molecules, namely CD4 and CD8, to phenotypically identify cytokine-secreting lymphocytes. Cells are then fixed in 2% p-formaldehyde solution and permeabilized to allow monoclonal antibodies access to the cytosol. After blocking Fc receptors and permeabilization, intracellular staining is performed using allophycocyanin-conjugated anti-IFN-γ antibodies and reagents provided with the Cytofix/Cytoperm Plus Kit (BD Pharmingen) in accordance with manufacturer guidelines. Data is collected on a BD FACSCanto II analyzed using BD FACSDiva™ software at the new Flow set-up in the Department of Infectious Disease and Immunology core facility, College of Veterinary Medicine, University of Florida.

Statistical analyses. All results are analyzed using the most appropriate statistical test from the SAS program to evaluate the relative significance or lack thereof of results obtained.

TABLE 2

Plasmids created for vaccine evaluation and development.

| Clone Bank Designation | Parent Vector | Gene/Size | Protein Synthesized in E. coli χ6212 (pYA232) | Protein Synthesized in Salmonella χ12509 |
|---|---|---|---|---|
| pG8R110 | NA | None | NA | NA |
| pG8R111 | NA | None | NA | NA |
| pG8R114 | NA | None | NA | NA |
| pG8R240 | pG8R110 | omp25/570 bp | No | No |
| pG8R241 | | omp22/564 bp | Yes | Yes |
| pG8R242 | | tf/1455 bp | Yes | No |
| pG8R243 | | bp26/666np | Yes | Yes |
| pG8R244 | pG8R111 | omp25/570 bp | No | No |
| pG8R245 | | omp22/564 bp | No | No |
| pG8R246 | | tf/1455 bp | No | No |
| pG8R247 | | bp26/666np | Yes | No |
| pG8R248 | pG8R114 | omp25/570 bp | No | Yes |
| pG8R249 | | omp22/564 bp | Yes | No |
| pG8R250 | | tf/1455 bp | Yes | Yes |
| pG8R251 | | bp26/666np | Yes | Yes |

TABLE 3

Plasmids created specifying fusion and non fusion antigens.

| pG8R # | Gene (Brucella) | Parent vector | ori |
|---|---|---|---|
| 231 | tf-bp26-omp31 | pG8R111 | pBR |
| 258 | btuB | pG8R111 | pBR |
| 259 | BLS-L7/L12-Cu/Zn SOD | pG8R111 | pBR |
| 260 | flgK | pG8R111 | pBR |
| 261 | omp31 | pG8R114 | pBR |

TABLE 4

| Antigen name | Gene/ Gene ID | Function | Signal peptide/ aa cute site | bp/aa (after deletion of signal sequence) | GC content before/after codon optimization | Percent Identity compared to *Brucella abortus* homologs | Reference |
|---|---|---|---|---|---|---|---|
| Omp 31 | omp31/ 29595531 | Outer Membrane Protein | Between aa 19 and 20 | 666/222 | 56.2/48 | 65% | (30, 31) |
| BtuB | btuB/ 29593454 | TonB-dependent receptor | NO | 1794/598 | 56.3/52% | 99% | (28) |
| FlgK | flgK/ 29595162 | Flagellar hook-associated protein FlgK | NO | 1455/485 | 58.1/51.2% | 99% | (28) |
| BLS | KJ401344.1 | lumazine synthase | NO | 477bp/158aa | 57/49 | 100% | (34, 35) |
| L7/L12 | L27819.1 | ribosomal protein | NO | 468bp/124aa | 55.3/49 | 100% | (36) |
| Cu/Zn | AGZ13506.1 | superoxide dismutase | NO | 522/172aa | 53/49 | 100% | (37) |

REFERENCES

1. Dean A S, Crump L, Greter H, Hattendorf J, Schelling E, Zinsstag J. Clinical manifestations of human brucellosis: a systematic review and meta-analysis. Plos Neglect Trop D. 2012; 6(12):e1929. Epub 2012/12/14. doi: 10.1371/journal.pntd.0001929. PubMed PMID: 23236528; PMCID: 3516581.
2. Corbel M J. Brucellosis: an overview. Emerg Infect Dis. 1997; 3(2):213-21. Epub 1997/04/01. doi: 10.3201/eid0302.970219. PubMed PMID: 9204307; PMCID: 2627605.
3. Pappas G, Papadimitriou P, Akritidis N, Christou L, Tsianos E V. The new global map of human brucellosis. The Lancet Infectious diseases. 2006; 6(2):91-9. Epub 2006/01/28. doi: 10.1016/S1473-3099(06)70382-6. PubMed PMID: 16439329.
4. Kruse H, kirkemo A M, Handeland K. Wildlife as source of zoonotic infections. Emerg Infect Dis. 2004; 10(12): 2067-72. Epub 2005/01/25. doi: 10.3201/eid1012.040707. PubMed PMID: 15663840; PMCID: PMC3323390.
5. Franz D R, Jahrling P B, Friedlander A M, McClain D J, Hoover D L, Bryne W R, Pavlin J A, Christopher C W, Eitzen E M. Clinical recognition and management of patients exposed to biological warfare agents. Jama-Journal of the American Medical Association. 1997; 278(5): 399-411. doi: DOI 10.1001/jama.278.5.399. PubMed PMID: ISI:A1997XN51800032.
6. Yang X, Skyberg J A, Cao L, Clapp B, Thornburg T, Pascual D W. Progress in *Brucella* vaccine development. Frontiers in biology. 2013; 8(1):60-77. doi: 10.1007/s11515-012-1196-0. PubMed PMID: 23730309; PMCID: 3666581.
7. Perkins S D, Smither S J, Atkins H S. Towards a *Brucella* vaccine for humans. Fems Microbiol Rev. 2010; 34(3): 379-94. Epub 2010/02/26. doi: 10.1111/j.1574-6976.2010.00211.x. PubMed PMID: 20180858.
8. Nicoletti P. Vaccination against *Brucella*. Advances in biotechnological processes. 1990; 13:147-68. Epub 1990/01/01. PubMed PMID: 2185782.
9. Beckett F W, MacDiarmid S C. The effect of reduced-dose *Brucella abortus* strain 19 vaccination in accredited dairy herds. The British veterinary journal. 1985; 141(5):507-14. Epub 1985/09/01. doi: 10.1016/0007-1935(85)90046-6. PubMed PMID: 4063777.
10. Blasco J M, Marin C M, Barberan M, Moriyon I, Diaz R. Immunization with *Brucella melitensis* Rev-1 against *Brucella ovis* infection of rams. Vet Microbiol. 1987; 14(4):381-92. doi: Doi 10.1016/0378-1135(87)90029-0. PubMed PMID: ISI:A1987K619100004.
11. Marianelli C, Ciuchini F, Tarantino M, Pasquali P, Adone R. Genetic bases of the rifampin resistance phenotype in *Brucella* spp. J Clin Microbiol. 2004; 42(12):5439-43. Epub 2004/12/08. doi: 10.1128/JCM.42.12.5439-5443.2004. PubMed PMID: 15583262; PMCID: 535235.
12. Franco M P, Mulder M, Gilman R H, Smits H L. Human brucellosis. The Lancet Infectious diseases. 2007; 7(12): 775-86. doi: 10.1016/S1473-3099(07)70286-4. PubMed PMID: 18045560.
13. Roy Curtiss, III, Zhang X, Wanda S-Y, Kang H Y, Konjufca V, Li Y, Gunn B, Wang S, Scarpellini G, Lee I S. Induction of host immune responses using *Salmonella*-vectored vaccines. Virulence Mechanisms of Bacterial Pathogens, Fourth Edition: American Society of Microbiology; 2007. p. 297-313.
14. Shi H, Santander J, Brenneman K E, Wanda S Y, Wang S, Senechal P, Sun W, Roland K L, Curtiss R, III. Live recombinant *Salmonella Typhi* vaccines constructed to investigate the role of rpoS in eliciting immunity to a heterologous antigen. PLoS One. 2010; 5(6):e11142. Epub 2010/06/30. doi: 10.1371/journal.pone.0011142. PubMed PMID: 20585446; PMCID: 2887840.
15. Wang S, Shi H, Li Y, Shi Z, Zhang X, Baek C H, Mothershead T, Curtiss R, III. A colanic acid operon deletion mutation enhances induction of early antibody responses by live attenuated *Salmonella* vaccine strains. Infect Immun. 2013; 81(9):3148-62. doi: 10.1128/IAI.00097-13. PubMed PMID: 23774599; PMCID: 3754205.
16. Clark-Curtiss J E, Curtiss R, 3rd. *Salmonella* Vaccines: Conduits for Protective Antigens. J Immunol. 2018; 200

(1):39-48. Epub 2017/12/20. doi: 10.4049/jimmunol.1600608. PubMed PMID: 29255088.
17. Kong W, Wanda S Y, Zhang X, Bollen W, Tinge S A, Roland K L, Curtiss R, III. Regulated programmed lysis of recombinant *Salmonella* in host tissues to release protective antigens and confer biological containment. Proc Natl Acad Sci USA. 2008; 105(27):9361-6. Epub 2008/07/09. doi: 0803801105 [pii] 10.1073/pnas.0803801105. PubMed PMID: 18607005; PMCID: 2453710.
18. Curtiss R, 3rd, Wanda S Y, Gunn B M, Zhang X, Tinge S A, Ananthnarayan V, Mo H, Wang S, Kong W. *Salmonella enterica* serovar *typhimurium* strains with regulated delayed attenuation in vivo. Infection and immunity. 2009; 77(3):1071-82. doi: 10.1128/IAI.00693-08. PubMed PMID: 19103774; PMCID: 2643627.
19. Juárez-Rodríguez M D, Yang J, Kader R, Alamuri P, Curtiss R, 3rd, Clark-Curtiss J E. Live attenuated *Salmonella* vaccines displaying regulated delayed lysis and delayed antigen synthesis to confer protection against *Mycobacterium tuberculosis*. Infect Immun. 2012; 80(2): 815-31. Epub 2011/12/07. doi: 10.1128/iai.05526-11. PubMed PMID: 22144485; PMCID: PMC3264310.
20. Torres-Escobar A, Juárez-Rodríguez M D, Gunn B M, Branger C G, Tinge S A, Curtiss R, 3rd. Fine-tuning synthesis of *Yersinia pestis* LcrV from runaway-like replication balanced-lethal plasmid in a *Salmonella enterica* serovar *typhimurium* vaccine induces protection against a lethal *Y. pestis* challenge in mice. Infect Immun. 2010; 78(6):2529-43. Epub 2010/03/24. doi: 10.1128/iai.00005-10. PubMed PMID: 20308296; PMCID: PMC2876574.
21. Sanapala S, Rahav H, Patel H, Sun W, Curtiss R, III. Multiple antigens of *Yersinia pestis* delivered by live recombinant attenuated *Salmonella* vaccine strains elicit protective immunity against plague. Vaccine. 2016; 34(21):2410-6. doi: 10.1016/j.vaccine.2016.03.094. PubMed PMID: 27060051.
22. Xin W, Wanda S Y, Li Y, Wang S, Mo H, Curtiss R, 3rd. Analysis of type II secretion of recombinant pneumococcal PspA and PspC in a *Salmonella enterica* serovar *Typhimurium* vaccine with regulated delayed antigen synthesis. Infect Immun. 2008; 76(7):3241-54. Epub 2008/05/07. doi: 10.1128/iai.01623-07. PubMed PMID: 18458067; PMCID: PMC2446722.
23. Liu Q, Liu Q, Yi J, Liang K, Hu B, Zhang X, Curtiss R, III, Kong Q. Outer membrane vesicles from flagellin-deficient *Salmonella enterica* serovar *Typhimurium* induce cross-reactive immunity and provide cross-protection against heterologous *Salmonella* challenge. Sci Rep. 2016; 6:34776. doi: 10.1038/srep34776. PubMed PMID: 27698383; PMCID: PMC5048178.
24. Kong W, Clark-Curtiss J, Curtiss R, 3rd. Utilizing *Salmonella* for antigen delivery: the aims and benefits of bacterial delivered vaccination. Expert Rev Vaccines. 2013; 12(4):345-7. Epub 2013/04/09. doi: 10.1586/erv.13.7. PubMed PMID: 23560914.
25. Kong W, Brovold M, Koeneman B A, Clark-Curtiss J, Curtiss R, III. Turning self-destructing *Salmonella* into a universal DNA vaccine delivery platform. Proc Natl Acad Sci USA. 2012; 109(47):19414-9. doi: 10.1073/pnas.1217554109. PubMed PMID: 23129620; PMCID: 3511069.
26. Gunn B M, Wanda S Y, Burshell D, Wang C, Curtiss R, 3rd. Construction of recombinant attenuated *Salmonella enterica* serovar *typhimurium* vaccine vector strains for safety in newborn and infant mice. Clin Vaccine Immunol. 2010; 17(3):354-62. Epub 2010/01/08. doi: 10.1128/cvi.00412-09. PubMed PMID: 20053874; PMCID: PMC2837962.
27. Kong Q, Six D A, Roland K L, Liu Q, Gu L, Reynolds C M, Wang X, Raetz C R, Curtiss R, 3rd. *Salmonella* synthesizing 1-dephosphorylated [corrected] lipopolysaccharide exhibits low endotoxic activity while retaining its immunogenicity. J Immunol. 2011; 187(1):412-23. Epub 2011/06/03. doi: 10.4049/jimmunol.1100339. PubMed PMID: 21632711; PMCID: PMC3119770.
28. Gomez G, Pei J, Mwangi W, Adams L G, Rice-Ficht A, Ficht T A. Immunogenic and invasive properties of *Brucella melitensis* 16M outer membrane protein vaccine candidates identified via a reverse vaccinology approach. PloS one. 2013; 8(3):e59751. doi: 10.1371/journal.pone.0059751. PubMed PMID: 23533646; PMCID: 3606113.
29. Bowden R A, Cloeckaert A, Zygmunt M S, Dubray G. Evaluation of immunogenicity and protective activity in BALB/c mice of the 25-kDa major outer-membrane protein of *Brucella melitensis* (Omp25) expressed in *Escherichia coli*. Journal of medical microbiology. 1998; 47(1): 39-48. doi: 10.1099/00222615-47-1-39. PubMed PMID: 9449948.
30. Ghasemi A, Salari M H, Zarnani A H, Pourmand M R, Ahmadi H, Mirshafiey A, Jeddi-Tehrani M. Immune reactivity of *Brucella melitensis*-vaccinated rabbit serum with recombinant Omp31 and DnaK proteins. Iran J Microbiol. 2013; 5(1):19-23. Epub 2013/03/08. PubMed PMID: 23467315; PMCID: PMC3577567.
31. Ghasemi A, Jeddi-Tehrani M, Mautner J, Salari M H, Zarnani A H. Simultaneous immunization of mice with Omp31 and TF provides protection against *Brucella melitensis* infection. Vaccine. 2015; 33(42):5532-8. doi: 10.1016/j.vaccine.2015.09.013. PubMed PMID: 26384448.
32. Yang X, Hudson M, Walters N, Bargatze R F, Pascual D W. Selection of protective epitopes for *Brucella melitensis* by DNA vaccination. Infection and immunity. 2005; 73(11):7297-303. doi: 10.1128/IAI.73.11.7297-7303.2005. PubMed PMID: 16239526; PMCID: 1273852.
33. Ghasemi A, Ranjbar R, Amani J. In silico analysis of chimeric TF, Omp31 and BP26 fragments of *Brucella melitensis* for development of a multi subunit vaccine candidate. Iran J Basic Med Sci. 2014; 17(3):172-80. Epub 2014/05/23. PubMed PMID: 24847419; PMCID: PMC4016687.
34. Velikovsky C A, Goldbaum F A, Cassataro J, Estein S, Bowden R A, Bruno L, Fossati C A, Giambartolomei G H. *Brucella lumazine* synthase elicits a mixed Th1-Th2 immune response and reduces infection in mice challenged with *Brucella* abortus 544 independently of the adjuvant formulation used. Infect Immun. 2003; 71(10): 5750-5. Epub 2003/09/23. PubMed PMID: 14500496; PMCID: PMC201088.
35. Sciutto E, Toledo A, Cruz C, Rosas G, Meneses G, Laplagne D, Ainciart N, Cervantes J, Fragoso G, Goldbaum F A. *Brucella* spp. lumazine synthase: a novel antigen delivery system. Vaccine. 2005; 23(21):2784-90. Epub 2005/03/23. doi: 10.1016/j.vaccine.2004.11.043. PubMed PMID: 15780726.
36. Oliveira S C, Splitter G A. Immunization of mice with recombinant L7/L12 ribosomal protein confers protection against *Brucella abortus* infection. Vaccine. 1996; 14(10): 959-62. Epub 1996/07/01. PubMed PMID: 8873388.

37. Sung K Y, Jung M, Shin M K, Park H E, Lee J J, Kim S, Yoo H S. Induction of immune responses by two recombinant proteins of *Brucella abortus*, outer membrane proteins 2b porin and Cu/Zn superoxide dismutase, in mouse model. J Microbiol Biotechnol. 2014; 24(6): 854-61. Epub 2014/03/13. PubMed PMID: 24608566.

38. Jiang Y, Mo H, Willingham C, Wang S, Park J Y, Kong W, Roland K L, Curtiss R, III. Protection Against Necrotic Enteritis in Broiler Chickens by Regulated Delayed Lysis *Salmonella* Vaccines. Avian diseases. 2015; 59(4):475-85. doi: 10.1637/11094-041715-Reg. PubMed PMID: 26629620.

39. Juárez-Rodríguez M D, Yang J, Kader R, Alamuri P, Curtiss R, III, Clark-Curtiss J E. Live attenuated *Salmonella* vaccines displaying regulated delayed lysis and delayed antigen synthesis to confer protection against *Mycobacterium tuberculosis*. Infect Immun. 2012; 80(2): 815-31. doi: 10.1128/IAI.05526-11. PubMed PMID: 22144485; PMCID: 3264310.

40. Wang S, Li Y, Scarpellini G, Kong W, Shi H, Baek C H, Gunn B, Wanda S Y, Roland K L, Zhang X, Senechal-Willis P, Curtiss R, 3rd. *Salmonella* vaccine vectors displaying delayed antigen synthesis in vivo to enhance immunogenicity. Infection and immunity. 2010; 78(9): 3969-80. doi: 10.1128/IAI.00444-10. PubMed PMID: 20605977; PMCID: 2937466.

41. Ashraf S, Kong W, Wang S, Yang J, Curtiss R, III. Protective cellular responses elicited by vaccination with influenza nucleoprotein delivered by a live recombinant attenuated *Salmonella* vaccine. Vaccine. 2011; 29(23): 3990-4002. doi: 10.1016/j.vaccine.2011.03.066. PubMed PMID: 21466806; PMCID: 3092860.

42. Xin W, Wanda S Y, Zhang X, Santander J, Scarpellini G, Ellis K, Alamuri P, Curtiss R, 3rd. The Asd(+)-DadB(+) dual-plasmid system offers a novel means to deliver multiple protective antigens by a recombinant attenuated *Salmonella* vaccine. Infection and immunity. 2012; 80(10):3621-33. doi: 10.1128/IAI.00620-12. PubMed PMID: 22868499; PMCID: 3457550.

43. Li Y, Wang S, Xin W, Scarpellini G, Shi Z, Gunn B, Roland K L, Curtiss R, III. A sopB deletion mutation enhances the immunogenicity and protective efficacy of a heterologous antigen delivered by live attenuated *Salmonella enterica* vaccines. Infect Immun. 2008; 76(11): 5238-46. PubMed PMID: 18765737.

44. Ameiss K, Ashraf S, Kong W, Pekosz A, Wu W H, Milich D, Billaud J N, Curtiss R, III. Delivery of woodchuck hepatitis virus-like particle presented influenza M2e by recombinant attenuated *Salmonella* displaying a delayed lysis phenotype. Vaccine. 2010; 28(41):6704-13. doi: 10.1016/j.vaccine.2010.07.083. PubMed PMID: 20691653; PMCID: 2939226.

45. Nakayama K, Kelly S M, Curtiss R, III Construction of an Asd+ expression-cloning Vector: stable maintenance and high level expression of cloned genes in a *Salmonella* vaccine strain. Nat Biotech. 1988; 6(6):693-7.

46. Ahman H, Kayhty H, Vuorela A, Leroy O, Eskola J. Dose dependency of antibody response in infants and children to pneumococcal polysaccharides conjugated to tetanus toxoid. Vaccine. 1999; 17(20-21):2726-32. PubMed PMID: 10418924.

47. Siegrist C. Vaccine immunology. In: Plotkin S A, Orenstein W, Offit P A, editors. Vaccines. 6th ed: Elsevier Inc.; 2013. p. 14-32.

48. Sun W, Olinzock J, Wang S, Sanapala S, Curtiss R, III. Evaluation of YadC protein delivered by live attenuated *Salmonella* as a vaccine against plague. Pathogens and disease. 2014; 70(2):119-31. doi: 10.1111/2049-632X.12076. PubMed PMID: 23913628; PMCID: 4028040.

49. Muralinath M, Kuehn M J, Roland K L, Curtiss R, 3rd. Immunization with *Salmonella enterica* serovar *Typhimurium*-derived outer membrane vesicles delivering the pneumococcal protein PspA confers protection against challenge with *Streptococcus pneumoniae*. Infect Immun. 2011; 79(2):887-94. Epub 2010/12/01. doi: 10.1128/iai.00950-10. PubMed PMID: 21115718; PMCID: PMC3028854.

50. Konjufca V, Jenkins M, Wang S, Juárez-Rodríguez M D, Curtiss R, III. Immunogenicity of recombinant attenuated *Salmonella enterica* serovar *Typhimurium* vaccine strains carrying a gene that encodes *Eimeria tenella* antigen SO7. Infect Immun. 2008; 76(12):5745-53. Epub 2008/09/24. doi: IAI.00897-08 [pii] 10.1128/IAI.00897-08. PubMed PMID: 18809658; PMCID: 2583560.

51. Curtiss R, III., Porter S B, Munson M, Tinge S A, Hassan J O, Gentry-Weeks C, Kelly S M. Nonrecombinant and recombinant avirulent *Salmonella* live vaccines for poultry. In: Blankenship L C, Bailey J H S, Cox N A, Stern N J, Meinersmann R J, editors. Colonization control of human bacterial enteropathogens in poultry. New York Academic Press 1991. p. 169-98.

52. Bertani G. Studies on lysogenesis. I. The mode of phage liberation by lysogenic *Escherichia coli*. J Bacteriol. 1951; 62(3):293-300. Epub 1951/09/01. PubMed PMID: 14888646.

53. Sambrook J, Russell D W. Molecular cloning: a laboratory manual. 3rd ed. Cold Spring Harbor, N.Y.: Cold Spring Harbor Laboratory Press; 2001.

54. Ehretsmann C P, Carpousis A J, Krisch H M. Specificity of *Escherichia coli* endoribonuclease RNase E: in vivo and in vitro analysis of mutants in a bacteriophage T4 mRNA processing site. Genes Dev. 1992; 6(1)149-59. Epub 1992/01/01. PubMed PMID: 1730408.

55. McDowall K J, Kaberdin V R, Wu S W, Cohen S N, Lin-Chao S. Site-specific RNase E cleavage of oligonucleotides and inhibition by stem-loops. Nature. 1995; 374(6519):287-90. Epub 1995/03/16. doi: 10.1038/374287a0. PubMed PMID: 7533896.

56. Lin-Chao S, Wong T T, McDowall K J, Cohen S N. Effects of nucleotide sequence on the specificity of rne-dependent and RNase E-mediated cleavages of RNA I encoded by the pBR322 plasmid. J Biol Chem. 1994; 269(14):10797-803. Epub 1994/04/08. PubMed PMID: 7511607.

57. Kong Q, Liu Q, Roland K L, Curtiss R, III. Regulated delayed expression of rfaH in an attenuated *Salmonella enterica* serovar *Typhimurium* vaccine enhances immunogenicity of outer membrane proteins and a heterologous antigen. Infect Immun. 2009; 77(12):5572-82. Epub 2009/10/07. doi: IA1.00831-09 [pii] 10.1128/IAI.00831-09. PubMed PMID: 19805538; PMCID: 2786485.

58. Hitchcock P J, Brown T M. Morphological heterogeneity among *Salmonella* lipopolysaccharide chemotypes in silver-stained polyacrylamide gels. Journal of bacteriology. 1983; 154(1):269-77. Epub 1983/04/01. PubMed PMID: 6187729.

59. Yang X, Clapp B, Thornburg T, Hoffman C, Pascual D W. Vaccination with a DeltanorD DeltaznuA *Brucella abortus* mutant confers potent protection against virulent challenge. Vaccine. 2016; 34(44):5290-7. doi: 10.1016/j.vaccine.2016.09.004. PubMed PMID: 27639282; PMCID: 5053898.

60. Herzberg M, Elberg S S. Immunization against *Brucella* infection. III. Response of mice and guinea pigs to injection of viable and nonviable suspensions of a streptomycin-dependent mutant of *Brucella melitensis*. J Bacteriol. 1955; 69(4):432-5. Epub 1955/04/01. PubMed PMID: 14367297; PMCID: PMC357555.
61. Thornton D H, Muskett J C. The use of laboratory animals in the potency test of *Brucella abortus* S19 vaccine. Response of guinea-pigs to graduated doses of vaccine and challenge. J Comp Pathol. 1972; 82(2):201-8. Epub 1972/04/01. PubMed PMID: 4625200.
62. Engvall E, Perlmann P. Enzyme-linked immunosorbent assay (ELISA). Quantitative assay of immunoglobulin G. Immunochemistry. 1971; 8(9):871-4. Epub 1971/09/01. PubMed PMID: 5135623.
63. Van Weemen B K, Schuurs A H. Immunoassay using antigen-enzyme conjugates. FEBS Lett. 1971; 15(3):232-6. Epub 1971/06/24. doi: 0014-5793(71)80319-8 [pii]. PubMed PMID: 11945853.
64. Kang H Y, Srinivasan J, Curtiss R, III. Immune responses to recombinant pneumococcal PspA antigen delivered by live attenuated *Salmonella enterica* serovar *Typhimurium* vaccine. Infect Immun. 2002; 70(4):1739-49.
65. Biagini R E, Sammons D L, Smith J P, MacKenzie B A, Striley C A, Semenova V, Steward-Clark E, Stamey K, Freeman A E, Quinn C P, Snawder J E. Comparison of a multiplexed fluorescent covalent microsphere immunoassay and an enzyme-linked immunosorbent assay for measurement of human immunoglobulin G antibodies to anthrax toxins. Clinical and diagnostic laboratory immunology. 2004; 11(1):50-5. Epub 2004/01/13. PubMed PMID: 14715544; PMCID: 321348.
66. Clapp B, Yang X, Thornburg T, Walters N, Pascual D W. Nasal vaccination stimulates CD8(+) T cells for potent protection against mucosal *Brucella melitensis* challenge. Immunol Cell Biol. 2016; 94(5):496-508. Epub 2016/01/12. doi: 10.1038/icb.2016.5. PubMed PMID: 26752510; PMCID: PMC4879022.
67. Lalsiamthara J, Gogia N, Goswami T K, Singh R K, Chaudhuri P. Intermediate rough *Brucella abortus* S19Deltaper mutant is DIVA enable, safe to pregnant guinea pigs and confers protection to mice. Vaccine. 2015; 33(22):2577-83. Epub 2015/04/15. doi: 10.1016/j.vaccine.2015.04.004. PubMed PMID: 25869887.
68. Miranda K L, Dorneles E M, Poester F P, Martins Filho P S, Pauletti R B, Lage A P. Different resistance patterns of reference and field strains of *Brucella abortus*. Braz J Microbiol. 2015; 46(1):265-9. Epub 2015/07/30. doi: 10.1590/s1517-838246120130625. PubMed PMID: 26221116; PMCID: PMC4512078.

What is claimed is:

1. An attenuated microorganism that comprises an expression construct engineered to synthesize two or more *Brucella* proteins, the expression construct comprising two or more polynucleotide sequences each encoding at least one of the two or more *Brucella* proteins, wherein upon administration to an animal host, the microorganism expresses and delivers the two or more *Brucella* proteins to the animal host,
   wherein the attenuated microorganism is a Enterobacteriaceae family bacterium that comprises
   a. one or more mutations conferring regulated delayed attenuation within the animal host selected from $\Delta P_{murA}$::TT araC $P_{araBAD}$ murA gene, $\Delta$asdA::TT araC $P_{araBAD}$ c2, $\Delta$waaL, $\Delta$paqL:TT rhaRS $P_{rhaBAD}$ waaL; and
   b. a genetic modification to enable regulated delayed synthesis of the one or more *Brucella* proteins encoded by the expression construct in the attenuated microorganism within the animal host, the genetic modification comprising a $\Delta$relA::araC $P_{araBAD}$lacI TT deletion-insertion mutation in the attenuated microorganism and a LacI regulatable promoter in the expression construct to drive expression of the two or more polynucleotide sequences;
   wherein the expression construct comprises a plasmid that comprises an asdA gene and/or a murA gene whose expression is driven by a presence of arabinose; and
   wherein the two or more *Brucella* proteins are selected from Omp22, Omp25, Omp31, Tf, Bp26, BtuB, FlgK, BLS, L7/L12 and Cu/Zn SOD, or codon-optimized versions thereof.

2. The attenuated microorganism claim 1 wherein the bacterium of the family Enterobacteriaceae is a *Salmonella enterica* bacterium.

3. The attenuated microorganism of claim 1 wherein the two or more selected polynucleotides are codon optimized to enable high-level synthesis in the microorganism, wherein the codon-optimized polynucleotides comprise reduced GC content relative to wild-type sequences in *Brucella*.

4. The attenuated microorganism of claim 1 wherein the expression construct further comprises an encoded secretory signal sequence associated with each of the two or more polynucleotide sequences such that a secretory signal molecule encoded by the secretory signal sequence is fused with the two or more *Brucella* proteins to facilitate secretion of the two or more *Brucella* proteins from the microorganism via a Type 2 secretion system.

5. The attenuated microorganism of claim 1 wherein the expression construct further comprises a secretory signal sequence associated with each of the two or more polynucleotide sequences such that a secretory signal molecule encoded by the secretory signal sequence is fused with the two or more *Brucella* proteins to facilitate secretion of the two or more *Brucella* proteins from the microorganism via a Type 3 secretion system.

6. The attenuated microorganism of claim 1, wherein the microorganism comprises a sifA mutation to enable the microorganism to escape the endosome after entry into a cell within the animal host such that synthesized proteins can be delivered by lysis in the cytosol of the cell to enhance induction of CD8-dependent cellular immunities.

7. A vaccine composition comprising the microorganism of claim 1 and a pharmaceutically acceptable carrier.

8. A method of eliciting an immune response against *Brucella*, the method comprising administrating a vaccine composition of claim 7 to an animal host.

9. The attenuated microorganism of claim 1, wherein the one or more mutations conferring regulated delayed attenuation within the animal host comprises $\Delta$waaL and/or $\Delta$pagL::TT rhaRS PrhaBAD waaL.

10. The attenuated microorganism of claim 1, wherein the two or more *Brucella* proteins are selected from Omp22, Omp25, Omp31, Tf, Bp26, BtuB, FlgK, and L7/L12.

* * * * *

SEQUENCE LISTING

```
<160> NUMBER OF SEQ ID NOS: 42

<210> SEQ ID NO 1
<211> LENGTH: 6607
<212> TYPE: DNA
<213> ORGANISM: Artificial Sequence
<220> FEATURE:
<223> OTHER INFORMATION: Synthetic: FIG. 27: Sequence for
      pG8R251(pG8R114 with bp26)

<400> SEQUENCE: 1
ggatcttccg gaagaccttc cattctgaaa tgagctgttg acaattaatc atccggctcg     60
tataatgtgt ggaattgtga gcggataaca atttcacaca ggaaacagac catgaaaaaa    120
caacatttcc gtgtcgccct tattcccttt tttgcggcat tttgccttcc tgtttttgct    180
cacccagaaa cgctggtgaa agtaaaagat gctgaactcg agcaggaaaa ccagatgacc    240
acccagccgg cgcgtatcgc tgttaccggt gaaggtatga tgaccgcttc tccggacatg    300
gctatcctga acctgtctgt tctgcgtcag gcgaaaaccg cgcgtgaagc gatgaccgcg    360
aacaacgaag ctatgaccaa agttctggac gcgatgaaaa aagcgggtat cgaagaccgt    420
gacctccaga ccggtggtat caacatccag ccgatctacg tttacccgga cgacaaaaac    480
aacctgaaag aaccgaccat caccggttac tctgtttcta cctctctgac cgttcgtgtt    540
cgtgaactgg cgaacgttgg taaaatcctg gacgaatctg ttaccctggg tgttaaccag    600
ggtggtgacc tgaacctggt taacgacaac ccgtctgctg ttatcaacga agcgcgtaaa    660
cgtgctgttg ctaacgctat cgctaaagcg aaaaccctgg ctgacgctgc gggtgttggt    720
ctgggtcgtg ttgttgaaat ctctgaactg tctcgtccgc cgatgccgat gccgatcgcg    780
cgtggtcagt tccgtaccat gctggcggct gctccggaca actctgttcc gatcgctgct    840
ggtgaaaact cttacaacgt ttctgttaac gttgttttcg aaatcaaacc taggcaccac    900
caccaccacc accctaggta actgcagcca agctcccaag cttggctgtt ttggcggatg    960
agagaagatt ttcagcctga tacagattaa atcagaacgc agaagcggtc tgataaaaca   1020
```

```
gaatttgcct ggcggcagta gcgcggtggt cccacctgac cccatgccga actcagaagt    1080
gaaacgccgt agcgccgatg gtagtgtggg gtctccccat gcgagagtag ggaactgcca    1140
ggcatcaaat aaaacgaaag gctcagtcga aagactgggc ctttcgtttt atctgttgtt    1200
tgtcggtgaa cgctctcctg agtaggacaa atccgccggg agcggatttg aacgttgcga    1260
agcaacggcc cggagggtgg cgggcaggac gcccgccata aactgccagg catcaaatta    1320
agcagaaggc catcctgacg gatggccttt ttgcgtttct acaaactctt ttgtttattt    1380
ttctaaatac attcaaatat gtatccgctc atgagacaat aaccctgata aatgcttcaa    1440
taatggaaga tcttccaaca tcacaggtaa acagaaacgt cgggtcgatc gggaaattct    1500
ttcccggacg gcgcggggtt gggcaagccg caggcgcgtc agtgcttttta gcgggtgtcg    1560 gggcgcagcc atgacccagt cacgtagcga tagcggagtg tatactggct taactatgcg    1620
gcatcagagc agattgtact gagagtgcac catatgcggt gtgaaatacc gcacagatgc    1680
gtaaggagaa ataccgcat caggcgctct tccgcttcct cgctcactga ctcgctgcgc    1740
tcggtcgttc ggctgcggcg agcggtatca gctcactcaa aggcggtaat acggttatcc    1800
acagaatcag gggataacgc aggaaagaac atgtgagcaa aaggccagca aaaggccagg    1860
aaccgtaaaa aggccgcgtt gctggcgttt ttccataggc tccgcccccc tgacgagcat    1920
cacaaaaatc gacgctcaag tcagaggtgg cgaaacccga caggactata aagataccag    1980
gcgtttcccc ctggaagctc cctcgtgcgc tctcctgttc cgaccctgcc gcttaccgga    2040
tacctgtccg cctttctccc ttcgggaagc gtggcgcttt ctcatagctc acgctgtagg    2100
tatctcagtt cggtgtaggt cgttcgctcc aagctgggct gtgtgcacga accccccgtt    2160
cagcccgacc gctgcgcctt atccggtaac tatcgtcttg agtccaaccc ggtaagacac    2220
gacttatcgc cactggcagc agccactggt aacaggatta gcagagcgag gtatgtaggc    2280
ggtgctacag agttcttgaa gtggtggcct aactacggct acactagaag gacagtattt    2340
ggtatctgcg ctctgctgaa gccagttacc ttcggaaaaa gagttggtag ctcttgatcc    2400
ggcaaacaaa ccaccgctgg tagcggtggt ttttttgttt gcaagcagca gattacgcgc    2460
agaaaaaaag gatctcaaga agatcctttg atcttttcta cggggtctga cgctcagtgg    2520
aacgaaaact cacgttaagg gattttggtc atgagattat caaaaaggat cttcacctag    2580
atccttttaa attaaaaatg aagttttaaa tcaatctaaa gtatatatga gtaaacttgg    2640
tctgacagtc tagaagatct agcccgccta atgagcgggc ttttttttaa ttcgcaattc    2700
cccgatgcat aatgtgcctg tcaaatggac gaagcaggga ttctgcaaac cctatgctac    2760
tccgtcaagc cgtcaattgt ctgattcgtt accaattatg acaacttgac ggctacatca    2820 ttcactttt cttcacaacc ggcacggaac tcgctcgggc tggccccggt gcatttttta    2880
aatacccgcg agaaatagag ttgatcgtca aaaccaacat tgcgaccgac ggtggcgata    2940
ggcatccggg tggtgctcaa aagcagcttc gcctggctga tacgttggtc ctcgcgccag    3000
cttaagacgc taatccctaa ctgctggcgg aaaagatgtg acagacgcga cggcgacaag    3060
caaacatgct gtgcgacgct ggcgatatca aaattgctgt ctgccaggtg atcgctgatg    3120
tactgacaag cctcgcgtac ccgattatcc atcggtggat ggagcgactc gttaatcgct    3180
tccatgcgcc gcagtaacaa ttgctcaagc agatttatcg ccagcagctc cgaatagcgc    3240
ccttcccctt gcccggcgtt aatgatttgc ccaaacaggt cgctgaaatg cggctggtgc    3300
gcttcatccg ggcgaaagaa cccgtattg gcaaatattg acggccagtt aagccattca    3360
```

```
tgccagtagg cgcgcggacg aaagtaaacc cactggtgat accattcgcg agcctccgga    3420
tgacgaccgt agtgatgaat ctctcctggc gggaacagca aaatatcacc cggtcggcaa    3480
acaaattctc gtccctgatt tttcaccacc ccctgaccgc gaatggtgag attgagaata    3540
taacctttca ttcccagcgg tcggtcgata aaaaaatcga gataaccgtt ggcctcaatc    3600
ggcgttaaac ccgccaccag atgggcatta acgagtatc ccggcagcag gggatcattt     3660
tgcgcttcag ccatactttt catactcccg ccattcagag aagaaaccaa ttgtccatat    3720
tgcatcagac attgccgtca ctgcgtcttt tactggctct ctcgctaac caaaccggta     3780
accccgctta ttaaaagcat tctgtaacaa agcgggacca aagccatgac aaaaacgcgt    3840
aacaaaagtg tctataatca cggcagaaaa gtccacattg attatttgca cggcgtcaca    3900
ctttgctatg ccatagcatt tttatccata agattagcgg atcctacctg acgcttttta    3960
tcgcaactct ctactgtttc tccatacccg tttttttggg ctagcgaatt ctgagaacaa    4020
actaagtgga taaatttcgt gttcagggge caacgaagct ccaggcgaa gtcacaattt     4080
ccggcgctaa aaatgctgct ctgcctatcc tttttgccgc actactggcg gaagaaccgg    4140
tagagatcca gaacgtcccg aaactgaaag acgtcgatac atcaatgaag ctgctaagcc    4200
agctgggtgc gaaagtagaa cgtaatggtt ctgtgcatat tgatgcccgc gacgttaatg    4260
tattctgcgc accttacgat ctggttaaaa ccatgcgtgc ttctatctgg gcgctggggc    4320
cgctggtagc gcgctttggt caggggcaag tttcactacc tggcggttgt acgatcggtg    4380
cgcgtccggt tgatctacac atttctggcc tcgaacaatt aggcgcgacc atcaaactgg    4440
aagaaggtta cgttaaagct tccgtcgatg gtcgtttgaa aggtgcacat atcgtgatgg    4500
ataaagtcag cgttggcgca acggtgacca tcatgtgtgc tgcaaccctg gcggaaggca    4560
ccacgattat tgaaaacgca gcgcgtgaac cggaaatcgt cgataccgcg aacttcctga    4620
ttacgctggg tgcgaaaatt agcggtcagg gcaccgatcg tatcgtcatc gaaggtgtgg    4680
aacgtttagg cggcggtgtc tatcgcgttc tgccggatcg tatcgaaacc ggtactttcc    4740
tggtggcggc ggcgattct cgcggcaaaa ttatctgccg taacgcgcag ccagatactc     4800
tcgacgccgt gctggcgaaa ctgcgtgacg ctggagcgga catcgaagtc ggcgaagact    4860
ggattagcct ggatatgcat ggcaaacgtc cgaaggctgt taacgtacgt accgcgccgc    4920
atccggcatt cccgaccgat atgcaggccc agttcacgct gttgaacctg gtggcagaag    4980
ggaccgggtt tatcaccgaa acggtctttg aaaaccgctt tatgcatgtg ccagagctga    5040
gccgtatggg cgcgcacgcc gaaatcgaaa gcaataccgt tatttgtcac ggtgttgaaa    5100
aactttctgg cgcacaggtt atggcaaccg atctgcgtgc atcagcaagc ctggtgctgg    5160
ctggctgtat tgcggaaggg acgacggtgg ttgatcgtat ttatcacatc gatcgtggct    5220
acgaacgcat tgaagacaaa ctgcgcgctt taggtgcaaa tattgagcgt gtgaaaggcg    5280
aataagaatt caaggcaaaa aacgctgtga aaaatgttgg ttttatcggc tggcgcggaa    5340
tggtcggctc tgttctcatg caacgcatgg tagaggagcg cgatttcgac gctattcgcc    5400
ctgttttctt ttctacctcc cagtttggac aggcggcgcc caccttcggc gacacctcca    5460
ccggcacgct acaggacgct tttgatctgg atgcgctaaa agcgctcgat atcatcgtga    5520
cctgccaggg cggcgattat accaacgaaa tttatccaaa gctgcgcgaa gcggatggc    5580
agggttactg gattgatgcg gcttctacgc tgcgcatgaa agatgatgcc attattattc    5640
tcgacccggt caaccaggac gtgattaccg acggcctgaa caatgcgtg aagacctttg     5700
tgggcggtaa ctgtaccgtt agcctgatgt tgatgtcgct gggcggtctc tttgcccata    5760
```

```
atctcgttga ctgggtatcc gtcgcgacct atcaggccgc ctccggcggc ggcgcgcgcc    5820
atatgcgcga gctgttaacc cagatgggtc agttgtatgg ccatgtcgcc gatgaactgg    5880
cgacgccgtc ttccgcaatt cttgatattg aacgcaaagt tacggcattg acccgcagcg    5940
gcgagctgcc ggttgataac tttggcgtac cgctggcggg aagcctgatc ccctggatcg    6000
acaaacagct cgataacggc cagagccgcg aagagtggaa aggccaggcg aaaccaaca    6060 agattctcaa tactgcctct gtgattccgg ttgatggttt gtgtgtgcgc gtcggcgcgc    6120
tgcgctgtca cagccaggcg ttcaccatca agctgaaaaa agaggtatcc attccgacgg    6180
tggaagaact gctggcggca cataatccgt gggcgaaagt ggtgccgaac gatcgtgata    6240
tcactatgcg cgaattaacc ccggcggcgg tgaccggcac gttgactacg ccggttggtc    6300
gtctgcgtaa gctgaacatg gggccagagt tcttgtcggc gtttaccgta ggcgaccagt    6360
tgttatgggg cgccgccgag ccgctgcgtc gaatgctgcg ccagttggcc tagtctaggg    6420
acgatgatgc aaccgatacc gtcgacggat cacatagact cgctccgaaa ttaaagaaca    6480
cttaaattat ctactaaagg aatctttagt caagtttatt taagatgact taactatgaa    6540
tacacaattg atgggtgagc gtaggagcat gcttatgcga aaggccatcc tgacggatgg    6600
ccttttt                                                              6607

<210> SEQ ID NO 2
<211> LENGTH: 717
<212> TYPE: DNA
<213> ORGANISM: Artificial Sequence
<220> FEATURE:
<223> OTHER INFORMATION: Synthetic: FIG. 28 >bp26  Codon Optimization

<400> SEQUENCE: 2
cccgggctcg agcaggaaaa ccagatgacc acccagccgg cgcgtatcgc tgttaccggt     60
gaaggtatga tgaccgcttc tccggacatg gctatcctga acctgtctgt tctgcgtcag    120
gcgaaaaccg cgcgtgaagc gatgaccgcg aacaacgaag ctatgaccaa agttctggac    180
gcgatgaaaa aagcgggtat cgaagaccgt gacctccaga ccggtggtat caacatccag    240
ccgatctacg tttaccccgga cgacaaaaac aacctgaaag aaccgaccat caccggttac    300 tctgttcta cctctctgac cgttcgtgtt cgtgaactgg cgaacgttgg taaaatcctg    360
gacgaatctg ttaccctggg tgttaaccag ggtggtgacc tgaacctggt taacgacaac    420
ccgtctgctg ttatcaacga agcgcgtaaa cgtgctgttg ctaacgctat cgctaaagcg    480
aaaaccctgg ctgacgctgc gggtgttggt ctgggtcgtg ttgttgaaat ctctgaactg    540
tctcgtccgc cgatgccgat gccgatcgcg cgtggtcagt tccgtaccat gctggcggct    600
gctccggaca actctgttcc gatcgctgct ggtgaaaact cttacaacgt ttctgttaac    660
gttgttttcg aaatcaaacc taggcaccac caccaccacc accctaggta actgcag      717

<210> SEQ ID NO 3
<211> LENGTH: 222
<212> TYPE: PRT
<213> ORGANISM: Artificial Sequence
<220> FEATURE:
<223> OTHER INFORMATION: Synthetic: FIG. 28 >bp26  Codon Optimization

<400> SEQUENCE: 3

Gln Glu Asn Gln Met Thr Thr Gln Pro Ala Arg Ile Ala Val Thr Gly
1               5                   10                  15

Glu Gly Met Met Thr Ala Ser Pro Asp Met Ala Ile Leu Asn Leu Ser
```

```
                    20                  25                  30
Val Leu Arg Gln Ala Lys Thr Ala Arg Glu Ala Met Thr Ala Asn Asn
                35                  40                  45

Glu Ala Met Thr Lys Val Leu Asp Ala Met Lys Lys Ala Gly Ile Glu
            50                  55                  60

Asp Arg Asp Leu Gln Thr Gly Gly Ile Asn Ile Gln Pro Ile Tyr Val
 65                 70                  75                  80

Tyr Pro Asp Asp Lys Asn Asn Leu Lys Glu Pro Thr Ile Thr Gly Tyr
                85                  90                  95

Ser Val Ser Thr Ser Leu Thr Val Arg Val Arg Glu Leu Ala Asn Val
            100                 105                 110

Gly Lys Ile Leu Asp Glu Ser Val Thr Leu Gly Val Asn Gln Gly Gly
            115                 120                 125

Asp Leu Asn Leu Val Asn Asp Asn Pro Ser Ala Val Ile Asn Glu Ala
            130                 135                 140

Arg Lys Arg Ala Val Ala Asn Ala Ile Ala Lys Ala Lys Thr Leu Ala
145                 150                 155                 160

Asp Ala Ala Gly Val Gly Leu Gly Arg Val Val Glu Ile Ser Glu Leu
                165                 170                 175

Ser Arg Pro Pro Met Pro Met Pro Ile Ala Arg Gly Gln Phe Arg Thr
            180                 185                 190

Met Leu Ala Ala Ala Pro Asp Asn Ser Val Pro Ile Ala Ala Gly Glu
            195                 200                 205

Asn Ser Tyr Asn Val Ser Val Asn Val Val Phe Glu Ile Lys
            210                 215                 220

<210> SEQ ID NO 4
<211> LENGTH: 6513
<212> TYPE: DNA
<213> ORGANISM: Artificial Sequence
<220> FEATURE:
<223> OTHER INFORMATION: Synthetic: FIG. 30: Sequence for pG8R241
      (pG8R110 with omp22)

<400> SEQUENCE: 4
atctagcccg cctaatgagc gggcttttttt ttaattcgca attccccgat gcataatgaa    60
actgcctgtc aaatggacga agcagggatt ctgcaaaccc tatgctactc cgtcaagccg   120
tcaattgtct gattcgttac caattatgac aacttgacgg ctacatcatt cacttttttct  180 tcacaaccgg cacgaaactc gctcgggctg gccccggtgc atttttaaa tactcgcgag    240 aaatagagtt gatcgtcaaa accaacattg cgaccgacgg tggcgatagg catccgggta   300
gtgctcaaaa gcagcttcgc ctgactaatg cgttggtcct cgcgccagct taagacgcta   360
atccctaact gctggcggaa agatgtgac agacgcgacg gcgacaagca acatgctgt    420 gcgacgctgg cgatatcaaa attgctgtct gccaggtgat cgctgatgta ctgacaagcc   480
tcgcgtaccc gattatccat cggtggatgg agcgactcgt taatcgcttc catgcgccgc   540
agtaacaatt gctcaagcag atttatcgcc agcagctccg aatagcgccc ttcccttgc    600 ccggcgttaa tgatttgccc aaacaggtcg ctgaaatgcg gctggtgcgc ttcatccggg   660
cgaaagaaac ccgtattggc aaatattgac ggccagttaa gccattcatg ccagtaggcg   720
cgcggacgaa agtaaaccca ctggtgatac cattcgcgag cctccggatg acgaccgtag   780
tgatgaatct ctcctggcgg gaacagcaaa atatcacccg gtcggcagac aaattctcgt   840
ccctgatttt tcaccacccc ctgaccgcga atggtgagat tgagaatata acctttcatt   900
```

```
cccagcggtc ggtcgataaa aaaatcgaga taaccgttgg cctcaatcgg cgttaaaccc    960
gccaccagat gggcattaaa cgagtatccc ggcagcaggg gatcattttg cgcttcagcc   1020
atacttttca tactcccgcc attcagagaa gaaaccaatt gtccatattg catcagacat   1080
tgccgtcact gcgtctttta ctggctcttc tcgctaacca aaccggtaac cccgcttatt   1140
aaaagcattc tgtaacaaag cgggaccaaa gccatgacaa aaacgcgtaa caaaagtgtc   1200
tataatcacg gcagaaaagt ccacattgat tatttgcacg gcgtcacact ttgctatgcc   1260
atagcatttt tatccataag attagcggat cctacctgac gcttttatc gcaactctct    1320
actgtttctc catacccgtt tttttgggct agcgaattct gagaacaaac taatggata    1380
aatttcgtgt tcaggggcca acgaagctcc agggcgaagt cacaatttcc ggcgctaaaa   1440
atgctgctct gcctatcctt tttgccgcac tactggcgga gaaccggta gagatccaga    1500
acgtcccgaa actgaaagac gtcgatacat caatgaagct gctaagccag ctgggtgcga   1560
aagtagaacg taatggttct gtgcatattg atgcccgcga cgttaatgta ttctgcgcac   1620
cttacgatct ggttaaaacc atgcgtgctt ctatctgggc gctggggccg ctggtagcgc   1680
gctttggtca gggcaagtt tcactacctg gcggttgtac gatcggtgcg cgtccggttg    1740
atctacacat ttctggcctc gaacaattag gcgcgaccat caaactggaa gaaggttacg   1800
ttaaagcttc cgtcgatggt cgtttgaaag gtgcacatat cgtgatggat aaagtcagcg   1860
ttggcgcaac ggtgaccatc atgtgtgctg caaccctggc ggaaggcacc acgattattg   1920
aaaacgcagc gcgtgaaccg gaaatcgtcg ataccgcgaa cttcctgatt acgctgggtg   1980
cgaaaattag cggtcaggc accgatcgta tcgtcatcga aggtgtggaa cgtttaggcg    2040
gcggtgtcta tcgcgttctg ccggatcgta tcgaaaccgg tactttcctg gtggcggcgg   2100
cgatttctcg cggcaaaatt atctgccgta acgcgcagcc agatactctc gacgccgtgc   2160
tggcgaaact gcgtgacgct ggagcggaca tcgaagtcgg cgaagactgg attagcctgg   2220
atatgcatgc caaacgtccg aaggctgtta acgtacgtac cgcgccgcat ccggcattcc   2280
cgaccgatat gcaggcccag ttcacgctgt tgaacctggt ggcagaaggg accgggttta   2340
tcaccgaaac ggtctttgaa aaccgcttta tgcatgtgcc agagctgagc cgtatgggcg   2400
cgcacgccga aatcgaaagc aataccgtta tttgtcacgg tgttgaaaaa ctttctggcg   2460
cacaggttat ggcaaccgat ctgcgtgcat cagcaagcct ggtgctggct ggctgtattg   2520
cggaagggac gacggtggtt gatcgtattt atcacatcga tcgtggctac gaacgcattg   2580
aagacaaact gcgcgcttta ggtgcaaata ttgagcgtgt gaaaggcgaa taagaattca   2640
ggaaaaaaac gctgtgaaaa atgttggttt tatcggctgg cgcggaatgg tcggctctgt   2700
tctcatgcaa cgcatggtag aggagcgcga tttcgacgct attcgccctg ttttctttc    2760
tacctcccag tttggacagg cggcgcccac cttcggcgac acctccaccg gcacgctaca   2820
ggacgctttt gatctggatg cgctaaaagc gctcgatatc atcgtgacct gccagggcgg   2880
cgattatacc aacgaaattt atccaaagct gcgcgaaagc ggatggcagg ttactggat    2940
tgatgcggct tctacgctgc gcatgaaaga tgatgccatt attattctcg acccggtcaa   3000
ccaggacgtg attaccgacg gcctgaacaa tggcgtgaag acctttgtgg gcggtaactg   3060
taccgttagc ctgatgttga tgtcgctggg cggtctcttt gcccataatc tcgttgactg   3120
ggtatccgtc gcgacctatc aggccgcctc cggcggcggc gcgcgccata tgcgcgagct   3180
gttaacccag atgggtcagt tgtatggcca tgtcgccgat gaactggcga cgccgtcttc   3240
cgcaattctt gatattgaac gcaaagttac ggcattgacc cgcagcggcg agctgccggt   3300
```

-continued

```
tgataacttt ggcgtaccgc tggcgggaag cctgatcccc tggatcgaca aacagctcga      3360
taacggccag agccgcgaag agtggaaagg ccaggcggaa accaacaaga ttctcaatac      3420
tgcctctgtg attccggttg atggtttgtg tgtgcgcgtc ggcgcgctgc gctgtcacag      3480
ccaggcgttc accatcaagc tgaaaaaaga ggtatccatt ccgacggtgg aagaactgct      3540
ggcggcacat aatccgtggg cgaaagtggt gccgaacgat cgtgatatca ctatgcgcga      3600
attaaccccg gcggcggtga ccggcacgtt gactacgccg gttggtcgtc tgcgtaagct      3660
gaacatgggg ccagagttct tgtcggcgtt taccgtaggc gaccagttgt tatggggcgc      3720
cgagccgagc cgctgcgtcg aatgctgcgc cagttggcgt agtctagctg cacgataccg      3780
tcgacttgta catagactcg ctccgaaatt aaagaacact taaattatct actaaaggaa      3840
tctttagtca agtttattta agatgactta actatgaata cacaattgat gggtgagcgt      3900
aggagcatgc ttatgcgaaa ggccatcctg acggatggcc tttttggatc ttccggaaga      3960
ccttccattc tgaaatgagc tgttgacaat taatcatccg gctcgtataa tgtgtggaat      4020
tgtgagcgga taacaatttc acacaggaaa cagaccatgg tgacaaaaat aactttatct      4080
ccccagaatt ttagaatcca aaacaggaaa accacactac taaagaaaaa atcaaccgag      4140
aaaaattctt tagcaaaaag tattctcgca gtaaaaaatc acttcatcga attaaggtca      4200
aaattatcgg aacgttttat ttcgcataag aacactgagt cttctgcaac acactttcac      4260
cgaggaagcg catctgaggg ccgggcagtg ttgacaaatg aattcgttgg atccgtcgac      4320
cccgggctcg aggcggacat gatgggtggt accgactaca cctacaacga cccggttgcg      4380
gcgggtccgc acgactggtc tggtaactac gttggtgcgc aggttggtgg ttcttcttct      4440
aaattcccgt ctccgttcgc gtctcgtacc ggtgcgctgg gtggtatcgt tgttggtaaa      4500
aacatgcaga acggtaacat cgtttttcggt gcggaactgg aaggtaactt cgcggaagcg      4560
gaacaccgta tcggtcacgg tggtaccccta cagcagtctt ggaacggtaa cgcgaaaggt      4620
aaagttggtt acaccttcga caaaaccctg gtttacggta ccgcgggtta cggtgttacc      4680
cgtttcaaag cgaaagacaa caccacctct gcgtctggtt gcgaaggtgg tgttctgatc      4740
ggtgcgggtg ttgaacaggc gctgtctggt ccgctgtctg ttaaagcgga atacgacttc      4800
cagcgtttca cgacgttaa atctcaggtt aacggtatcg aacagcgtaa caacctgaaa      4860
aaccactcta tcaaagcggg tctgaactac aaattcccta ggcaccacca ccaccaccac      4920
cctaggtagc tgcagccaag ctcccaagct tggctgtttt ggcggatgag agaagatttt      4980
cagcttctga tacagattaa atcagaacgc agaagcggtc tgataaaaca gaatttgcct      5040
ggcggcagta gcgcggtggt cccacctgac cccatgccga actcagaagt gaaacgccgt      5100
agcgccgatg gtagtgtggg gtctccccat gcgagagtag gaactgcca ggcatcaaat      5160 aaaacgaaag gctcagtcga aagactgggc ctttcgtttt atctgttgtt tgtcggtgaa      5220
cgctctcctg agtaggacaa atccgccggg agcggatttg aacgttgcga agcaacggcc      5280
cggagggtgg cgggcaggac gcccgccata aactgccagg catcaaatta agcagaaggc      5340
catcctgacg gatggccttt ttgcgtttct acaaactctt tgtttatttt tctaaatac      5400 attcaaatat gtatccgctc atgagacaat aaccctgata aatgcttcaa taatggaaga      5460
tcttccaaca tcacaggtaa acagaaacgt cgggtcgatc gggaaattct ttcccggacg      5520
gcgcggggtt gggcaagccg caggcgcgtc agtgctttta gcgggtgtcg gggcgcagcc      5580
atgacccagt cacgtagcgc tagcggagtg tatactggct tactatgttg gcactgatga      5640
```

| | |
|---|---|
| gggtgtcagt gaagtgcttc atgtggcagg agaaaaaagg ctgcaccggt gcgtcagcag | 5700 |
| aatatgtgat acaggatata ttccgcttcc tcgctcactg actcgctacg ctcggtcgtt | 5760 |
| cgactgcggc gagcggaaat ggcttacgaa cggggcggag atttcctgga agatgccagg | 5820 |
| aagatactta acagggaagt gagagggccg cggcaaagcc gttttccat aggctccgcc | 5880 |
| cccctgacaa gcatcacgaa atctgacgct caaatcagtg gtggcgaaac ccgacaggac | 5940 |
| tataaagata ccaggcgttt cccctggcg ctccctcgt gcgctctcct gttcctgcct | 6000 |
| ttcggtttac cggtgtcatt ccgctgttat ggccgcgttt gtctcattcc acgcctgaca | 6060 |
| ctcagttccg ggtaggcagt tcgctccaag ctggactgta tgcacgaacc ccccgttcag | 6120 |
| tccgaccgct gcgccttatc cggtaactat cgtcttgagt ccaacccgga agacatgca | 6180 |
| aaagcaccac tggcagcagc cactggtaat tgatttagag gagttagtct tgaagtcatg | 6240 |
| cgccggttaa ggctaaactg aaaggacaag ttttggtgac tgcgctcctc caagccagtt | 6300 |
| acctcggttc aaagagttgg tagctcagag aaccttcgaa aaaccgccct gcaaggcggt | 6360 |
| ttttcgttt tcagagcaag agattacgcg cagaccaaaa cgatctcaag aagatcatct | 6420 |
| tattaatcag ataaaatatt tctagatttc agtgcaattt atctcttcaa atgtagcacc | 6480 |
| tgaagtcagc cccatacgat ataagttgtt gga | 6513 |

<210> SEQ ID NO 5
<211> LENGTH: 615
<212> TYPE: DNA
<213> ORGANISM: Artificial Sequence
<220> FEATURE:
<223> OTHER INFORMATION: Synthetic: FIG. 31: >omp22  Codon Optimization

<400> SEQUENCE: 5

| | |
|---|---|
| cccgggctcg aggcggacat gatgggtggt accgactaca cctacaacga cccggttgcg | 60 |
| gcgggtccgc acgactggtc tggtaactac gttggtgcgc aggttggtgg ttcttcttct | 120 |
| aaattcccgt ctccgttcgc gtctcgtacc ggtgcgctgg gtggtatcgt tgttggtaaa | 180 |
| aacatgcaga acggtaacat cgttttcggt gcggaactgg aagtaacttt cgcggaagcg | 240 |
| gaacaccgta tcggtcacgg tggtacccta cagcagtctt ggaacggtaa cgcgaaaggt | 300 |
| aaagttggtt acaccttcga caaaaccctg gtttacggta ccgcgggtta cggtgttacc | 360 |
| cgtttcaaag cgaaagacaa caccaccctct cgtctggtt gcgaaggtgg tgttctgatc | 420 |
| ggtgcgggtg ttgaacaggc gctgtctggt ccgctgtctg ttaaagcgga atacgacttc | 480 |
| cagcgtttca cgacgttaa atctcaggtt aacggtatcg aacagcgtaa caacctgaaa | 540 |
| aaccactcta tcaaagcggg tctgaactac aaattcccta ggcaccacca ccaccaccac | 600 |
| cctaggtaac tgcag | 615 |

<210> SEQ ID NO 6
<211> LENGTH: 188
<212> TYPE: PRT
<213> ORGANISM: Artificial Sequence
<220> FEATURE:
<223> OTHER INFORMATION: Synthetic: FIG. 31: >omp22  Codon Optimization

<400> SEQUENCE: 6

Ala Asp Met Met Gly Gly Thr Asp Tyr Thr Tyr Asn Asp Pro Val Ala
1               5                   10                  15

Ala Gly Pro His Asp Trp Ser Gly Asn Tyr Val Gly Ala Gln Val Gly
            20                  25                  30

Gly Ser Ser Ser Lys Phe Pro Ser Pro Phe Ala Ser Arg Thr Gly Ala

```
                   35                  40                  45

Leu Gly Gly Ile Val Val Gly Lys Asn Met Gln Asn Gly Asn Ile Val
     50                  55                  60

Phe Gly Ala Glu Leu Glu Gly Asn Phe Ala Glu Ala Glu His Arg Ile
 65                  70                  75                  80

Gly His Gly Gly Thr Leu Gln Gln Ser Trp Asn Gly Asn Ala Lys Gly
                 85                  90                  95

Lys Val Gly Tyr Thr Phe Asp Lys Thr Leu Val Tyr Gly Thr Ala Gly
            100                 105                 110

Tyr Gly Val Thr Arg Phe Lys Ala Lys Asp Asn Thr Thr Ser Ala Ser
            115                 120                 125

Gly Cys Glu Gly Gly Val Leu Ile Gly Ala Gly Val Glu Gln Ala Leu
        130                 135                 140

Ser Gly Pro Leu Ser Val Lys Ala Glu Tyr Asp Phe Gln Arg Phe Asn
145                 150                 155                 160

Asp Val Lys Ser Gln Val Asn Gly Ile Glu Gln Arg Asn Asn Leu Lys
                165                 170                 175

Asn His Ser Ile Lys Ala Gly Leu Asn Tyr Lys Phe
            180                 185

<210> SEQ ID NO 7
<211> LENGTH: 6618
<212> TYPE: DNA
<213> ORGANISM: Artificial Sequence
<220> FEATURE:
<223> OTHER INFORMATION: Synthetic: FIG. 33: Sequence for pG8R243
      (pG8R110 with bp26)

<400> SEQUENCE: 7
atctagcccg cctaatgagc gggcttttttt ttaattcgca attccccgat gcataatgaa    60
actgcctgtc aaatggacga agcagggatt ctgcaaaccc tatgctactc cgtcaagccg   120
tcaattgtct gattcgttac caattatgac aacttgacgg ctacatcatt cactttttct   180
tcacaaccgg cacgaaactc gctcgggctg gccccggtgc attttttaaa tactcgcgag   240
aaatagagtt gatcgtcaaa accaacattg cgaccgacgg tggcgatagg catccgggta   300
gtgctcaaaa gcagcttcgc ctgactaatg cgttggtcct cgcgccagct taagacgcta   360
atccctaact gctggcggaa aagatgtgac agacgcgacg cgacaagca aacatgctgt    420 gcgacgctgg cgatatcaaa attgctgtct gccaggtgat cgctgatgta ctgacaagcc   480
tcgcgtaccc gattatccat cggtggatgg agcgactcgt taatcgcttc catgcgccgc   540
agtaacaatt gctcaagcag atttatcgcc agcagctccg aatagcgccc ttccccttgc   600
ccggcgttaa tgatttgccc aaacaggtcg ctgaaatgcg gctggtgcgc ttcatccggg   660
cgaaagaaac ccgtattggc aaatattgac ggccagttaa gccattcatg ccagtaggcg   720
cgcggacgaa agtaaaccca ctggtgatac cattcgcgag cctccggatg acgaccgtag   780
tgatgaatct ctcctggcgg aacagcaaaa tatcacccg tcggcagac aaattctcgt     840 ccctgatttt tcaccacccc ctgaccgcga atggtgagat tgagaatata acctttcatt   900
cccagcggtc ggtcgataaa aaatcgaga taaccgttgg cctcaatcgg cgttaaaccc    960
gccaccagat gggcattaaa cgagtatccc ggcagcaggg atcattttg cgcttcagcc   1020 atacttttca tactcccgcc attcagagaa gaaaccaatt gtccatattg catcagacat   1080
tgccgtcact gcgtcttta ctggctcttc tcgctaacca aaccggtaac ccgcttattt   1140
aaaagcattc tgtaacaaag cgggaccaaa gccatgacaa aaacgcgtaa caaaagtgtc   1200
```

```
tataatcacg gcagaaaagt ccacattgat tatttgcacg gcgtcacact ttgctatgcc   1260
atagcatttt tatccataag attagcggat cctacctgac gcttttatc gcaactctct    1320 actgtttctc catacccgtt tttttgggct agcgaattct gagaacaaac taaatggata   1380
aatttcgtgt tcaggggcca acgaagctcc agggcgaagt cacaatttcc ggcgctaaaa   1440
atgctgctct gcctatcctt tttgccgcac tactggcgga agaaccggta gagatccaga   1500
acgtcccgaa actgaaagac gtcgatacat caatgaagct gctaagccag ctgggtgcga   1560
aagtagaacg taatggttct gtgcatattg atgcccgcga cgttaatgta ttctgcgcac   1620
cttacgatct ggttaaaacc atgcgtgctt ctatctgggc gctggggccg ctggtagcgc   1680
gctttggtca ggggcaagtt tcactacctg gcggttgtac gatcggtgcg cgtccggttg   1740
atctacacat ttctggcctc gaacaattag gcgcgaccat caaactggaa gaaggttacg   1800
ttaaagcttc cgtcgatggt cgtttgaaag gtgcacatat cgtgatggat aaagtcagcg   1860
ttggcgcaac ggtgaccatc atgtgtgctg caaccctggc ggaaggcacc acgattattg   1920
aaaacgcagc gcgtgaaccg gaaatcgtcg ataccgcgaa cttcctgatt acgctgggtg   1980
cgaaaattag cggtcagggc accgatcgta tcgtcatcga aggtgtggaa cgtttaggcg   2040
gcggtgtcta tcgcgttctg ccggatcgta tcgaaaccgg tactttcctg gtggcggcgg   2100
cgatttctcg cggcaaaatt atctgccgta acgcgcagcc agatactctc gacgccgtgc   2160
tggcgaaact gcgtgacgct ggagcggaca tcgaagtcgg cgaagactgg attagcctgg   2220
atatgcatgg caaacgtccg aaggctgtta acgtacgtac cgcgccgcat ccggcattcc   2280
cgaccgatat gcaggcccag ttcacgctgt tgaacctggt ggcagaaggg accgggttta   2340
tcaccgaaac ggtctttgaa aaccgcttta tgcatgtgcc agagctgagc cgtatgggcg   2400
cgcacgccga atcgaaagc aataccgtta tttgtcacgg tgttgaaaaa ctttctggcg   2460
cacaggttat ggcaaccgat ctgcgtgcat cagcaagcct ggtgctggct ggctgtattg   2520
cggaagggac gacggtggtt gatcgtattt atcacatcga tcgtggctac gaacgcattg   2580 aagacaaaact gcgcgcttta ggtgcaaata ttgagcgtgt gaaaggcgaa taagaattca   2640
ggaaaaaaac gctgtgaaaa atgttggttt tatcggctgg cgcggaatgg tcggctctgt   2700
tctcatgcaa cgcatggtag aggagcgcga tttcgacgct attcgccctg ttttcttttc   2760
tacctcccag tttggacagg cggcgccac cttcggcgac acctccaccg gcacgctaca   2820
ggacgctttt gatctggatg cgctaaaagc gctcgatatc atcgtgacct gccagggcgg   2880
cgattatacc aacgaaattt atccaaagct gcgcgaaagc ggatggcagg ttactggat   2940 tgatgcggct tctacgctgc gcatgaaaga tgatgccatt attattctcg acccggtcaa   3000
ccaggacgtg attaccgacg gcctgaacaa tggcgtgaag acctttgtgg gcggtaactg   3060
taccgttagc ctgatgttga tgtcgctggg cggtctcttt gcccataatc tcgttgactg   3120
ggtatccgtc gcgacctatc aggccgcctc cggcggcggc gcgcgccata tgcgcgagct   3180
gttaacccag atgggtcagt tgtatggcca tgtcgccgat gaactggcga cgccgtcttc   3240
cgcaattctt gatattgaac gcaaagttac ggcattgacc cgcagcggcg agctgccggt   3300
tgataacttt ggcgtaccgc tggcgggaag cctgatcccc tggatcgaca aacagctcga   3360
taacggccag agccgcgaag agtggaaagg ccaggcggaa accaacaaga ttctcaatac   3420
tgcctctgtg attccggttg atggtttgtg tgtgcgcgtc ggcgcgctgc gctgtcacag   3480
ccaggcgttc accatcaagc tgaaaaaaga ggtatccatt ccgacggtgg aagaactgct   3540
```

```
ggcggcacat aatccgtggg cgaaagtggt gccgaacgat cgtgatatca ctatgcgcga    3600
attaaccccg gcggcggtga ccggcacgtt gactacgccg gttggtcgtc tgcgtaagct    3660
gaacatgggg ccagagttct tgtcggcgtt taccgtaggc gaccagttgt tatggggcgc    3720
cgagccgagc cgctgcgtcg aatgctgcgc cagttggcgt agtctagctg cacgataccg    3780
tcgacttgta catagactcg ctccgaaatt aaagaacact taaattatct actaaaggaa    3840
tctttagtca agtttattta agatgactta actatgaata cacaattgat gggtgagcgt    3900
aggagcatgc ttatgcgaaa ggccatcctg acggatggcc tttttggatc ttccggaaga    3960
ccttccattc tgaaatgagc tgttgacaat taatcatccg gctcgtataa tgtgtggaat    4020
tgtgagcgga taacaatttc acacaggaaa cagaccatgg tgacaaaaat aactttatct    4080
ccccagaatt ttagaatcca aaaacaggaa accacactac taaagaaaaa atcaaccgag    4140
aaaaattctt tagcaaaaag tattctcgca gtaaaaaatc acttcatcga attaaggtca    4200
aaattatcgg aacgttttat ttcgcataag aacactgagt cttctgcaac acactttcac    4260
cgaggaagcg catctgaggg ccgggcagtg ttgacaaatg aattcgttgg atccgtcgac    4320
cccgggctcg agcaggaaaa ccagatgacc acccagccgg cgcgtatcgc tgttaccggt    4380
gaaggtatga tgaccgcttc tccggacatg gctatcctga acctgtctgt tctgcgtcag    4440
gcgaaaaccg cgcgtgaagc gatgaccgcg aacaacgaag ctatgaccaa agttctggac    4500
gcgatgaaaa aagcgggtat cgaagaccgt gacctccaga ccggtggtat caacatccag    4560
ccgatctacg tttacccgga cgacaaaaac aacctgaaag aaccgaccat caccggttac    4620
tctgttttcta cctctctgac cgttcgtgtt cgtgaactgg cgaacgttgg taaaatcctg    4680
gacgaatctg ttaccctggg tgttaaccag ggtggtgacc tgaacctggt taacgacaac    4740
ccgtctgctg ttatcaacga agcgcgtaaa cgtgctgttg ctaacgctat cgctaaagcg    4800
aaaaccctgg ctgacgctgc gggtgttggt ctgggtcgtg ttgttgaaat ctctgaactg    4860
tctcgtccgc cgatgccgat gccgatcgcg cgtggtcagt tccgtaccat gctggcggct    4920
gctccggaca actctgttcc gatcgctgct ggtgaaaact cttacaacgt ttctgttaac    4980
gttgttttcg aaatcaaacc taggcaccac caccaccacc accctaggta atgactgcag    5040
ccaagctccc aagcttggct gttttggcgg atgagagaag attttcagct tctgatacag    5100
attaaatcag aacgcagaag cggtctgata aaacagaatt tgcctggcgg cagtagcgcg    5160
gtggtcccac ctgaccccat gccgaactca gaagtgaaac gccgtagcgc cgatggtagt    5220
gtggggtctc cccatgcgag agtagggaac tgccaggcat caaataaaac gaaaggctca    5280
gtcgaaagac tgggcctttc gttttatctg ttgtttgtcg gtgaacgctc tcctgagtag    5340
gacaaatccg ccgggagcgg atttgaacgt tgcgaagcaa cggcccggag ggtggcgggc    5400
aggacgcccg ccataaactg ccaggcatca aattaagcag aaggccatcc tgacggatgg    5460
ccttttttgcg tttctacaaa ctcttttgtt tattttttcta aatacattca aatatgtatc    5520
cgctcatgag acaataaccc tgataaatgc ttcaataatg gaagatcttc caacatcaca    5580
ggtaaacaga aacgtcgggt cgatcgggaa attctttccc ggacggcgcg gggttgggca    5640
agccgcaggc gcgtcagtgc ttttagcggg tgtcggggcg cagccatgac ccagtcacgt    5700
agcgctagcg gagtgtatac tggcttacta tgttggcact gatgagggtg tcagtgaagt    5760
gcttcatgtg gcaggagaaa aaaggctgca ccggtgcgtc agcagaatat gtgatacagg    5820
atatattccg cttcctcgct cactgactcg ctacgctcgg tcgttcgact gcggcgagcg    5880
gaaatggctt acgaacgggg cggagatttc ctggaagatg ccaggaagat acttaacagg    5940
```

```
gaagtgagag ggccgcggca agccgttttt tccataggct ccgcccccct gacaagcatc    6000
acgaaatctg acgctcaaat cagtggtggc gaaacccgac aggactataa agataccagg    6060
cgtttccccc tggcggctcc ctcgtgcgct ctcctgttcc tgcctttcgg tttaccggtg    6120
tcattccgct gttatggccg cgtttgtctc attccacgcc tgacactcag ttccgggtag    6180
gcagttcgct ccaagctgga ctgtatgcac gaaccccccg ttcagtccga ccgctgcgcc    6240
ttatccggta actatcgtct tgagtccaac ccggaaagac atgcaaaagc accactggca    6300
gcagccactg gtaattgatt tagaggagtt agtcttgaag tcatgcgccg gttaaggcta    6360
aactgaaagg acaagttttg gtgactgcgc tcctccaagc cagttacctc ggttcaaaga    6420
gttggtagct cagagaacct tcgaaaaacc gccctgcaag gcggttttt  cgttttcaga    6480 gcaagagatt acgcgcagac caaaacgatc tcaagaagat catcttatta atcagataaa    6540
atatttctag atttcagtgc aatttatctc ttcaaatgta gcacctgaag tcagccccat    6600
acgatataag ttgttgga                                                  6618

<210> SEQ ID NO 8
<211> LENGTH: 717
<212> TYPE: DNA
<213> ORGANISM: Artificial Sequence
<220> FEATURE:
<223> OTHER INFORMATION: Synthetic: FIG. 34 >bp26   Codon Optimization

<400> SEQUENCE: 8
cccgggctcg agcaggaaaa ccagatgacc acccagccgg cgcgtatcgc tgttaccggt      60
gaaggtatga tgaccgcttc tccggacatg gctatcctga acctgtctgt tctgcgtcag     120
gcgaaaaccg cgcgtgaagc gatgaccgcg aacaacgaag ctatgaccaa agttctggac     180
gcgatgaaaa aagcgggtat cgaagaccgt gacctccaga ccggtggtat caacatccag     240
ccgatctacg tttaccccgga cgacaaaaac aacctgaaag aaccgaccat caccggttac     300 tctgttttcta cctctctgac cgttcgtgtt cgtgaactgg cgaacgttgg taaaatcctg     360
gacgaatctg ttaccctggg tgttaaccag ggtggtgacc tgaacctggt taacgacaac     420
ccgtctgctg ttatcaacga agcgcgtaaa cgtgctgttg ctaacgctat cgctaaagcg     480
aaaaccctgg ctgacgctgc gggtgttggt ctgggtcgtg ttgttgaaat ctctgaactg     540
tctcgtccgc cgatgccgat gccgatcgcg cgtggtcagt tccgtaccat gctggcggct     600
gctccggaca actctgttcc gatcgctgct ggtgaaaact cttacaacgt ttctgttaac     660
gttgttttcg aaatcaaacc taggcaccac caccaccacc accctaggta actgcag       717

<210> SEQ ID NO 9
<211> LENGTH: 222
<212> TYPE: PRT
<213> ORGANISM: Artificial Sequence
<220> FEATURE:
<223> OTHER INFORMATION: Synthetic: FIG. 34 >bp26   Codon Optimization

<400> SEQUENCE: 9

Gln Glu Asn Gln Met Thr Thr Gln Pro Ala Arg Ile Ala Val Thr Gly
1               5                   10                  15

Glu Gly Met Met Thr Ala Ser Pro Asp Met Ala Ile Leu Asn Leu Ser
            20                  25                  30

Val Leu Arg Gln Ala Lys Thr Ala Arg Glu Ala Met Thr Ala Asn Asn
        35                  40                  45

Glu Ala Met Thr Lys Val Leu Asp Ala Met Lys Lys Ala Gly Ile Glu
```

```
            50                  55                  60
Asp Arg Asp Leu Gln Thr Gly Gly Ile Asn Ile Gln Pro Ile Tyr Val
 65                  70                  75                  80

Tyr Pro Asp Asp Lys Asn Asn Leu Lys Glu Pro Thr Ile Thr Gly Tyr
                 85                  90                  95

Ser Val Ser Thr Ser Leu Thr Val Arg Val Arg Glu Leu Ala Asn Val
                100                 105                 110

Gly Lys Ile Leu Asp Glu Ser Val Thr Leu Gly Val Asn Gln Gly Gly
            115                 120                 125

Asp Leu Asn Leu Val Asn Asp Asn Pro Ser Ala Val Ile Asn Glu Ala
        130                 135                 140

Arg Lys Arg Ala Val Ala Asn Ala Ile Ala Lys Ala Lys Thr Leu Ala
145                 150                 155                 160

Asp Ala Ala Gly Val Gly Leu Gly Arg Val Val Glu Ile Ser Glu Leu
                165                 170                 175

Ser Arg Pro Pro Met Pro Met Pro Ile Ala Arg Gly Gln Phe Arg Thr
            180                 185                 190

Met Leu Ala Ala Ala Pro Asp Asn Ser Val Pro Ile Ala Ala Gly Glu
        195                 200                 205

Asn Ser Tyr Asn Val Ser Val Asn Val Val Phe Glu Ile Lys
    210                 215                 220

<210> SEQ ID NO 10
<211> LENGTH: 7396
<212> TYPE: DNA
<213> ORGANISM: Artificial Sequence
<220> FEATURE:
<223> OTHER INFORMATION: Synthetic: FIG. 36: Sequence for pG8R250
      (pG8R114 with tf)

<400> SEQUENCE: 10
ggatcttccg gaagaccttc cattctgaaa tgagctgttg acaattaatc atccggctcg      60
tataatgtgt ggaattgtga gcggataaca atttcacaca ggaaacagac catgaaaaaa     120
caacatttcc gtgtcgccct tattcccttt tttgcggcat tttgccttcc tgttttttgct    180 cacccagaaa cgctggtgaa agtaaaagat gctgaactcg agatgacccg ttctgaaggt     240
ctgaacatgc aggttaccga aaccctgaac gaaggtctga acgtgaaat caaagttgtt     300 gttccggcgg gtgacctgga agcgaaactg gcggaacgtc tggaaaccgc gcgtggtcgt     360
gcgcgtatca acggtttccg tccgggtaaa gttccgaccg cgcacctgcg taaaatgtac     420
ggtaaatctt tcatggcgga aatcgttaac gaaatcctga cgactcttc cgttctatc      480 ctggcggaac gtaacgaaaa atctgcgacc cagccggaag ttatcatgtc tgaagacgaa     540
aaagaagcgg aaaagttct ggacggtaaa gcggacttcg ttttctctct gaactacgaa      600
gttctgccgg cgatcgaagt taaagacttc tctaaaatcg cggttaccccg tgaagttgtt     660 gacatctctg acgaagaagt tgacgaacag gttaaacgta tcgcgtcttc tacccgtacc     720
tttgaaacca aaaaggtaa agcggaaaac gaagatcgtg ttaccatcga ctacctgggt     780
aaactggacg tgaaccgtt cgaaggtggt gcggacaacg acgcgcagct ggttctgggt     840
tctggtcagt tcattccggg tttcgaagaa cagctgatcg tctgaaagc gggtgacgaa     900 aaagttatca ccgttacgtt cccggcggaa tacggtgcgg cgcacctggc gggtaaagaa     960
gcgaccttcg acatcaaagt taagaagtt gcgaaaccga acgaactggt tctggacgac    1020
gaaaccgcga aaaactggg tatcgaatct ctggaacgtc tgcgtcaggt tgttcgtgaa    1080
```

```
cagatcgaat ctcagtacgg tcagatcacc cgtcagaaag ttaaacgtca gatcctggac   1140
gcgctggacg gtgactacca gttcgaaacc ccgcagaaac tggttgacgc ggaattcaac   1200
aacatctggc agcagatcaa cttcgacctc cagcaggcgg gtcgtacctt cgaagacgaa   1260
gaaaccaccg aagaagcggc gcgtgaagaa taccgtaaac tggcggaacg tcgtgttcgt   1320
ctgggtctgg ttctgtctga atcggtgaa aaagcgggtg ttgaagttac cgaagaagaa    1380
ctccagcgtg cggtttacga ccaggttcgt cgttatccgg gtcaggaaaa agaaatctac   1440
gacttcctgc gtcgtacccc ggacgcggtt gcgaacctgc gtgcgccgat cttcgaagaa   1500
aaagttgttg accacctgct ggcgaacatc aacgttaccg acaaaaaagt ttctaaagaa   1560
gaactgaccg cggaagacga agacgcggcg tctgaagcga accggcgaa aaaagcggcg    1620 gcgaaaaaaa aagcggcgcc gaaaaaaaaa gcggaagaag gtaaatctga agaagcgcct   1680
aggcaccacc accaccacca ccctaggtga ctgcagccaa gctcccaagc ttggctgttt   1740
tggcggatga gaagagattt tcagcctgat acagattaaa tcagaacgca gaagcggtct   1800
gataaaacag aatttgcctg gcggcagtag cgcggtggtc ccacctgacc ccatgccgaa   1860
ctcagaagtg aaacgccgta gcgccgatgg tagtgtgggg tctccccatg cgagagtagg   1920
gaactgccag gcatcaaata aaacgaaagg ctcagtcgaa agactgggcc tttcgtttta   1980
tctgttgttt gtcggtgaac gctctcctga gtaggacaaa tccgccggga gcggatttga   2040
acgttgcgaa gcaacggccc ggagggtggc gggcaggacg cccgccataa actgccaggc   2100
atcaaattaa gcagaaggcc atcctgacgg atggcctttt tgcgtttcta caaactcttt   2160
tgtttatttt tctaaataca ttcaaatatg tatccgctca tgagacaata accctgataa   2220
atgcttcaat aatggaagat cttccaacat cacaggtaaa cagaaacgtc gggtcgatcg   2280
ggaaattctt tcccggacgg cgcggggttg gcaagccgc aggcgcgtca gtgcttttag    2340
cgggtgtcgg ggcgcagcca tgacccagtc acgtagcgat agcggagtgt atactggctt   2400
aactatgcgg catcagagca gattgtactg agagtgcacc atatgcggtg tgaaataccg   2460
cacagatgcg taaggagaaa ataccgcatc aggcgctctt ccgcttcctc gctcactgac   2520
tcgctgcgct cggtcgttcg gctgcggcga gcggtatcag ctcactcaaa ggcggtaata   2580
cggttatcca cagaatcagg ggataacgca ggaaagaaca tgtgagcaaa aggccagcaa   2640
aaggccagga accgtaaaaa ggccgcgttg ctggcgtttt tccataggct ccgcccccct   2700
gacgagcatc acaaaaatcg acgctcaagt cagaggtggc gaaacccgac aggactataa   2760
agataccagg cgtttccccc tggaagctcc ctcgtgcgct ctcctgttcc gaccctgccg   2820
cttaccggat acctgtccgc ctttctccct tcgggaagcg tggcgctttc tcatagctca   2880
cgctgtaggt atctcagttc ggtgtaggtc gttcgctcca agctgggctg tgtgcacgaa   2940
ccccccgttc agcccgaccg ctgcgcctta tccggtaact atcgtcttga gtccaacccg   3000
gtaagacacg acttatcgcc actggcagca gccactggta acaggattag cagagcgagg   3060
tatgtaggcg gtgctacaga gttcttgaag tggtggccta actacggcta cactagaagg   3120
acagtatttg gtatctgcgc tctgctgaag ccagttacct tcggaaaaag agttggtagc   3180
tcttgatccg gcaaacaaac caccgctggt agcggtggtt ttttgtttg caagcagcag    3240 attacgcgca gaaaaaaagg atctcaagaa gatcctttga tcttttctac ggggtctgac   3300
gctcagtgga acgaaaactc acgttaaggg attttggtca tgagattatc aaaaaggatc   3360
ttcacctaga tccttttaaa ttaaaaatga agttttaaat caatctaaag tatatatgag   3420
taaacttggt ctgacagtct agaagatcta gcccgcctaa tgagcgggct ttttttttaat   3480
```

```
tcgcaattcc ccgatgcata atgtgcctgt caaatggacg aagcagggat tctgcaaacc   3540
ctatgctact ccgtcaagcc gtcaattgtc tgattcgtta ccaattatga caacttgacg   3600
gctacatcat tcactttttc ttcacaaccg gcacggaact cgctcgggct ggccccggtg   3660
cattttttaa atacccgcga gaaatagagt tgatcgtcaa aaccaacatt gcgaccgacg   3720
gtggcgatag gcatccgggt ggtgctcaaa agcagcttcg cctggctgat acgttggtcc   3780
tcgcgccagc ttaagacgct aatccctaac tgctggcgga aaagatgtga cagacgcgac   3840
ggcgacaagc aaacatgctg tgcgacgctg gcgatatcaa aattgctgtc tgccaggtga   3900
tcgctgatgt actgacaagc ctcgcgtacc cgattatcca tcggtggatg gagcgactcg   3960
ttaatcgctt ccatgcgccg cagtaacaat tgctcaagca gatttatcgc cagcagctcc   4020
gaatagcgcc cttccccttg cccggcgtta atgatttgcc caaacaggtc gctgaaatgc   4080
ggctggtgcg cttcatccgg gcgaaagaac cccgtattgg caaatattga cggccagtta   4140
agccattcat gccagtaggc gcgcggacga aagtaaaccc actggtgata ccattcgcga   4200
gcctccggat gacgaccgta gtgatgaatc tctcctggcg ggaacagcaa aatatcaccc   4260
ggtcggcaaa caaattctcg tccctgattt ttcaccaccc cctgaccgcg aatggtgaga   4320
ttgagaatat aacctttcat tcccagcggt cggtcgataa aaaaatcgag ataaccgttg   4380
gcctcaatcg gcgttaaacc cgccaccaga tgggcattaa acgagtatcc cggcagcagg   4440
ggatcatttt gcgcttcagc catactttc atactcccgc cattcagaga agaaaccaat   4500
tgtccatatt gcatcagaca ttgccgtcac tgcgtctttt actggctctt ctcgctaacc   4560
aaaccggtaa ccccgcttat taaaagcatt ctgtaacaaa gcgggaccaa agccatgaca   4620
aaaacgcgta acaaaagtgt ctataatcac ggcagaaaag tccacattga ttatttgcac   4680
ggcgtcacac tttgctatgc catagcattt ttatccataa gattagcgga tcctacctga   4740
cgctttttat cgcaactctc tactgtttct ccatacccgt ttttttgggc tagcgaattc   4800
tgagaacaaa ctaagtggat aaatttcgtg ttcaggggcc aacgaagctc cagggcgaag   4860
tcacaatttc cggcgctaaa aatgctgctc tgcctatcct ttttgccgca ctactggcgg   4920
aagaaccggt agagatccag aacgtcccga aactgaaaga cgtcgataca tcaatgaagc   4980
tgctaagcca gctgggtgcg aaagtagaac gtaatggttc tgtgcatatt gatgcccgcg   5040
acgttaatgt attctgcgca ccttacgatc tggttaaaac catgcgtgct tctatctggg   5100
cgctggggcc gctggtagcg cgctttggtc aggggcaagt ttcactacct ggcggttgta   5160
cgatcggtgc gcgtccggtt gatctacaca tttctggcct cgaacaatta ggcgcgacca   5220
tcaaactgga agaaggttac gttaaagctt ccgtcgatgg tcgtttgaaa ggtgcacata   5280
tcgtgatgga taaagtcagc gttggcgcaa cggtgaccat catgtgtgct gcaaccctgg   5340
cggaaggcac cacgattatt gaaaacgcag cgcgtgaacc ggaaatcgtc gataccgcga   5400
acttcctgat tacgctgggt gcgaaaatta gcggtcaggg caccgatcgt atcgtcatcg   5460
aaggtgtgga acgtttaggc ggcggtgtct atcgcgttct gccggatcgt atcgaaaccg   5520
gtactttcct ggtggcggcg gcgatttctc gcggcaaaat tatctgccgt aacgcgcagc   5580
cagatactct cgacgccgtg ctggcgaaac tgcgtgacgc tggagcggac atcgaagtcg   5640
gcgaagactg gattagcctg gatatgcatg gcaaacgtcc gaaggctgtt aacgtacgta   5700
ccgcgccgca tccggcattc ccgaccgata tgcaggccca gttcacgctg ttgaacctgg   5760
tggcagaagg gaccggggttt atcaccgaaa cggtctttga aaaccgcttt atgcatgtgc   5820
```

| | |
|---|---|
| cagagctgag ccgtatgggc gcgcacgccg aaatcgaaag caataccgtt atttgtcacg | 5880 |
| gtgttgaaaa actttctggc gcacaggtta tggcaaccga tctgcgtgca tcagcaagcc | 5940 |
| tggtgctggc tggctgtatt gcggaaggga cgacggtggt tgatcgtatt tatcacatcg | 6000 |
| atcgtggcta cgaacgcatt gaagacaaac tgcgcgcttt aggtgcaaat attgagcgtg | 6060 |
| tgaaaggcga ataagaattc aaggcaaaaa acgctgtgaa aaatgttggt tttatcggct | 6120 |
| ggcgcggaat ggtcggctct gttctcatgc aacgcatggt agaggagcgc gatttcgacg | 6180 |
| ctattcgccc tgttttcttt tctacctccc agtttggaca ggcggcgccc accttcggcg | 6240 |
| acacctccac cggcacgcta caggacgctt tgatctgga tgcgctaaaa gcgctcgata | 6300 |
| tcatcgtgac ctgccagggc ggcgattata ccaacgaaat ttatccaaag ctgcgcgaaa | 6360 |
| gcggatggca gggttactgg attgatgcgg cttctacgct gcgcatgaaa gatgatgcca | 6420 |
| ttattattct cgacccggtc aaccaggacg tgattaccga cggcctgaac aatggcgtga | 6480 |
| agaccttttgt gggcggtaac tgtaccgtta gcctgatgtt gatgtcgctg ggcggtctct | 6540 |
| ttgcccataa tctcgttgac tgggtatccg tcgcgaccta tcaggccgcc tccggcggcg | 6600 |
| gcgcgcgcca tatgcgcgag ctgttaaccc agatgggtca gttgtatggc catgtcgccg | 6660 |
| atgaactggc gacgccgtct tccgcaattc ttgatattga acgcaaagtt acggcattga | 6720 |
| cccgcagcgg cgagctgccg gttgataact ttggcgtacc gctggcggga agcctgatcc | 6780 |
| cctggatcga caaacagctc gataacggcc agagccgcga agagtggaaa ggccaggcgg | 6840 |
| aaaccaacaa gattctcaat actgcctctg tgattccggt tgatggtttg tgtgtgcgcg | 6900 |
| tcggcgcgct gcgctgtcac agccaggcgt tcaccatcaa gctgaaaaaa gaggtatcca | 6960 |
| ttccgacggt ggaagaactg ctggcggcac ataatccgtg ggcgaaagtg gtgccgaacg | 7020 |
| atcgtgatat cactatgcgc gaattaaccc cggcggcgt gaccggcacg ttgactacgc | 7080 |
| cggttggtcg tctgcgtaag ctgaacatgg ggccagagtt cttgtcggcg tttaccgtag | 7140 |
| gcgaccagtt gttatgggc gccgccgagc cgctgcgtcg aatgctgcgc cagttggcct | 7200 |
| agtctaggga cgatgatgca accgataccg tcgacggatc acatagactc gctccgaaat | 7260 |
| taaagaacac ttaaattatc tactaaagga atctttagtc aagtttatt aagatgactt | 7320 |
| aactatgaat acacaattga tgggtgagcg taggagcatg cttatgcgaa aggccatcct | 7380 |
| gacggatggc ctttt | 7396 |

<210> SEQ ID NO 11
<211> LENGTH: 1506
<212> TYPE: DNA
<213> ORGANISM: Artificial Sequence
<220> FEATURE:
<223> OTHER INFORMATION: Synthetic: FIG. 37: >Tf Codon optimization

<400> SEQUENCE: 11

| | |
|---|---|
| cccgggctcg agatgacccg ttctgaaggt ctgaacatgc aggttaccga aaccctgaac | 60 |
| gaaggtctga acgtgaaat caaagttgtt gttccggcgg tgacctgga agcgaaactg | 120 |
| gcggaacgtc tggaaaccgc gcgtggtcgt gcgcgtatca acggtttccg tccgggtaaa | 180 |
| gttccgaccg cgcacctgcg taaaatgtac ggtaaatctt tcatggcgga aatcgttaac | 240 |
| gaaatcctga cgactcttc tcgttctatc ctggcggaac gtaacgaaaa atctgcgacc | 300 |
| cagccggaag ttatcatgtc tgaagacgaa aagaagcgg aaaagttct ggacggtaaa | 360 |
| gcggacttcg ttttctctct gaactacgaa gttctgccgg cgatcgaagt taagacttc | 420 |
| tctaaaatcg cggttacccg tgaagttgtt gacatctctg acgaagaagt tgacgaacag | 480 |

```
gttaaacgta tcgcgtcttc tacccgtacc tttgaaacca aaaaaggtaa agcggaaaac    540
gaagatcgtg ttaccatcga ctacctgggt aaactggacg gtgaaccgtt cgaaggtggt    600
gcggacaacg acgcgcagct ggttctgggt tctggtcagt tcattccggg tttcgaagaa    660
cagctgatcg gtctgaaagc gggtgacgaa aaagttatca ccgttacgtt cccggcggaa    720
tacggtgcgg cgcacctggc gggtaaagaa gcgaccttcg acatcaaagt taagaagtt     780 gcgaaaccga cgaactggt tctggacgac gaaaccgcga aaaaactggg tatcgaatct    840
ctggaacgtc tgcgtcaggt tgttcgtgaa cagatcgaat ctcagtacgg tcagatcacc    900
cgtcagaaag ttaaacgtca gatcctggac gcgctggacg tgactacca gttcgaaacc    960 ccgcagaaac tggttgacgc ggaattcaac aacatctggc agcagatcaa cttcgacctc    1020
cagcaggcgg tcgtaccctt cgaagacgaa gaaaccaccg aagaagcggc gcgtgaagaa    1080
taccgtaaac tggcggaacg tcgtgttcgt ctgggtctgg ttctgtctga atcggtgaa     1140 aaagcgggtg ttgaagttac cgaagaagaa ctccagcgtg cggtttacga ccaggttcgt    1200
cgttatccgg gtcaggaaaa agaaatctac gacttcctgc gtcgtacccc ggacgcggtt    1260
gcgaacctgc gtcgcgccgat cttcgaagaa aaagttgttg accacctgct ggcgaacatc    1320
aacgttaccg acaaaaaagt ttctaaagaa gaactgaccg cggaagacga agacgcggcg    1380
tctgaagcga accggcgaa aaaagcggcg cgaaaaaaa aagcggcgcc gaaaaaaaaa    1440
gcggaagaag gtaaatctga agaagcgcct aggcaccacc accaccacca ccctaggtaa    1500
ctgcag                                                              1506
```

<210> SEQ ID NO 12
<211> LENGTH: 485
<212> TYPE: PRT
<213> ORGANISM: Artificial Sequence
<220> FEATURE:
<223> OTHER INFORMATION: Synthetic: FIG. 37: >Tf Codon optimization

<400> SEQUENCE: 12

```
Met Thr Arg Ser Glu Gly Leu Asn Met Gln Val Thr Glu Thr Leu Asn
1               5                   10                  15

Glu Gly Leu Lys Arg Glu Ile Lys Val Val Pro Ala Gly Asp Leu
                20                  25                  30

Glu Ala Lys Leu Ala Glu Arg Leu Glu Thr Ala Arg Gly Arg Ala Arg
        35                  40                  45

Ile Asn Gly Phe Arg Pro Gly Lys Val Pro Thr Ala His Leu Arg Lys
    50                  55                  60

Met Tyr Gly Lys Ser Phe Met Ala Glu Ile Val Asn Glu Ile Leu Asn
65                  70                  75                  80

Asp Ser Ser Arg Ser Ile Leu Ala Glu Arg Asn Glu Lys Ser Ala Thr
                85                  90                  95

Gln Pro Glu Val Ile Met Ser Glu Asp Glu Lys Glu Ala Glu Lys Val
            100                 105                 110

Leu Asp Gly Lys Ala Asp Phe Val Phe Ser Leu Asn Tyr Glu Val Leu
        115                 120                 125

Pro Ala Ile Glu Val Lys Asp Phe Ser Lys Ile Ala Val Thr Arg Glu
    130                 135                 140

Val Val Asp Ile Ser Asp Glu Glu Val Asp Glu Gln Val Lys Arg Ile
145                 150                 155                 160

Ala Ser Ser Thr Arg Thr Phe Glu Thr Lys Lys Gly Lys Ala Glu Asn
                165                 170                 175
```

```
Glu Asp Arg Val Thr Ile Asp Tyr Leu Gly Lys Leu Asp Gly Glu Pro
            180                 185                 190

Phe Glu Gly Gly Ala Asp Asn Asp Ala Gln Leu Val Leu Gly Ser Gly
            195                 200                 205

Gln Phe Ile Pro Gly Phe Glu Glu Gln Leu Ile Gly Leu Lys Ala Gly
210                 215                 220

Asp Glu Lys Val Ile Thr Val Thr Phe Pro Ala Glu Tyr Gly Ala Ala
225                 230                 235                 240

His Leu Ala Gly Lys Glu Ala Thr Phe Asp Ile Lys Val Lys Glu Val
            245                 250                 255

Ala Lys Pro Asn Glu Leu Val Leu Asp Asp Thr Ala Lys Lys Leu
            260                 265                 270

Gly Ile Glu Ser Leu Glu Arg Leu Arg Gln Val Val Arg Glu Gln Ile
            275                 280                 285

Glu Ser Gln Tyr Gly Gln Ile Thr Arg Gln Lys Val Lys Arg Gln Ile
            290                 295                 300

Leu Asp Ala Leu Asp Gly Asp Tyr Gln Phe Glu Thr Pro Gln Lys Leu
305                 310                 315                 320

Val Asp Ala Glu Phe Asn Asn Ile Trp Gln Gln Ile Asn Phe Asp Leu
                325                 330                 335

Gln Gln Ala Gly Arg Thr Phe Glu Asp Glu Thr Thr Glu Glu Ala
            340                 345                 350

Ala Arg Glu Glu Tyr Arg Lys Leu Ala Glu Arg Val Arg Leu Gly
            355                 360                 365

Leu Val Leu Ser Glu Ile Gly Glu Lys Ala Gly Val Glu Val Thr Glu
            370                 375                 380

Glu Glu Leu Gln Arg Ala Val Tyr Asp Gln Val Arg Arg Tyr Pro Gly
385                 390                 395                 400

Gln Glu Lys Glu Ile Tyr Asp Phe Leu Arg Arg Thr Pro Asp Ala Val
                405                 410                 415

Ala Asn Leu Arg Ala Pro Ile Phe Glu Glu Lys Val Val Asp His Leu
            420                 425                 430

Leu Ala Asn Ile Asn Val Thr Asp Lys Lys Val Ser Lys Glu Glu Leu
            435                 440                 445

Thr Ala Glu Asp Glu Asp Ala Ala Ser Glu Ala Lys Pro Ala Lys Lys
450                 455                 460

Ala Ala Ala Lys Lys Lys Ala Ala Pro Lys Lys Lys Ala Glu Glu Gly
465                 470                 475                 480

Lys Ser Glu Glu Ala
            485

<210> SEQ ID NO 13
<211> LENGTH: 6511
<212> TYPE: DNA
<213> ORGANISM: Artificial Sequence
<220> FEATURE:
<223> OTHER INFORMATION: Synthetic: FIG. 39: Sequence for pG8R248
      (pG8R114 with omp25)

<400> SEQUENCE: 13
ggatcttccg aagaccttc cattctgaaa tgagctgttg acaattaatc atccggctcg      60
tataatgtgt ggaattgtga gcggataaca atttcacaca ggaaacagac catgaaaaaa     120
caacatttcc gtgtcgccct tattcccttt tttgcggcat tttgccttcc tgttttgct     180 caccagaaa cgctggtgaa agtaaaagat gctgaactcg aggcggacgc gatccaggaa     240
```

```
cagccgccgg ttccggctcc ggttgaagtt gctccgcagt actcttgggc tggtgggtac    300
accggtctgt acctgggtta cggttggaac aaagcgaaaa cctctaccgt tggttctatc    360
aaaccggacg actggaaagc tggtgctttc gctggttgga acttccagca ggaccagatc    420
gtttacggtg ttgaaggtga cgcgggttac tcttgggcta aaaaatctaa agacggtctg    480
gaagttaaac agggtttcga aggttctctg cgtgcgcgtg ttggttacga cctgaacccg    540
gttatgccgt acctgaccgc tggtatcgcg ggttctcaga tcaaactgaa caacggtctg    600
gacgacgaat ctaaattccg tgttggttgg accgctggtg ctggtctgga agctaaactg    660
accgacaaca tcctgggtcg tgttgaatac cgttacaccc agtacggtaa caaaaactac    720
gacctggctg gtaccaccgt tcgtaacaaa ctggacaccc aggacttccg tgttggtatc    780
ggttacaaat tccctaggca ccaccaccac caccaccctg gtaactgca gccaagctcc    840 caagcttggc tgttttggcg gatgagagaa gattttcagc ctgatacaga ttaaatcaga    900
acgcagaagc ggtctgataa aacagaattt gcctggcggc agtagcgcgg tggtcccacc    960
tgaccccatg ccgaactcag aagtgaaacg ccgtagcgcc gatggtagtg tggggtctcc   1020
ccatgcgaga gtagggaact gccaggcatc aaataaaacg aaaggctcag tcgaaagact   1080
gggcctttcg ttttatctgt tgtttgtcgg tgaacgctct cctgagtagg acaaatccgc   1140
cgggagcgga tttgaacgtt gcgaagcaac ggcccgaagg gtggcgggca ggacgcccgc   1200
cataaactgc caggcatcaa attaagcaga aggccatcct gacggatggc cttttgcgt   1260 ttctacaaac tcttttgttt attttttctaa atacattcaa atatgtatcc gctcatgaga   1320 caataacccct gataaatgct tcaataatgg aagatcttcc aacatcacag gtaaacagaa   1380
acgtcgggtc gatcgggaaa ttctttcccg gacggcgcgg ggttgggcaa gccgcaggcg   1440
cgtcagtgct tttagcgggt gtcggggcgc agccatgacc cagtcacgta gcgatagcgg   1500
agtgtatact ggcttaacta tgcggcatca gagcagattg tactgagagt gcaccatatg   1560
cggtgtgaaa taccgcacag atgcgtaagg agaaaatacc gcatcaggcg ctcttccgct   1620
tcctcgctca ctgactcgct gcgctcggtc gttcggctgc ggcgagcggt atcagctcac   1680
tcaaaggcgg taatacggtt atccacagaa tcagggatt acgcaggaaa gaacatgtga   1740
gcaaaaggcc agcaaaaggc caggaaccgt aaaaaggccg cgttgctggc gtttttccat   1800
aggctccgcc cccctgacga gcatcacaaa aatcgacgct caagtcagag gtggcgaaac   1860
ccgacaggac tataaagata ccaggcgttt ccccctggaa gctccctcgt gcgctctcct   1920
gttccgaccc tgccgcttac cggatacctg tccgcctttc tcccttcggg aagcgtggcg   1980
ctttctcata gctcacgctg taggtatctc agttcggtgt aggtcgttcg ctccaagctg   2040
ggctgtgtgc acgaaccccc cgttcagccc gaccgctgcg ccttatccgg taactatcgt   2100
cttgagtcca acccggtaag acacgactta tcgccactgg cagcagccac tggtaacagg   2160
attagcagag cgaggtatgt aggcggtgct acagagttct tgaagtggtg gcctaactac   2220
ggctacacta gaaggacagt atttggtatc tgcgctctgc tgaagccagt taccttcgga   2280
aaaagagttg gtagctcttg atccggcaaa caaaccaccg ctggtagcgg tggtttttt   2340 gtttgcaagc agcagattac gcgcagaaaa aaaggatctc aagaagatcc tttgatcttt   2400
tctacggggt ctgacgctca gtggaacgaa aactcacgtt aagggatttt ggtcatgaga   2460
ttatcaaaaa ggatcttcac ctagatcctt ttaaattaaa aatgaagttt taaatcaatc   2520
taaagtatat atgagtaaac ttggtctgac agttctagaag atctagcccg cctaatgagc   2580
```

```
gggcttttttt ttaattcgca attccccgat gcataatgtg cctgtcaaat ggacgaagca    2640
gggattctgc aaaccctatg ctactccgtc aagccgtcaa ttgtctgatt cgttaccaat    2700
tatgacaact tgacggctac atcattcact ttttcttcac aaccggcacg gaactcgctc    2760
gggctggccc cggtgcattt tttaaatacc cgcgagaaat agagttgatc gtcaaaacca    2820
acattgcgac cgacggtggc gataggcatc cgggtggtgc tcaaaagcag cttcgcctgg    2880
ctgatacgtt ggtcctcgcg ccagcttaag acgctaatcc ctaactctg gcggaaaaga    2940
tgtgacagac gcgacggcga caagcaaaca tgctgtgcga cgctggcgat atcaaaattg    3000
ctgtctgcca ggtgatcgct gatgtactga caagcctcgc gtacccgatt atccatcggt    3060
ggatggagcg actcgttaat cgcttccatg cgccgcagta acaattgctc aagcagattt    3120
atcgccagca gctccgaata gcgcccttcc ccttgcccgg cgttaatgat ttgcccaaac    3180
aggtcgctga aatgcggctg gtgcgcttca tccgggcgaa agaaccccgt attggcaaat    3240
attgacggcc agttaagcca ttcatgccag taggcgcgcg gacgaaagta aacccactgg    3300
tgataccatt cgcgagcctc cggatgacga ccgtagtgat gaatctctcc tggcgggaac    3360
agcaaaatat cacccggtcg gcaaacaaat tctcgtccct gattttttcac cacccctga    3420
ccgcgaatgg tgagattgag aatataacct ttcattccca gcggtcggtc gataaaaaaa    3480
tcgagataac cgttggcctc aatcggcgtt aaacccgcca ccagatgggc attaaacgag    3540
tatcccggca gcaggggatc attttgcgct tcagccatac ttttcatact cccgccattc    3600
agagaagaaa ccaattgtcc atattgcatc agacattgcc gtcactgcgt cttttactgg    3660
ctcttctcgc taaccaaacc ggtaacccg cttattaaaa gcattctgta acaaagcggg    3720
accaaagcca tgacaaaaac gcgtaacaaa agtgtctata atcacggcag aaaagtccac    3780
attgattatt tgcacggcgt cacactttgc tatgccatag catttttatc cataagatta    3840
gcggatccta cctgacgctt tttatcgcaa ctctctactg tttctccata cccgttttt    3900
tgggctagcg aattctgaga acaaactaag tggataaatt tcgtgttcag gggccaacga    3960
agctccaggg cgaagtcaca atttccggcg ctaaaaatgc tgctctgcct atccttttg    4020
ccgcactact ggcggaagaa ccggtagaga tccagaacgt cccgaaactg aaagacgtcg    4080
atacatcaat gaagctgcta agccagctgg gtgcgaaagt agaacgtaat ggttctgtgc    4140
atattgatgc ccgcgacgtt aatgtattct gcgcaccta cgatctggtt aaaaccatgc    4200
gtgcttctat ctgggcgctg gggccgctgg tagcgcgctt tggtcagggg caagtttcac    4260
tacctggcgg ttgtacgatc ggtgcgcgtc cggttgatct acacatttct ggcctcgaac    4320
aattaggcgc gaccatcaaa ctggaagaag gttacgttaa agcttccgtc gatggtcgtt    4380
tgaaaggtgc acatatcgtg atggataaag tcagcgttgg cgcaacggtg accatcatgt    4440
gtgctgcaac cctggcggaa ggcaccacga ttattgaaaa cgcagcgcgt gaaccggaaa    4500
tcgtcgatac cgcgaacttc ctgattacgc tgggtgcgaa aattagcggt cagggcaccg    4560
atcgtatcgt catcgaaggt gtggaacgtt taggcggcgg tgtctatcgc gttctgccgg    4620
atcgtatcga aaccggtact ttcctggtgg cggcggcgat ttctcgcggc aaaattatct    4680
gccgtaacgc gcagccagat actctcgacg ccgtgctgg gaaactgcgt gacgctggag    4740
cggacatcga agtcggcgaa gactggatta gcctggatat gcatggcaaa cgtccgaagg    4800
ctgttaacgt acgtaccgcg ccgcatccgg cattcccgac cgatatgcag gcccagttca    4860
cgctgttgaa cctggtggca gaagggaccg ggtttatcac cgaaacgtc tttgaaaacc    4920
gctttatgca tgtgccagag ctgagccgta tgggcgcgca cgccgaaatc gaaagcaata    4980
```

-continued

```
ccgttatttg tcacggtgtt gaaaaacttt ctggcgcaca ggttatggca accgatctgc    5040
gtgcatcagc aagcctggtg ctggctggct gtattgcgga agggacgacg gtggttgatc    5100
gtatttatca catcgatcgt ggctacgaac gcattgaaga caaactgcgc gctttaggtg    5160
caaatattga gcgtgtgaaa ggcgaataag aattcaaggc aaaaaacgct gtgaaaaatg    5220
ttggttttat cggctggcgc ggaatggtcg gctctgttct catgcaacgc atggtagagg    5280
agcgcgattt cgacgctatt cgccctgttt tcttttctac ctcccagttt ggacaggcgg    5340
cgcccacctt cggcgacacc tccaccggca cgctacagga cgcttttgat ctggatgcgc    5400
taaaagcgct cgatatcatc gtgacctgcc agggcggcgca ttataccaac gaaatttatc    5460
caaagctgcg cgaaagcgga tggcaggggtt actggattga tgcggcttct acgctgcgca    5520
tgaaagatga tgccattatt attctcgacc cggtcaacca ggacgtgatt accgacggcc    5580
tgaacaatgg cgtgaagacc tttgtgggcg gtaactgtac cgttagcctg atgttgatgt    5640
cgctgggcgt tctctttgcc cataatctcg ttgactgggt atccgtcgcg acctatcagg    5700
ccgcctccgg cggcggcgcg cgccatatgc gcgagctgtt aacccagatg ggtcagttgt    5760
atggccatgt cgccgatgaa ctggcgacgc cgtcttccgc aattcttgat attgaacgca    5820
aagttacggc attgacccgc agcggcgagc tgccggttga taactttggc gtaccgctgg    5880
cgggaagcct gatcccctgg atcgacaaac agctcgataa cggccagagc cgcgaagagt    5940
ggaaaggcca ggcggaaacc aacaagattc tcaatactgc ctctgtgatt ccggttgatg    6000
gtttgtgtgt gcgcgtcggc gcgctgcgct gtcacagcca ggcgttcacc atcaagctga    6060
aaaaagaggt atccattccg acggtggaag aactgctggc ggcacataat ccgtgggcga    6120
aagtggtgcc gaacgatcgt gatatcacta tgcgcgaatt aaccccggcg gcggtgaccg    6180
gcacgttgac tacgccggtt ggtcgtctgc gtaagctgaa catggggcca gagttcttgt    6240
cggcgtttac cgtaggcgac cagttgttat ggggcgccgc cgagccgctg cgtcgaatgc    6300
tgcgccagtt ggcctagtct agggacgatg atgcaaccga taccgtcgac ggatcacata    6360
gactcgctcc gaaattaaag aacacttaaa ttatctacta aaggaatctt tagtcaagtt    6420
tatttaagat gacttaacta tgaatacaca attgatgggt gagcgtagga gcatgcttat    6480
gcgaaaggcc atcctgacgg atggccttt t                                    6511
```

<210> SEQ ID NO 14
<211> LENGTH: 621
<212> TYPE: DNA
<213> ORGANISM: Artificial Sequence
<220> FEATURE:
<223> OTHER INFORMATION: Synthetic: FIG. 40: >omp25

<400> SEQUENCE: 14

```
cccgggctcg aggcggacgc gatccaggaa cagccgccgg ttccggctcc ggttgaagtt     60
gctccgcagt actcttgggc tggtgggtac accggtctgt acctgggtta cggttggaac    120
aaagcgaaaa cctctaccgt tggttctatc aaaccggacg actggaaagc tggtgctttc    180
gctggttgga acttccagca ggaccagatc gtttacggtg ttgaaggtga cgcgggttac    240 tctttgggcta aaaaatctaa agacggtctg gaagttaaac agggtttcga aggttctctg    300
cgtgcgcgtg ttggttacga cctgaacccg gttatgccgt acctgaccgc tggtatcgcg    360
ggttctcaga tcaaactgaa caacggtctg gacgacgaat ctaaattccg tgttggttgg    420
accgctggtg ctggtctgga agctaaactg accgacaaca tcctgggtcg tgttgaatac    480
```

```
cgttacaccc agtacggtaa caaaaactac gacctggctg gtaccaccgt tcgtaacaaa      540
ctggacaccc aggacttccg tgttggtatc ggttacaaat tccctaggca ccaccaccac      600
caccacccta ggtaactgca g                                                621
```

```
<210> SEQ ID NO 15
<211> LENGTH: 190
<212> TYPE: PRT
<213> ORGANISM: Artificial Sequence
<220> FEATURE:
<223> OTHER INFORMATION: Synthetic: FIG. 40: >omp25

<400> SEQUENCE: 15
```

```
Ala Asp Ala Ile Gln Glu Gln Pro Pro Val Pro Ala Pro Val Glu Val
1               5                   10                  15

Ala Pro Gln Tyr Ser Trp Ala Gly Gly Tyr Thr Gly Leu Tyr Leu Gly
            20                  25                  30

Tyr Gly Trp Asn Lys Ala Lys Thr Ser Thr Val Gly Ser Ile Lys Pro
        35                  40                  45

Asp Asp Trp Lys Ala Gly Ala Phe Ala Gly Trp Asn Phe Gln Gln Asp
    50                  55                  60

Gln Ile Val Tyr Gly Val Glu Gly Asp Ala Gly Tyr Ser Trp Ala Lys
65                  70                  75                  80

Lys Ser Lys Asp Gly Leu Glu Val Lys Gln Gly Phe Glu Gly Ser Leu
                85                  90                  95

Arg Ala Arg Val Gly Tyr Asp Leu Asn Pro Val Met Pro Tyr Leu Thr
            100                 105                 110

Ala Gly Ile Ala Gly Ser Gln Ile Lys Leu Asn Asn Gly Leu Asp Asp
        115                 120                 125

Glu Ser Lys Phe Arg Val Gly Trp Thr Ala Gly Ala Gly Leu Glu Ala
    130                 135                 140

Lys Leu Thr Asp Asn Ile Leu Gly Arg Val Glu Tyr Arg Tyr Thr Gln
145                 150                 155                 160

Tyr Gly Asn Lys Asn Tyr Asp Leu Ala Gly Thr Thr Val Arg Asn Lys
                165                 170                 175

Leu Asp Thr Gln Asp Phe Arg Val Gly Ile Gly Tyr Lys Phe
            180                 185                 190
```

```
<210> SEQ ID NO 16
<211> LENGTH: 18
<212> TYPE: DNA
<213> ORGANISM: Artificial Sequence
<220> FEATURE:
<223> OTHER INFORMATION: Synthetic: HIS Tag

<400> SEQUENCE: 16
caccaccacc accaccac                                                    18
```

```
<210> SEQ ID NO 17
<211> LENGTH: 6
<212> TYPE: PRT
<213> ORGANISM: Artificial Sequence
<220> FEATURE:
<223> OTHER INFORMATION: Synthetic: HIS Tag

<400> SEQUENCE: 17

His His His His His His
1               5
```

```
<210> SEQ ID NO 18
```

<211> LENGTH: 485
<212> TYPE: PRT
<213> ORGANISM: Artificial Sequence
<220> FEATURE:
<223> OTHER INFORMATION: Synthetic: figK

<400> SEQUENCE: 18

```
Met Glu Ser Leu Ser Ser Ala Leu Leu Thr Ala Lys Ser Ser Leu Ala
1               5                   10                  15

Ala Thr Ser Lys Gln Thr Ser Val Val Ser Arg Asn Ile Ser Gly Ala
            20                  25                  30

Lys Asp Ala Asp Tyr Ser Arg Arg Thr Ala Ser Leu Val Ser Gly Pro
        35                  40                  45

Tyr Gly Ser Leu Tyr Val Gly Ile Ser Arg Ser Ala Asp Glu Ala Met
    50                  55                  60

Phe Asn Arg Tyr Ile Gln Ser Asn Ser Ala Ala Ser Ala Ser Ser Thr
65                  70                  75                  80

Leu Ala Asp Gly Leu Asp Arg Leu Ser Ala Leu Tyr Ser Ala Asp Asn
                85                  90                  95

Tyr Ser Gly Ser Pro Ser Gly Leu Ile Gly Asp Leu Arg Asp Ala Leu
            100                 105                 110

Gln Thr Tyr Val Ala Ser Pro Ser Asn Ser Ala Leu Gly Asp Ser Val
        115                 120                 125

Val Ser Val Ala Gln Ser Leu Ala Asn Ala Leu Asn Asp Cys Thr Arg
130                 135                 140

Gln Val Gln Ser Leu Arg Asn Asp Ala Asp Arg Glu Ile Ala Asp Ser
                150                 155                 160
145

Val Ala Asn Ile Asn Asp Leu Leu Ala Lys Phe Glu Lys Val Asn Gln
            165                 170                 175

Asn Val Val Gly Gly Thr Arg Met Gly Arg Asp Val Ser Asp Tyr Leu
            180                 185                 190

Asp Gln Arg Asp Ala Leu Leu Lys Gln Leu Ser Gly Glu Ile Gly Ile
        195                 200                 205

Thr Thr Met Met Arg Gly Asp Asn Asp Met Val Ile Phe Ala Glu Asn
210                 215                 220

Gly Val Thr Leu Phe Glu Thr Thr Ala Arg Lys Val Thr Phe Glu Gln
225                 230                 235                 240

Ser Ala Val Leu Thr Pro Gly Val Ala Gly Lys Ala Val Thr Val Asp
                245                 250                 255

Gly Val Pro Leu Ser His Asp Thr Phe Asp Gln Pro Phe Gly Thr Gly
            260                 265                 270

Arg Leu Ser Gly Leu Leu Gln Leu Arg Asp Gln Ile Ala Pro Gln Tyr
        275                 280                 285

Gln Met Gln Leu Asp Glu Ile Ala Arg Gly Leu Val Thr Val Phe Ala
    290                 295                 300

Glu Ser Asp Gln Thr Gly Ser Ser Pro Asp Gln Thr Gly Leu Phe Ser
305                 310                 315                 320

Trp Ser Gly Ser Pro Ala Ile Pro Gly Ala Gly Leu Ser Ala Gly Ile
                325                 330                 335

Ala Gly Thr Ile Glu Val Ser Val Pro Phe Ile Ala Ser Glu Gly Gly
            340                 345                 350

Ser Ala Leu Leu Leu Arg Asp Gly Gly Ala Asn Gly Ala Asn Tyr Lys
        355                 360                 365

Tyr Asn Val Gln Gly Ala Ala Gly Phe Ser Asp Arg Leu Arg Ala Leu
    370                 375                 380
```

Asn Glu Ala Phe Ser Glu Pro Met Val Phe Asp Ala Ala Gly Ile
385                 390                 395                 400

Ser Ser Ser Ser Leu Ile Gly Tyr Ser Ala Ser Ser Leu Gly Trp
            405                 410                 415

Leu Glu Gly Lys Arg Gln Lys Ala Asn Ser Glu Phe Thr Tyr Asn Gly
            420                 425                 430

Thr Val Ala Ser Gln Ala Asp Phe Ala Leu Ser Asn Ala Thr Gly Val
            435                 440                 445

Asp Ile Asp Thr Glu Met Ala Leu Leu Leu Asp Leu Glu His Ser Tyr
            450                 455                 460

Gln Ala Ser Ser Arg Val Leu Thr Thr Val Ser Ala Met Leu Asp Asp
465                 470                 475                 480

Leu Leu Asn Ala Val
            485

<210> SEQ ID NO 19
<211> LENGTH: 1452
<212> TYPE: DNA
<213> ORGANISM: Artificial Sequence
<220> FEATURE:
<223> OTHER INFORMATION: Synthetic: figK

<400> SEQUENCE: 19
atgtcactta gttctgctct tctgacggcc aaaagttcac ttgcggcaac gtccaagcag      60
acgtccgtgg tttcccgcaa tatttcaggg gcgaaagatg cggattattc ccggcgcacg     120
gcctcccttg tatcgggccc ctatggctcc ctttatgtgg ggatcagccg gtcggcggat     180
gaagcgatgt tcaatcgcta tccagtcg aacagcgccg cttccgcatc gtccactctc       240
gcagacggtc tggaccgcct ttccgcgctt tattcggcgg ataattattc cggctcccct     300
tccggcctta tcggcgatct gcgcgacgca ctccagacct atgtcgcttc gccttccaac     360
agcgcgcttg gcgatagcgt ggtctcggtt gcgcagtcgc ttgccaatgc gttgaatgac     420
tgtacgcggc aggtgcagtc gctgcgcaac gatgccgacc gggaaattgc ggattccgtc     480
gccaatatca cgatcttct ggcaaaaattc gagaaggcca atcagaacgt ggttggtggc    540
acccgcatgg ggcgggacgt gtcggattat ctcgatcagc gcgatgcatt gctgaaacag     600
ctttcaggcg agatcggcat cacaaccatg atgcgcggtg acaacgacat ggttattttc     660
gccgaaaacg gcgtcaccct gtttgagacg acggcacgca aggtcacttt cgagcaatcc     720
gccgttctga cgcccgggcgt ggcgggcaag gcggtgacgg tcgatggcgt gccgctcagc    780
catgatacgt tcgaccagcc ttttggtacg ggccgcttga gcgggctttt gcaattgcgc     840
gaccagatcg caccgcaata ccagatgcag cttgatgaaa tcgcacgcgg gctggtgacg     900
gtgtttgccg aaagcgacca gacgggttct agcccggacc agaccgggct tttcagctgg     960
agcggctcgc cgccataccc gggtgcaggc ctttctgccg gtatcgccgg aacgatcgag    1020
gtgtccgtgc cgttcattgc ttctgaaggc ggcagcgcgc ttcttctgcg cgacggcggg    1080
gccaatggcg cgaattataa gtataatgtg caaggcgctg ccgggtttag tgatcgcctg    1140
cgcgcgctga cgaagccctt tccgaaccca tggttttttg atgcagcggc ggggatttcc    1200
tccagttcaa gcctgatcgg ctacagcgcc tcgtctctgg gctggcttga aggcaagcgc    1260
cagaaagcca atagcgaatt tacctataat gggacggtcg ccagccaggc cgattttgct    1320 cttttccaacg ccactggcgt cgatatcgac actgaaatgc gctgcttctc ggacttggaa    1380
cattcctatc aggcatcaag ccgggtgctg acgacggtta gcgcaatgct tgatgatctt    1440
cttaacgcgg tg                                                    1452

<210> SEQ ID NO 20
<211> LENGTH: 1455
<212> TYPE: DNA
<213> ORGANISM: Artificial Sequence
<220> FEATURE:
<223> OTHER INFORMATION: Synthetic: figK

<400> SEQUENCE: 20

```
atggaatctc tgtcttctgc gctgctgacc gcgaaatctt ctctggcggc gacctctaaa    60
cagacctctg ttgtttctcg taacatctct ggtgcgaaag acgcggacta ctctcgtcgt   120
accgcgtctc tggtttctgg tccgtacggt tctctgtacg ttggtatctc tcgttctgcg   180
gacgaagcga tgttcaaccg ttacatccag tctaactctg cggcgtctgc gtcttctacc   240
ctggcggacg gtctggaccg tctgtctgcg ctgtactctg cggacaacta ctctggttct   300
ccgtctggtc tgatcggtga cctgcgtgac gcgctgcaga cctacgttgc gtctccgtct   360
aactctgcgc tgggtgactc tgttgtttct gttgcgcagt ctctggcgaa cgcgctgaac   420
gactgcaccc gtcaggttca gtctctgcgt aacgacgcgg accgtgaaat cgcggactct   480
gttgcgaaca tcaacgacct gctggcgaaa ttcgaaaaag ttaaccagaa cgttgttggt   540
ggtacccgta tgggtcgtga cgtttctgac tacctggacc agcgtgacgc gctgctgaaa   600
cagctgtctg gtgaaatcgg tatcaccacc atgatgcgtg gtgacaacga catggttatc   660
ttcgcggaaa acgtgttac cctgttcgaa accaccgcgc gtaaagttac cttcgaacag   720
tctgcggttc tgactcctgg cgttgcgggt aaagcggtta ccgttgacgg tgttccgctg   780
tctcacgaca ccttcgacca gccgttcggt accggtcgtc tgtctggtct gctgcagctg   840
cgtgaccaga tcgcgccgca gtaccagatg cagctggacg aaatcgcgcg tggtctggtt   900
accgttttcg cggaatctga ccagaccggt tcttctccgg accagaccgg tctgttctct   960
tggtctggtt ctccggcgat tcctggcgcg ggtctgtctg cgggtatcgc gggtaccatc  1020
gaagtttctg ttccgttcat cgcgtctgaa ggtggttctg cgctgctgct gcgtgacggt  1080
ggtgcgaacg gtgcgaacta caaatacaac gttcagggtg cggcgggttt ctctgaccgt  1140
ctgcgtgcgc tgaacgaagc gttctctgaa ccgatggttt tcgacgcggc ggcgggtatc  1200
tcttcttctt cttctctgat cggttactct gcgtcttctc tgggttggct ggaaggtaaa  1260
cgtcagaaag cgaactctga attcacctac aacggtaccg ttgcgtctca ggcggacttc  1320
gcgctgtcta acgcgaccgg tgttgacatc gacaccgaaa tggcgctgct gctggacctg  1380
gaacactctt accaggcgtc ttctcgtgtt ctgaccaccg tttctgcgat gctggacgac  1440
ctgctgaacg cggtt                                                  1455
```

<210> SEQ ID NO 21
<211> LENGTH: 720
<212> TYPE: DNA
<213> ORGANISM: Artificial Sequence
<220> FEATURE:
<223> OTHER INFORMATION: Synthetic: omp31

<400> SEQUENCE: 21

```
atgaaatccg taattttggc gtccatcgcc gctatgttcg ccacgtccgc tatggctgcc    60
gacgtggttg tttctgaacc ttccgccccc actgctgctc ctgttgacac cttctcgtgg   120
accggcggct atatcggtat caacgccggt tacgcaggcg gcaagttcaa gcatccattt   180
```

-continued

```
tctagctttg acaaggaaga caacgaacag gtttccggtt cgctcgacgt aacagctggc    240
ggcttcgtcg gtggtgttca ggccggttac aactggcagc tcgacaacgg cgtcgtgctc    300
ggcgcggaaa ccgacttcca gggatcgagc gttacgggtt cgatttcagc cggtgccagc    360
ggtctcgaag gcaaagctga aaccaaggtc gagtggttcg gcacagttcg tgcccgtctt    420
ggctacacgg ctaccgaacg cctcatggtt tatggtaccg gcggtctggc ctatggtaag    480
gtcaagtctg cgttcaacct gggtgatgat gcaagtgccc tgcacacgtg gtccgacaag    540
acgaaagctg gctggaccct cggcgctggt gctgaatatg ccatcaacaa caactggacg    600
ctcaagtcgg aatacctcta caccgacctc ggcaagcgca acctcgtcga cgttgacaat    660
agcttccttg agagcaaggt caatttccac actgttcgcg tcggtctgaa ctacaagttc    720
```

<210> SEQ ID NO 22
<211> LENGTH: 663
<212> TYPE: DNA
<213> ORGANISM: Artificial Sequence
<220> FEATURE:
<223> OTHER INFORMATION: Synthetic: omp31

<400> SEQUENCE: 22

```
gcggacgttg ttgtttctga accgtctgcg ccgaccgcgg cgccggttga caccttctct     60
tggaccggtg gttacatcgg tatcaacgcg ggttacgcgg gtggtaaatt caaacacccg    120
ttctcttctt tcgacaaaga agacaacgaa caggttctg gttctctgga cgttaccgcg    180
ggtggtttcg ttggtggtgt tcaggcgggt tacaactggc agctggacaa cggtgttgtt    240
ctgggtgcga aaccgacttc caggggttct tctgttaccg gttctatctc tgcgggtgcg    300
tctggtctgg aaggtaaagc ggaaaccaaa gttgaatggt tcggtaccgt tcgtgcgcgt    360
ctgggttaca ccgcgaccga acgtctgatg gtttacggta ccggtggtct ggcgtacggt    420
aaagttaaat ctgcgttcaa cctgggtgac gacgcgtctg cgctgcacac ctggtctgac    480
aaaaccaaag cgggttggac cctgggtgcg ggtgcggaat acgcgatcaa caacaactgg    540
accctgaaat ctgaataccct gtacaccgac ctgggtaaac gtaacctggt tgacgttgac    600 aactcttttcc tggaatctaa agttaacttc cacaccgttc gtgttggtct gaactacaaa    660
ttc                                                                   663
```

<210> SEQ ID NO 23
<211> LENGTH: 221
<212> TYPE: PRT
<213> ORGANISM: Artificial Sequence
<220> FEATURE:
<223> OTHER INFORMATION: Synthetic: omp31

<400> SEQUENCE: 23

```
Ala Asp Val Val Val Ser Glu Pro Ser Ala Pro Thr Ala Ala Pro Val
 1               5                   10                  15

Asp Thr Phe Ser Trp Thr Gly Gly Tyr Ile Gly Ile Asn Ala Gly Tyr
             20                  25                  30

Ala Gly Gly Lys Phe Lys His Pro Phe Ser Ser Phe Asp Lys Glu Asp
         35                  40                  45

Asn Glu Gln Val Ser Gly Ser Leu Asp Val Thr Ala Gly Gly Phe Val
     50                  55                  60

Gly Gly Val Gln Ala Gly Tyr Asn Trp Gln Leu Asp Asn Gly Val Val
 65                  70                  75                  80

Leu Gly Ala Glu Thr Asp Phe Gln Gly Ser Ser Val Thr Gly Ser Ile
                 85                  90                  95
```

```
Ser Ala Gly Ala Ser Gly Leu Glu Gly Lys Ala Glu Thr Lys Val Glu
            100                 105                 110

Trp Phe Gly Thr Val Arg Ala Arg Leu Gly Tyr Thr Ala Thr Glu Arg
        115                 120                 125

Leu Met Val Tyr Gly Thr Gly Leu Ala Tyr Gly Lys Val Lys Ser
    130                 135                 140

Ala Phe Asn Leu Gly Asp Asp Ala Ser Ala Leu His Thr Trp Ser Asp
145                 150                 155                 160

Lys Thr Lys Ala Gly Trp Thr Leu Gly Ala Gly Ala Glu Tyr Ala Ile
                165                 170                 175

Asn Asn Asn Trp Thr Leu Lys Ser Glu Tyr Leu Tyr Thr Asp Leu Gly
            180                 185                 190

Lys Arg Asn Leu Val Asp Val Asp Asn Ser Phe Leu Glu Ser Lys Val
        195                 200                 205

Asn Phe His Thr Val Arg Val Gly Leu Asn Tyr Lys Phe
    210                 215                 220

<210> SEQ ID NO 24
<211> LENGTH: 1797
<212> TYPE: DNA
<213> ORGANISM: Artificial Sequence
<220> FEATURE:
<223> OTHER INFORMATION: Synthetic: btuB

<400> SEQUENCE: 24
atggcgcagg atggcgggga taaggatgat ggtgtcacac ttgatactat cgtggtgaca      60
ccgctccgcc gggcctcgtc gcttcagcga tccacgtcct cggtgagcgt tattgacgct    120
gccgatatcg aacggtccgc cgcgcccgat ctgcaatcct tgctgcaaac ctatagcggc    180
atttcggtca agacgaatgg tgggcagggg tcttccgccg atatctatat gcgcggcatg    240
tcgtcgaagc agacggtcgt gctggtcaat ggggtgcgca cggcttcggg aacgagtgga    300
tcgaccgcgc ttgccaatat tccgctgacc tccatcgaac gtatcgagat tgccaggggc    360
gcgcattcct cgcaatatgg cgcggatgca atcggcggtg tcatcaatat catcaccaaa    420
cagggcgggg cctgcggcga acgcgcatgg tgcggcagcg tttcaacagg cgtgtcgcat    480
ccatggggcg gttatgcatc gggttcgtta caaggccgca gcagcgacgg tatcgattat    540
gccgtagggg cagcgtttac cggcactcaa ggctatgatt tcaccacgcc ggaagcattc    600
ggccacgagc cggacgatga tggtttcctg cagggctcgt caatttttgc gctgtcgaaa    660
gatttcgact ggggcaaaat ctatgcggac ggcctcttca gccgtgggcg caaccagtat    720
gatgcgaccg cacccgcatt caacgaagcg gatagtacgg cctttaccgg caaggtcggc    780
acacggatcg accatacggc cgactggtcc tcgacggtgg aattcagcac gggatcgac    840 aatagccgga atttccgcaa ggggatcgaa ggttcggact ggttcgagac caggcgttac    900
ggggtgttcg cctcgaccga aaaagcttc gataccggca aggtctcgca tgttgtgact    960
ggcggcgttg aagcctatcg ggaaaaaatc aatacgacca tcgattatga cgagacaggc   1020
cgcgatcttg ccgccgtgtt cgggcaatat tcgctggaat atgatgcatt gcgtttcgat   1080
ggcggcattc gctacgacca taatggccag ttcggcaatg tgaccaccta taatcttggc   1140
gcgagctatg aaatcctgcc tgatctggtg ctgcgttcat cctatgcgac gggtttccgc   1200
gccccgactt tcaacgagct ttattatccg ggctttgcca atcccgacct gcaacccgaa   1260
aaatcccgtt ctgtggaagt cgggctgaac tggcaggcga cggcttcgac aagcctcgac   1320
```

| | |
|---|---:|
| atggcactct atcagacccg gctcagcgat gcaatcatga gcactgcgcc gtcctatatt | 1380 |
| ccgtataata ttgcaagcgc gaaggtgacc ggccttgaag cgacactcag ccatagcttc | 1440 |
| aacgaacaat ggggcatcaa gggaatggtg gacctcaagc ggcctgtcga tgaagatagc | 1500 |
| gggaatgatc ttccctatcg cgaacgtttc aaggcggccg ccgaagtgaa cttcaagccg | 1560 |
| gtggaaaagc tcgatctgac ggcacgggtg ctctatggcg gttcgcgcta taccaatgcg | 1620 |
| aaaaatacga gaaactcgg cgattatgtc accgcggatt ttgtggcgct ctattcgatc | 1680 |
| gacaaacaat cgcagttgaa gttctcggtg gagaatatct tcgacaagga ttacgagacg | 1740 |
| agttccggct atgttgcgcc gggccgcacc atcactatcg ggctgacccg taatttc | 1797 |

<210> SEQ ID NO 25
<211> LENGTH: 1797
<212> TYPE: DNA
<213> ORGANISM: Artificial Sequence
<220> FEATURE:
<223> OTHER INFORMATION: Synthetic: btuB

<400> SEQUENCE: 25

| | |
|---|---:|
| atggaacaag atggtggtga taaagatgat ggtgttacac tggacactat cgtagtaact | 60 |
| cctctgcgtc gtgcatcttc tctgcagcgt tctacctctt ctgtttctgt tatcgacgcg | 120 |
| gcggacatcg aacgttctgc ggcgccggac ctgcagtctc tgctgcagac ctactctggt | 180 |
| atctctgtta aaaccaacgg tggtcagggt tcttctgcgg acatctacat gcgtggtatg | 240 |
| tcttctaaac agaccgttgt tctggttaac ggtgttcgta ccgcgtctgc gacctctggt | 300 |
| tctaccgcgc tggcgaacat cccgctgacc tctatcgaac gtatcgaaat cgcgcgtggt | 360 |
| gcgcactctt ctcagtacgg tgcggacgcg atcggtggtg ttatcaacat catcaccaaa | 420 |
| cagggtggtc gtgcggtga acgtgcgtgg tgcggttctg tttctaccgg tgtttctcac | 480 |
| ccgtggggtg gttacgcgtc tggttctctg cagggtcgtt cttctgacgg tatcgactac | 540 |
| gcggttggtg cggcgttcac cggtacccag ggttacgact tcaccaccc ggaagcgttc | 600 |
| ggtcacgaac cggacgacga cggtttcctg cagggttctt tcaacttcgc gctgtctaaa | 660 |
| gacttcgact ggggtaaaat ctacgcggac ggtctgttct ctcgtggtcg taaccagtac | 720 |
| gacgcgaccg cgccggcgtt caacgaagcg gactctaccg cgttcaccgg taaagttggt | 780 |
| acccgtatcg accacaccgc ggactggtct tctaccgttg aattctctac cggtatcgac | 840 |
| aactctcgta acttccgtaa aggtatcgaa ggttctgact ggttcgaaac ccgtcgttac | 900 |
| ggtgttttcg cgtctaccga aaatctttc gacaccggta agtttctca cgttgttacc | 960 |
| ggtggtgttg aagcgtaccg tgaaaaaatc aacaccacca tcgactacga cgaaaccggt | 1020 |
| cgtgacctgg cggcggtttt cggtcagtac tctctggaat acgacgcgct gcgtttcgac | 1080 |
| ggtggtatcc gttacgacca caacggtcag ttcggtaacg ttaccaccta aacctgggt | 1140 |
| gcgtcttacg aaatcctgcc ggacctggtt ctgcgttctt cttacgcgac cggtttccgt | 1200 |
| gcgccgacct tcaacgaact gtactatcct ggcttcgcga acccgacct gcagccggaa | 1260 |
| aaatctcgtt ctgttgaagt tggtctgaac tggcaggcga ccgcgtctac ctctctggac | 1320 |
| atggcgctgt accagacccg tctgtctgac gcgatcatgt ctaccgcgcc gtcttacatc | 1380 |
| ccgtacaaca tcgcgtctgc gaaagttacc ggtctggaag cgaccctgtc tcactctttc | 1440 |
| aacgaacagt ggggtatcaa aggtatggtt gacctgaaac gtccggttga cgaagactct | 1500 |
| ggtaacgacc tgccgtaccg tgaacgtttc aaagcggcgg cggaagttaa cttcaaaccg | 1560 |
| gttgaaaaac tggacctgac cgcgcgtgtt ctgtacggtg gttctcgtta caccaacgcg | 1620 |

```
aaaaacacca aaaaactggg tgactacgtt accgcggact tcgttgcgct gtactctatc    1680
gacaaacagt ctcagctgaa attctctgtt gaaaacatct tcgacaaaga ctacgaaacc    1740
tcttctggtt acgttgcgcc gggtcgtacc atcaccatcg gtctgacccg taacttc       1797
```

<210> SEQ ID NO 26
<211> LENGTH: 599
<212> TYPE: PRT
<213> ORGANISM: Artificial Sequence
<220> FEATURE:
<223> OTHER INFORMATION: Synthetic: btuB

<400> SEQUENCE: 26

```
Met Glu Gln Asp Gly Gly Asp Lys Asp Asp Gly Val Thr Leu Asp Thr
1               5                   10                  15

Ile Val Val Thr Pro Leu Arg Arg Ala Ser Ser Leu Gln Arg Ser Thr
            20                  25                  30

Ser Ser Val Ser Val Ile Asp Ala Ala Asp Ile Glu Arg Ser Ala Ala
        35                  40                  45

Pro Asp Leu Gln Ser Leu Leu Gln Thr Tyr Ser Gly Ile Ser Val Lys
    50                  55                  60

Thr Asn Gly Gly Gln Gly Ser Ser Ala Asp Ile Tyr Met Arg Gly Met
65                  70                  75                  80

Ser Ser Lys Gln Thr Val Val Leu Val Asn Gly Val Arg Thr Ala Ser
                85                  90                  95

Ala Thr Ser Gly Ser Thr Ala Leu Ala Asn Ile Pro Leu Thr Ser Ile
            100                 105                 110

Glu Arg Ile Glu Ile Ala Arg Gly Ala His Ser Ser Gln Tyr Gly Ala
        115                 120                 125

Asp Ala Ile Gly Gly Val Ile Asn Ile Ile Thr Lys Gln Gly Gly Ala
    130                 135                 140

Cys Gly Glu Arg Ala Trp Cys Gly Ser Val Ser Thr Gly Val Ser His
145                 150                 155                 160

Pro Trp Gly Gly Tyr Ala Ser Gly Ser Leu Gln Gly Arg Ser Ser Asp
                165                 170                 175

Gly Ile Asp Tyr Ala Val Gly Ala Ala Phe Thr Gly Thr Gln Gly Tyr
            180                 185                 190

Asp Phe Thr Thr Pro Glu Ala Phe Gly His Glu Pro Asp Asp Asp Gly
        195                 200                 205

Phe Leu Gln Gly Ser Phe Asn Phe Ala Leu Ser Lys Asp Phe Asp Trp
    210                 215                 220

Gly Lys Ile Tyr Ala Asp Gly Leu Phe Ser Arg Gly Arg Asn Gln Tyr
225                 230                 235                 240

Asp Ala Thr Ala Pro Ala Phe Asn Glu Ala Asp Ser Thr Ala Phe Thr
                245                 250                 255

Gly Lys Val Gly Thr Arg Ile Asp His Thr Ala Asp Trp Ser Ser Thr
            260                 265                 270

Val Glu Phe Ser Thr Gly Ile Asp Asn Ser Arg Asn Phe Arg Lys Gly
        275                 280                 285

Ile Glu Gly Ser Asp Trp Phe Glu Thr Arg Arg Tyr Gly Val Phe Ala
    290                 295                 300

Ser Thr Glu Lys Ser Phe Asp Thr Gly Lys Val Ser His Val Val Thr
305                 310                 315                 320

Gly Gly Val Glu Ala Tyr Arg Glu Lys Ile Asn Thr Thr Ile Asp Tyr
                325                 330                 335
```

```
Asp Glu Thr Gly Arg Asp Leu Ala Ala Val Phe Gly Gln Tyr Ser Leu
            340                 345                 350

Glu Tyr Asp Ala Leu Arg Phe Asp Gly Gly Ile Arg Tyr Asp His Asn
        355                 360                 365

Gly Gln Phe Gly Asn Val Thr Thr Tyr Asn Leu Gly Ala Ser Tyr Glu
    370                 375                 380

Ile Leu Pro Asp Leu Val Leu Arg Ser Ser Tyr Ala Thr Gly Phe Arg
385                 390                 395                 400

Ala Pro Thr Phe Asn Glu Leu Tyr Tyr Pro Gly Phe Ala Asn Pro Asp
                405                 410                 415

Leu Gln Pro Glu Lys Ser Arg Ser Val Glu Val Gly Leu Asn Trp Gln
            420                 425                 430

Ala Thr Ala Ser Thr Ser Leu Asp Met Ala Leu Tyr Gln Thr Arg Leu
        435                 440                 445

Ser Asp Ala Ile Met Ser Thr Ala Pro Ser Tyr Ile Pro Tyr Asn Ile
    450                 455                 460

Ala Ser Ala Lys Val Thr Gly Leu Glu Ala Thr Leu Ser His Ser Phe
465                 470                 475                 480

Asn Glu Gln Trp Gly Ile Lys Gly Met Val Asp Leu Lys Arg Pro Val
                485                 490                 495

Asp Glu Asp Ser Gly Asn Asp Leu Pro Tyr Arg Glu Arg Phe Lys Ala
            500                 505                 510

Ala Ala Glu Val Asn Phe Lys Pro Val Glu Lys Leu Asp Leu Thr Ala
        515                 520                 525

Arg Val Leu Tyr Gly Gly Ser Arg Tyr Thr Asn Ala Lys Asn Thr Lys
    530                 535                 540

Lys Leu Gly Asp Tyr Val Thr Ala Asp Phe Val Ala Leu Tyr Ser Ile
545                 550                 555                 560

Asp Lys Gln Ser Gln Leu Lys Phe Ser Val Glu Asn Ile Phe Asp Lys
                565                 570                 575

Asp Tyr Glu Thr Ser Ser Gly Tyr Val Ala Pro Gly Arg Thr Ile Thr
            580                 585                 590

Ile Gly Leu Thr Arg Asn Phe
            595

<210> SEQ ID NO 27
<211> LENGTH: 1596
<212> TYPE: DNA
<213> ORGANISM: Artificial Sequence
<220> FEATURE:
<223> OTHER INFORMATION: Synthetic: Chimeric construct including TF,
      BP2693-111 and Omp3148-74

<400> SEQUENCE: 27
atgacaagaa gtgaaggttt gaacatgcag gttaccgaaa cgctcaatga agggctgaag      60
cgcgagatca aagtcgtggt tccggccggg gatcttgaag ccaagctcgc tgagcggctc     120
gaaaccgcgc gcggccgcgc ccgcatcaac ggcttccgtc cgggcaaggt gccgacggct     180
cacctgcgca agatgtacgg caagtccttc atggccgaga tcgtcaacga atcctcaac     240 gattcgtcgc gttccatcct tgccgaacgc aacgaaaagt cggcgaccca gcctgaagtc     300
atcatgtcgg aagacgaaaa agaagccgag aaggttctcg acggcaaggc cgatttcgtt     360
ttctcgctga actatgaagt gctgccggca atcgaggtca aggacttctc caagatcgcc     420
gtgacccgtg aagtcgtcga catttccgat gaggaagtcg atgaacaggt caagcgcatt     480
```

| | |
|---|---|
| gcgtcgtcga cccgcacctt tgaaaccaag aagggcaagg ccgaaaacga agatcgcgtc | 540 |
| acgatcgact atctgggcaa gctcgacggc gagccgtttg aaggcggtgc agacaatgac | 600 |
| gcacagctcg ttctcggttc cggccagttc attccgggct ttgaagaaca gctcattggc | 660 |
| ttgaaggctg gcgacgagaa ggtcatcacc gtaacgttcc cggctgaata cggcgctgcg | 720 |
| catctggctg gcaaggaagc aaccttcgac atcaaggtga aggaagttgc caagccgaac | 780 |
| gaactcgttc tcgatgacga aaccgcaaag aagctcggca ttgagtcgct tgagcgtctg | 840 |
| cgtcaggttg tgcgcgaaca gatcgaaagc cagtacggcc agatcacccg ccagaaagtg | 900 |
| aagcgtcaga ttctcgacgc ccttgatggt gattatcagt ttgaaacccc gcagaagctg | 960 |
| gttgacgccg agttcaacaa catctggcag cagatcaact tcgacctgca gcaggctggc | 1020 |
| cgcacctttg aagacgagga aacgacggaa gaagctgctc gcgaagaata tcgcaagctt | 1080 |
| gcagaacgcc gcgttcgtct tggcctcgtt ctctccgaaa tcggcgagaa ggcaggcgtg | 1140 |
| gaagtgaccg aagaagaact gcagcgcgct gtttacgatc aggttcgccg ctatccgggt | 1200 |
| caggaaaagg aaatctacga cttcctgcgc cgtacgccgg atgccgtcgc caatctgcgc | 1260 |
| gcgccgatct tgaagaaaa ggtcgtcgat catctgctgg ccaacatcaa tgtgaccgac | 1320 |
| aagaaggtct cgaaggaaga gctgacggct gaagacgaag atgcagcttc ggaagcaaag | 1380 |
| cctgccaaga aggcggctgc gaagaagaag gctgcgccga agaagaaggc cgaagaaggc | 1440 |
| aagtccgaag aggctcgcga tctccagaca ggcggcatca atatccagcc gatttatgtc | 1500 |
| tatcctgaca cgccggtta cgcaggcggc aagttcaagc atccattttc tagctttgac | 1560 |
| aaggaagaca cgaacaggt ttccggttcg aagctc | 1596 |

<210> SEQ ID NO 28
<211> LENGTH: 1662
<212> TYPE: DNA
<213> ORGANISM: Artificial Sequence
<220> FEATURE:
<223> OTHER INFORMATION: Synthetic: Chimeric construct including TF, BP2693-111 and Omp3148-74

<400> SEQUENCE: 28

| | |
|---|---|
| atgactcgtt ccgagggcct gaacatgcag gttaccgaaa ccctgaacga aggtctgaaa | 60 |
| cgcgaaatta aggttgtggt tccggcaggc gatctggaag caaaactggc tgaacgcctg | 120 |
| gagactgcgc gtggtcgcgc acgcattaac ggtttccgtc cgggcaaagt tccgaccgct | 180 |
| catctgcgca aaatgtacgg taagtctttc atggcggaaa ttgttaacga gattctgaac | 240 |
| gattctagcc gttctatcct ggcagagcgc aacgaaaaat ccgcgactca gccggaagtg | 300 |
| atcatgtctg aagacgagaa agaggcggag aaagttctgg atggtaaagc agactttgtt | 360 |
| ttctctctga actacgaggt tctgccggct atcgaggtga agattctc taaaatcgcg | 420 |
| gtgacccgtg aagttgtgga tatttccgac gaggaggtgg atgaacaggt taaacgtatc | 480 |
| gcgtcttcta cccgcacctt cgagaccaag aaaggtaagg ctgaaaacga ggatcgcgtt | 540 |
| accattgact acctgggtaa actggacggc gagccgtttg agggtggtgc agacaacgat | 600 |
| gcacagctgg ttctgggctc cggtcagttc attccgggct ttgaagagca gctgatcggc | 660 |
| ctgaaggctg gcgacgaaaa ggttattact gtgaccttc cggcggaata cggtgcggca | 720 |
| catctggctg gtaaggaggc gacctttgac atcaaagtga aggaggttgc gaaaccgaac | 780 |
| gaactggtgc tggatgatga accgcaaag aagctgggca tcgaatctct ggaacgtctg | 840 |
| cgtcaggttg ttcgtgaaca gatcgagtct cagtacggtc agattacccg tcagaaggtt | 900 |

```
aagcgccaga tcctggacgc tctggacggt gactatcagt ttgaaacccc gcagaaactg    960
gttgacgcgg agtttaacaa catttggcag cagatcaact tcgacctgca gcaggctggt   1020
cgtactttcg aggatgaaga gaccactgaa gaagcagcgc gtgaagaata ccgtaagctg   1080
gcggagcgtc gtgtgcgcct gggtctggtt ctgtctgaga tcggtgagaa agcgggcgtt   1140
gaggtgactg aggaagaact gcagcgtgcg gtgtatgacc aggtgcgccg ttatccgggc   1200
caggagaagg aaatttacga cttcctgcgt cgcactccgg acgcggtggc gaacctgcgt   1260
gcaccgattt ttgaggaaaa agttgttgac cacctgctgg ctaacatcaa cgttactgac   1320
aaaaaggtgt ctaaagagga gctgactgca gaagatgagg acgctgcgag cgaggcaaaa   1380
ccggctaaaa aagctgctgc gaagaagaag gcagcaccga aaagaaagc tgaagagggc    1440 aagagcgaag aggcagaagc ggctgctaag gaagctgcgg ctaagaaaaa ggcaggcatt   1500
gaagaccgtg acctgcagac tggtggcatc aacattcagc cgatctacgt gtacccggat   1560
gaggcggcag cgaaaaacgc tggttacgcg ggtggcaagt ttaagcaccc gttctcttct   1620
ttcgacaagg aagataacga gcaggtttct ggtagcaagc tt                      1662
```

<210> SEQ ID NO 29
<211> LENGTH: 554
<212> TYPE: PRT
<213> ORGANISM: Artificial Sequence
<220> FEATURE:
<223> OTHER INFORMATION: Synthetic: Chimeric construct including TF, BP2693-111 and Omp3148-74

<400> SEQUENCE: 29

```
Met Thr Arg Ser Glu Gly Leu Asn Met Gln Val Thr Glu Thr Leu Asn
1               5                   10                  15

Glu Gly Leu Lys Arg Glu Ile Lys Val Val Pro Ala Gly Asp Leu
            20                  25                  30

Glu Ala Lys Leu Ala Glu Arg Leu Glu Thr Ala Arg Gly Arg Ala Arg
        35                  40                  45

Ile Asn Gly Phe Arg Pro Gly Lys Val Pro Thr Ala His Leu Arg Lys
    50                  55                  60

Met Tyr Gly Lys Ser Phe Met Ala Glu Ile Val Asn Glu Ile Leu Asn
65                  70                  75                  80

Asp Ser Ser Arg Ser Ile Leu Ala Glu Arg Asn Glu Lys Ser Ala Thr
                85                  90                  95

Gln Pro Glu Val Ile Met Ser Glu Asp Glu Lys Glu Ala Glu Lys Val
            100                 105                 110

Leu Asp Gly Lys Ala Asp Phe Val Phe Ser Leu Asn Tyr Glu Val Leu
        115                 120                 125

Pro Ala Ile Glu Val Lys Asp Phe Ser Lys Ile Ala Val Thr Arg Glu
    130                 135                 140

Val Val Asp Ile Ser Asp Glu Glu Val Asp Glu Gln Val Lys Arg Ile
145                 150                 155                 160

Ala Ser Ser Thr Arg Thr Phe Glu Thr Lys Gly Lys Ala Glu Asn
                165                 170                 175

Glu Asp Arg Val Thr Ile Asp Tyr Leu Gly Lys Leu Asp Gly Glu Pro
            180                 185                 190

Phe Glu Gly Gly Ala Asp Asn Asp Ala Gln Leu Val Leu Gly Ser Gly
        195                 200                 205

Gln Phe Ile Pro Gly Phe Glu Gln Leu Ile Gly Leu Lys Ala Gly
    210                 215                 220
```

```
Asp Glu Lys Val Ile Thr Val Thr Phe Pro Ala Glu Tyr Gly Ala Ala
225                 230                 235                 240

His Leu Ala Gly Lys Glu Ala Thr Phe Asp Ile Lys Val Lys Glu Val
                245                 250                 255

Ala Lys Pro Asn Glu Leu Val Leu Asp Asp Glu Thr Ala Lys Lys Leu
            260                 265                 270

Gly Ile Glu Ser Leu Glu Arg Leu Arg Gln Val Val Arg Glu Gln Ile
        275                 280                 285

Glu Ser Gln Tyr Gly Gln Ile Thr Arg Gln Lys Val Lys Arg Gln Ile
    290                 295                 300

Leu Asp Ala Leu Asp Gly Asp Tyr Gln Phe Glu Thr Pro Gln Lys Leu
305                 310                 315                 320

Val Asp Ala Glu Phe Asn Asn Ile Trp Gln Gln Ile Asn Phe Asp Leu
                325                 330                 335

Gln Gln Ala Gly Arg Thr Phe Glu Asp Glu Thr Thr Glu Glu Ala
            340                 345                 350

Ala Arg Glu Glu Tyr Arg Lys Leu Ala Glu Arg Val Arg Leu Gly
            355                 360                 365

Leu Val Leu Ser Glu Ile Gly Glu Lys Ala Gly Val Glu Val Thr Glu
370                 375                 380

Glu Glu Leu Gln Arg Ala Val Tyr Asp Gln Val Arg Arg Tyr Pro Gly
385                 390                 395                 400

Gln Glu Lys Glu Ile Tyr Asp Phe Leu Arg Arg Thr Pro Asp Ala Val
                405                 410                 415

Ala Asn Leu Arg Ala Pro Ile Phe Glu Glu Lys Val Val Asp His Leu
            420                 425                 430

Leu Ala Asn Ile Asn Val Thr Asp Lys Lys Val Ser Lys Glu Glu Leu
        435                 440                 445

Thr Ala Glu Asp Glu Asp Ala Ala Ser Glu Ala Lys Pro Ala Lys Lys
    450                 455                 460

Ala Ala Ala Lys Lys Ala Ala Pro Lys Lys Ala Glu Glu Gly
465                 470                 475                 480

Lys Ser Glu Glu Ala Glu Ala Ala Lys Glu Ala Ala Lys Lys
                485                 490                 495

Lys Ala Gly Ile Glu Asp Arg Asp Leu Gln Thr Gly Gly Ile Asn Ile
            500                 505                 510

Gln Pro Ile Tyr Val Tyr Pro Asp Glu Ala Ala Ala Lys Asn Ala Gly
        515                 520                 525

Tyr Ala Gly Gly Lys Phe Lys His Pro Phe Ser Ser Phe Asp Lys Glu
    530                 535                 540

Asp Asn Glu Gln Val Ser Gly Ser Lys Leu
545                 550
```

<210> SEQ ID NO 30
<211> LENGTH: 1302
<212> TYPE: DNA
<213> ORGANISM: Artificial Sequence
<220> FEATURE:
<223> OTHER INFORMATION: Synthetic: Chimeric including BLS, ribosomal
      protein L7/L12 and Cu/Zn superoxide dismutase

<400> SEQUENCE: 30

```
atgaaccaaa gctgtccgaa caagacatcc tttaaaatcg cattcattca ggcccgctgg      60
cacgccgaca tcgttgacga agcgcgcaaa agctttgtcg ccgaactggc cgcaaagacg     120
ggtggcagcg tcgaggtaga gatattcgac gtgccgggtg catatgaaat tccccttcac     180
```

```
gccaagacat tggccagaac cgggcgctat gcagccatcg tcggtgcggc cttcgtgatc    240
gacggcggca tctatcgtca tgatttcgtg gcgacggccg ttatcaacgg catgatgcag    300
gtgcagcttg aaacggaagt gccggtgctg agcgtcgtgc tgacgccgca ccatttccat    360
gaaagcaagg agcatcacga cttcttccat gctcatttca aggtgaaggg cgtggaagcg    420
gcccatgccg ccttgcagat cgtgagcgag cgcagccgca tcgccgcgct tgtcgctgat    480
ctcgcaaaga tcgttgaaga cctttcggcc ctgaccgttc tggaagccgc tgagctgtcc    540
aagcttctcg aagagaagtg gggcgtttcg gctgctgctc cggtcgctgt tgctgctgcc    600
ggtggcgctg cccctgctgc tgccgcagaa gaaaagaccg aattcgacgt cgttctcgct    660
gacggcggcg ctaacaagat caacgtgatc aaggaagtgc gcgcactcac cggtctcggc    720
ctcaaggaag ccaaggacct ggtcgaaggc gctccgaagg ctgtcaagga aggcgcctcg    780
aaggacgaag ctgagaagat caaggcacag ctcgaagctg ctggcgccaa ggttgaactc    840
aagagcacga cggtaaaaat gtatgaggcg ctgccgaccg gaccgggtaa agaagttggc    900
accgtggtca tttccgaagc cccgggcggg ctgcacttca aggtgaatat ggagaagctg    960
acgccgggct atcatggctt tcatgttcac gaaaatccaa gctgcgctcc gggagaaaaa   1020
gacggcaaga tcgtaccggc tcttgctgcc ggcgggcatt atgatccggg taatacccat   1080
caccatttag ggcctgaagg tgatggacat atgggcgatt gccacgcct gagcgccaat    1140 gctgacggca aggtgagtga aaccgttgtc gctccacatc tcaagaaatt ggcggaaatc   1200
aagcagcgtt ctttgatggt ccatgtcgga ggggataatt attccgataa gcctgagccg   1260
cttggtggcg gtggtgcccg ttttgcctgc ggcgtgatcg aa                     1302

<210> SEQ ID NO 31
<211> LENGTH: 1335
<212> TYPE: DNA
<213> ORGANISM: Artificial Sequence
<220> FEATURE:
<223> OTHER INFORMATION: Synthetic: Chimeric including BLS, ribosomal
      protein L7/L12 and Cu/Zn superoxide dismutase

<400> SEQUENCE: 31
atgaatcaat catgtcctaa taaaacatca tttaaaatag catttattca agcacgttgg     60
catgcagata tagttgacga agcgcgtaaa tctttcgttg cggaactggc ggcgaaaacc    120
ggtggttctg ttgaagttga atcttcgac gttccgggtg cgtacgaaat cccgctgcac    180
gcgaaaaccc tggcgcgtac cggtcgttac gcggcgatcg ttggtgcggc gttcgttatc    240
gacggtggta tctaccgtca cgacttcgtt gcgaccgcgg ttatcaacgg tatgatgcag    300
gttcagctgg aaaccgaagt tccggttctg tctgttgttc tgaccccgca ccacttccac    360
gaatctaaag aacaccacga cttcttccac gcgcacttca agttaaaggg tgttgaagcg    420
gcacacgcag cactccagat cgtttctgaa cgttctcgta tcgcggcact ggttgaagcg    480
gcagcaaaag cggacctggc gaaatcgtt gaagacctgt ctgcgctgac cgttctggaa    540
gcggcggaac tgtctaaact gctggaagaa aaatggggtg tttctgcggc agcgccggtt    600
gcggttgcgg cagcaggtgg tgcagcaccg gcagcagcag cagaagaaaa aaccgaattt    660
gacgttgttc tggcggacgg tggtgcaaac aaaatcaacg ttatcaaaga agttcgtgca    720
ctgaccggtc tgggtctgaa agaagcaaaa gacctggttg aaggtgcgcc gaaagcggtt    780
aaagaaggtg tgtctaaaga cgaagcgaaa aaatcaaag cgcagctgga agcggcgggt    840
gcgaaagttg aactgaaaga agcggcggcg aaagaatcta ccaccgttaa aatgtacgaa    900
```

```
gcgctgccga ccggtccggg taaagaagtt ggtaccgttg ttatctctga agcgccgggt      960
ggtctgcact tcaaagttaa catggaaaaa ctgactcctg ttaccacgg tttccacgtt     1020 cacgaaaacc cgtcttgcgc gccgggtgaa aagacggca agattgttcc ggcgctggcg     1080
gcgggtggtc actacgatcc gggtaacacc caccaccacc tgggtccgga aggtgacggt     1140
cacatgggtg acctgccgcg tctgtctgcg aacgcggacg gtaaagtttc tgaaaccgtt     1200
gttgcgccgc acctgaaaaa actggcggaa atcaaacagc gttctctgat ggttcacgtt     1260
ggtggtgaca actactctga caaaccggaa ccgctgggtg gtggtggtgc gcgtttcgcg     1320
tgcggtgtta tcgaa                                                     1335
```

<210> SEQ ID NO 32
<211> LENGTH: 445
<212> TYPE: PRT
<213> ORGANISM: Artificial Sequence
<220> FEATURE:
<223> OTHER INFORMATION: Synthetic: Chimeric including BLS, ribosomal
      protein L7/L12 and Cu/Zn superoxide dismutase

<400> SEQUENCE: 32

```
Met Asn Gln Ser Cys Pro Asn Lys Thr Ser Phe Lys Ile Ala Phe Ile
1               5                   10                  15

Gln Ala Arg Trp His Ala Asp Ile Val Asp Glu Ala Arg Lys Ser Phe
            20                  25                  30

Val Ala Glu Leu Ala Ala Lys Thr Gly Gly Ser Val Glu Val Glu Ile
        35                  40                  45

Phe Asp Val Pro Gly Ala Tyr Glu Ile Pro Leu His Ala Lys Thr Leu
    50                  55                  60

Ala Arg Thr Gly Arg Tyr Ala Ala Ile Val Gly Ala Ala Phe Val Ile
65                  70                  75                  80

Asp Gly Gly Ile Tyr Arg His Asp Phe Val Ala Thr Ala Val Ile Asn
                85                  90                  95

Gly Met Met Gln Val Gln Leu Glu Thr Glu Val Pro Val Leu Ser Val
            100                 105                 110

Val Leu Thr Pro His His Phe His Glu Ser Lys Glu His His Asp Phe
        115                 120                 125

Phe His Ala His Phe Lys Val Lys Gly Val Glu Ala Ala His Ala Ala
    130                 135                 140

Leu Gln Ile Val Ser Glu Arg Ser Arg Ile Ala Ala Leu Val Glu Ala
145                 150                 155                 160

Ala Ala Lys Ala Asp Leu Ala Lys Ile Val Glu Asp Leu Ser Ala Leu
                165                 170                 175

Thr Val Leu Glu Ala Ala Glu Leu Ser Lys Leu Leu Glu Glu Lys Trp
            180                 185                 190

Gly Val Ser Ala Ala Ala Pro Val Ala Val Ala Ala Gly Gly Ala
        195                 200                 205

Ala Pro Ala Ala Ala Ala Glu Glu Lys Thr Glu Phe Asp Val Val Leu
    210                 215                 220

Ala Asp Gly Gly Ala Asn Lys Ile Asn Val Ile Lys Glu Val Arg Ala
225                 230                 235                 240

Leu Thr Gly Leu Gly Leu Lys Glu Ala Lys Asp Leu Val Glu Gly Ala
                245                 250                 255

Pro Lys Val Lys Glu Gly Ala Ser Lys Asp Glu Ala Glu Lys Ile
            260                 265                 270
```

```
Lys Ala Gln Leu Glu Ala Ala Gly Ala Lys Val Glu Leu Lys Glu Ala
            275                 280                 285
Ala Ala Lys Glu Ser Thr Thr Val Lys Met Tyr Glu Ala Leu Pro Thr
        290                 295                 300
Gly Pro Gly Lys Glu Val Gly Thr Val Val Ile Ser Glu Ala Pro Gly
305                 310                 315                 320
Gly Leu His Phe Lys Val Asn Met Glu Lys Leu Thr Pro Gly Tyr His
                325                 330                 335
Gly Phe His Val His Glu Asn Pro Ser Cys Ala Pro Gly Glu Lys Asp
            340                 345                 350
Gly Lys Ile Val Pro Ala Leu Ala Ala Gly Gly His Tyr Asp Pro Gly
        355                 360                 365
Asn Thr His His His Leu Gly Pro Glu Gly Asp Gly His Met Gly Asp
370                 375                 380
Leu Pro Arg Leu Ser Ala Asn Ala Asp Gly Lys Val Ser Glu Thr Val
385                 390                 395                 400
Val Ala Pro His Leu Lys Lys Leu Ala Glu Ile Lys Gln Arg Ser Leu
                405                 410                 415
Met Val His Val Gly Gly Asp Asn Tyr Ser Asp Lys Pro Glu Pro Leu
            420                 425                 430
Gly Gly Gly Gly Ala Arg Phe Ala Cys Gly Val Ile Glu
        435                 440                 445

<210> SEQ ID NO 33
<211> LENGTH: 21
<212> TYPE: DNA
<213> ORGANISM: Artificial Sequence
<220> FEATURE:
<223> OTHER INFORMATION: Synthetic: pG8R_consensus_F

<400> SEQUENCE: 33
caattgatgg gtgagcgtag g                                          21

<210> SEQ ID NO 34
<211> LENGTH: 20
<212> TYPE: DNA
<213> ORGANISM: Artificial Sequence
<220> FEATURE:
<223> OTHER INFORMATION: Synthetic: pG8R_consensus_R

<400> SEQUENCE: 34
tctctcatcc gccaaaacag                                            20

<210> SEQ ID NO 35
<211> LENGTH: 20
<212> TYPE: DNA
<213> ORGANISM: Artificial Sequence
<220> FEATURE:
<223> OTHER INFORMATION: Synthetic: bp26_CO_F

<400> SEQUENCE: 35
caggaaaacc agatgaccac                                            20

<210> SEQ ID NO 36
<211> LENGTH: 20
<212> TYPE: DNA
<213> ORGANISM: Artificial Sequence
<220> FEATURE:
<223> OTHER INFORMATION: Synthetic: bp26_CO_R

<400> SEQUENCE: 36
```
agcgatcgga acagagttgt                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic: omp22_CO_F

<400> SEQUENCE: 37
gggtggtacc gactacacct                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic: omp22_CO_R

<400> SEQUENCE: 38
tcaggttgtt acgctgttcg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic: tf_CO_F

<400> SEQUENCE: 39
ccctgaacga aggtctgaaa                                              20

<210> SEQ ID NO 40
<211> LENGTH: 22
<212> TYPE: DNA
<213> ORGANISM: Artificial Sequence
<220> FEATURE:
<223> OTHER INFORMATION: Synthetic: tf_CO_R

<400> SEQUENCE: 40
cagatttacc ttcttccgct tt                                           22

<210> SEQ ID NO 41
<211> LENGTH: 20
<212> TYPE: DNA
<213> ORGANISM: Artificial Sequence
<220> FEATURE:
<223> OTHER INFORMATION: Synthetic: omp25_CO_F

<400> SEQUENCE: 41
tactcttggg ctggtgggta                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic: omp25_CO_R

<400> SEQUENCE: 42
ccgataccaa cacggaagtc                                              20